United States Patent
Henderson et al.

(10) Patent No.: US 11,471,206 B2
(45) Date of Patent: Oct. 18, 2022

(54) METHOD FOR CONTROLLING A MODULAR ENERGY SYSTEM USER INTERFACE

(71) Applicant: Ethicon LLC, Guaynabo, PR (US)

(72) Inventors: Joshua Henderson, Cincinnati, OH (US); Joshua P. Morgan, Loveland, OH (US); Andrew W. Carroll, Cincinnati, OH (US); Jeffrey L. Aldridge, Lebanon, OH (US); Eitan T. Wiener, Cincinnati, OH (US); James M. Vachon, West Chester, OH (US); Gregory J. Bakos, Mason, OH (US)

(73) Assignee: Cilag GmbH International, Zug (CH)

( * ) Notice: Subject to any disclaimer, the term of this patent is extended or adjusted under 35 U.S.C. 154(b) by 361 days.

(21) Appl. No.: 16/562,144

(22) Filed: Sep. 5, 2019

(65) Prior Publication Data

US 2020/0078106 A1 Mar. 12, 2020

Related U.S. Application Data

(60) Provisional application No. 62/826,584, filed on Mar. 29, 2019, provisional application No. 62/826,588, (Continued)

(51) Int. Cl.
*A61B 18/00* (2006.01)
*A61B 34/35* (2016.01)
(Continued)

(52) U.S. Cl.
CPC ............ *A61B 18/00* (2013.01); *A61B 17/072* (2013.01); *A61B 17/320068* (2013.01);
(Continued)

(58) Field of Classification Search
CPC ......... A61B 18/00; A61B 34/20; A61B 34/25; A61B 34/35; A61B 34/74; A61B 90/361;
(Continued)

(56) References Cited

U.S. PATENT DOCUMENTS

| 4,171,700 A | 10/1979 | Farin |
| 4,849,752 A | 7/1989 | Bryant |

(Continued)

FOREIGN PATENT DOCUMENTS

| EP | 0408160 A1 | 1/1991 |
| EP | 0473987 A1 | 3/1992 |

(Continued)

OTHER PUBLICATIONS

Sorrells, P., "Application Note AN680. Passive RFID Basics," retrieved from http://ww1.microchip.com/downloads/en/AppNotes/00680b.pdf on Feb. 26, 2020, Dec. 31, 1998, pp. 1-7.

(Continued)

*Primary Examiner* — Aaron F Roane

(57) ABSTRACT

A method for controlling a user interface of a modular energy system. The modular energy system comprises a header module and a display screen on which the user interface is displayed. The modular energy system can detect attachment of a first module thereto, control the user interface to display one or more first user interface elements corresponding to the first module, detect attachment of a second module to the modular energy system, control the user interface to resize the one or more first user interface elements to accommodate display of one or more second user interface elements corresponding to the second module, and control the user interface to display the one or more second user interface elements. The various UI elements can correspond to the particular module type that is being connected to the modular energy system.

20 Claims, 63 Drawing Sheets

Related U.S. Application Data filed on Mar. 29, 2019, provisional application No. 62/826,587, filed on Mar. 29, 2019, provisional application No. 62/826,592, filed on Mar. 29, 2019, provisional application No. 62/728,480, filed on Sep. 7, 2018.

(51) Int. Cl.

| | | |
|---|---|---|
| A61B 34/20 | (2016.01) | |
| A61B 90/00 | (2016.01) | |
| A61B 34/00 | (2016.01) | |
| A61B 17/32 | (2006.01) | |
| A61B 18/12 | (2006.01) | |
| G16H 20/40 | (2018.01) | |
| A61B 18/14 | (2006.01) | |
| H04L 49/25 | (2022.01) | |
| H04L 9/40 | (2022.01) | |
| H04L 67/10 | (2022.01) | |
| H04L 67/12 | (2022.01) | |
| A61B 18/16 | (2006.01) | |
| H04B 5/00 | (2006.01) | |
| A61B 17/072 | (2006.01) | |
| H01R 43/26 | (2006.01) | |
| A61B 90/90 | (2016.01) | |
| A61B 17/00 | (2006.01) | |
| A61B 90/30 | (2016.01) | |
| A61B 34/30 | (2016.01) | |
| H04L 27/04 | (2006.01) | |
| A61B 34/37 | (2016.01) | |

(52) U.S. Cl.
CPC .. *A61B 17/320092* (2013.01); *A61B 18/1206* (2013.01); *A61B 18/1233* (2013.01); *A61B 18/1445* (2013.01); *A61B 18/16* (2013.01); *A61B 34/20* (2016.02); *A61B 34/25* (2016.02); *A61B 34/35* (2016.02); *A61B 34/74* (2016.02); *A61B 90/361* (2016.02); *A61B 90/90* (2016.02); *G16H 20/40* (2018.01); *H01R 43/26* (2013.01); *H04B 5/0031* (2013.01); *H04L 49/25* (2013.01); *H04L 63/0245* (2013.01); *H04L 67/10* (2013.01); *H04L 67/12* (2013.01); *A61B 34/37* (2016.02); *A61B 90/30* (2016.02); *A61B 90/37* (2016.02); *A61B 2017/00026* (2013.01); *A61B 2017/00199* (2013.01); *A61B 2017/00221* (2013.01); *A61B 2017/00225* (2013.01); *A61B 2017/00398* (2013.01); *A61B 2017/00477* (2013.01); *A61B 2017/00526* (2013.01); *A61B 2017/00973* (2013.01); *A61B 2017/07257* (2013.01); *A61B 2017/07271* (2013.01); *A61B 2017/07285* (2013.01); *A61B 2017/320074* (2017.08); *A61B 2018/0063* (2013.01); *A61B 2018/0072* (2013.01); *A61B 2018/0094* (2013.01); *A61B 2018/00178* (2013.01); *A61B 2018/00208* (2013.01); *A61B 2018/00601* (2013.01); *A61B 2018/00642* (2013.01); *A61B 2018/00732* (2013.01); *A61B 2018/00767* (2013.01); *A61B 2018/00845* (2013.01); *A61B 2018/00875* (2013.01); *A61B 2018/00916* (2013.01); *A61B 2018/00958* (2013.01); *A61B 2018/00994* (2013.01); *A61B 2018/126* (2013.01); *A61B 2018/128* (2013.01); *A61B 2018/1253* (2013.01); *A61B 2018/1273* (2013.01); *A61B 2018/1286* (2013.01); *A61B 2018/165* (2013.01); *A61B 2034/2048* (2016.02); *A61B 2034/2055* (2016.02); *A61B 2034/305* (2016.02); *A61B 2090/371* (2016.02); *A61B 2090/378* (2016.02); *A61B 2218/002* (2013.01); *A61B 2218/007* (2013.01); *A61B 2218/008* (2013.01); *A61B 2560/0443* (2013.01); *A61B 2560/0456* (2013.01); *H01R 2201/12* (2013.01); *H04L 27/04* (2013.01)

(58) Field of Classification Search
CPC .................. A61B 90/90; A61B 17/072; A61B 17/320068; A61B 17/320092; A61B 18/1206; A61B 18/1233; A61B 18/1445; A61B 18/16; A61B 2034/2048; A61B 2034/2055; A61B 2034/305; A61B 34/37; A61B 90/30; A61B 90/37; A61B 2090/371; A61B 2090/378; A61B 2017/320074; A61B 2017/00026; A61B 2017/00199; A61B 2017/00221; A61B 2017/00225; A61B 2017/00398; A61B 2017/00477; A61B 2017/00526; A61B 2017/00973; A61B 2017/07257; A61B 2017/07271; A61B 2017/07285; A61B 2018/00178; A61B 2018/00208; A61B 2018/00601; A61B 2018/0063; A61B 2018/00642; A61B 2018/0072; A61B 2018/00732; A61B 2018/00767; A61B 2018/00845; A61B 2018/00875; A61B 2018/00916; A61B 2018/0094; A61B 2018/00958; A61B 2018/00994; A61B 2018/1253; A61B 2018/126; A61B 2018/1273; A61B 2018/128; A61B 2018/1286; A61B 2018/165; A61B 2218/002; A61B 2218/007; A61B 2218/008; A61B 2560/0443; A61B 2560/0456; G16H 20/40; H01R 43/26; H01R 2201/12; H04B 5/0031; H04L 49/25; H04L 63/0245; H04L 67/10; H04L 67/12; H04L 27/04

USPC .......................................................... 606/1

See application file for complete search history.

(56) References Cited

U.S. PATENT DOCUMENTS

| | | |
|---|---|---|
| D303,787 S | 10/1989 | Messenger et al. |
| D327,061 S | 6/1992 | Soren et al. |
| 5,189,277 A | 2/1993 | Boisvert et al. |
| 5,204,669 A | 4/1993 | Dorfe et al. |
| 5,318,563 A | 6/1994 | Malis et al. |
| D379,346 S | 5/1997 | Mieki |
| 5,693,042 A | 12/1997 | Boiarski et al. |
| 5,724,468 A | 3/1998 | Leone et al. |
| 6,049,467 A | 4/2000 | Tamarkin et al. |
| 6,055,458 A | 4/2000 | Cochran et al. |
| D431,811 S | 10/2000 | Nishio et al. |
| 6,269,411 B1 | 7/2001 | Reasoner |
| 6,416,471 B1 | 7/2002 | Kumar et al. |
| 6,546,270 B1 | 4/2003 | Goldin et al. |
| 6,584,358 B2 | 6/2003 | Carter et al. |
| 6,611,793 B1 | 8/2003 | Burnside et al. |
| 6,731,514 B2 | 5/2004 | Evans |
| 6,760,218 B2 | 7/2004 | Fan |
| 6,839,238 B2 | 1/2005 | Derr et al. |
| 6,913,471 B2 | 7/2005 | Smith |
| 7,009,511 B2 | 3/2006 | Mazar et al. |
| 7,044,949 B2 | 5/2006 | Orszulak et al. |
| 7,074,205 B1 | 7/2006 | Duffy et al. |
| 7,134,994 B2 | 11/2006 | Alpert et al. |
| 7,217,269 B2 | 5/2007 | El-Galley et al. |
| 7,252,664 B2 | 8/2007 | Nasab et al. |
| 7,344,532 B2 | 3/2008 | Goble et al. |
| 7,353,068 B2 | 4/2008 | Tanaka et al. |

(56) References Cited

U.S. PATENT DOCUMENTS

| | | |
|---|---|---|
| 7,408,439 B2 | 8/2008 | Wang et al. |
| D579,876 S | 11/2008 | Novotney et al. |
| D583,328 S | 12/2008 | Chiang |
| 7,496,418 B2 | 2/2009 | Kim et al. |
| D589,447 S | 3/2009 | Sasada et al. |
| 7,500,747 B2 | 3/2009 | Howell et al. |
| 7,518,502 B2 | 4/2009 | Austin et al. |
| 7,563,259 B2 | 7/2009 | Takahashi |
| 7,637,907 B2 | 12/2009 | Blaha |
| 7,656,671 B2 | 2/2010 | Liu et al. |
| 7,757,028 B2 | 7/2010 | Druke et al. |
| D631,252 S | 1/2011 | Leslie |
| 7,932,826 B2 | 4/2011 | Fritchie et al. |
| 7,945,065 B2 | 5/2011 | Menzl et al. |
| 7,945,342 B2 | 5/2011 | Tsai et al. |
| 7,982,776 B2 | 7/2011 | Dunki-Jacobs et al. |
| 7,995,045 B2 | 8/2011 | Dunki-Jacobs |
| 8,019,094 B2 | 9/2011 | Hsieh et al. |
| D655,678 S | 3/2012 | Kobayashi et al. |
| D657,368 S | 4/2012 | Magee et al. |
| 8,239,066 B2 | 8/2012 | Jennings et al. |
| D667,838 S | 9/2012 | Magee et al. |
| D675,164 S | 1/2013 | Kobayashi et al. |
| D676,392 S | 2/2013 | Gassauer |
| D678,196 S | 3/2013 | Miyauchi et al. |
| D678,304 S | 3/2013 | Yakoub et al. |
| 8,423,182 B2 | 4/2013 | Robinson et al. |
| D687,146 S | 7/2013 | Juzkiw et al. |
| 8,540,709 B2 | 9/2013 | Allen |
| 8,567,393 B2 | 10/2013 | Hickle et al. |
| D704,839 S | 5/2014 | Juzkiw et al. |
| 8,795,001 B1 | 8/2014 | Lam et al. |
| 8,819,581 B2 | 8/2014 | Nakamura et al. |
| D716,333 S | 10/2014 | Chotin et al. |
| 8,917,513 B1 | 12/2014 | Hazzard |
| 8,920,186 B2 | 12/2014 | Shishikura |
| 8,923,012 B2 | 12/2014 | Kaufman et al. |
| 8,968,296 B2 | 3/2015 | McPherson |
| 8,986,288 B2 | 3/2015 | Konishi |
| D729,267 S | 5/2015 | Yoo et al. |
| 9,055,870 B2 | 6/2015 | Meador et al. |
| 9,160,853 B1 | 10/2015 | Daddi et al. |
| 9,168,054 B2 | 10/2015 | Turner et al. |
| 9,168,091 B2 | 10/2015 | Janssen et al. |
| 9,198,711 B2 | 12/2015 | Joseph |
| 9,226,766 B2 | 1/2016 | Aldridge et al. |
| 9,226,791 B2 | 1/2016 | McCarthy et al. |
| 9,237,921 B2 | 1/2016 | Messerly et al. |
| 9,265,429 B2 | 2/2016 | St. Pierre et al. |
| 9,277,961 B2 | 3/2016 | Panescu et al. |
| 9,277,969 B2 | 3/2016 | Brannan et al. |
| 9,345,481 B2 | 5/2016 | Hall et al. |
| 9,345,900 B2 | 5/2016 | Wu et al. |
| 9,351,653 B1 | 5/2016 | Harrison |
| 9,463,646 B2 | 10/2016 | Payne et al. |
| 9,474,565 B2 | 10/2016 | Shikhman et al. |
| D772,252 S | 11/2016 | Myers et al. |
| 9,486,271 B2 | 11/2016 | Dunning |
| 9,532,827 B2 | 1/2017 | Morgan et al. |
| 9,600,031 B2 | 3/2017 | Kaneko et al. |
| 9,603,277 B2 | 3/2017 | Morgan et al. |
| D783,675 S | 4/2017 | Yagisawa et al. |
| D784,270 S | 4/2017 | Bhattacharya |
| 9,713,503 B2 | 7/2017 | Goldschmidt |
| 9,750,563 B2 | 9/2017 | Shikhman et al. |
| 9,782,214 B2 | 10/2017 | Houser et al. |
| 9,788,907 B1 | 10/2017 | Alvi et al. |
| 9,867,670 B2 | 1/2018 | Brannan et al. |
| 9,907,196 B2 | 2/2018 | Susini et al. |
| 9,974,595 B2 | 5/2018 | Anderson et al. |
| 9,987,068 B2 | 6/2018 | Anderson et al. |
| 9,987,072 B2 | 6/2018 | McPherson |
| 10,028,402 B1 | 7/2018 | Walker |
| 10,039,589 B2 | 8/2018 | Virshek et al. |
| D832,211 S | 10/2018 | Ladd et al. |
| 10,098,527 B2 | 10/2018 | Weisenburgh, II et al. |
| 10,105,470 B2 | 10/2018 | Reasoner et al. |
| D834,541 S | 11/2018 | You et al. |
| 10,117,702 B2 | 11/2018 | Danziger et al. |
| 10,136,954 B2 | 11/2018 | Johnson et al. |
| 10,137,245 B2 | 11/2018 | Melker et al. |
| 10,147,148 B2 | 12/2018 | Wu et al. |
| 10,166,061 B2 | 1/2019 | Berry et al. |
| 10,201,365 B2 | 2/2019 | Boudreaux et al. |
| 10,339,496 B2 | 7/2019 | Matson et al. |
| 10,357,184 B2 | 7/2019 | Crawford et al. |
| 10,386,990 B2 | 8/2019 | Shikhman et al. |
| 10,499,847 B2 | 12/2019 | Latimer et al. |
| 10,531,579 B2 | 1/2020 | Hsiao et al. |
| D876,466 S | 2/2020 | Kobayashi et al. |
| 10,561,753 B2 | 2/2020 | Thompson et al. |
| 10,602,007 B2 | 3/2020 | Takano |
| 10,624,667 B2 | 4/2020 | Faller et al. |
| 10,624,691 B2 | 4/2020 | Wiener et al. |
| 10,675,100 B2 | 6/2020 | Frushour |
| 10,687,884 B2 | 6/2020 | Wiener et al. |
| 10,743,872 B2 | 8/2020 | Leimbach et al. |
| 10,772,673 B2 | 9/2020 | Allen, IV et al. |
| 10,881,399 B2 | 1/2021 | Shelton, IV et al. |
| 10,898,256 B2 | 1/2021 | Yates et al. |
| 10,932,772 B2 | 3/2021 | Shelton, IV et al. |
| 10,950,982 B2 | 3/2021 | Regnier et al. |
| D924,139 S | 7/2021 | Jayme |
| D928,725 S | 8/2021 | Oberkircher et al. |
| D928,726 S | 8/2021 | Asher et al. |
| D939,545 S | 12/2021 | Oberkircher et al. |
| 11,218,822 B2 | 1/2022 | Morgan et al. |
| 2001/0029315 A1 | 10/2001 | Sakurai et al. |
| 2003/0078631 A1 | 4/2003 | Nelson et al. |
| 2003/0199864 A1 | 10/2003 | Eick |
| 2004/0030328 A1 | 2/2004 | Eggers et al. |
| 2004/0059323 A1 | 3/2004 | Sturm et al. |
| 2004/0111045 A1 | 6/2004 | Sullivan et al. |
| 2005/0010209 A1 | 1/2005 | Lee et al. |
| 2005/0013459 A1 | 1/2005 | Maekawa |
| 2005/0113823 A1 | 5/2005 | Reschke et al. |
| 2005/0165390 A1 | 7/2005 | Mauti et al. |
| 2005/0229110 A1 | 10/2005 | Gegner et al. |
| 2005/0251233 A1 | 11/2005 | Kanzius |
| 2006/0136622 A1 | 6/2006 | Rouvelin et al. |
| 2007/0282321 A1 | 12/2007 | Shah et al. |
| 2008/0072896 A1 | 3/2008 | Setzer et al. |
| 2008/0129465 A1 | 6/2008 | Rao |
| 2008/0249377 A1 | 10/2008 | Molducci et al. |
| 2009/0131929 A1 | 5/2009 | Shimizu |
| 2009/0234352 A1 | 9/2009 | Behnke et al. |
| 2010/0069939 A1 | 3/2010 | Konishi |
| 2010/0092006 A1 | 4/2010 | Rosen |
| 2010/0120266 A1 | 5/2010 | Rimborg |
| 2010/0198200 A1 | 8/2010 | Horvath |
| 2011/0125149 A1 | 5/2011 | El-Galley et al. |
| 2011/0245630 A1 | 10/2011 | St. Pierre et al. |
| 2011/0273465 A1 | 11/2011 | Konishi et al. |
| 2011/0306840 A1 | 12/2011 | Allen et al. |
| 2013/0031201 A1 | 1/2013 | Kagan et al. |
| 2013/0197503 A1 | 8/2013 | Orszulak |
| 2013/0268283 A1 | 10/2013 | Vann et al. |
| 2014/0009894 A1 | 1/2014 | Yu |
| 2014/0058714 A1 | 2/2014 | Boyer |
| 2014/0087573 A1 | 3/2014 | Kroeckel |
| 2014/0226572 A1 | 8/2014 | Thota et al. |
| 2014/0262598 A1 | 9/2014 | Miki et al. |
| 2014/0263552 A1 | 9/2014 | Hall et al. |
| 2015/0190189 A1 | 7/2015 | Yates et al. |
| 2015/0289929 A1 | 10/2015 | Toth et al. |
| 2016/0045247 A1 | 2/2016 | Heim et al. |
| 2016/0287312 A1 | 10/2016 | Tegg et al. |
| 2017/0202595 A1 | 7/2017 | Shelton, IV |
| 2017/0251305 A1 | 8/2017 | Fathollahi |
| 2017/0252091 A1 | 9/2017 | Honda |
| 2017/0296213 A1 | 10/2017 | Swensgard et al. |
| 2017/0319259 A1 | 11/2017 | Dunning |
| 2018/0042659 A1 | 2/2018 | Rupp et al. |
| 2018/0065248 A1 | 3/2018 | Barral et al. |

(56) References Cited

U.S. PATENT DOCUMENTS

| | | |
|---|---|---|
| 2018/0221005 A1 | 8/2018 | Hamel et al. |
| 2018/0228528 A1 | 8/2018 | Fraasch et al. |
| 2018/0262916 A1 | 9/2018 | Polley et al. |
| 2018/0333207 A1 | 11/2018 | Moctezuma De la Barrera |
| 2019/0000478 A1 | 1/2019 | Messerly et al. |
| 2019/0201137 A1 | 7/2019 | Shelton, IV et al. |
| 2019/0224434 A1 | 7/2019 | Silver et al. |
| 2019/0247141 A1 | 8/2019 | Batchelor et al. |
| 2019/0278262 A1 | 9/2019 | Taylor et al. |
| 2020/0004487 A1 | 1/2020 | Hanajima et al. |
| 2020/0038120 A1 | 2/2020 | Ziraknejad et al. |
| 2020/0078070 A1 | 3/2020 | Henderson et al. |
| 2020/0078071 A1 | 3/2020 | Asher |
| 2020/0078076 A1 | 3/2020 | Henderson et al. |
| 2020/0078077 A1 | 3/2020 | Henderson et al. |
| 2020/0078078 A1 | 3/2020 | Henderson et al. |
| 2020/0078079 A1 | 3/2020 | Morgan et al. |
| 2020/0078080 A1 | 3/2020 | Henderson et al. |
| 2020/0078081 A1 | 3/2020 | Jayme et al. |
| 2020/0078082 A1 | 3/2020 | Henderson et al. |
| 2020/0078089 A1 | 3/2020 | Henderson et al. |
| 2020/0078110 A1 | 3/2020 | Henderson et al. |
| 2020/0078111 A1 | 3/2020 | Oberkircher et al. |
| 2020/0078112 A1 | 3/2020 | Henderson et al. |
| 2020/0078113 A1 | 3/2020 | Sawhney et al. |
| 2020/0078114 A1 | 3/2020 | Asher et al. |
| 2020/0078115 A1 | 3/2020 | Asher et al. |
| 2020/0078116 A1 | 3/2020 | Oberkircher et al. |
| 2020/0078117 A1 | 3/2020 | Henderson et al. |
| 2020/0078118 A1 | 3/2020 | Henderson et al. |
| 2020/0078119 A1 | 3/2020 | Henderson et al. |
| 2020/0078120 A1 | 3/2020 | Aldridge et al. |
| 2020/0081585 A1 | 3/2020 | Petre et al. |
| 2020/0090808 A1 | 3/2020 | Carroll et al. |
| 2020/0100825 A1 | 4/2020 | Henderson et al. |
| 2020/0100830 A1 | 4/2020 | Henderson et al. |
| 2020/0106220 A1 | 4/2020 | Henderson et al. |
| 2020/0305924 A1 | 10/2020 | Carroll |
| 2020/0305945 A1 | 10/2020 | Morgan et al. |
| 2021/0203889 A1 | 7/2021 | Fung et al. |
| 2021/0212717 A1 | 7/2021 | Yates et al. |
| 2021/0236755 A1 | 8/2021 | King et al. |

FOREIGN PATENT DOCUMENTS

| | | |
|---|---|---|
| EP | 0929263 B1 | 7/1999 |
| EP | 2942023 A2 | 11/2015 |
| JP | 2001029353 A | 2/2001 |
| WO | WO-0112089 A1 | 2/2001 |
| WO | WO-2008053485 A1 | 5/2008 |
| WO | WO-2014031800 A1 | 2/2014 |
| WO | WO-2014071184 A1 | 5/2014 |
| WO | WO-2017058617 | 4/2017 |
| WO | WO-2018116247 A1 | 6/2018 |

OTHER PUBLICATIONS

IEEE Std 802.3-2012 (Revision of IEEE Std 802.3-2008, published Dec. 28, 2012.

"ATM-MPLS Network Interworking Version 2.0, af-aic-0178.001" ATM Standard, The ATM Forum Technical Committee, published Aug. 2003.

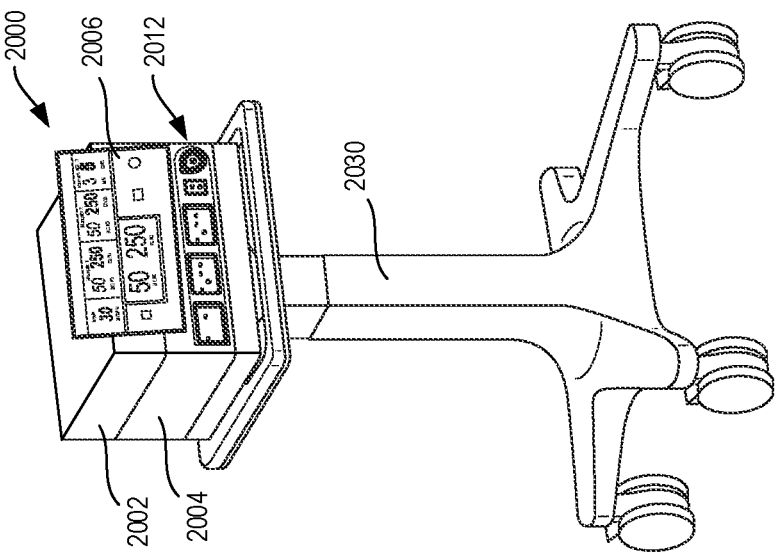
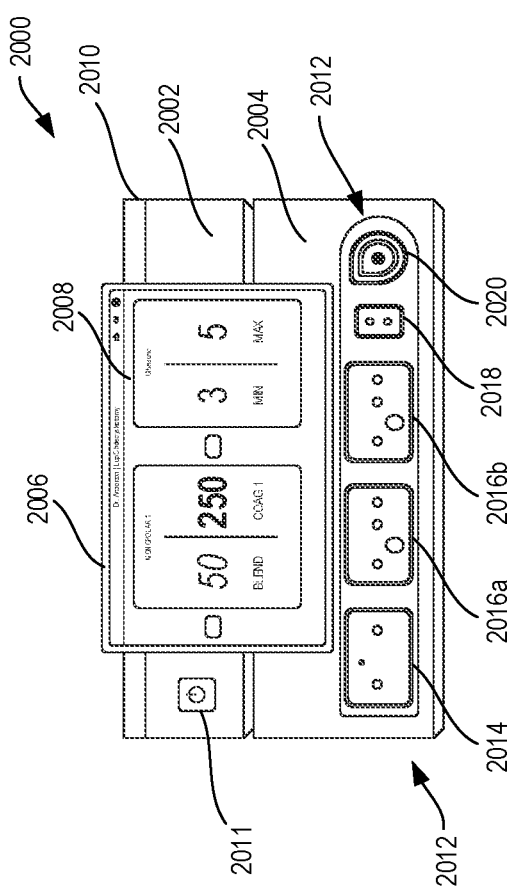
FIG. 25A
FIG. 25B

METHOD FOR CONTROLLING A MODULAR ENERGY SYSTEM USER INTERFACE

CROSS-REFERENCE TO RELATED APPLICATIONS

The present application claims priority under 35 U.S.C. § 119(e) to U.S. Provisional Patent Application Ser. No. 62/826,584, titled MODULAR SURGICAL PLATFORM ELECTRICAL ARCHITECTURE, filed Mar. 29, 2019, the disclosure of which is herein incorporated by reference in its entirety.

The present application claims priority under 35 U.S.C. § 119(e) to U.S. Provisional Patent Application Ser. No. 62/826,587, titled MODULAR ENERGY SYSTEM CONNECTIVITY, filed Mar. 29, 2019, the disclosure of which is herein incorporated by reference in its entirety.

The present application claims priority under 35 U.S.C. § 119(e) to U.S. Provisional Patent Application Ser. No. 62/826,588, titled MODULAR ENERGY SYSTEM INSTRUMENT COMMUNICATION TECHNIQUES, filed Mar. 29, 2019, the disclosure of which is herein incorporated by reference in its entirety.

The present application claims priority under 35 U.S.C. § 119(e) to U.S. Provisional Patent Application Ser. No. 62/826,592, titled MODULAR ENERGY DELIVERY SYSTEM, filed Mar. 29, 2019, the disclosure of which is herein incorporated by reference in its entirety.

The present application claims priority under 35 U.S.C. § 119(e) to U.S. Provisional Patent Application Ser. No. 62/728,480, titled MODULAR ENERGY SYSTEM AND USER INTERFACE, filed Sep. 7, 2018, the disclosure of which is herein incorporated by reference in its entirety.

BACKGROUND

The present disclosure relates to various surgical systems, including modular electrosurgical and/or ultrasonic surgical systems. Operating rooms (ORs) are in need of streamlined capital solutions because ORs are a tangled web of cords, devices, and people due to the number of different devices that are needed to complete each surgical procedure. This is a reality of every OR in every market throughout the globe. Capital equipment is a major offender in creating clutter within ORs because most capital equipment performs one task or job, and each type of capital equipment requires unique techniques or methods to use and has a unique user interface. Accordingly, there are unmet consumer needs for capital equipment and other surgical technology to be consolidated in order to decrease the equipment footprint within the OR, streamline the equipment's interfaces, and improve surgical staff efficiency during a surgical procedure by reducing the number of devices that surgical staff members need to interact with.

SUMMARY

In one general aspect, a method for controlling a user interface (UI) of a modular energy system. The modular energy system comprises a header module and a display screen on which the UI is displayed. The method comprises: detecting attachment of a first module to the modular energy system; controlling the UI to display one or more first UI elements corresponding to the first module, the one or more first UI elements configured to provide information or controls pertaining to the first module; detecting attachment of a second module to the modular energy system; controlling the UI to resize the one or more first UI elements to accommodate display of one or more second UI elements corresponding to the second module; and controlling the UI to display the one or more second UI elements, the one or more second UI elements configured to display information or controls provide information or controls pertaining to the second module.

FIGURES

The various aspects described herein, both as to organization and methods of operation, together with further objects and advantages thereof, may best be understood by reference to the following description, taken in conjunction with the accompanying drawings as follows.

FIG. 25A is a first illustrative modular energy system configuration including a header module and a display screen that renders a graphical user interface (GUI) for relaying information regarding modules connected to the header module, in accordance with at least one aspect of the present disclosure.

FIG. 25B is the modular energy system shown in FIG. 25A mounted to a cart, in accordance with at least one aspect of the present disclosure.

DESCRIPTION

Figure 1:
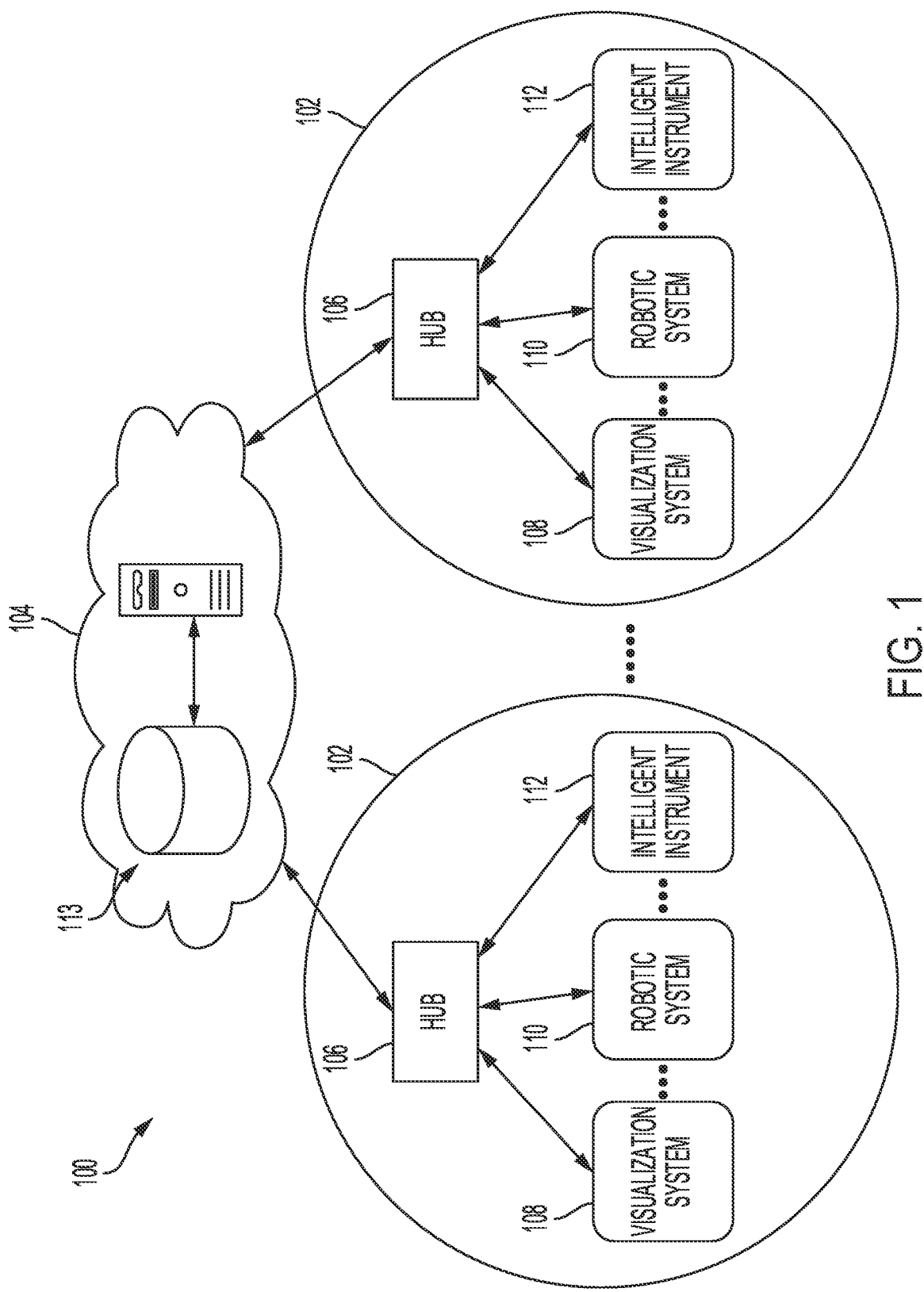
FIG. 1 is a block diagram of a computer-implemented interactive surgical system, in accordance with at least one aspect of the present disclosure.

Applicant of the present application owns the following U.S. patent applications filed on Sep. 5, 2019, the disclosures of each of which are herein incorporated by reference in their entireties:

U.S. patent application Ser. No. 16/562,123, titled METHOD FOR CONSTRUCTING AND USING A MODULAR SURGICAL ENERGY SYSTEM WITH MULTIPLE DEVICES, now U.S. Patent Application Publication No. 2020/0100830;

U.S. patent application Ser. No. 16/562,142, titled METHOD FOR ENERGY DISTRIBUTION IN A SURGICAL MODULAR ENERGY SYSTEM, now U.S. Patent Application Publication No. 2020/0078070;

U.S. patent application Ser. No. 16/562,169, titled SURGICAL MODULAR ENERGY SYSTEM WITH A SEGMENTED BACKPLANE, now U.S. Patent Application Publication No. 2020/0078112;

U.S. patent application Ser. No. 16/562,185, titled SURGICAL MODULAR ENERGY SYSTEM WITH FOOTER MODULE, now U.S. Patent Application Publication No. 2020/0078115;

U.S. patent application Ser. No. 16/562,203, titled POWER AND COMMUNICATION MITIGATION ARRANGEMENT FOR MODULAR SURGICAL ENERGY SYSTEM, now U.S. Patent Application Publication No. 2020/0078118;

U.S. patent application Ser. No. 16/562,212, titled MODULAR SURGICAL ENERGY SYSTEM WITH MODULE POSITIONAL AWARENESS SENSING WITH VOLTAGE DETECTION, now U.S. Patent Application Publication No. 2020/0078119;

U.S. patent application Ser. No. 16/562,234, titled MODULAR SURGICAL ENERGY SYSTEM WITH MODULE POSITIONAL AWARENESS SENSING WITH TIME COUNTER, now U.S. Patent Application Publication No. 2020/0305945;

U.S. patent application Ser. No. 16/562,243, titled MODULAR SURGICAL ENERGY SYSTEM WITH MODULE POSITIONAL AWARENESS WITH DIGITAL LOGIC, now U.S. Patent Application Publication No. 2020/0078120;

U.S. patent application Ser. No. 16/562,135, titled METHOD FOR CONTROLLING AN ENERGY MODULE OUTPUT, now U.S. Patent Application Publication No. 2020/0078076;

U.S. patent application Ser. No. 16/562,180, titled ENERGY MODULE FOR DRIVING MULTIPLE ENERGY MODALITIES, now U.S. Patent Application Publication No. 2020/0078080;

U.S. patent application Ser. No. 16/562,184, titled GROUNDING ARRANGEMENT OF ENERGY MODULES, now U.S. Patent Application Publication No. 2020/0078081;

U.S. patent application Ser. No. 16/562,188, titled BACKPLANE CONNECTOR DESIGN TO CONNECT STACKED ENERGY MODULES, now U.S. Patent Application Publication No. 2020/0078116;

U.S. patent application Ser. No. 16/562,195, titled ENERGY MODULE FOR DRIVING MULTIPLE ENERGY MODALITIES THROUGH A PORT, now U.S. Patent Application Publication No. 2020/0078117;

U.S. patent application Ser. No. 16/562,202, titled SURGICAL INSTRUMENT UTILIZING DRIVE SIGNAL TO POWER SECONDARY FUNCTION, now U.S. Patent Application Publication No. 2020/0078082;

U.S. patent application Ser. No. 16/562,151, titled PASSIVE HEADER MODULE FOR A MODULAR ENERGY SYSTEM, now U.S. Patent Application Publication No. 2020/0078110;

U.S. patent application Ser. No. 16/562,157, titled CONSOLIDATED USER INTERFACE FOR MODULAR ENERGY SYSTEM, now U.S. Patent Application Publication No. 2020/0081585;

U.S. patent application Ser. No. 16/562,159, titled AUDIO TONE CONSTRUCTION FOR AN ENERGY MODULE OF A MODULAR ENERGY SYSTEM, now U.S. Pat. No. 11,218,822;

U.S. patent application Ser. No. 16/562,163, titled ADAPTABLY CONNECTABLE AND REASSIGNABLE SYSTEM ACCESSORIES FOR MODULAR ENERGY SYSTEM, now U.S. Patent Application Publication No. 2020/0078111;

U.S. patent application Ser. No. 16/562,125, titled METHOD FOR COMMUNICATING BETWEEN MODULES AND DEVICES IN A MODULAR SURGICAL SYSTEM, now U.S. Patent Application Publication No. 2020/0100825;

U.S. patent application Ser. No. 16/562,137, titled FLEXIBLE HAND-SWITCH CIRCUIT, now U.S. Patent Application Publication No. 2020/0106220;

U.S. patent application Ser. No. 16/562,143, titled FIRST AND SECOND COMMUNICATION PROTOCOL ARRANGEMENT FOR DRIVING PRIMARY AND SECONDARY DEVICES THROUGH A SINGLE PORT, now U.S. Patent Application Publication No. 2020/0090808;

U.S. patent application Ser. No. 16/562,148, titled FLEXIBLE NEUTRAL ELECTRODE, now U.S. Pat. No. 11,350,978;

U.S. patent application Ser. No. 16/562,154, titled SMART RETURN PAD SENSING THROUGH MODULATION OF NEAR FIELD COMMUNICATION AND CONTACT QUALITY MONITORING SIGNALS, now U.S. Patent Application Publication No. 2020/0078089;

U.S. patent application Ser. No. 16/562,162, titled AUTOMATIC ULTRASONIC ENERGY ACTIVATION CIRCUIT DESIGN FOR MODULAR SURGICAL SYSTEMS, now U.S. Patent Application Publication No. 2020/0305924;

U.S. patent application Ser. No. 16/562,167, titled COORDINATED ENERGY OUTPUTS OF SEPARATE BUT CONNECTED MODULES, now U.S. Patent Application Publication No. 2020/0078078;

U.S. patent application Ser. No. 16/562,170, titled MANAGING SIMULTANEOUS MONOPOLAR OUTPUTS USING DUTY CYCLE AND SYNCHRONIZATION, now U.S. Patent Application Publication No. 2020/0078079;

U.S. patent application Ser. No. 16/562,172, titled PORT PRESENCE DETECTION SYSTEM FOR MODULAR ENERGY SYSTEM, now U.S. Patent Application Publication No. 2020/0078113;

U.S. patent application Ser. No. 16/562,175, titled INSTRUMENT TRACKING ARRANGEMENT BASED ON REAL TIME CLOCK INFORMATION, now U.S. Patent Application Publication No. 2020/0078071;

U.S. patent application Ser. No. 16/562,177, titled REGIONAL LOCATION TRACKING OF COMPONENTS OF A MODULAR ENERGY SYSTEM, now U.S. Patent Application Publication No. 2020/0078114;

U.S. patent application Ser. No. 29/704,610, titled ENERGY MODULE, now U.S. Pat. No. D928,725;

U.S. patent application Ser. No. 29/704,614, titled ENERGY MODULE MONOPOLAR PORT, now U.S. Pat. No. D928,726;

U.S. patent application Ser. No. 29/704,616, titled ENERGY MODULE WITH A BACKPLANE CONNECTOR, now U.S. Pat. No. D924,139; and U.S. patent application Ser. No. 29/704,617, titled DISPLAY PANAL OR PORTION THEREOF WITH GRAPHICAL USER INTERFACE FOR ENERGY MODULE, now U.S. Pat. No. D939,545.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Various aspects are directed to improved ultrasonic surgical devices, electrosurgical devices and generators for use therewith. Aspects of the ultrasonic surgical devices can be configured for transecting and/or coagulating tissue during surgical procedures, for example. Aspects of the electrosurgical devices can be configured for transecting, coagulating, scaling, welding and/or desiccating tissue during surgical procedures, for example.

Surgical System Hardware

Referring to FIG. 1, a computer-implemented interactive surgical system 100 includes one or more surgical systems 102 and a cloud-based system (e.g., the cloud 104 that may include a remote server 113 coupled to a storage device 105). Each surgical system 102 includes at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P are integers greater than or equal to one.

Figure 2:
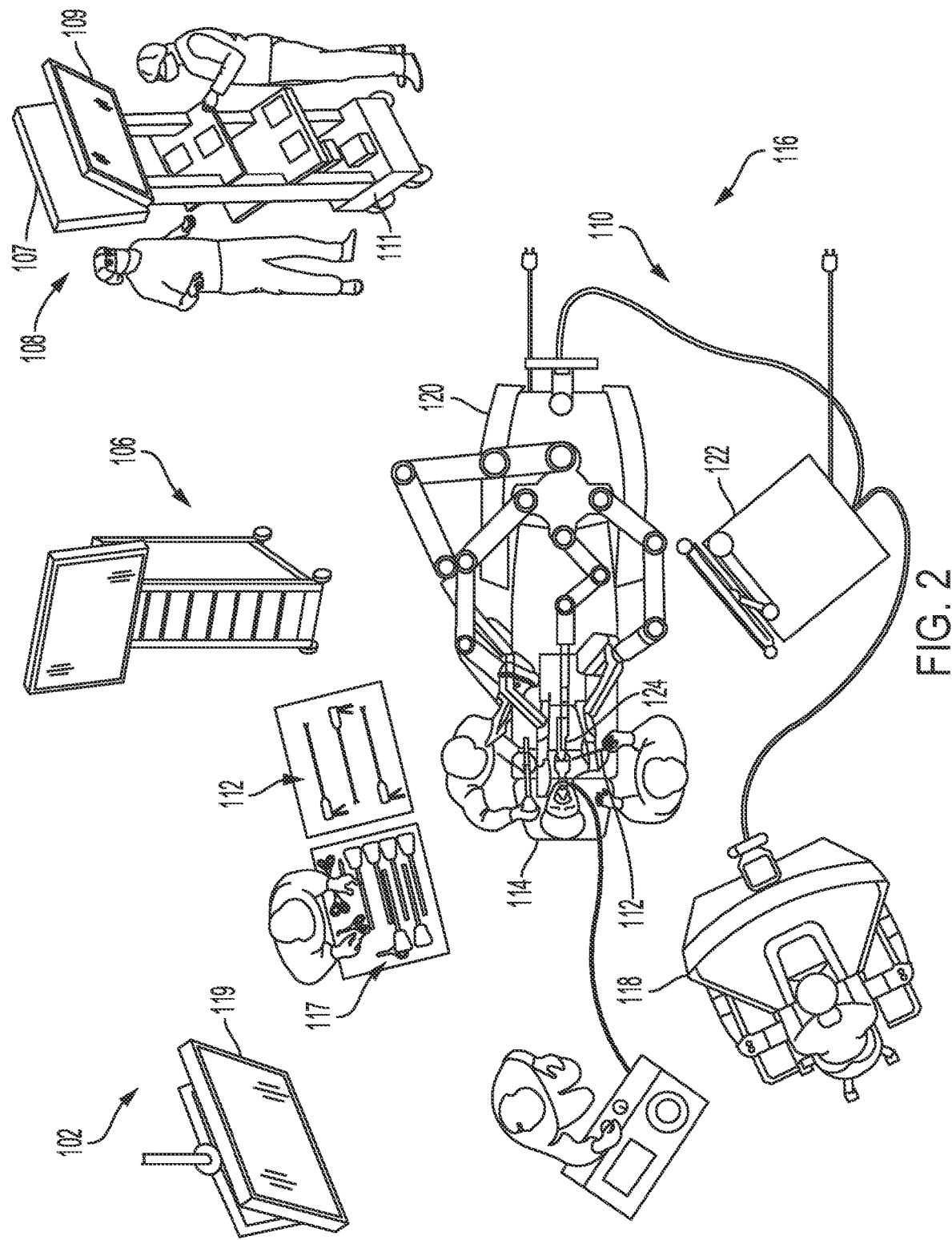
FIG. 2 is a surgical system being used to perform a surgical procedure in an operating room, in accordance with at least one aspect of the present disclosure.

FIG. 2 depicts an example of a surgical system 102 being used to perform a surgical procedure on a patient who is lying down on an operating table 114 in a surgical operating room 116. A robotic system 110 is used in the surgical procedure as a part of the surgical system 102. The robotic system 110 includes a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Provisional Patent Application Ser. No. 62/611,339, titled ROBOT ASSISTED SURGICAL PLATFORM, filed Dec. 28, 2017, the disclosure of which is herein incorporated by reference in its entirety.

Various examples of cloud-based analytics that are performed by the cloud 104, and are suitable for use with the present disclosure, are described in U.S. Provisional Patent Application Ser. No. 62/611,340, titled CLOUD-BASED MEDICAL ANALYTICS, filed Dec. 28, 2017, the disclosure of which is herein incorporated by reference in its entirety.

In various aspects, the imaging device 124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngoneproscope, sigmoidoscope, thoracoscope, and ureteroscope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area. In various aspects, the visualization system 108 includes one or more imaging sensors, one or more image-processing units, one or more storage arrays, and one or more displays that are strategically arranged with respect to the sterile field, as illustrated in FIG. 2. In one aspect, the visualization system 108 includes an interface for HL7, PACS, and EMR. Various components of the visualization system 108 are described under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 includes a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snapshot of a surgical site, as recorded by an imaging device 124, on a non-sterile display 107 or 109, while maintaining a live feed of the surgical site on the primary display 119. The snapshot on the non-sterile display 107 or 109 can permit a non-sterile operator to perform a diagnostic step relevant to the surgical procedure, for example.

In one aspect, the hub 106 is also configured to route a diagnostic input or feedback entered by a non-sterile operator at the visualization tower 111 to the primary display 119 within the sterile field, where it can be viewed by a sterile operator at the operating table. In one example, the input can be in the form of a modification to the snapshot displayed on the non-sterile display 107 or 109, which can be routed to the primary display 119 by the hub 106.

Referring to FIG. 2, a surgical instrument 112 is being used in the surgical procedure as part of the surgical system 102. The hub 106 is also configured to coordinate information flow to a display of the surgical instrument 112. For example, in U.S. Provisional Patent Application Ser. No. 62/611,341, titled INTERACTIVE SURGICAL PLATFORM, filed Dec. 28, 2017, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading SURGICAL INSTRUMENT HARDWARE and in U.S. Provisional Patent Application Ser. No. 62/611,341, titled INTERACTIVE SURGICAL PLATFORM, filed Dec. 28, 2017, the disclosure of which is herein incorporated by reference in its entirety, for example.

Figure 3:
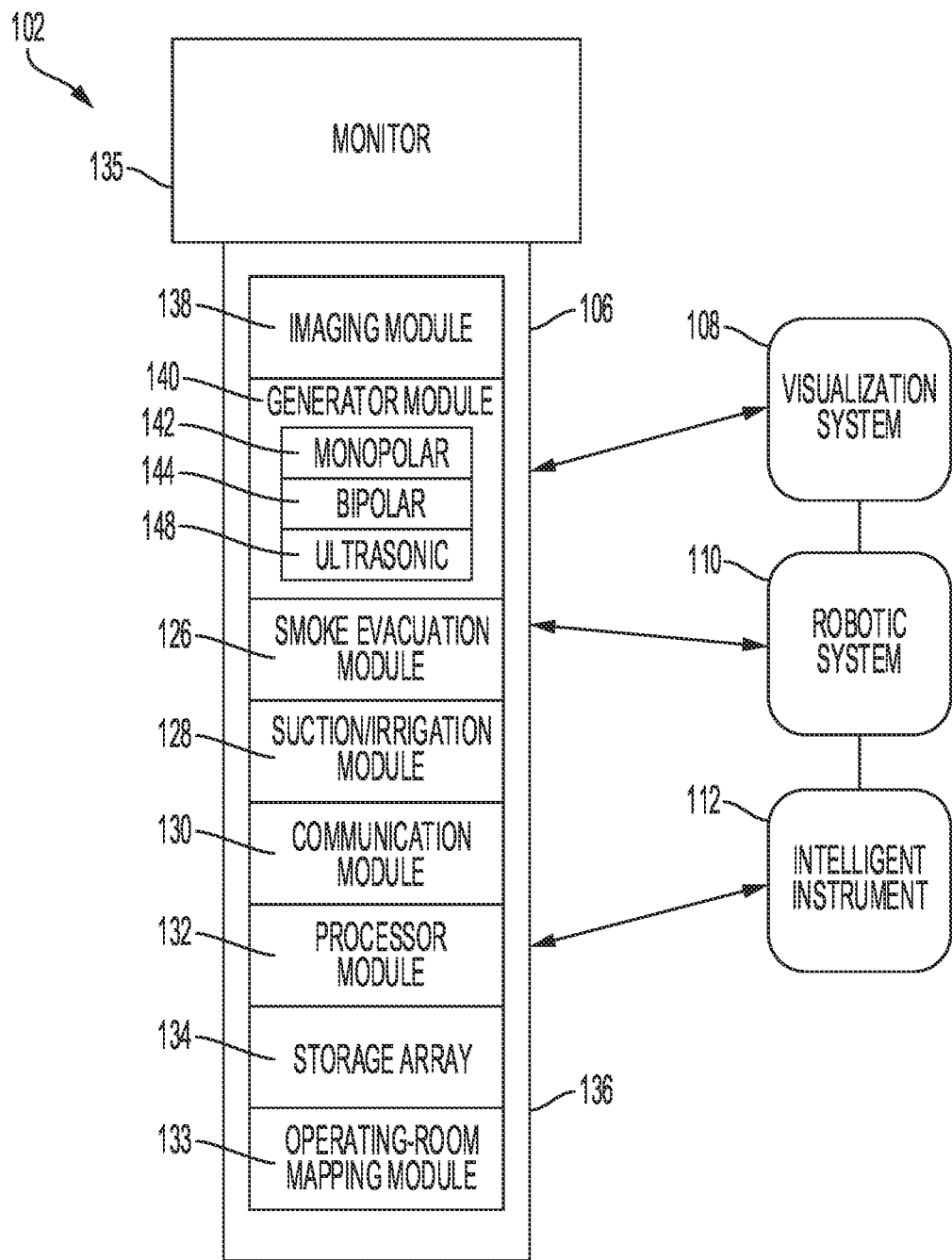
FIG. 3 is a surgical hub paired with a visualization system, a robotic system, and an intelligent instrument, in accordance with at least one aspect of the present disclosure.

Referring now to FIG. 3, a hub 106 is depicted in communication with a visualization system 108, a robotic system 110, and a handheld intelligent surgical instrument 112. The hub 106 includes a hub display 135, an imaging module 138, a generator module 140, a communication module 130, a processor module 132, and a storage array 134. In certain aspects, as illustrated in FIG. 3, the hub 106 further includes a smoke evacuation module 126 and/or a suction/irrigation module 128.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts, Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts.

In addition, the modular surgical enclosure also includes a communication bus between the first docking port and the second docking port, configured to facilitate communication between the first energy-generator module and the second energy-generator module.

Figure 4:
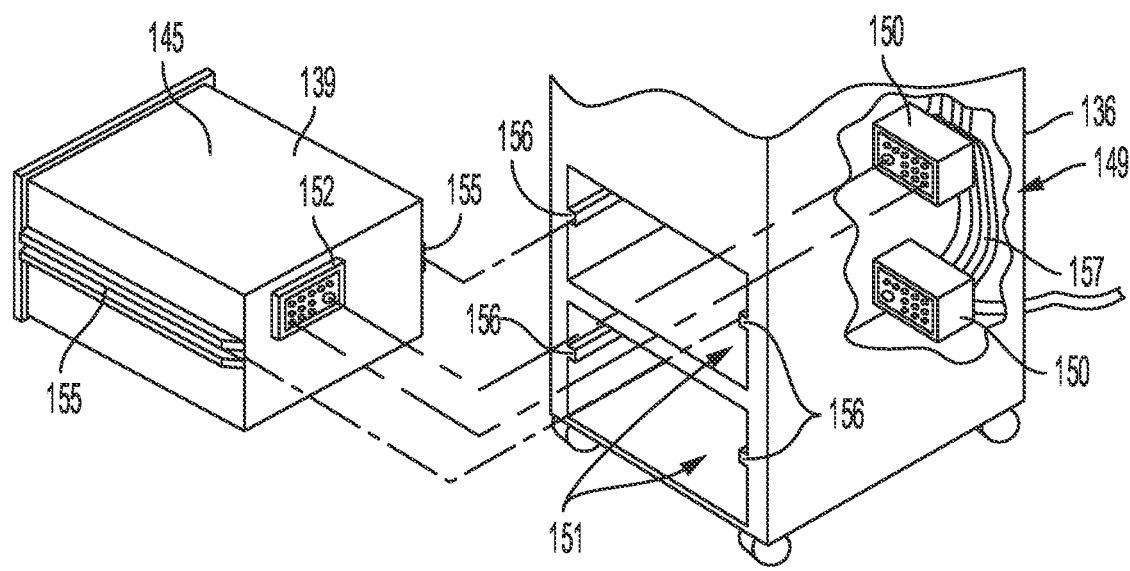
FIG. 4 is a partial perspective view of a surgical hub enclosure, and of a combo generator module slidably receivable in a drawer of the surgical hub enclosure, in accordance with at least one aspect of the present disclosure.
Figure 5:
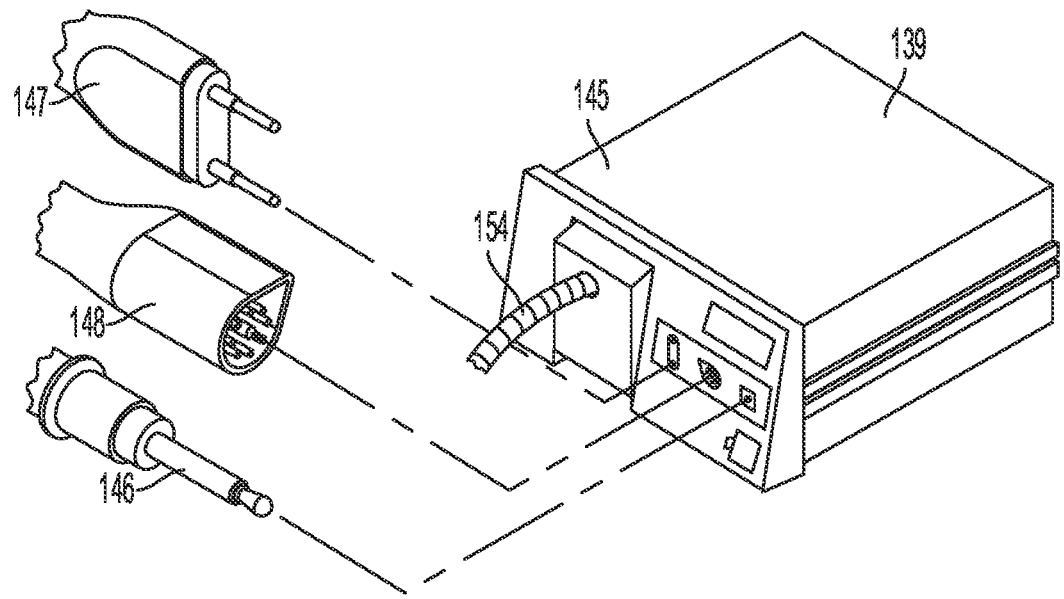
FIG. 5 is a perspective view of a combo generator module with bipolar, ultrasonic, and monopolar contacts and a smoke evacuation component, in accordance with at least one aspect of the present disclosure.

Referring to FIGS. 3-7, aspects of the present disclosure are presented for a hub modular enclosure 136 that allows the modular integration of a generator module 140, a smoke evacuation module 126, and a suction/irrigation module 128. The hub modular enclosure 136 further facilitates interactive communication between the modules 140, 126, 128. As illustrated in FIG. 5, the generator module 140 can be a generator module with integrated monopolar, bipolar, and ultrasonic components supported in a single housing unit 139 slidably insertable into the hub modular enclosure 136. As illustrated in FIG. 5, the generator module 140 can be configured to connect to a monopolar device 146, a bipolar device 147, and an ultrasonic device 148. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

In one aspect, the hub modular enclosure 136 comprises a modular power and communication backplane 149 with external and wireless communication headers to enable the removable attachment of the modules 140, 126, 128 and interactive communication therebetween.

In one aspect, the hub modular enclosure 136 includes docking stations, or drawers, 151, herein also referred to as drawers, which are configured to slidably receive the modules 140, 126, 128. FIG. 4 illustrates a partial perspective view of a surgical hub enclosure 136, and a combo generator module 145 slidably receivable in a docking station 151 of the surgical hub enclosure 136. A docking port 152 with power and data contacts on a rear side of the combo generator module 145 is configured to engage a corresponding docking port 150 with power and data contacts of a corresponding docking station 151 of the hub modular enclosure 136 as the combo generator module 145 is slid into position within the corresponding docking station 151 of the hub module enclosure 136. In one aspect, the combo generator module 145 includes a bipolar, ultrasonic, and monopolar module and a smoke evacuation module integrated together into a single housing unit 139, as illustrated in FIG. 5.

In various aspects, the smoke evacuation module 126 includes a fluid line 154 that conveys captured/collected smoke and/or fluid away from a surgical site and to, for example, the smoke evacuation module 126. Vacuum suction originating from the smoke evacuation module 126 can draw the smoke into an opening of a utility conduit at the surgical site. The utility conduit, coupled to the fluid line, can be in the form of a flexible tube terminating at the smoke evacuation module 126. The utility conduit and the fluid line define a fluid path extending toward the smoke evacuation module 126 that is received in the hub enclosure 136.

In various aspects, the suction/irrigation module 128 is coupled to a surgical tool comprising an aspiration fluid line and a suction fluid line. In one example, the aspiration and suction fluid lines are in the form of flexible tubes extending from the surgical site toward the suction/irrigation module

128. One or more drive systems can be configured to cause irrigation and aspiration of fluids to and from the surgical site.

In one aspect, the surgical tool includes a shaft having an end effector at a distal end thereof and at least one energy treatment associated with the end effector, an aspiration tube, and an irrigation tube. The aspiration tube can have an inlet port at a distal end thereof and the aspiration tube extends through the shaft. Similarly, an irrigation tube can extend through the shaft and can have an inlet port in proximity to the energy deliver implement. The energy deliver implement is configured to deliver ultrasonic and/or RF energy to the surgical site and is coupled to the generator module 140 by a cable extending initially through the shaft.

The irrigation tube can be in fluid communication with a fluid source, and the aspiration tube can be in fluid communication with a vacuum source. The fluid source and/or the vacuum source can be housed in the suction/irrigation module 128. In one example, the fluid source and/or the vacuum source can be housed in the hub enclosure 136 separately from the suction/irrigation module 128. In such example, a fluid interface can be configured to connect the suction/irrigation module 128 to the fluid source and/or the vacuum source.

In one aspect, the modules 140, 126, 128 and/or their corresponding docking stations on the hub modular enclosure 136 may include alignment features that are configured to align the docking ports of the modules into engagement with their counterparts in the docking stations of the hub modular enclosure 136. For example, as illustrated in FIG. 4, the combo generator module 145 includes side brackets 155 that are configured to slidably engage with corresponding brackets 156 of the corresponding docking station 151 of the hub modular enclosure 136. The brackets cooperate to guide the docking port contacts of the combo generator module 145 into an electrical engagement with the docking port contacts of the hub modular enclosure 136.

In some aspects, the drawers 151 of the hub modular enclosure 136 are the same, or substantially the same size, and the modules are adjusted in size to be received in the drawers 151. For example, the side brackets 155 and/or 156 can be larger or smaller depending on the size of the module. In other aspects, the drawers 151 are different in size and are each designed to accommodate a particular module.

Furthermore, the contacts of a particular module can be keyed for engagement with the contacts of a particular drawer to avoid inserting a module into a drawer with mismatching contacts.

As illustrated in FIG. 4, the docking port 150 of one drawer 151 can be coupled to the docking port 150 of another drawer 151 through a communications link 157 to facilitate an interactive communication between the modules housed in the hub modular enclosure 136. The docking ports 150 of the hub modular enclosure 136 may alternatively, or additionally, facilitate a wireless interactive communication between the modules housed in the hub modular enclosure 136. Any suitable wireless communication can be employed, such as for example Air Titan-Bluetooth.

Figure 6:
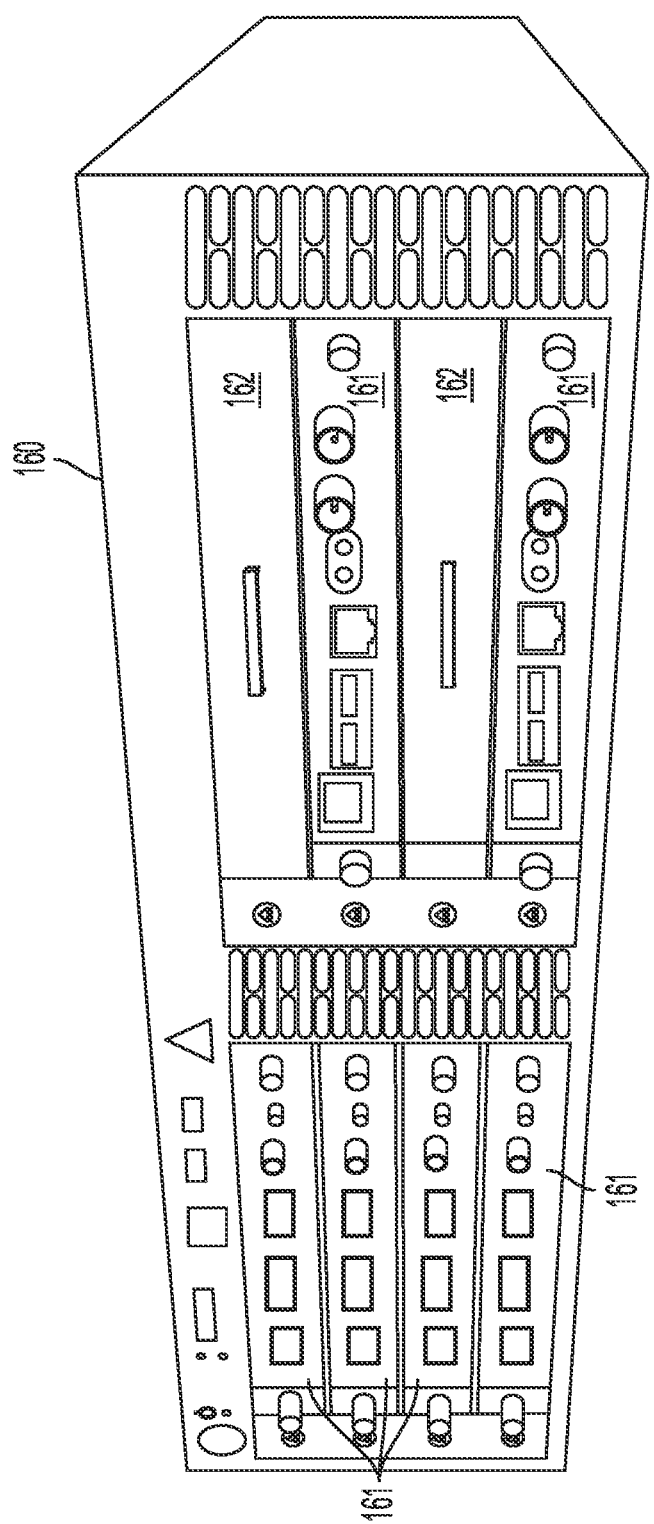
FIG. 6 illustrates individual power bus attachments for a plurality of lateral docking ports of a lateral modular housing configured to receive a plurality of modules, in accordance with at least one aspect of the present disclosure.

FIG. 6 illustrates individual power bus attachments for a plurality of lateral docking ports of a lateral modular housing 160 configured to receive a plurality of modules of a surgical hub 206. The lateral modular housing 160 is configured to laterally receive and interconnect the modules 161. The modules 161 are slidably inserted into docking stations 162 of lateral modular housing 160, which includes a backplane for interconnecting the modules 161. As illustrated in FIG. 6, the modules 161 are arranged laterally in the lateral modular housing 160. Alternatively, the modules 161 may be arranged vertically in a lateral modular housing.

Figure 7:
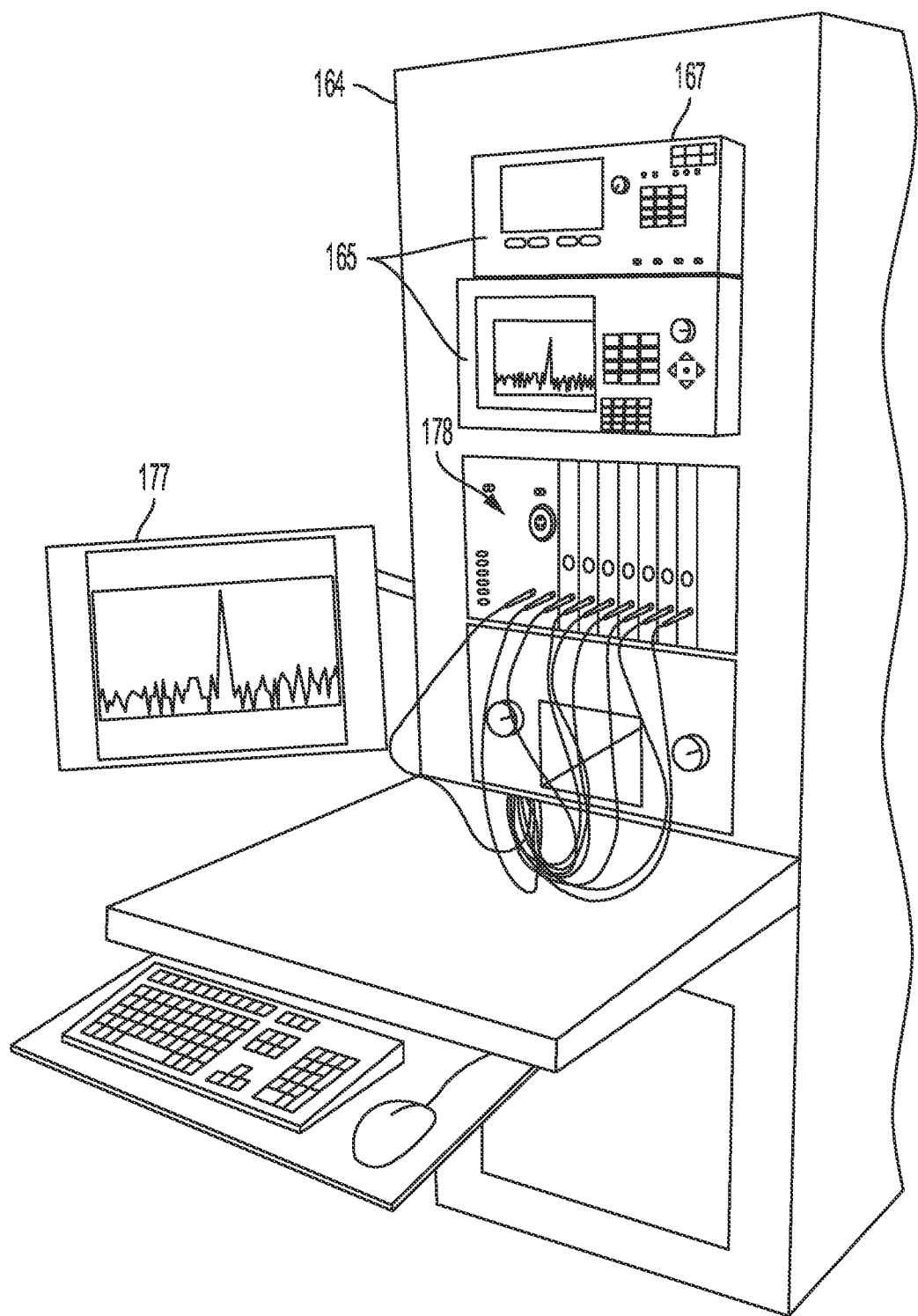
FIG. 7 illustrates a vertical modular housing configured to receive a plurality of modules, in accordance with at least one aspect of the present disclosure.

FIG. 7 illustrates a vertical modular housing 164 configured to receive a plurality of modules 165 of the surgical hub 106. The modules 165 are slidably inserted into docking stations, or drawers, 167 of vertical modular housing 164, which includes a backplane for interconnecting the modules 165. Although the drawers 167 of the vertical modular housing 164 are arranged vertically, in certain instances, a vertical modular housing 164 may include drawers that are arranged laterally. Furthermore, the modules 165 may interact with one another through the docking ports of the vertical modular housing 164. In the example of FIG. 7, a display 177 is provided for displaying data relevant to the operation of the modules 165. In addition, the vertical modular housing 164 includes a master module 178 housing a plurality of sub-modules that are slidably received in the master module 178.

In various aspects, the imaging module 138 comprises an integrated video processor and a modular light source and is adapted for use with various imaging devices. In one aspect, the imaging device is comprised of a modular housing that can be assembled with a light source module and a camera module. The housing can be a disposable housing. In at least one example, the disposable housing is removably coupled to a reusable controller, a light source module, and a camera module. The light source module and/or the camera module can be selectively chosen depending on the type of surgical procedure. In one aspect, the camera module comprises a CCD sensor. In another aspect, the camera module comprises a CMOS sensor. In another aspect, the camera module is configured for scanned beam imaging. Likewise, the light source module can be configured to deliver a white light or a different light, depending on the surgical procedure.

During a surgical procedure, removing a surgical device from the surgical field and replacing it with another surgical device that includes a different camera or a different light source can be inefficient. Temporarily losing sight of the surgical field may lead to undesirable consequences. The module imaging device of the present disclosure is configured to permit the replacement of a light source module or a camera module midstream during a surgical procedure, without having to remove the imaging device from the surgical field.

In one aspect, the imaging device comprises a tubular housing that includes a plurality of channels. A first channel is configured to slidably receive the camera module, which can be configured for a snap-fit engagement with the first channel. A second channel is configured to slidably receive the light source module, which can be configured for a snap-fit engagement with the second channel. In another example, the camera module and/or the light source module can be rotated into a final position within their respective channels. A threaded engagement can be employed in lieu of the snap-fit engagement.

In various examples, multiple imaging devices are placed at different positions in the surgical field to provide multiple views. The imaging module 138 can be configured to switch between the imaging devices to provide an optimal view. In various aspects, the imaging module 138 can be configured to integrate the images from the different imaging device.

Various image processors and imaging devices suitable for use with the present disclosure are described in U.S. Pat. No. 7,995,045, titled COMBINED SBI AND CONVENTIONAL IMAGE PROCESSOR, which issued on Aug. 9, 2011, which is herein incorporated by reference in its entirety. In addition, U.S. Pat. No. 7,982,776, titled SBI MOTION ARTIFACT REMOVAL APPARATUS AND METHOD, which issued on Jul. 19, 2011, which is herein incorporated by reference in its entirety, describes various systems for removing motion artifacts from image data. Such systems can be integrated with the imaging module 138. Furthermore, U.S. Patent Application Publication No. 2011/0306840, titled CONTROLLABLE MAGNETIC SOURCE TO FIXTURE INTRACORPOREAL APPARATUS, which published on Dec. 15, 2011, and U.S. Patent Application Publication No. 2014/0243597, titled SYSTEM FOR PERFORMING A MINIMALLY INVASIVE SURGICAL PROCEDURE, which published on Aug. 28, 2014, each of which is herein incorporated by reference in its entirety.

Figure 8:
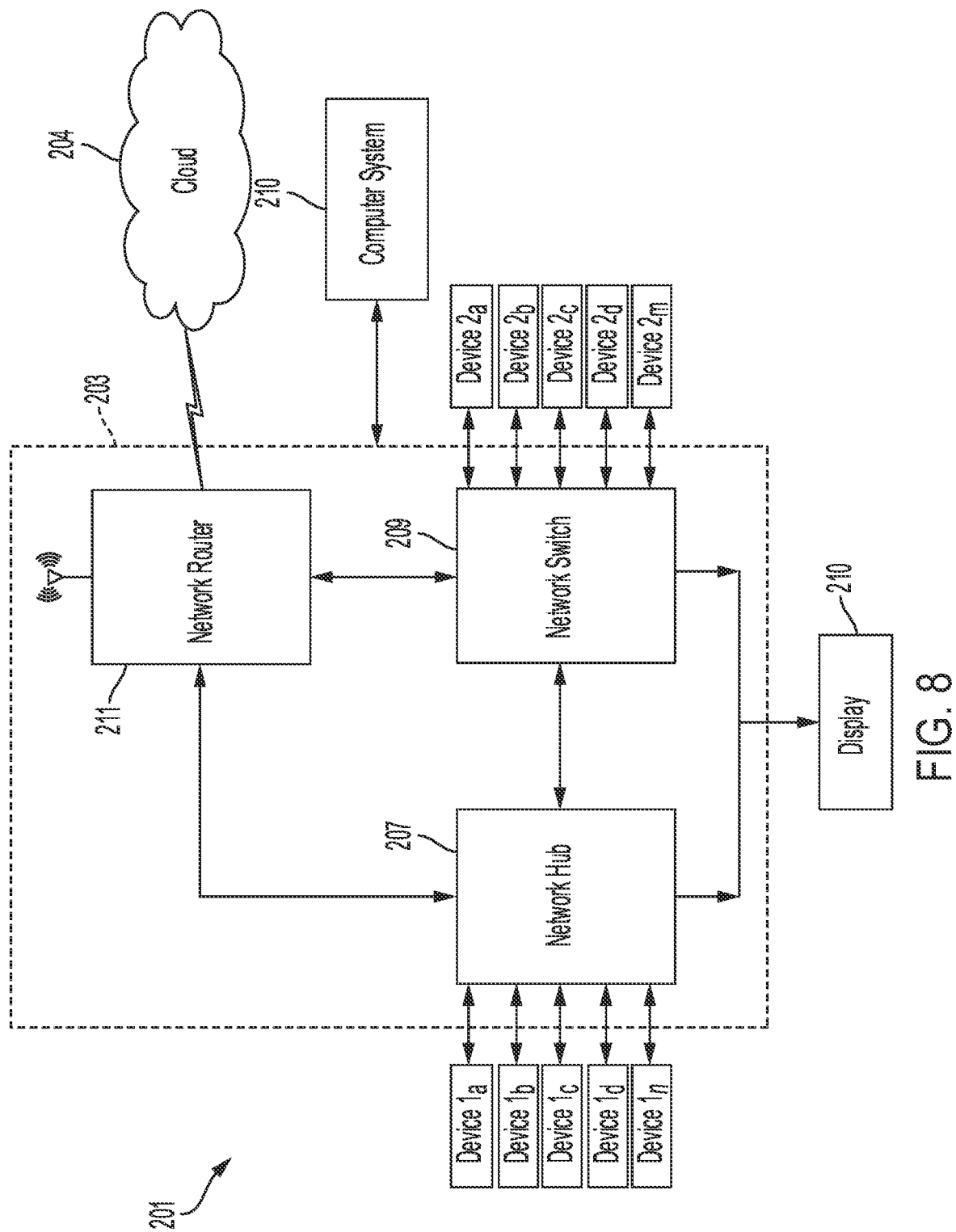
FIG. 8 illustrates a surgical data network comprising a modular communication hub configured to connect modular devices located in one or more operating theaters of a healthcare facility, or any room in a healthcare facility specially equipped for surgical operations, to the cloud, in accordance with at least one aspect of the present disclosure.

FIG. 8 illustrates a surgical data network 201 comprising a modular communication hub 203 configured to connect modular devices located in one or more operating theaters of a healthcare facility, or any room in a healthcare facility specially equipped for surgical operations, to a cloud-based system (e.g., the cloud 204 that may include a remote server 213 coupled to a storage device 205). In one aspect, the modular communication hub 203 comprises a network hub 207 and/or a network switch 209 in communication with a network router. The modular communication hub 203 also can be coupled to a local computer system 210 to provide local computer processing and data manipulation. The surgical data network 201 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 207 or network switch 209. An intelligent surgical data network may be referred to as a manageable hub or switch. A switching hub reads the destination address of each packet and then forwards the packet to the correct port.

Modular devices 1a-1n located in the operating theater may be coupled to the modular communication hub 203. The network hub 207 and/or the network switch 209 may be coupled to a network router 211 to connect the devices 1a-1n to the cloud 204 or the local computer system 210. Data associated with the devices 1a-1n may be transferred to cloud-based computers via the router for remote data processing and manipulation. Data associated with the devices 1a-1n may also be transferred to the local computer system 210 for local data processing and manipulation. Modular devices 2a-2m located in the same operating theater also may be coupled to a network switch 209. The network switch 209 may be coupled to the network hub 207 and/or the network router 211 to connect to the devices 2a-2m to the cloud 204. Data associated with the devices 2a-2n may be transferred to the cloud 204 via the network router 211 for data processing and manipulation. Data associated with the devices 2a-2m may also be transferred to the local computer system 210 for local data processing and manipulation.

It will be appreciated that the surgical data network 201 may be expanded by interconnecting multiple network hubs 207 and/or multiple network switches 209 with multiple network routers 211. The modular communication hub 203 may be contained in a modular control tower configured to receive multiple devices 1a-1n/2a-2m. The local computer system 210 also may be contained in a modular control tower. The modular communication hub 203 is connected to a display 212 to display images obtained by some of the devices 1a-1n/2a-2m, for example during surgical procedures. In various aspects, the devices 1a-1n/2a-2m may include, for example, various modules such as an imaging module 138 coupled to an endoscope, a generator module 140 coupled to an energy-based surgical device, a smoke evacuation module 126, a suction/irrigation module 128, a communication module 130, a processor module 132, a storage array 134, a surgical device coupled to a display, and/or a non-contact sensor module, among other modular devices that may be connected to the modular communication hub 203 of the surgical data network 201.

In one aspect, the surgical data network 201 may comprise a combination of network hub(s), network switch(es), and network router(s) connecting the devices 1a-1n/2a-2m to the cloud. Any one of or all of the devices 1a-1n/2a-2m coupled to the network hub or network switch may collect data in real time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 203 and/or computer system 210 located in the surgical theater (e.g., a fixed, mobile, temporary, or field operating room or space) and to devices connected to the modular communication hub 203 and/or computer system 210 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

Applying cloud computer data processing techniques on the data collected by the devices 1a-1n/2a-2m, the surgical data network provides improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This includes localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud 204 or the local computer system 210 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing, and using standardized approaches may provide beneficial feedback to either confirm surgical treatments and the behavior of the surgeon or suggest modifications to surgical treatments and the behavior of the surgeon.

In one implementation, the operating theater devices 1a-1n may be connected to the modular communication hub 203 over a wired channel or a wireless channel depending on the configuration of the devices 1a-1n to a network hub. The network hub 207 may be implemented, in one aspect, as a local network broadcast device that works on the physical layer of the Open System Interconnection (OSI) model. The network hub provides connectivity to the devices 1a-1n located in the same operating theater network. The network hub 207 collects data in the form of packets and sends them to the router in half duplex mode. The network hub 207 does not store any media access control/Internet Protocol (MAC/IP) to transfer the device data. Only one of the devices 1a-1n can send data at a time through the network hub 207. The network hub 207 has no routing tables or intelligence regarding where to send information and broadcasts all network data across each connection and to a remote server 213 (FIG. 9) over the cloud 204. The network hub 207 can detect basic network errors such as collisions, but having all information broadcast to multiple ports can be a security risk and cause bottlenecks.

In another implementation, the operating theater devices 2a-2m may be connected to a network switch 209 over a wired channel or a wireless channel. The network switch 209 works in the data link layer of the OSI model. The network switch 209 is a multicast device for connecting the devices 2a-2m located in the same operating theater to the network. The network switch 209 sends data in the form of frames to the network router 211 and works in full duplex mode. Multiple devices 2a-2m can send data at the same time through the network switch 209. The network switch 209 stores and uses MAC addresses of the devices 2a-2m to transfer data.

The network hub 207 and/or the network switch 209 are coupled to the network router 211 for connection to the cloud 204. The network router 211 works in the network layer of the OSI model. The network router 211 creates a route for transmitting data packets received from the network hub 207 and/or network switch 211 to cloud-based computer resources for further processing and manipulation of the data collected by any one of or all the devices 1a-1n/2a-2m. The network router 211 may be employed to connect two or more different networks located in different locations, such as, for example, different operating theaters of the same healthcare facility or different networks located in different operating theaters of different healthcare facilities. The network router 211 sends data in the form of packets to the cloud 204 and works in full duplex mode. Multiple devices can send data at the same time. The network router 211 uses IP addresses to transfer data.

In one example, the network hub 207 may be implemented as a USB hub, which allows multiple USB devices to be connected to a host computer. The USB hub may expand a single USB port into several tiers so that there are more ports available to connect devices to the host system computer. The network hub 207 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In other examples, the operating theater devices 1a-1n/2a-2m may communicate to the modular communication hub 203 via Bluetooth wireless technology standard for exchanging data over short distances (using short-wavelength UHF radio waves in the ISM band from 2.4 to 2.485 GHz) from fixed and mobile devices and building personal area networks (PANs). In other aspects, the operating theater devices 1a-1n/2a-2m may communicate to the modular communication hub 203 via a number of wireless or wired communication standards or protocols, including but not limited to Wi-Fi (IEEE 802.11 family), WiMAX (IEEE 802.16 family), IEEE 802.20, long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth, and a second communication module may be dedicated to longer-range wireless communications such as GPS, EDGE, GPRS, CDMA, WiMAX, LTE, Ev-DO, and others.

The modular communication hub 203 may serve as a central connection for one or all of the operating theater devices 1a-1n/2a-2m and handles a data type known as frames. Frames carry the data generated by the devices 1a-1n/2a-2m. When a frame is received by the modular communication hub 203, it is amplified and transmitted to the network router 211, which transfers the data to the cloud computing resources by using a number of wireless or wired communication standards or protocols, as described herein.

The modular communication hub 203 can be used as a standalone device or be connected to compatible network hubs and network switches to form a larger network. The modular communication hub 203 is generally easy to install, configure, and maintain, making it a good option for networking the operating theater devices 1a-1n/2a-2m.

Figure 9:
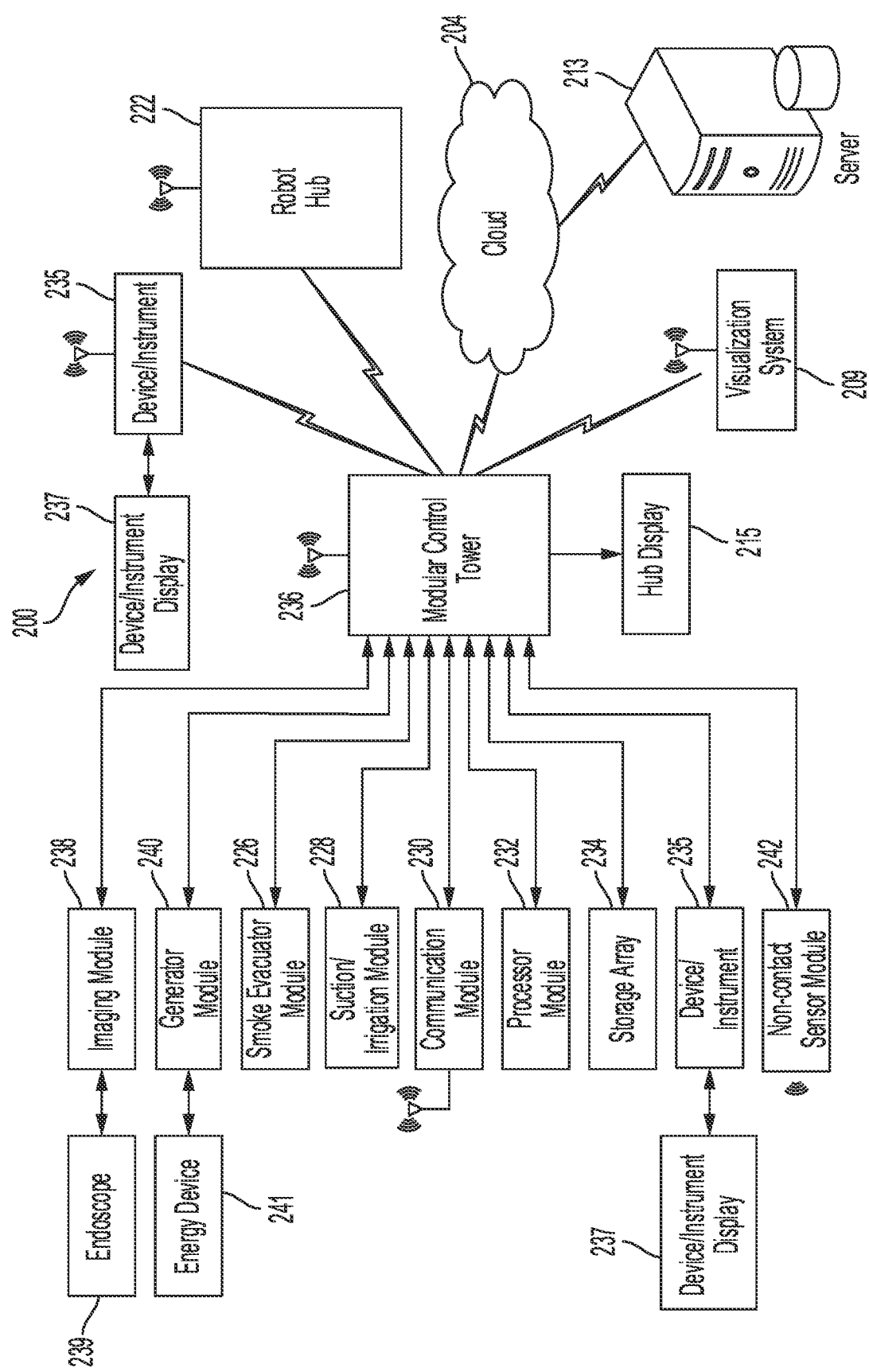
FIG. 9 illustrates a computer-implemented interactive surgical system, in accordance with at least one aspect of the present disclosure.
Figure 10:
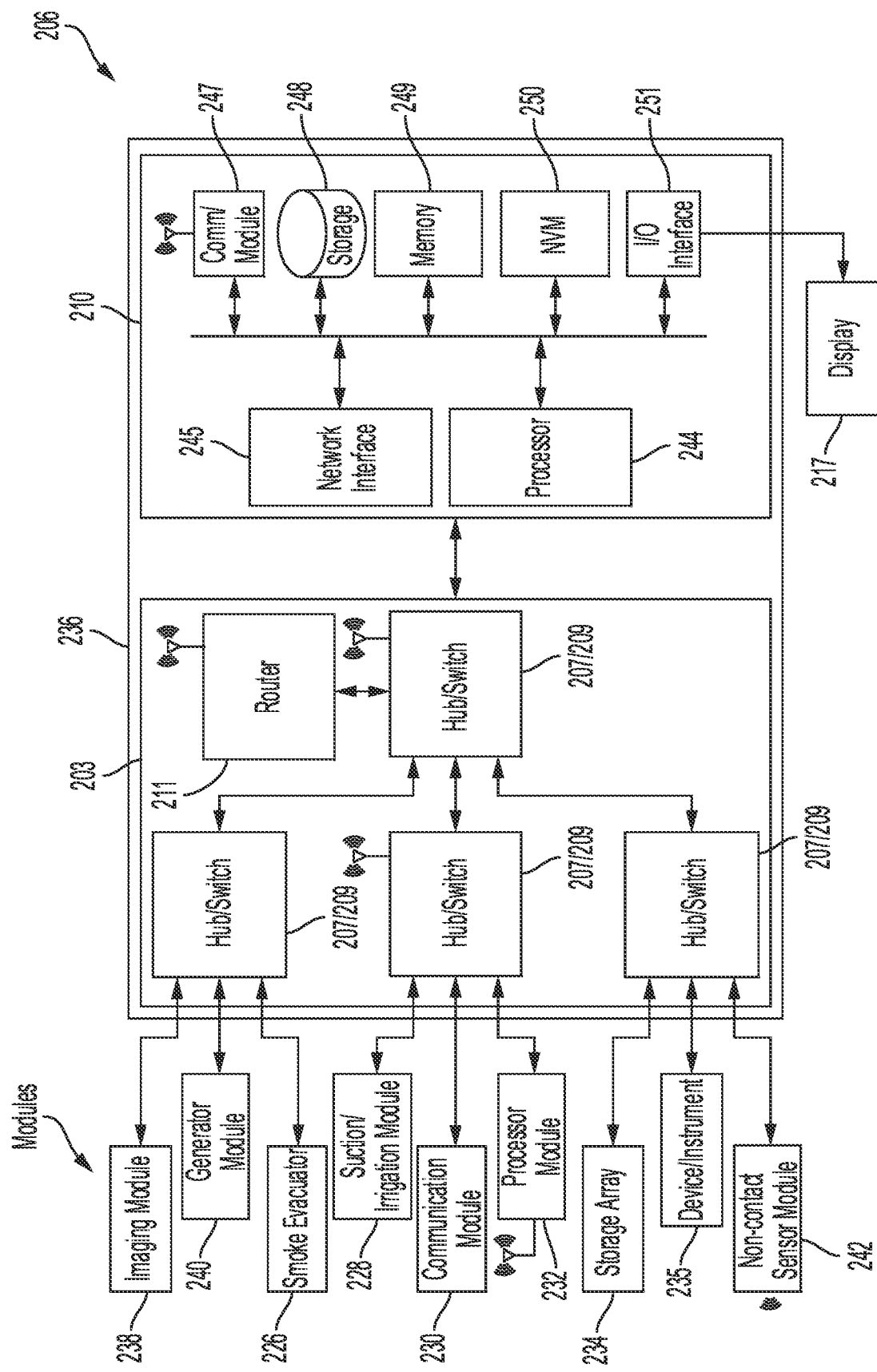
FIG. 10 illustrates a surgical hub comprising a plurality of modules coupled to the modular control tower, in accordance with at least one aspect of the present disclosure.

FIG. 9 illustrates a computer-implemented interactive surgical system 200. The computer-implemented interactive surgical system 200 is similar in many respects to the computer-implemented interactive surgical system 100. For example, the computer-implemented interactive surgical system 200 includes one or more surgical systems 202, which are similar in many respects to the surgical systems 102. Each surgical system 202 includes at least one surgical hub 206 in communication with a cloud 204 that may include a remote server 213. In one aspect, the computer-implemented interactive surgical system 200 comprises a modular control tower 236 connected to multiple operating theater devices such as, for example, intelligent surgical instruments, robots, and other computerized devices located in the operating theater. As shown in FIG. 10, the modular control tower 236 comprises a modular communication hub 203 coupled to a computer system 210. As illustrated in the example of FIG. 9, the modular control tower 236 is coupled to an imaging module 238 that is coupled to an endoscope 239, a generator module 240 that is coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242. The operating theater devices are coupled to cloud computing resources and data storage via the modular control tower 236. A robot hub 222 also may be connected to the modular control tower 236 and to the cloud computing resources. The devices/instruments 235, visualization systems 208, among others, may be coupled to the modular control tower 236 via wired or wireless communication standards or protocols, as described herein. The modular control tower 236 may be coupled to a hub display 215 (e.g., monitor, screen) to display and overlay images received from the imaging module, device/instrument display, and/or other visualization systems 208. The hub display also may display data received from devices connected to the modular control tower in conjunction with images and overlaid images.

FIG. 10 illustrates a surgical hub 206 comprising a plurality of modules coupled to the modular control tower 236. The modular control tower 236 comprises a modular communication hub 203, e.g., a network connectivity device, and a computer system 210 to provide local processing, visualization, and imaging, for example. As shown in FIG. 10, the modular communication hub 203 may be connected in a tiered configuration to expand the number of modules (e.g., devices) that may be connected to the modular communication hub 203 and transfer data associated with the modules to the computer system 210, cloud computing resources, or both. As shown in FIG. 10, each of the network hubs/switches in the modular communication hub 203 includes three downstream ports and one upstream port. The upstream network hub/switch is connected to a processor to provide a communication connection to the cloud computing resources and a local display 217. Communication to the cloud 204 may be made either through a wired or a wireless communication channel.

The surgical hub 206 employs a non-contact sensor module 242 to measure the dimensions of the operating theater and generate a map of the surgical theater using either ultrasonic or laser-type non-contact measurement devices. An ultrasound-based non-contact sensor module scans the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety, in which the sensor module is configured to determine the size of the operating theater and to adjust Bluetooth-pairing distance limits. A laser-based non-contact sensor module scans the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 210 comprises a processor 244 and a network interface 245. The processor 244 is coupled to a communication module 247, storage 248, memory 249, non-volatile memory 250, and input/output interface 251 via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 244 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In one aspect, the processor 244 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory includes volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 210 also includes removable/non-removable, volatile/non-volatile computer storage media, such as for example disk storage. The disk storage includes, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 210 includes software that acts as an intermediary between users and the basic computer resources described in a suitable operating environment. Such software includes an operating system. The operating system, which can be stored on the disk storage, acts to control and allocate resources of the computer system. System applications take advantage of the management of resources by the operating system through program modules and program data stored either in the system memory or on the disk storage. It is to be appreciated that various components described herein can be implemented with various operating systems or combinations of operating systems.

A user enters commands or information into the computer system 210 through input device(s) coupled to the I/O interface 251. The input devices include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output information from the computer system to an output device. An output adapter is provided to illustrate that there are some output devices like monitors, displays, speakers, and printers, among other output devices that require special adapters. The output adapters include, by way of illustration and not limitation, video and sound cards that provide a means of connection between the output device and the system bus. It should be noted that other devices and/or systems of devices, such as remote computer(s), provide both input and output capabilities.

The computer system 210 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) is logically connected to the computer system through a network interface and then physically connected via a communication connection. The network interface encompasses communication networks such as local area networks (LANs) and wide area networks (WANs). LAN technologies include Fiber Distributed Data Interface (FDDI), Copper Distributed Data Interface (CDDI), Ethernet/IEEE 802.3, Token Ring/IEEE 802.5 and the like. WAN technologies include, but are not limited to, point-to-point links, circuit-switching networks like Integrated Services Digital Networks (ISDN) and variations thereof, packet-switching networks, and Digital Subscriber Lines (DSL).

In various aspects, the computer system 210 of FIG. 10, the imaging module 238 and/or visualization system 208, and/or the processor module 232 of FIGS. 9-10, may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) refers to the hardware/software employed to connect the network interface to the bus. While the communication connection is shown for illustrative clarity inside the computer system, it can also be external to the computer system 210. The hardware/software necessary for connection to the network interface includes, for illustrative purposes only, internal and external technologies such as modems, including regular telephone-grade modems, cable modems, and DSL modems, ISDN adapters, and Ethernet cards.

Figure 11:
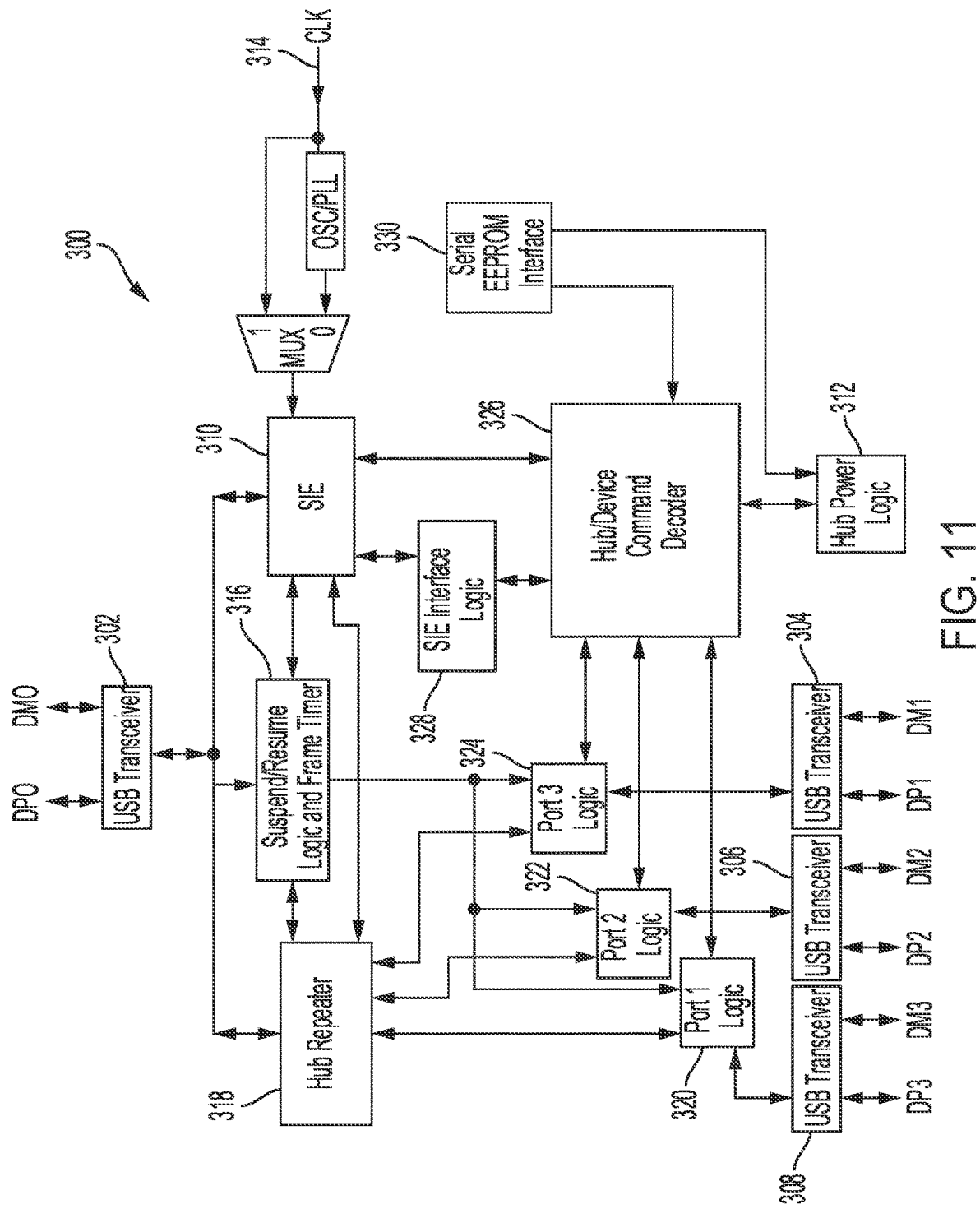
FIG. 11 illustrates one aspect of a Universal Serial Bus (USB) network hub device, in accordance with at least one aspect of the present disclosure.

FIG. 11 illustrates a functional block diagram of one aspect of a USB network hub 300 device, in accordance with at least one aspect of the present disclosure. In the illustrated aspect, the USB network hub device 300 employs a TUSB2036 integrated circuit hub by Texas Instruments. The USB network hub 300 is a CMOS device that provides an upstream USB transceiver port 302 and up to three downstream USB transceiver ports 304, 306, 308 in compliance with the USB 2.0 specification. The upstream USB transceiver port 302 is a differential root data port comprising a differential data minus (DM0) input paired with a differential data plus (DP0) input. The three downstream USB transceiver ports 304, 306, 308 are differential data ports where each port includes differential data plus (DP1-DP3) outputs paired with differential data minus (DM1-DM3) outputs.

The USB network hub 300 device is implemented with a digital state machine instead of a microcontroller, and no firmware programming is required. Fully compliant USB transceivers are integrated into the circuit for the upstream USB transceiver port 302 and all downstream USB transceiver ports 304, 306, 308. The downstream USB transceiver ports 304, 306, 308 support both full-speed and low-speed devices by automatically setting the slew rate according to the speed of the device attached to the ports. The USB network hub 300 device may be configured either in bus-powered or self-powered mode and includes a hub power logic 312 to manage power.

The USB network hub 300 device includes a serial interface engine 310 (SIE). The SIE 310 is the front end of the USB network hub 300 hardware and handles most of the protocol described in chapter 8 of the USB specification. The SIE 310 typically comprehends signaling up to the transaction level. The functions that it handles could include: packet recognition, transaction sequencing, SOP, EOP, RESET, and RESUME signal detection/generation, clock/data separation, non-return-to-zero invert (NRZI) data encoding/decoding and bit-stuffing, CRC generation and checking (token and data), packet ID (PID) generation and checking/decoding, and/or serial-parallel/parallel-serial conversion. The 310 receives a clock input 314 and is coupled to a suspend/resume logic and frame timer 316 circuit and a hub repeater circuit 318 to control communication between the upstream USB transceiver port 302 and the downstream USB transceiver ports 304, 306, 308 through port logic circuits 320, 322, 324. The SIE 310 is coupled to a command decoder 326 via interface logic to control commands from a serial EEPROM via a serial EEPROM interface 330.

In various aspects, the USB network hub 300 can connect 127 functions configured in up to six logical layers (tiers) to a single computer. Further, the USB network hub 300 can connect to all peripherals using a standardized four-wire cable that provides both communication and power distribution. The power configurations are bus-powered and self-powered modes. The USB network hub 300 may be configured to support four modes of power management: a bus-powered hub, with either individual-port power management or ganged-port power management, and the self-powered hub, with either individual-port power management or ganged-port power management. In one aspect, using a USB cable, the USB network hub 300, the upstream USB transceiver port 302 is plugged into a USB host controller, and the downstream USB transceiver ports 304, 306, 308 are exposed for connecting USB compatible devices, and so forth.

Surgical Instrument Hardware

Figure 12:
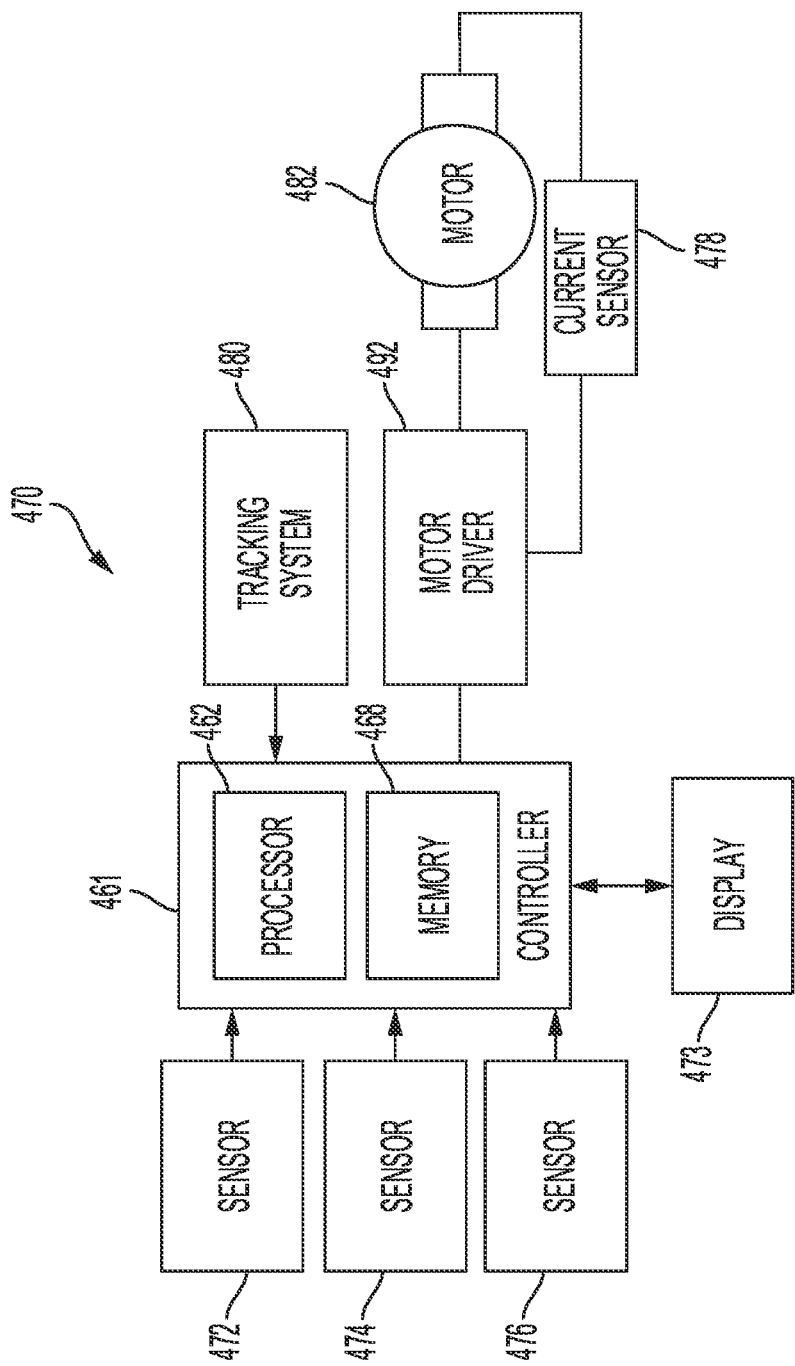
FIG. 12 illustrates a logic diagram of a control system of a surgical instrument or tool, in accordance with at least one aspect of the present disclosure.

FIG. 12 illustrates a logic diagram of a control system 470 of a surgical instrument or tool in accordance with one or more aspects of the present disclosure. The system 470 comprises a control circuit. The control circuit includes a microcontroller 461 comprising a processor 462 and a memory 468. One or more of sensors 472, 474, 476, for example, provide real-time feedback to the processor 462. A motor 482, driven by a motor driver 492, operably couples a longitudinally movable displacement member to drive a clamp arm closure member. A tracking system 480 is configured to determine the position of the longitudinally movable displacement member. The position information is provided to the processor 462, which can be programmed or configured to determine the position of the longitudinally movable drive member as well as the position of the closure member. Additional motors may be provided at the tool driver interface to control closure tube travel, shaft rotation, articulation, or clamp arm closure, or a combination of the above. A display 473 displays a variety of operating conditions of the instruments and may include touch screen functionality for data input. Information displayed on the display 473 may be overlaid with images acquired via endoscopic imaging modules.

In one aspect, the microcontroller 461 may be any single-core or multicore processor such as those known under the trade name ARM Cortex by Texas Instruments. In one aspect, the main microcontroller 461 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

In one aspect, the microcontroller 461 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 461 may be programmed to perform various functions such as precise control over the speed and position of the knife, articulation systems, clamp arm, or a combination of the above. In one aspect, the microcontroller 461 includes a processor 462 and a memory 468. The electric motor 482 may be a brushed direct current (DC) motor with a gearbox and mechanical links to an articulation or knife system. In one aspect, a motor driver 492 may be an A3941 available from Allegro Microsystems, Inc. Other motor drivers may be readily substituted for use in the tracking system 480 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 461 may be programmed to provide precise control over the speed and position of displacement members and articulation systems. The microcontroller 461 may be configured to compute a response in the software of the microcontroller 461. The computed response is compared to a measured response of the actual system to obtain an "observed" response, which is used for actual feedback decisions. The observed response is a favorable, tuned value that balances the smooth, continuous nature of the simulated response with the measured response, which can detect outside influences on the system.

In one aspect, the motor 482 may be controlled by the motor driver 492 and can be employed by the firing system of the surgical instrument or tool. In various forms, the motor 482 may be a brushed DC driving motor having a maximum rotational speed of approximately 25,000 RPM. In other arrangements, the motor 482 may include a brushless motor, a cordless motor, a synchronous motor, a stepper motor, or any other suitable electric motor. The motor driver 492 may comprise an H-bridge driver comprising field-effect transistors (FETs), for example. The motor 482 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable battery cells. In at least one example, the battery cells can be lithium-ion batteries which can be couplable to and separable from the power assembly.

The motor driver 492 may be an A3941 available from Allegro Microsystems, Inc. The A3941 492 is a full-bridge controller for use with external N-channel power metal-oxide semiconductor field-effect transistors (MOSFETs) specifically designed for inductive loads, such as brush DC motors. The driver 492 comprises a unique charge pump regulator that provides full (>10 V) gate drive for battery voltages down to 7 V and allows the A3941 to operate with a reduced gate drive, down to 5.5 V. A bootstrap capacitor may be employed to provide the above battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the low-side FETs. The power FETs are protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 480 comprising an absolute positioning system.

The tracking system 480 comprises a controlled motor drive circuit arrangement comprising a position sensor 472 according to one aspect of this disclosure. The position sensor 472 for an absolute positioning system provides a unique position signal corresponding to the location of a displacement member. In one aspect, the displacement member represents a longitudinally movable drive member comprising a rack of drive teeth for meshing engagement with a corresponding drive gear of a gear reducer assembly. In other aspects, the displacement member represents the firing member, which could be adapted and configured to include a rack of drive teeth. In yet another aspect, the displacement member represents a longitudinal displacement member to open and close a clamp arm, which can be adapted and configured to include a rack of drive teeth. In other aspects, the displacement member represents a clamp arm closure member configured to close and to open a clamp arm of a stapler, ultrasonic, or electrosurgical device, or combinations of the above. Accordingly, as used herein, the term displacement member is used generically to refer to any movable member of the surgical instrument or tool such as the drive member, the clamp arm, or any element that can be displaced. Accordingly, the absolute positioning system can, in effect, track the displacement of the clamp arm by tracking the linear displacement of the longitudinally movable drive member. In other aspects, the absolute positioning system can be configured to track the position of a clamp arm in the process of closing or opening. In various other aspects, the displacement member may be coupled to any position sensor 472 suitable for measuring linear displacement. Thus, the longitudinally movable drive member, or clamp arm, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photo diodes or photo detectors, or any combination thereof.

The electric motor 482 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 472 element corresponds to some linear longitudinal translation of the displacement member. An arrangement of gearing and sensors can be connected to the linear actuator, via a rack and pinion arrangement, or a rotary actuator, via a spur gear or other connection. A power source supplies power to the absolute positioning system and an output indicator may display the output of the absolute positioning system. The displacement member represents the longitudinally movable drive member comprising a rack of drive teeth formed thereon for meshing engagement with a corresponding drive gear of the gear reducer assembly. The displacement member represents the longitudinally movable firing member to open and close a clamp arm.

A single revolution of the sensor element associated with the position sensor 472 is equivalent to a longitudinal linear displacement $d_1$ of the displacement member, where $d_1$ is the longitudinal linear distance that the displacement member moves from point "a" to point "b" after a single revolution of the sensor element coupled to the displacement member. The sensor arrangement may be connected via a gear reduction that results in the position sensor 472 completing one or more revolutions for the full stroke of the displacement member. The position sensor 472 may complete multiple revolutions for the full stroke of the displacement member.

A series of switches, where n is an integer greater than one, may be employed alone or in combination with a gear reduction to provide a unique position signal for more than one revolution of the position sensor 472. The state of the switches are fed back to the microcontroller 461 that applies logic to determine a unique position signal corresponding to the longitudinal linear displacement $d_1+d_2+\ldots d_n$ of the displacement member. The output of the position sensor 472 is provided to the microcontroller 461. The position sensor 472 of the sensor arrangement may comprise a magnetic sensor, an analog rotary sensor like a potentiometer, or an array of analog Hall-effect elements, which output a unique combination of position signals or values.

The position sensor 472 may comprise any number of magnetic sensing elements, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

In one aspect, the position sensor 472 for the tracking system 480 comprising an absolute positioning system comprises a magnetic rotary absolute positioning system. The position sensor 472 may be implemented as an AS5055EQFT single-chip magnetic rotary position sensor available from Austria Microsystems, AG. The position sensor 472 is interfaced with the microcontroller 461 to provide an absolute positioning system. The position sensor 472 is a low-voltage and low-power component and includes four Hall-effect elements in an area of the position sensor 472 that is located above a magnet. A high-resolution ADC and a smart power management controller are also provided on the chip. A coordinate rotation digital computer (CORDIC) processor, also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface, such as a serial peripheral interface (SPI) interface, to the microcontroller 461. The position sensor 472 provides 12 or 14 bits of resolution. The position sensor 472 may be an AS5055 chip provided in a small QFN 16-pin 4×4×0.85 mm package.

The tracking system 480 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 472. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system takes into account properties like mass, inertia, viscous friction, inductance resistance, etc., to predict what the states and outputs of the physical system will be by knowing the input.

The absolute positioning system provides an absolute position of the displacement member upon power-up of the instrument, without retracting or advancing the displacement member to a reset (zero or home) position as may be required with conventional rotary encoders that merely count the number of steps forwards or backwards that the motor 482 has taken to infer the position of a device actuator, drive bar, knife, or the like.

A sensor 474, such as, for example, a strain gauge or a micro-strain gauge, is configured to measure one or more parameters of the end effector, such as, for example, the amplitude of the strain exerted on the anvil during a clamping operation, which can be indicative of the closure forces applied to the anvil. The measured strain is converted to a digital signal and provided to the processor 462. Alternatively, or in addition to the sensor 474, a sensor 476, such as, for example, a load sensor, can measure the closure force applied by the closure drive system to the anvil in a stapler or a clamp arm in an ultrasonic or electrosurgical instrument. The sensor 476, such as, for example, a load sensor, can measure the firing force applied to a closure member coupled to a clamp arm of the surgical instrument or tool or the force applied by a clamp arm to tissue located in the jaws of an ultrasonic or electrosurgical instrument. Alternatively, a current sensor 478 can be employed to measure the current drawn by the motor 482. The displacement member also may be configured to engage a clamp arm to open or close the clamp arm. The force sensor may be configured to measure the clamping force on tissue. The force required to advance the displacement member can correspond to the current drawn by the motor 482, for example. The measured force is converted to a digital signal and provided to the processor 462.

In one form, the strain gauge sensor 474 can be used to measure the force applied to the tissue by the end effector. A strain gauge can be coupled to the end effector to measure the force on the tissue being treated by the end effector. A system for measuring forces applied to the tissue grasped by the end effector comprises a strain gauge sensor 474, such as, for example, a micro-strain gauge, that is configured to measure one or more parameters of the end effector, for example. In one aspect, the strain gauge sensor 474 can measure the amplitude or magnitude of the strain exerted on a jaw member of an end effector during a clamping operation, which can be indicative of the tissue compression. The measured strain is converted to a digital signal and provided to a processor 462 of the microcontroller 461. A load sensor 476 can measure the force used to operate the knife element, for example, to cut the tissue captured between the anvil and the staple cartridge. A load sensor 476 can measure the force used to operate the clamp arm element, for example, to capture tissue between the clamp arm and an ultrasonic blade or to capture tissue between the clamp arm and a jaw of an electrosurgical instrument. A magnetic field sensor can be employed to measure the thickness of the captured tissue. The measurement of the magnetic field sensor also may be converted to a digital signal and provided to the processor 462.

The measurements of the tissue compression, the tissue thickness, and/or the force required to close the end effector on the tissue, as respectively measured by the sensors 474, 476, can be used by the microcontroller 461 to characterize the selected position of the firing member and/or the corresponding value of the speed of the firing member. In one instance, a memory 468 may store a technique, an equation, and/or a lookup table which can be employed by the microcontroller 461 in the assessment.

The control system 470 of the surgical instrument or tool also may comprise wired or wireless communication circuits to communicate with the modular communication hub as shown in FIGS. 8-11.

Figure 13:
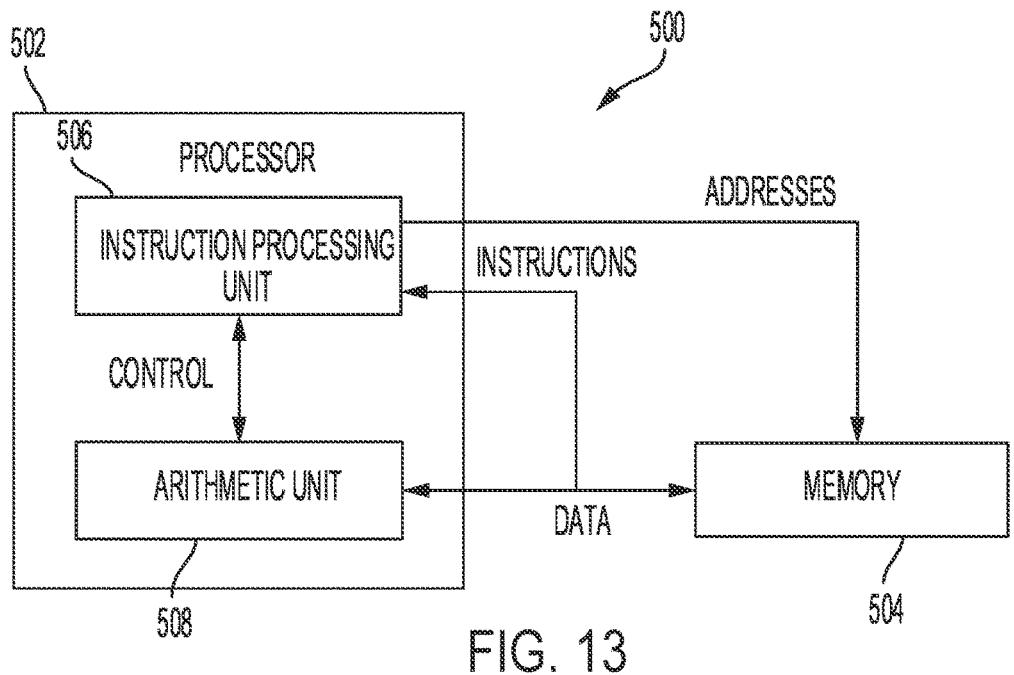
FIG. 13 illustrates a control circuit configured to control aspects of the surgical instrument or tool, in accordance with at least one aspect of the present disclosure.

FIG. 13 illustrates a control circuit 500 configured to control aspects of the surgical instrument or tool according to one aspect of this disclosure. The control circuit 500 can be configured to implement various processes described herein. The control circuit 500 may comprise a microcontroller comprising one or more processors 502 (e.g., microprocessor, microcontroller) coupled to at least one memory circuit 504. The memory circuit 504 stores machine-executable instructions that, when executed by the processor 502, cause the processor 502 to execute machine instructions to implement various processes described herein. The processor 502 may be any one of a number of single-core or multicore processors known in the art. The memory circuit 504 may comprise volatile and non-volatile storage media. The processor 502 may include an instruction processing unit 506 and an arithmetic unit 508. The instruction processing unit may be configured to receive instructions from the memory circuit 504 of this disclosure.

Figure 14:
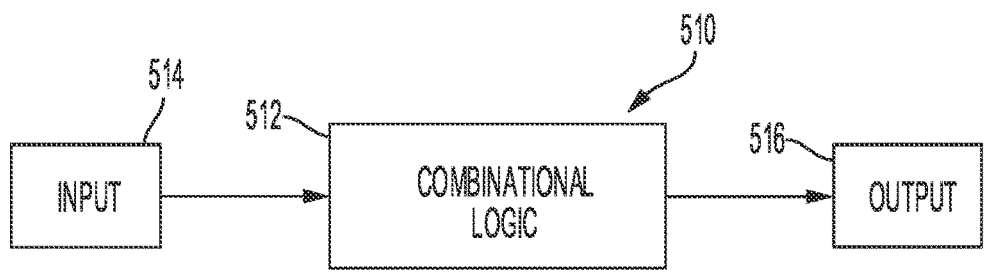
FIG. 14 illustrates a combinational logic circuit configured to control aspects of the surgical instrument or tool, in accordance with at least one aspect of the present disclosure.

FIG. 14 illustrates a combinational logic circuit 510 configured to control aspects of the surgical instrument or tool according to one aspect of this disclosure. The combinational logic circuit 510 can be configured to implement various processes described herein. The combinational logic circuit 510 may comprise a finite state machine comprising a combinational logic 512 configured to receive data associated with the surgical instrument or tool at an input 514, process the data by the combinational logic 512, and provide an output 516.

Figure 15:
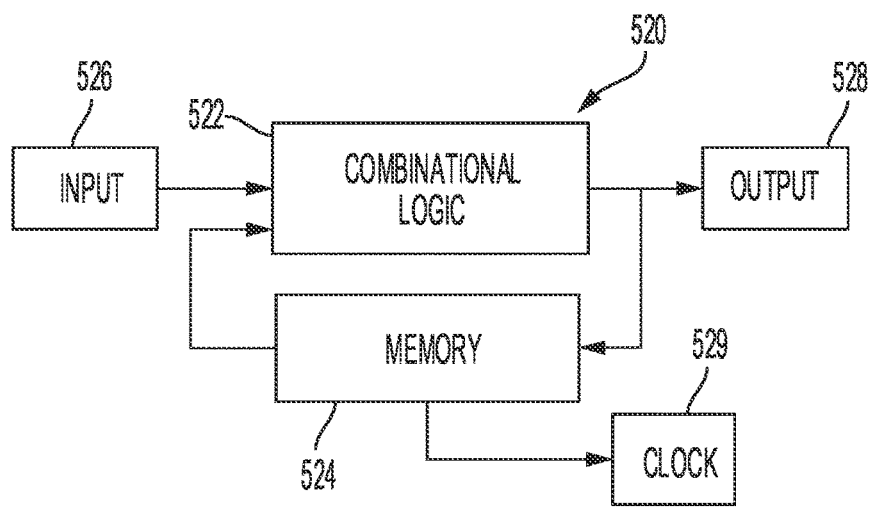
FIG. 15 illustrates a sequential logic circuit configured to control aspects of the surgical instrument or tool, in accordance with at least one aspect of the present disclosure.

FIG. 15 illustrates a sequential logic circuit 520 configured to control aspects of the surgical instrument or tool according to one aspect of this disclosure. The sequential logic circuit 520 or the combinational logic 522 can be configured to implement various processes described herein. The sequential logic circuit 520 may comprise a finite state machine. The sequential logic circuit 520 may comprise a combinational logic 522, at least one memory circuit 524, and a clock 529, for example. The at least one memory circuit 524 can store a current state of the finite state machine. In certain instances, the sequential logic circuit 520 may be synchronous or asynchronous. The combinational logic 522 is configured to receive data associated with the surgical instrument or tool from an input 526, process the data by the combinational logic 522, and provide an output 528. In other aspects, the circuit may comprise a combination of a processor (e.g., processor 502, FIG. 13) and a finite state machine to implement various processes herein. In other aspects, the finite state machine may comprise a combination of a combinational logic circuit (e.g., combinational logic circuit 510, FIG. 14) and the sequential logic circuit 520.

Figure 16:
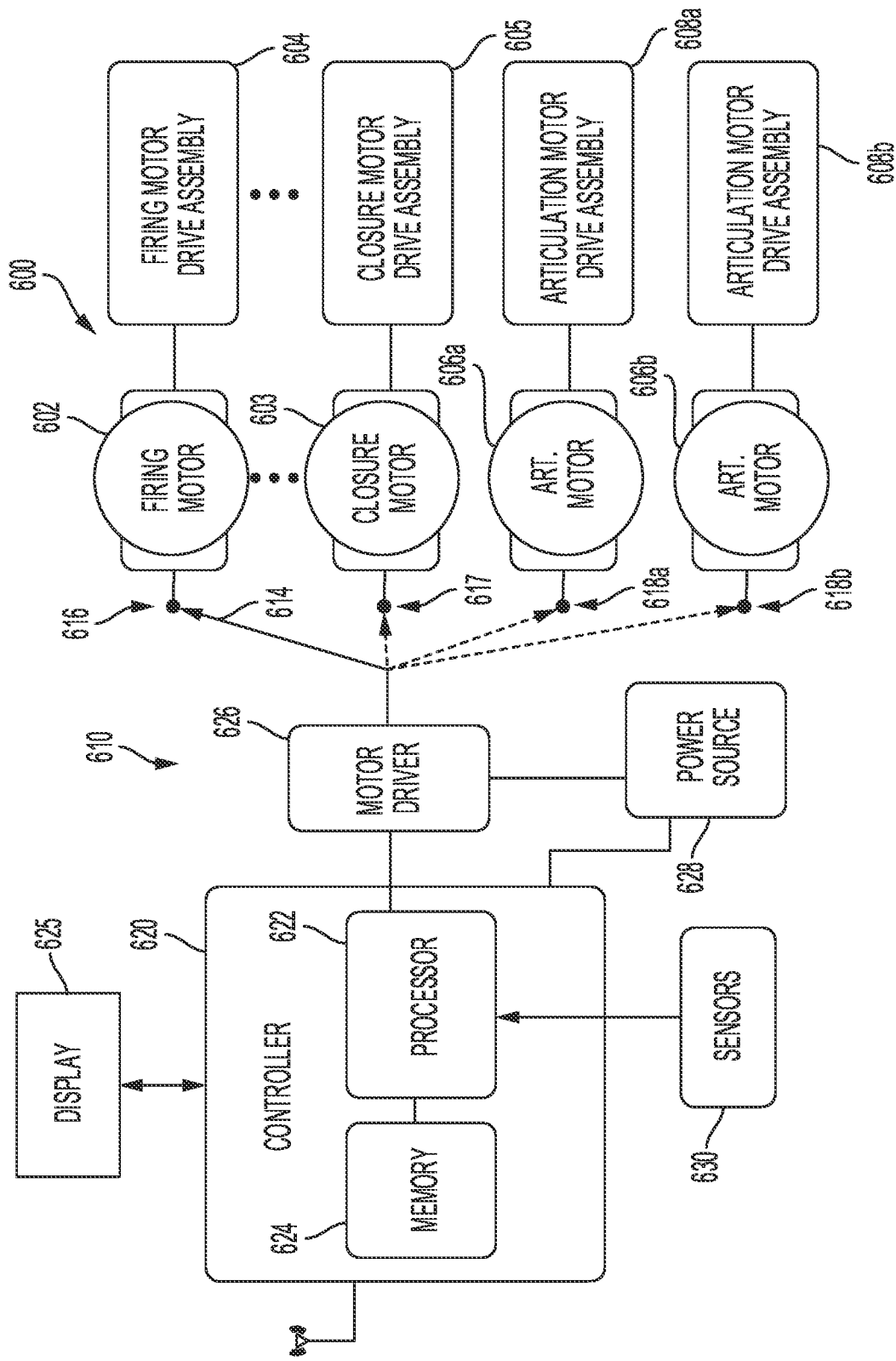
FIG. 16 illustrates a surgical instrument or tool comprising a plurality of motors which can be activated to perform various functions, in accordance with at least one aspect of the present disclosure.

FIG. 16 illustrates a surgical instrument or tool comprising a plurality of motors which can be activated to perform various functions. In certain instances, a first motor can be activated to perform a first function, a second motor can be activated to perform a second function, a third motor can be activated to perform a third function, a fourth motor can be activated to perform a fourth function, and so on. In certain instances, the plurality of motors of robotic surgical instrument 600 can be individually activated to cause firing, closure, and/or articulation motions in the end effector. The firing, closure, and/or articulation motions can be transmitted to the end effector through a shaft assembly, for example.

In certain instances, the surgical instrument system or tool may include a firing motor 602. The firing motor 602 may be operably coupled to a firing motor drive assembly 604 which can be configured to transmit firing motions, generated by the motor 602 to the end effector, in particular to displace the clamp arm closure member. The closure member may be retracted by reversing the direction of the motor 602, which also causes the clamp arm to open.

In certain instances, the surgical instrument or tool may include a closure motor 603. The closure motor 603 may be operably coupled to a closure motor drive assembly 605 which can be configured to transmit closure motions, generated by the motor 603 to the end effector, in particular to displace a closure tube to close the anvil and compress tissue between the anvil and the staple cartridge. The closure motor 603 may be operably coupled to a closure motor drive assembly 605 which can be configured to transmit closure motions, generated by the motor 603 to the end effector, in particular to displace a closure tube to close the clamp arm and compress tissue between the clamp arm and either an ultrasonic blade or jaw member of an electrosurgical device. The closure motions may cause the end effector to transition from an open configuration to an approximated configuration to capture tissue, for example. The end effector may be transitioned to an open position by reversing the direction of the motor 603.

In certain instances, the surgical instrument or tool may include one or more articulation motors 606a, 606b, for example. The motors 606a, 606b may be operably coupled to respective articulation motor drive assemblies 608a, 608b, which can be configured to transmit articulation motions generated by the motors 606a, 606b to the end effector. In certain instances, the articulation motions may cause the end effector to articulate relative to the shaft, for example.

As described above, the surgical instrument or tool may include a plurality of motors which may be configured to perform various independent functions. In certain instances, the plurality of motors of the surgical instrument or tool can be individually or separately activated to perform one or more functions while the other motors remain inactive. For example, the articulation motors 606a, 606b can be activated to cause the end effector to be articulated while the firing motor 602 remains inactive. Alternatively, the firing motor 602 can be activated to fire the plurality of staples, and/or to advance the cutting edge, while the articulation motor 606 remains inactive. Furthermore, the closure motor 603 may be activated simultaneously with the firing motor 602 to cause the closure tube or closure member to advance distally as described in more detail hereinbelow.

In certain instances, the surgical instrument or tool may include a common control module 610 which can be employed with a plurality of motors of the surgical instrument or tool. In certain instances, the common control module 610 may accommodate one of the plurality of motors at a time. For example, the common control module 610 can be couplable to and separable from the plurality of motors of the robotic surgical instrument individually. In certain instances, a plurality of the motors of the surgical instrument or tool may share one or more common control modules such as the common control module 610. In certain instances, a plurality of motors of the surgical instrument or tool can be individually and selectively engaged with the common control module 610. In certain instances, the common control module 610 can be selectively switched from interfacing with one of a plurality of motors of the surgical instrument or tool to interfacing with another one of the plurality of motors of the surgical instrument or tool.

In at least one example, the common control module 610 can be selectively switched between operable engagement with the articulation motors 606a, 606b and operable engagement with either the firing motor 602 or the closure motor 603. In at least one example, as illustrated in FIG. 16, a switch 614 can be moved or transitioned between a plurality of positions and/or states. In a first position 616, the switch 614 may electrically couple the common control module 610 to the firing motor 602; in a second position 617, the switch 614 may electrically couple the common control module 610 to the closure motor 603; in a third position 618a, the switch 614 may electrically couple the common control module 610 to the first articulation motor 606a; and in a fourth position 618b, the switch 614 may electrically couple the common control module 610 to the second articulation motor 606b, for example. In certain instances, separate common control modules 610 can be electrically coupled to the firing motor 602, the closure motor 603, and the articulations motor 606a, 606b at the same time. In certain instances, the switch 614 may be a mechanical switch, an electromechanical switch, a solid-state switch, or any suitable switching mechanism.

Each of the motors 602, 603, 606a, 606b may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, as illustrated in FIG. 16, the common control module 610 may comprise a motor driver 626 which may comprise one or more H-Bridge FETs. The motor driver 626 may modulate the power transmitted from a power source 628 to a motor coupled to the common control module 610 based on input from a microcontroller 620 (the "controller"), for example. In certain instances, the microcontroller 620 can be employed to determine the current drawn by the motor, for example, while the motor is coupled to the common control module 610, as described above.

In certain instances, the microcontroller 620 may include a microprocessor 622 (the "processor") and one or more non-transitory computer-readable mediums or memory units 624 (the "memory"). In certain instances, the memory 624 may store various program instructions, which when executed may cause the processor 622 to perform a plurality of functions and/or calculations described herein. In certain instances, one or more of the memory units 624 may be coupled to the processor 622, for example. In various aspects, the microcontroller 620 may communicate over a wired or wireless channel, or combinations thereof.

In certain instances, the power source 628 can be employed to supply power to the microcontroller 620, for example. In certain instances, the power source 628 may comprise a battery (or "battery pack" or "power pack"), such as a lithium-ion battery, for example. In certain instances, the battery pack may be configured to be releasably mounted to a handle for supplying power to the surgical instrument 600. A number of battery cells connected in series may be used as the power source 628. In certain instances, the power source 628 may be replaceable and/or rechargeable, for example.

In various instances, the processor 622 may control the motor driver 626 to control the position, direction of rotation, and/or velocity of a motor that is coupled to the common control module 610. In certain instances, the processor 622 can signal the motor driver 626 to stop and/or disable a motor that is coupled to the common control module 610. It should be understood that the term "processor" as used herein includes any suitable microprocessor, microcontroller, or other basic computing device that incorporates the functions of a computer's central processing unit (CPU) on an integrated circuit or, at most, a few integrated circuits. The processor 622 is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one instance, the processor 622 may be any single-core or multicore processor such as those known under the trade name ARM Cortex by Texas Instruments. In certain instances, the microcontroller 620 may be an LM 4F230H5QR, available from Texas Instruments, for example. In at least one example, the Texas Instruments LM4F230H5QR is an ARM Cortex-M4F Processor Core comprising an on-chip memory of 256 KB single-cycle flash memory, or other non-volatile memory, up to 40 MHz, a prefetch buffer to improve performance above 40 MHz, a 32 KB single-cycle SRAM, an internal ROM loaded with StellarisWare® software, a 2 KB EEPROM, one or more PWM modules, one or more QEI analogs, one or more 12-bit ADCs with 12 analog input channels, among other features that are readily available for the product datasheet. Other microcontrollers may be readily substituted for use with the module 4410. Accordingly, the present disclosure should not be limited in this context.

In certain instances, the memory 624 may include program instructions for controlling each of the motors of the surgical instrument 600 that are couplable to the common control module 610. For example, the memory 624 may include program instructions for controlling the firing motor 602, the closure motor 603, and the articulation motors 606a, 606b. Such program instructions may cause the processor 622 to control the firing, closure, and articulation functions in accordance with inputs from algorithms or control programs of the surgical instrument or tool.

In certain instances, one or more mechanisms and/or sensors such as, for example, sensors 630 can be employed to alert the processor 622 to the program instructions that should be used in a particular setting. For example, the sensors 630 may alert the processor 622 to use the program instructions associated with firing, closing, and articulating the end effector. In certain instances, the sensors 630 may comprise position sensors which can be employed to sense the position of the switch 614, for example. Accordingly, the processor 622 may use the program instructions associated with firing the closure member coupled to the clamp arm of the end effector upon detecting, through the sensors 630 for example, that the switch 614 is in the first position 616; the processor 622 may use the program instructions associated with closing the anvil upon detecting, through the sensors 630 for example, that the switch 614 is in the second position 617; and the processor 622 may use the program instructions associated with articulating the end effector upon detecting, through the sensors 630 for example, that the switch 614 is in the third or fourth position 618a, 618b.

Figure 17:
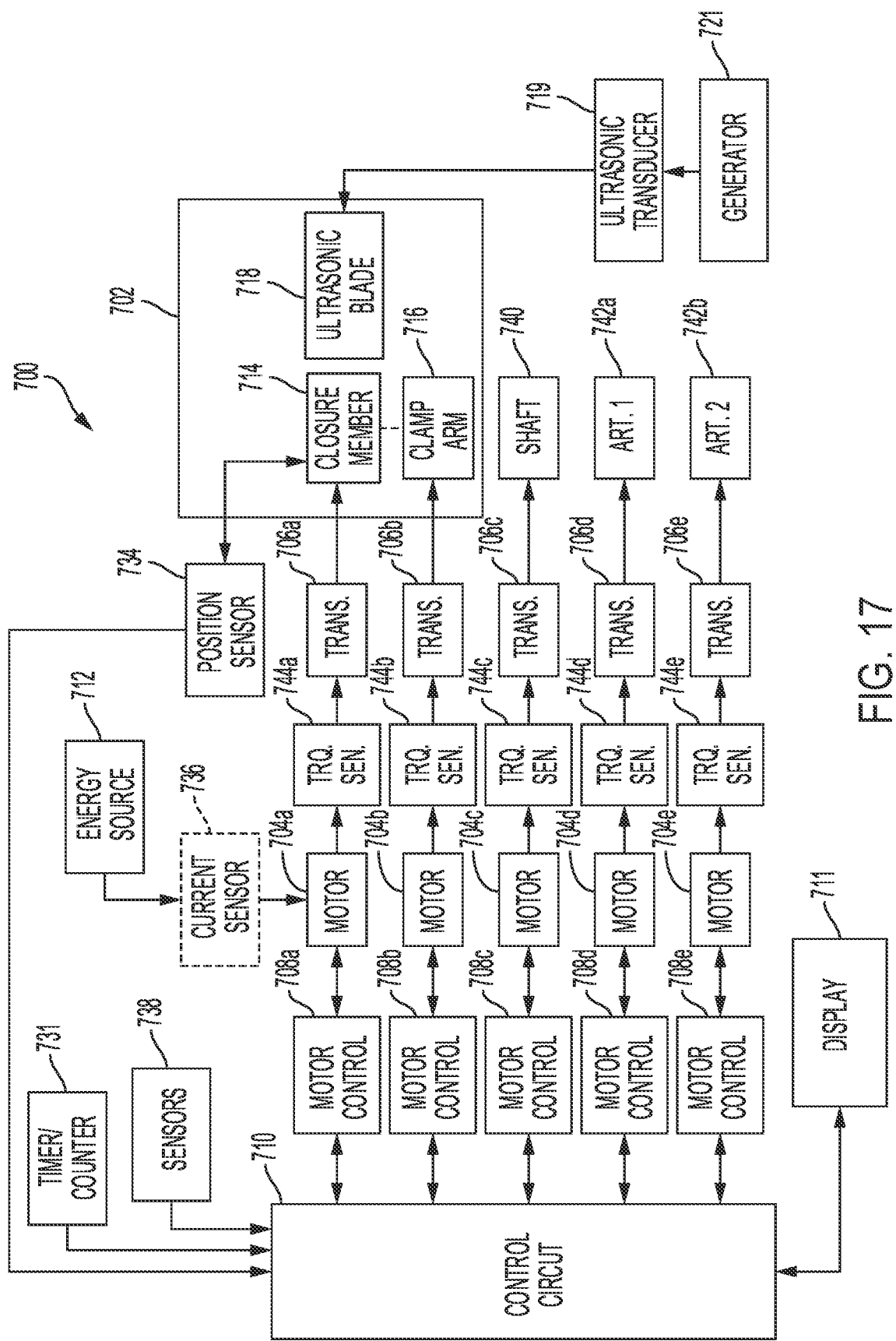
FIG. 17 is a schematic diagram of a robotic surgical instrument configured to operate a surgical tool described herein, in accordance with at least one aspect of the present disclosure.

FIG. 17 is a schematic diagram of a robotic surgical instrument 700 configured to operate a surgical tool described herein according to one aspect of this disclosure. The robotic surgical instrument 700 may be programmed or configured to control distal/proximal translation of a displacement member, distal/proximal displacement of a closure tube, shaft rotation, and articulation, either with single or multiple articulation drive links. In one aspect, the surgical instrument 700 may be programmed or configured to individually control a firing member, a closure member, a shaft member, or one or more articulation members, or combinations thereof. The surgical instrument 700 comprises a control circuit 710 configured to control motor-driven firing members, closure members, shaft members, or one or more articulation members, or combinations thereof.

In one aspect, the robotic surgical instrument 700 comprises a control circuit 710 configured to control a clamp arm 716 and a closure member 714 portion of an end effector 702, an ultrasonic blade 718 coupled to an ultrasonic transducer 719 excited by an ultrasonic generator 721, a shaft 740, and one or more articulation members 742a, 742b via a plurality of motors 704a-704e. A position sensor 734 may be configured to provide position feedback of the closure member 714 to the control circuit 710. Other sensors 738 may be configured to provide feedback to the control circuit 710. A timer/counter 731 provides timing and counting information to the control circuit 710. An energy source 712 may be provided to operate the motors 704a-704e, and a current sensor 736 provides motor current feedback to the control circuit 710. The motors 704a-704e can be operated individually by the control circuit 710 in an open-loop or closed-loop feedback control.

In one aspect, the control circuit 710 may comprise one or more microcontrollers, microprocessors, or other suitable processors for executing instructions that cause the processor or processors to perform one or more tasks. In one aspect, a timer/counter 731 provides an output signal, such as the elapsed time or a digital count, to the control circuit 710 to correlate the position of the closure member 714 as determined by the position sensor 734 with the output of the timer/counter 731 such that the control circuit 710 can determine the position of the closure member 714 at a specific time (t) relative to a starting position or the time (t) when the closure member 714 is at a specific position relative to a starting position. The timer/counter 731 may be configured to measure elapsed time, count external events, or time external events.

In one aspect, the control circuit 710 may be programmed to control functions of the end effector 702 based on one or more tissue conditions. The control circuit 710 may be programmed to sense tissue conditions, such as thickness, either directly or indirectly, as described herein. The control circuit 710 may be programmed to select a firing control program or closure control program based on tissue conditions. A firing control program may describe the distal motion of the displacement member. Different firing control programs may be selected to better treat different tissue conditions. For example, when thicker tissue is present, the control circuit 710 may be programmed to translate the displacement member at a lower velocity and/or with lower power. When thinner tissue is present, the control circuit 710 may be programmed to translate the displacement member at a higher velocity and/or with higher power. A closure control program may control the closure force applied to the tissue by the clamp arm 716. Other control programs control the rotation of the shaft 740 and the articulation members 742a, 742b.

In one aspect, the control circuit 710 may generate motor set point signals. The motor set point signals may be provided to various motor controllers 708a-708e. The motor controllers 708a-708e may comprise one or more circuits configured to provide motor drive signals to the motors 704a-704e to drive the motors 704a-704e as described herein. In some examples, the motors 704a-704e may be brushed DC electric motors. For example, the velocity of the motors 704a-704e may be proportional to the respective motor drive signals. In some examples, the motors 704a-704e may be brushless DC electric motors, and the respective motor drive signals may comprise a PWM signal provided to one or more stator windings of the motors 704a-704e. Also, in some examples, the motor controllers 708a-708e may be omitted and the control circuit 710 may generate the motor drive signals directly.

In one aspect, the control circuit 710 may initially operate each of the motors 704a-704e in an open-loop configuration for a first open-loop portion of a stroke of the displacement member. Based on the response of the robotic surgical instrument 700 during the open-loop portion of the stroke, the control circuit 710 may select a firing control program in a closed-loop configuration. The response of the instrument may include a translation distance of the displacement member during the open-loop portion, a time elapsed during the open-loop portion, the energy provided to one of the motors 704a-704e during the open-loop portion, a sum of pulse widths of a motor drive signal, etc. After the open-loop portion, the control circuit 710 may implement the selected firing control program for a second portion of the displacement member stroke. For example, during a closed-loop portion of the stroke, the control circuit 710 may modulate one of the motors 704a-704e based on translation data describing a position of the displacement member in a closed-loop manner to translate the displacement member at a constant velocity.

In one aspect, the motors 704a-704e may receive power from an energy source 712. The energy source 712 may be a DC power supply driven by a main alternating current power source, a battery, a super capacitor, or any other suitable energy source. The motors 704a-704e may be mechanically coupled to individual movable mechanical elements such as the closure member 714, clamp arm 716, shaft 740, articulation 742a, and articulation 742b via respective transmissions 706a-706e. The transmissions 706a-706e may include one or more gears or other linkage components to couple the motors 704a-704e to movable mechanical elements. A position sensor 734 may sense a position of the closure member 714. The position sensor 734 may be or include any type of sensor that is capable of generating position data that indicate a position of the closure member 714. In some examples, the position sensor 734 may include an encoder configured to provide a series of pulses to the control circuit 710 as the closure member 714 translates distally and proximally. The control circuit 710 may track the pulses to determine the position of the closure member 714. Other suitable position sensors may be used, including, for example, a proximity sensor. Other types of position sensors may provide other signals indicating motion of the closure member 714. Also, in some examples, the position sensor 734 may be omitted. Where any of the motors 704a-704e is a stepper motor, the control circuit 710 may track the position of the closure member 714 by aggregating the number and direction of steps that the motor 704 has been instructed to execute. The position sensor 734 may be located in the end effector 702 or at any other portion of the instrument. The outputs of each of the motors 704a-704e include a torque sensor 744a-744e to sense force and have an encoder to sense rotation of the drive shaft.

In one aspect, the control circuit 710 is configured to drive a firing member such as the closure member 714 portion of the end effector 702. The control circuit 710 provides a motor set point to a motor control 708a, which provides a drive signal to the motor 704a. The output shaft of the motor 704a is coupled to a torque sensor 744a. The torque sensor 744a is coupled to a transmission 706a which is coupled to the closure member 714. The transmission 706a comprises movable mechanical elements such as rotating elements and a firing member to control the movement of the closure member 714 distally and proximally along a longitudinal axis of the end effector 702. In one aspect, the motor 704a may be coupled to the knife gear assembly, which includes a knife gear reduction set that includes a first knife drive gear and a second knife drive gear. A torque sensor 744a provides a firing force feedback signal to the control circuit 710. The firing force signal represents the force required to fire or displace the closure member 714. A position sensor 734 may be configured to provide the position of the closure member 714 along the firing stroke or the position of the firing member as a feedback signal to the control circuit 710. The end effector 702 may include additional sensors 738 configured to provide feedback signals to the control circuit 710. When ready to use, the control circuit 710 may provide a firing signal to the motor control 708a. In response to the firing signal, the motor 704a may drive the firing member distally along the longitudinal axis of the end effector 702 from a proximal stroke start position to a stroke end position distal to the stroke start position. As the closure member 714 translates distally, the clamp arm 716 closes towards the ultrasonic blade 718.

In one aspect, the control circuit 710 is configured to drive a closure member such as the clamp arm 716 portion of the end effector 702. The control circuit 710 provides a motor set point to a motor control 708b, which provides a drive signal to the motor 704b. The output shaft of the motor 704b is coupled to a torque sensor 744b. The torque sensor 744b is coupled to a transmission 706b which is coupled to the clamp arm 716. The transmission 706b comprises movable mechanical elements such as rotating elements and a closure member to control the movement of the clamp arm 716 from the open and closed positions. In one aspect, the motor 704b is coupled to a closure gear assembly, which includes a closure reduction gear set that is supported in meshing engagement with the closure spur gear. The torque sensor 744b provides a closure force feedback signal to the control circuit 710. The closure force feedback signal represents the closure force applied to the clamp arm 716. The position sensor 734 may be configured to provide the position of the closure member as a feedback signal to the control circuit 710. Additional sensors 738 in the end effector 702 may provide the closure force feedback signal to the control circuit 710. The pivotable clamp arm 716 is positioned opposite the ultrasonic blade 718. When ready to use, the control circuit 710 may provide a closure signal to the motor control 708b. In response to the closure signal, the motor 704b advances a closure member to grasp tissue between the clamp arm 716 and the ultrasonic blade 718.

In one aspect, the control circuit 710 is configured to rotate a shaft member such as the shaft 740 to rotate the end effector 702. The control circuit 710 provides a motor set point to a motor control 708c, which provides a drive signal to the motor 704c. The output shaft of the motor 704c is coupled to a torque sensor 744c. The torque sensor 744c is coupled to a transmission 706c which is coupled to the shaft 740. The transmission 706c comprises movable mechanical elements such as rotating elements to control the rotation of the shaft 740 clockwise or counterclockwise up to and over 360°. In one aspect, the motor 704c is coupled to the rotational transmission assembly, which includes a tube gear segment that is formed on (or attached to) the proximal end of the proximal closure tube for operable engagement by a rotational gear assembly that is operably supported on the tool mounting plate. The torque sensor 744c provides a rotation force feedback signal to the control circuit 710. The rotation force feedback signal represents the rotation force applied to the shaft 740. The position sensor 734 may be configured to provide the position of the closure member as a feedback signal to the control circuit 710. Additional sensors 738 such as a shaft encoder may provide the rotational position of the shaft 740 to the control circuit 710.

In one aspect, the control circuit 710 is configured to articulate the end effector 702. The control circuit 710 provides a motor set point to a motor control 708d, which provides a drive signal to the motor 704d. The output shaft of the motor 704d is coupled to a torque sensor 744d. The torque sensor 744d is coupled to a transmission 706d which is coupled to an articulation member 742a. The transmission 706d comprises movable mechanical elements such as articulation elements to control the articulation of the end effector 702 ±65°. In one aspect, the motor 704d is coupled to an articulation nut, which is rotatably journaled on the proximal end portion of the distal spine portion and is rotatably driven thereon by an articulation gear assembly. The torque sensor 744d provides an articulation force feedback signal to the control circuit 710. The articulation force feedback signal represents the articulation force applied to the end effector 702. Sensors 738, such as an articulation encoder, may provide the articulation position of the end effector 702 to the control circuit 710.

In another aspect, the articulation function of the robotic surgical system 700 may comprise two articulation members, or links, 742a, 742b. These articulation members 742a, 742b are driven by separate disks on the robot interface (the rack) which are driven by the two motors 708d, 708e. When the separate firing motor 704a is provided, each of articulation links 742a, 742b can be antagonistically driven with respect to the other link in order to provide a resistive holding motion and a load to the head when it is not moving and to provide an articulation motion as the head is articulated. The articulation members 742a, 742b attach to the head at a fixed radius as the head is rotated. Accordingly, the mechanical advantage of the push-and-pull link changes as the head is rotated. This change in the mechanical advantage may be more pronounced with other articulation link drive systems.

In one aspect, the one or more motors 704a-704e may comprise a brushed DC motor with a gearbox and mechanical links to a firing member, closure member, or articulation member. Another example includes electric motors 704a-704e that operate the movable mechanical elements such as the displacement member, articulation links, closure tube, and shaft. An outside influence is an unmeasured, unpredictable influence of things like tissue, surrounding bodies, and friction on the physical system. Such outside influence can be referred to as drag, which acts in opposition to one of electric motors 704a-704e. The outside influence, such as drag, may cause the operation of the physical system to deviate from a desired operation of the physical system.

In one aspect, the position sensor 734 may be implemented as an absolute positioning system. In one aspect, the position sensor 734 may comprise a magnetic rotary absolute positioning system implemented as an AS5055EQFT single-chip magnetic rotary position sensor available from Austria Microsystems, AG. The position sensor 734 may interface with the control circuit 710 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the control circuit 710 may be in communication with one or more sensors 738. The sensors 738 may be positioned on the end effector 702 and adapted to operate with the robotic surgical instrument 700 to measure the various derived parameters such as the gap distance versus time, tissue compression versus time, and anvil strain versus time. The sensors 738 may comprise a magnetic sensor, a magnetic field sensor, a strain gauge, a load cell, a pressure sensor, a force sensor, a torque sensor, an inductive sensor such as an eddy current sensor, a resistive sensor, a capacitive sensor, an optical sensor, and/or any other suitable sensor for measuring one or more parameters of the end effector 702. The sensors 738 may include one or more sensors. The sensors 738 may be located on the clamp arm 716 to determine tissue location using segmented electrodes. The torque sensors 744a-744e may be configured to sense force such as firing force, closure force, and/or articulation force, among others. Accordingly, the control circuit 710 can sense (1) the closure load experienced by the distal closure tube and its position, (2) the firing member at the rack and its position, (3) what portion of the ultrasonic blade 718 has tissue on it, and (4) the load and position on both articulation rods.

In one aspect, the one or more sensors 738 may comprise a strain gauge, such as a micro-strain gauge, configured to measure the magnitude of the strain in the clamp arm 716 during a clamped condition. The strain gauge provides an electrical signal whose amplitude varies with the magnitude of the strain. The sensors 738 may comprise a pressure sensor configured to detect a pressure generated by the presence of compressed tissue between the clamp arm 716 and the ultrasonic blade 718. The sensors 738 may be configured to detect impedance of a tissue section located between the clamp arm 716 and the ultrasonic blade 718 that is indicative of the thickness and/or fullness of tissue located therebetween.

In one aspect, the sensors 738 may be implemented as one or more limit switches, electromechanical devices, solid-state switches, Hall-effect devices, magneto-resistive (MR) devices, giant magneto-resistive (GMR) devices, magnetometers, among others. In other implementations, the sensors 738 may be implemented as solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 738 may include electrical conductorless switches, ultrasonic switches, accelerometers, and inertial sensors, among others.

In one aspect, the sensors 738 may be configured to measure forces exerted on the clamp arm 716 by the closure drive system. For example, one or more sensors 738 can be at an interaction point between the closure tube and the clamp arm 716 to detect the closure forces applied by the closure tube to the clamp arm 716. The forces exerted on the clamp arm 716 can be representative of the tissue compression experienced by the tissue section captured between the clamp arm 716 and the ultrasonic blade 718. The one or more sensors 738 can be positioned at various interaction points along the closure drive system to detect the closure forces applied to the clamp arm 716 by the closure drive system. The one or more sensors 738 may be sampled in real time during a clamping operation by the processor of the control circuit 710. The control circuit 710 receives real-time sample measurements to provide and analyze time-based information and assess, in real time, closure forces applied to the clamp arm 716.

In one aspect, a current sensor 736 can be employed to measure the current drawn by each of the motors 704a-704e. The force required to advance any of the movable mechanical elements such as the closure member 714 corresponds to the current drawn by one of the motors 704a-704e. The force is converted to a digital signal and provided to the control circuit 710. The control circuit 710 can be configured to simulate the response of the actual system of the instrument in the software of the controller. A displacement member can be actuated to move the closure member 714 in the end effector 702 at or near a target velocity. The robotic surgical instrument 700 can include a feedback controller, which can be one of any feedback controllers, including, but not limited to a PID, a state feedback, a linear-quadratic (LQR), and/or an adaptive controller, for example. The robotic surgical instrument 700 can include a power source to convert the signal from the feedback controller into a physical input such as case voltage, PWM voltage, frequency modulated voltage, current, torque, and/or force, for example. Additional details are disclosed in U.S. patent application Ser. No. 15/636,829, titled CLOSED LOOP VELOCITY CONTROL TECHNIQUES FOR ROBOTIC SURGICAL INSTRUMENT, filed Jun. 29, 2017, which is herein incorporated by reference in its entirety.

Figure 18:
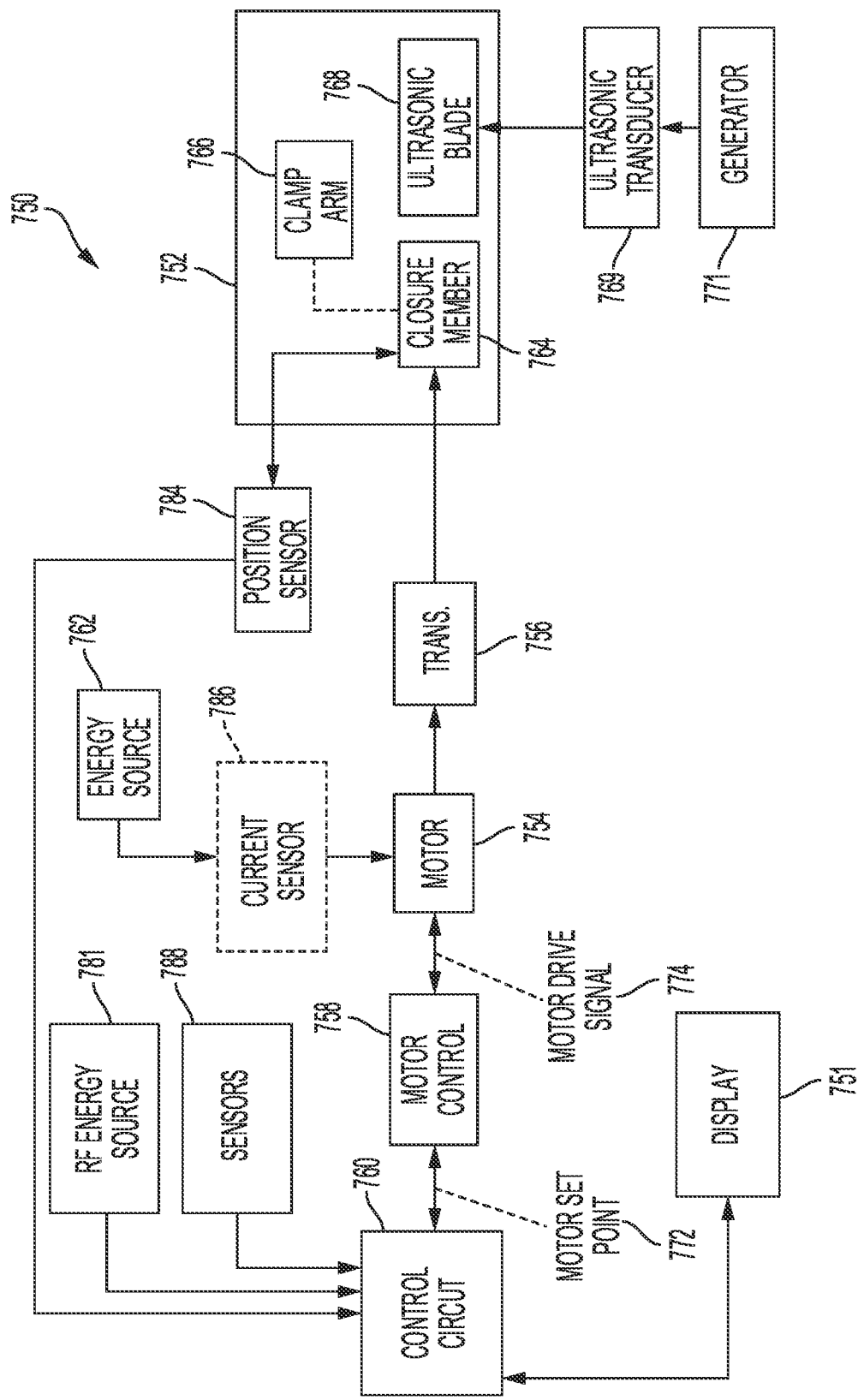
FIG. 18 illustrates a block diagram of a surgical instrument programmed to control the distal translation of a displacement member, in accordance with at least one aspect of the present disclosure.

FIG. 18 illustrates a schematic diagram of a surgical instrument 750 configured to control the distal translation of a displacement member according to one aspect of this disclosure. In one aspect, the surgical instrument 750 is programmed to control the distal translation of a displacement member such as the closure member 764. The surgical instrument 750 comprises an end effector 752 that may comprise a clamp arm 766, a closure member 764, and an ultrasonic blade 768 coupled to an ultrasonic transducer 769 driven by an ultrasonic generator 771.

The position, movement, displacement, and/or translation of a linear displacement member, such as the closure member 764, can be measured by an absolute positioning system, sensor arrangement, and position sensor 784. Because the closure member 764 is coupled to a longitudinally movable drive member, the position of the closure member 764 can be determined by measuring the position of the longitudinally movable drive member employing the position sensor 784. Accordingly, in the following description, the position, displacement, and/or translation of the closure member 764 can be achieved by the position sensor 784 as described herein. A control circuit 760 may be programmed to control the translation of the displacement member, such as the closure member 764. The control circuit 760, in some examples, may comprise one or more microcontrollers, microprocessors, or other suitable processors for executing instructions that cause the processor or processors to control the displacement member, e.g., the closure member 764, in the manner described. In one aspect, a timer/counter 781 provides an output signal, such as the elapsed time or a digital count, to the control circuit 760 to correlate the position of the closure member 764 as determined by the position sensor 784 with the output of the timer/counter 781 such that the control circuit 760 can determine the position of the closure member 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the closure member 764 via a transmission 756. The transmission 756 may include one or more gears or other linkage components to couple the motor 754 to the closure member 764. A position sensor 784 may sense a position of the closure member 764. The position sensor 784 may be or include any type of sensor that is capable of generating position data that indicate a position of the closure member 764. In some examples, the position sensor 784 may include an encoder configured to provide a series of pulses to the control circuit 760 as the closure member 764 translates distally and proximally. The control circuit 760 may track the pulses to determine the position of the closure member 764. Other suitable position sensors may be used, including, for example, a proximity sensor. Other types of position sensors may provide other signals indicating motion of the closure member 764. Also, in some examples, the position sensor 784 may be omitted. Where the motor 754 is a stepper motor, the control circuit 760 may track the position of the closure member 764 by aggregating the number and direction of steps that the motor 754 has been instructed to execute. The position sensor 784 may be located in the end effector 752 or at any other portion of the instrument.

The control circuit 760 may be in communication with one or more sensors 788. The sensors 788 may be positioned on the end effector 752 and adapted to operate with the surgical instrument 750 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 752. The sensors 788 may include one or more sensors.

The one or more sensors 788 may comprise a strain gauge, such as a micro-strain gauge, configured to measure the magnitude of the strain in the clamp arm 766 during a clamped condition. The strain gauge provides an electrical signal whose amplitude varies with the magnitude of the strain. The sensors 788 may comprise a pressure sensor configured to detect a pressure generated by the presence of compressed tissue between the clamp arm 766 and the ultrasonic blade 768. The sensors 788 may be configured to detect impedance of a tissue section located between the clamp arm 766 and the ultrasonic blade 768 that is indicative of the thickness and/or fullness of tissue located therebetween.

The sensors 788 may be is configured to measure forces exerted on the clamp arm 766 by a closure drive system. For example, one or more sensors 788 can be at an interaction point between a closure tube and the clamp arm 766 to detect the closure forces applied by a closure tube to the clamp arm 766. The forces exerted on the clamp arm 766 can be representative of the tissue compression experienced by the tissue section captured between the clamp arm 766 and the ultrasonic blade 768. The one or more sensors 788 can be positioned at various interaction points along the closure drive system to detect the closure forces applied to the clamp arm 766 by the closure drive system. The one or more sensors 788 may be sampled in real time during a clamping operation by a processor of the control circuit 760. The control circuit 760 receives real-time sample measurements to provide and analyze time-based information and assess, in real time, closure forces applied to the clamp arm 766.

A current sensor 786 can be employed to measure the current drawn by the motor 754. The force required to advance the closure member 764 corresponds to the current drawn by the motor 754. The force is converted to a digital signal and provided to the control circuit 760.

The control circuit 760 can be configured to simulate the response of the actual system of the instrument in the software of the controller. A displacement member can be actuated to move a closure member 764 in the end effector 752 at or near a target velocity. The surgical instrument 750 can include a feedback controller, which can be one of any feedback controllers, including, but not limited to a PID, a state feedback, LQR, and/or an adaptive controller, for example. The surgical instrument 750 can include a power source to convert the signal from the feedback controller into a physical input such as case voltage, PWM voltage, frequency modulated voltage, current, torque, and/or force, for example.

The actual drive system of the surgical instrument 750 is configured to drive the displacement member, cutting member, or closure member 764, by a brushed DC motor with gearbox and mechanical links to an articulation and/or knife system. Another example is the electric motor 754 that operates the displacement member and the articulation driver, for example, of an interchangeable shaft assembly. An outside influence is an unmeasured, unpredictable influence of things like tissue, surrounding bodies and friction on the physical system. Such outside influence can be referred to as drag which acts in opposition to the electric motor 754. The outside influence, such as drag, may cause the operation of the physical system to deviate from a desired operation of the physical system.

Various example aspects are directed to a surgical instrument 750 comprising an end effector 752 with motor-driven surgical sealing and cutting implements. For example, a motor 754 may drive a displacement member distally and proximally along a longitudinal axis of the end effector 752. The end effector 752 may comprise a pivotable clamp arm 766 and, when configured for use, an ultrasonic blade 768 positioned opposite the clamp arm 766. A clinician may grasp tissue between the clamp arm 766 and the ultrasonic blade 768, as described herein. When ready to use the instrument 750, the clinician may provide a firing signal, for example by depressing a trigger of the instrument 750. In response to the firing signal, the motor 754 may drive the displacement member distally along the longitudinal axis of the end effector 752 from a proximal stroke begin position to a stroke end position distal of the stroke begin position. As the displacement member translates distally, the closure member 764 with a cutting element positioned at a distal end, may cut the tissue between the ultrasonic blade 768 and the clamp arm 766.

In various examples, the surgical instrument 750 may comprise a control circuit 760 programmed to control the distal translation of the displacement member, such as the closure member 764, for example, based on one or more tissue conditions. The control circuit 760 may be programmed to sense tissue conditions, such as thickness, either directly or indirectly, as described herein. The control circuit 760 may be programmed to select a control program based on tissue conditions. A control program may describe the distal motion of the displacement member. Different control programs may be selected to better treat different tissue conditions. For example, when thicker tissue is present, the control circuit 760 may be programmed to translate the displacement member at a lower velocity and/or with lower power. When thinner tissue is present, the control circuit 760 may be programmed to translate the displacement member at a higher velocity and/or with higher power.

In some examples, the control circuit 760 may initially operate the motor 754 in an open loop configuration for a first open loop portion of a stroke of the displacement member. Based on a response of the instrument 750 during the open loop portion of the stroke, the control circuit 760 may select a firing control program. The response of the instrument may include, a translation distance of the displacement member during the open loop portion, a time elapsed during the open loop portion, energy provided to the motor 754 during the open loop portion, a sum of pulse widths of a motor drive signal, etc. After the open loop portion, the control circuit 760 may implement the selected firing control program for a second portion of the displacement member stroke. For example, during the closed loop portion of the stroke, the control circuit 760 may modulate the motor 754 based on translation data describing a position of the displacement member in a closed loop manner to translate the displacement member at a constant velocity. Additional details are disclosed in U.S. patent application Ser. No. 15/720,852, titled SYSTEM AND METHODS FOR CONTROLLING A DISPLAY OF A SURGICAL INSTRUMENT, filed Sep. 29, 2017, which is herein incorporated by reference in its entirety.

Figure 19:
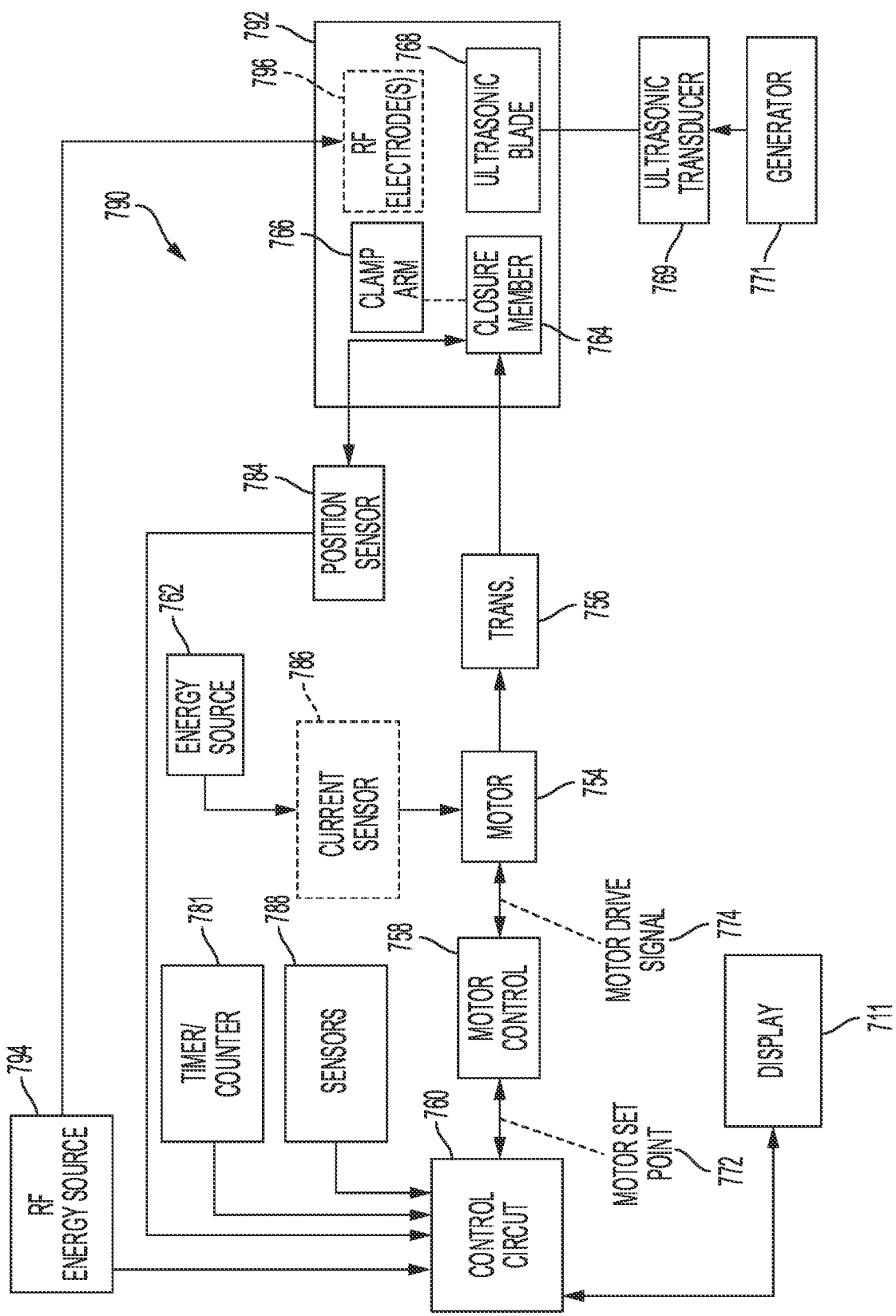
FIG. 19 is a schematic diagram of a surgical instrument configured to control various functions, in accordance with at least one aspect of the present disclosure.

FIG. 19 is a schematic diagram of a surgical instrument 790 configured to control various functions according to one aspect of this disclosure. In one aspect, the surgical instrument 790 is programmed to control distal translation of a displacement member such as the closure member 764. The surgical instrument 790 comprises an end effector 792 that may comprise a clamp arm 766, a closure member 764, and an ultrasonic blade 768 which may be interchanged with or work in conjunction with one or more RF electrodes 796 (shown in dashed line). The ultrasonic blade 768 is coupled to an ultrasonic transducer 769 driven by an ultrasonic generator 771.

In one aspect, sensors 788 may be implemented as a limit switch, electromechanical device, solid-state switches, Hall-effect devices, MR devices, GMR devices, magnetometers, among others. In other implementations, the sensors 638 may be solid-state switches that operate under the influence of light, such as optical sensors, IR sensors, ultraviolet sensors, among others. Still, the switches may be solid-state devices such as transistors (e.g., FET, junction FET, MOS-FET, bipolar, and the like). In other implementations, the sensors 788 may include electrical conductorless switches, ultrasonic switches, accelerometers, and inertial sensors, among others.

In one aspect, the position sensor 784 may be implemented as an absolute positioning system comprising a magnetic rotary absolute positioning system implemented as an AS5055EQFT single-chip magnetic rotary position sensor available from Austria Microsystems, AG. The position sensor 784 may interface with the control circuit 760 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In some examples, the position sensor 784 may be omitted. Where the motor 754 is a stepper motor, the control circuit 760 may track the position of the closure member 764 by aggregating the number and direction of steps that the motor has been instructed to execute. The position sensor 784 may be located in the end effector 792 or at any other portion of the instrument.

The control circuit 760 may be in communication with one or more sensors 788. The sensors 788 may be positioned on the end effector 792 and adapted to operate with the surgical instrument 790 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 792. The sensors 788 may include one or more sensors.

An RF energy source 794 is coupled to the end effector 792 and is applied to the RF electrode 796 when the RF electrode 796 is provided in the end effector 792 in place of the ultrasonic blade 768 or to work in conjunction with the ultrasonic blade 768. For example, the ultrasonic blade is made of electrically conductive metal and may be employed as the return path for electrosurgical RF current. The control circuit 760 controls the delivery of the RF energy to the RF electrode 796.

Additional details are disclosed in U.S. patent application Ser. No. 15/636,096, titled SURGICAL SYSTEM COUPLABLE WITH STAPLE CARTRIDGE AND RADIO FREQUENCY CARTRIDGE, AND METHOD OF USING SAME, filed Jun. 28, 2017, which is herein incorporated by reference in its entirety.

Generator Hardware

In various aspects smart ultrasonic energy devices may comprise adaptive algorithms to control the operation of the ultrasonic blade. In one aspect, the ultrasonic blade adaptive control algorithms are configured to identify tissue type and adjust device parameters. In one aspect, the ultrasonic blade control algorithms are configured to parameterize tissue type. An algorithm to detect the collagen/elastic ratio of tissue to tune the amplitude of the distal tip of the ultrasonic blade is described in the following section of the present disclosure. Various aspects of smart ultrasonic energy devices are described herein in connection with FIGS. 12-19, for example. Accordingly, the following description of adaptive ultrasonic blade control algorithms should be read in conjunction with FIGS. 12-19 and the description associated therewith.

In certain surgical procedures it would be desirable to employ adaptive ultrasonic blade control algorithms. In one aspect, adaptive ultrasonic blade control algorithms may be employed to adjust the parameters of the ultrasonic device based on the type of tissue in contact with the ultrasonic blade. In one aspect, the parameters of the ultrasonic device may be adjusted based on the location of the tissue within the jaws of the ultrasonic end effector, for example, the location of the tissue between the clamp arm and the ultrasonic blade. The impedance of the ultrasonic transducer may be employed to differentiate what percentage of the tissue is located in the distal or proximal end of the end effector. The reactions of the ultrasonic device may be based on the tissue type or compressibility of the tissue. In another aspect, the parameters of the ultrasonic device may be adjusted based on the identified tissue type or parameterization. For example, the mechanical displacement amplitude of the distal tip of the ultrasonic blade may be tuned based on the ration of collagen to elastin tissue detected during the tissue identification procedure. The ratio of collagen to elastin tissue may be detected used a variety of techniques including infrared (IR) surface reflectance and emissivity. The force applied to the tissue by the clamp arm and/or the stroke of the clamp arm to produce gap and compression. Electrical continuity across a jaw equipped with electrodes may be employed to determine what percentage of the jaw is covered with tissue.

Figure 20:
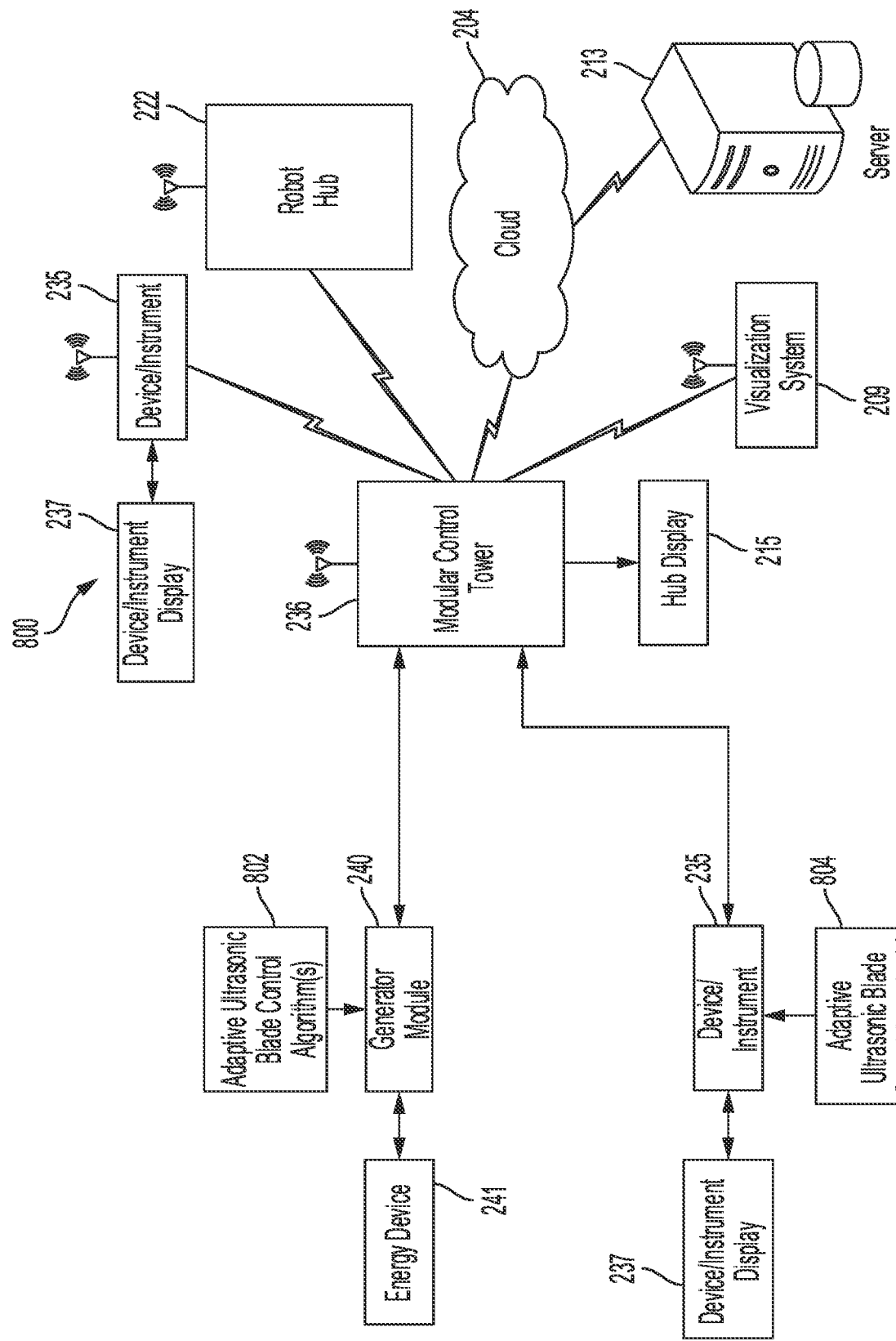
FIG. 20 is a system configured to execute adaptive ultrasonic blade control algorithms in a surgical data network comprising a modular communication hub, in accordance with at least one aspect of the present disclosure.

FIG. 20 is a system 800 configured to execute adaptive ultrasonic blade control algorithms in a surgical data network comprising a modular communication hub, in accordance with at least one aspect of the present disclosure. In one aspect, the generator module 240 is configured to execute the adaptive ultrasonic blade control algorithm(s) 802. In another aspect, the device/instrument 235 is configured to execute the adaptive ultrasonic blade control algorithm(s) 804. In another aspect, both the generator module 240 and the device/instrument 235 are configured to execute the adaptive ultrasonic blade control algorithms 802, 804.

The generator module 240 may comprise a patient isolated stage in communication with a non-isolated stage via a power transformer. A secondary winding of the power transformer is contained in the isolated stage and may comprise a tapped configuration (e.g., a center-tapped or a non-center-tapped configuration) to define drive signal outputs for delivering drive signals to different surgical instruments, such as, for example, an ultrasonic surgical instrument, an RF electrosurgical instrument, and a multifunction surgical instrument which includes ultrasonic and RF energy modes that can be delivered alone or simultaneously. In particular, the drive signal outputs may output an ultrasonic drive signal (e.g., a 420V root-mean-square (RMS) drive signal) to an ultrasonic surgical instrument 241, and the drive signal outputs may output an RF electrosurgical drive signal (e.g., a 100V RMS drive signal) to an RF electrosurgical instrument 241. Aspects of the generator module 240 are described herein with reference to FIGS. 21-22.

The generator module 240 or the device/instrument 235 or both are coupled the modular control tower 236 connected to multiple operating theater devices such as, for example, intelligent surgical instruments, robots, and other computerized devices located in the operating theater, as described with reference to FIGS. 8-11, for example.

Figure 21:
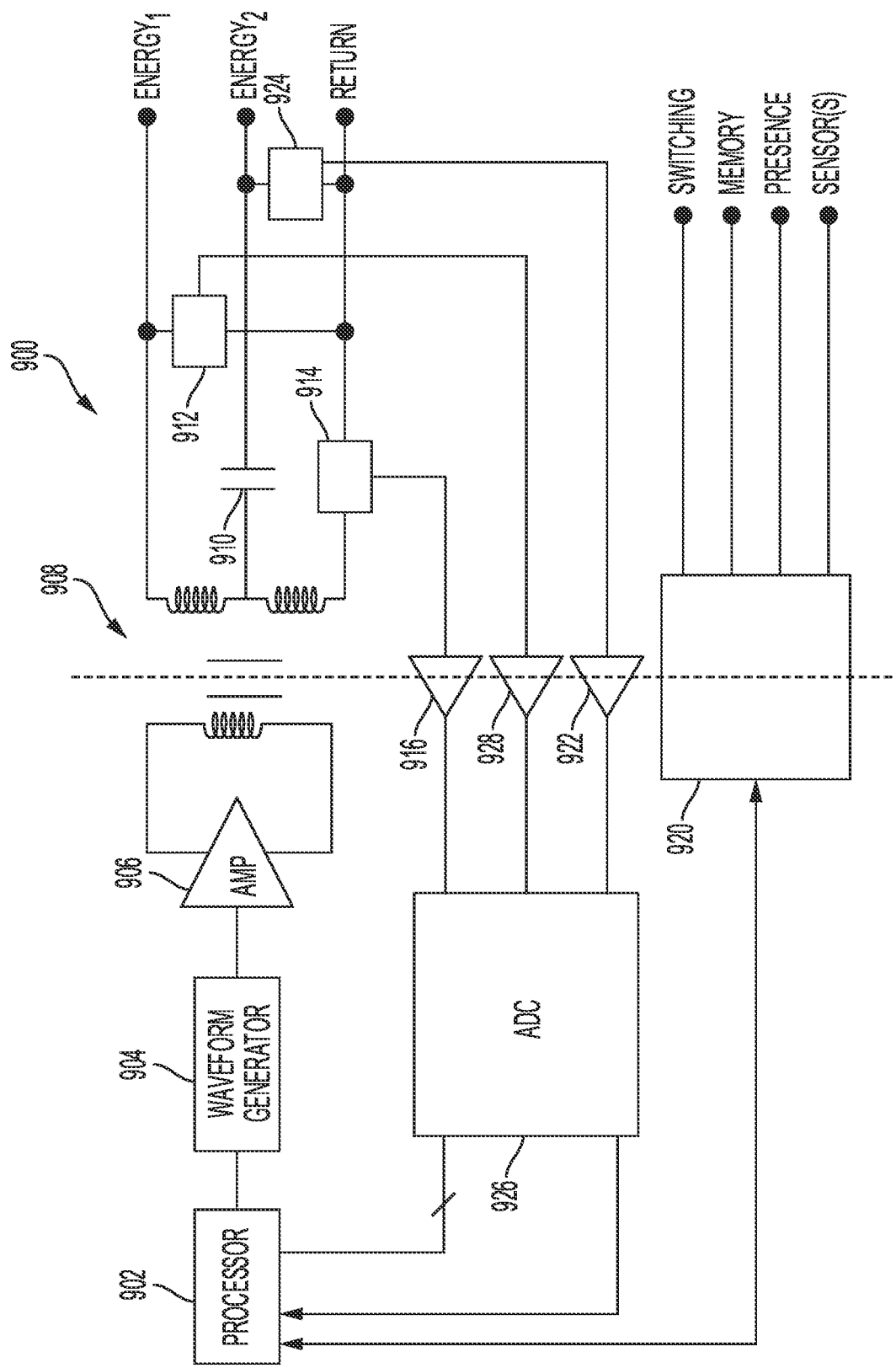
FIG. 21 illustrates an example of a generator, in accordance with at least one aspect of the present disclosure.

FIG. 21 illustrates an example of a generator 900, which is one form of a generator configured to couple to an ultrasonic instrument and further configured to execute adaptive ultrasonic blade control algorithms in a surgical data network comprising a modular communication hub as shown in FIG. 20. The generator 900 is configured to deliver multiple energy modalities to a surgical instrument. The generator 900 provides RF and ultrasonic signals for delivering energy to a surgical instrument either independently or simultaneously. The RF and ultrasonic signals may be provided alone or in combination and may be provided simultaneously. As noted above, at least one generator output can deliver multiple energy modalities (e.g., ultrasonic, bipolar or monopolar RF, irreversible and/or reversible electroporation, and/or microwave energy, among others) through a single port, and these signals can be delivered separately or simultaneously to the end effector to treat tissue. The generator 900 comprises a processor 902 coupled to a waveform generator 904. The processor 902 and waveform generator 904 are configured to generate a variety of signal waveforms based on information stored in a memory coupled to the processor 902, not shown for clarity of disclosure. The digital information associated with a waveform is provided to the waveform generator 904 which includes one or more DAC circuits to convert the digital input into an analog output. The analog output is fed to an amplifier 1106 for signal conditioning and amplification. The conditioned and amplified output of the amplifier 906 is coupled to a power transformer 908. The signals are coupled across the power transformer 908 to the secondary side, which is in the patient isolation side. A first signal of a first energy modality is provided to the surgical instrument between the terminals labeled $ENERGY_1$ and RETURN. A second signal of a second energy modality is coupled across a capacitor 910 and is provided to the surgical instrument between the terminals labeled $ENERGY_2$ and RETURN. It will be appreciated that more than two energy modalities may be output and thus the subscript "n" may be used to designate that up to n $ENERGY_n$ terminals may be provided, where n is a positive integer greater than 1. It also will be appreciated that up to "n" return paths $RETURN_n$ may be provided without departing from the scope of the present disclosure.

A first voltage sensing circuit 912 is coupled across the terminals labeled $ENERGY_1$ and the RETURN path to measure the output voltage therebetween. A second voltage sensing circuit 924 is coupled across the terminals labeled $ENERGY_2$ and the RETURN path to measure the output voltage therebetween. A current sensing circuit 914 is disposed in series with the RETURN leg of the secondary side of the power transformer 908 as shown to measure the output current for either energy modality. If different return paths are provided for each energy modality, then a separate current sensing circuit should be provided in each return leg. The outputs of the first and second voltage sensing circuits 912, 924 are provided to respective isolation transformers 916, 922 and the output of the current sensing circuit 914 is provided to another isolation transformer 918. The outputs of the isolation transformers 916, 928, 922 in the on the primary side of the power transformer 908 (non-patient isolated side) are provided to a one or more ADC circuit 926. The digitized output of the ADC circuit 926 is provided to the processor 902 for further processing and computation. The output voltages and output current feedback information can be employed to adjust the output voltage and current provided to the surgical instrument and to compute output impedance, among other parameters. Input/output communications between the processor 902 and patient isolated circuits is provided through an interface circuit 920. Sensors also may be in electrical communication with the processor 902 by way of the interface circuit 920.

In one aspect, the impedance may be determined by the processor 902 by dividing the output of either the first voltage sensing circuit 912 coupled across the terminals labeled $ENERGY_1$/RETURN or the second voltage sensing circuit 924 coupled across the terminals labeled $ENERGY_2$/RETURN by the output of the current sensing circuit 914 disposed in series with the RETURN leg of the secondary side of the power transformer 908. The outputs of the first and second voltage sensing circuits 912, 924 are provided to separate isolations transformers 916, 922 and the output of the current sensing circuit 914 is provided to another isolation transformer 916. The digitized voltage and current sensing measurements from the ADC circuit 926 are provided the processor 902 for computing impedance. As an example, the first energy modality $ENERGY_1$ may be ultrasonic energy and the second energy modality $ENERGY_2$ may be RF energy. Nevertheless, in addition to ultrasonic and bipolar or monopolar RF energy modalities, other energy modalities include irreversible and/or reversible electroporation and/or microwave energy, among others. Also, although the example illustrated in FIG. 21 shows a single return path RETURN may be provided for two or more energy modalities, in other aspects, multiple return paths $RETURN_n$ may be provided for each energy modality $ENERGY_n$. Thus, as described herein, the ultrasonic transducer impedance may be measured by dividing the output of the first voltage sensing circuit 912 by the current sensing circuit 914 and the tissue impedance may be measured by dividing the output of the second voltage sensing circuit 924 by the current sensing circuit 914.

As shown in FIG. 21, the generator 900 comprising at least one output port can include a power transformer 908 with a single output and with multiple taps to provide power in the form of one or more energy modalities, such as ultrasonic, bipolar or monopolar RF, irreversible and/or reversible electroporation, and/or microwave energy, among others, for example, to the end effector depending on the type of treatment of tissue being performed. For example, the generator 900 can deliver energy with higher voltage and lower current to drive an ultrasonic transducer, with lower voltage and higher current to drive RF electrodes for sealing tissue, or with a coagulation waveform for spot coagulation using either monopolar or bipolar RF electrosurgical electrodes. The output waveform from the generator 900 can be steered, switched, or filtered to provide the frequency to the end effector of the surgical instrument. The connection of an ultrasonic transducer to the generator 900 output would be preferably located between the output labeled $ENERGY_1$ and RETURN as shown in FIG. 21. In one example, a connection of RF bipolar electrodes to the generator 900 output would be preferably located between the output labeled ENERGY$_2$ and RETURN. In the case of monopolar output, the preferred connections would be active electrode (e.g., pencil or other probe) to the ENERGY$_2$ output and a suitable return pad connected to the RETURN output.

Additional details are disclosed in U.S. Patent Application Publication No. 2017/0086914, titled TECHNIQUES FOR OPERATING GENERATOR FOR DIGITALLY GENERATING ELECTRICAL SIGNAL WAVEFORMS AND SURGICAL INSTRUMENTS, which published on Mar. 30, 2017, which is herein incorporated by reference in its entirety.

As used throughout this description, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some aspects they might not. The communication module may implement any of a number of wireless or wired communication standards or protocols, including but not limited to Wi-Fi (IEEE 802.11 family), WMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, Ethernet derivatives thereof, as well as any other wireless and wired protocols that are designated as 3G, 4G, 5G, and beyond. The computing module may include a plurality of communication modules. For instance, a first communication module may be dedicated to shorter range wireless communications such as Wi-Fi and Bluetooth and a second communication module may be dedicated to longer range wireless communications such as GPS, EDGE, GPRS, CDMA, WiMAX, LTE, Ev-DO, and others.

As used herein a processor or processing unit is an electronic circuit which performs operations on some external data source, usually memory or some other data stream. The term is used herein to refer to the central processor (central processing unit) in a system or computer systems (especially systems on a chip (SoCs)) that combine a number of specialized "processors."

As used herein, a system on a chip or system on chip (SoC or SOC) is an integrated circuit (also known as an "IC" or "chip") that integrates all components of a computer or other electronic systems. It may contain digital, analog, mixed-signal, and often radio-frequency functions—all on a single substrate. A SoC integrates a microcontroller (or microprocessor) with advanced peripherals like graphics processing unit (GPU), Wi-Fi module, or coprocessor. A SoC may or may not contain built-in memory.

As used herein, a microcontroller or controller is a system that integrates a microprocessor with peripheral circuits and memory. A microcontroller (or MCU for microcontroller unit) may be implemented as a small computer on a single integrated circuit. It may be similar to a SoC; a SoC may include a microcontroller as one of its components. A microcontroller may contain one or more core processing units (CPUs) along with memory and programmable input/output peripherals. Program memory in the form of Ferroelectric RAM, NOR flash or OTP ROM is also often included on chip, as well as a small amount of RAM. Microcontrollers may be employed for embedded applications, in contrast to the microprocessors used in personal computers or other general purpose applications consisting of various discrete chips.

As used herein, the term controller or microcontroller may be a stand-alone IC or chip device that interfaces with a peripheral device. This may be a link between two parts of a computer or a controller on an external device that manages the operation of (and connection with) that device.

Any of the processors or microcontrollers described herein, may be implemented by any single core or multicore processor such as those known under the trade name ARM Cortex by Texas Instruments. In one aspect, the processor may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

In one aspect, the processor may comprise a safety controller comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

Modular devices include the modules (as described in connection with FIGS. 3 and 9, for example) that are receivable within a surgical hub and the surgical devices or instruments that can be connected to the various modules in order to connect or pair with the corresponding surgical hub. The modular devices include, for example, intelligent surgical instruments, medical imaging devices, suction/irrigation devices, smoke evacuators, energy generators, ventilators, insufflators, and displays. The modular devices described herein can be controlled by control algorithms. The control algorithms can be executed on the modular device itself, on the surgical hub to which the particular modular device is paired, or on both the modular device and the surgical hub (e.g., via a distributed computing architecture). In some exemplifications, the modular devices' control algorithms control the devices based on data sensed by the modular device itself (i.e., by sensors in, on, or connected to the modular device). This data can be related to the patient being operated on (e.g., tissue properties or insufflation pressure) or the modular device itself (e.g., the rate at which a knife is being advanced, motor current, or energy levels). For example, a control algorithm for a surgical stapling and cutting instrument can control the rate at which the instrument's motor drives its knife through tissue according to resistance encountered by the knife as it advances.

Figure 22:
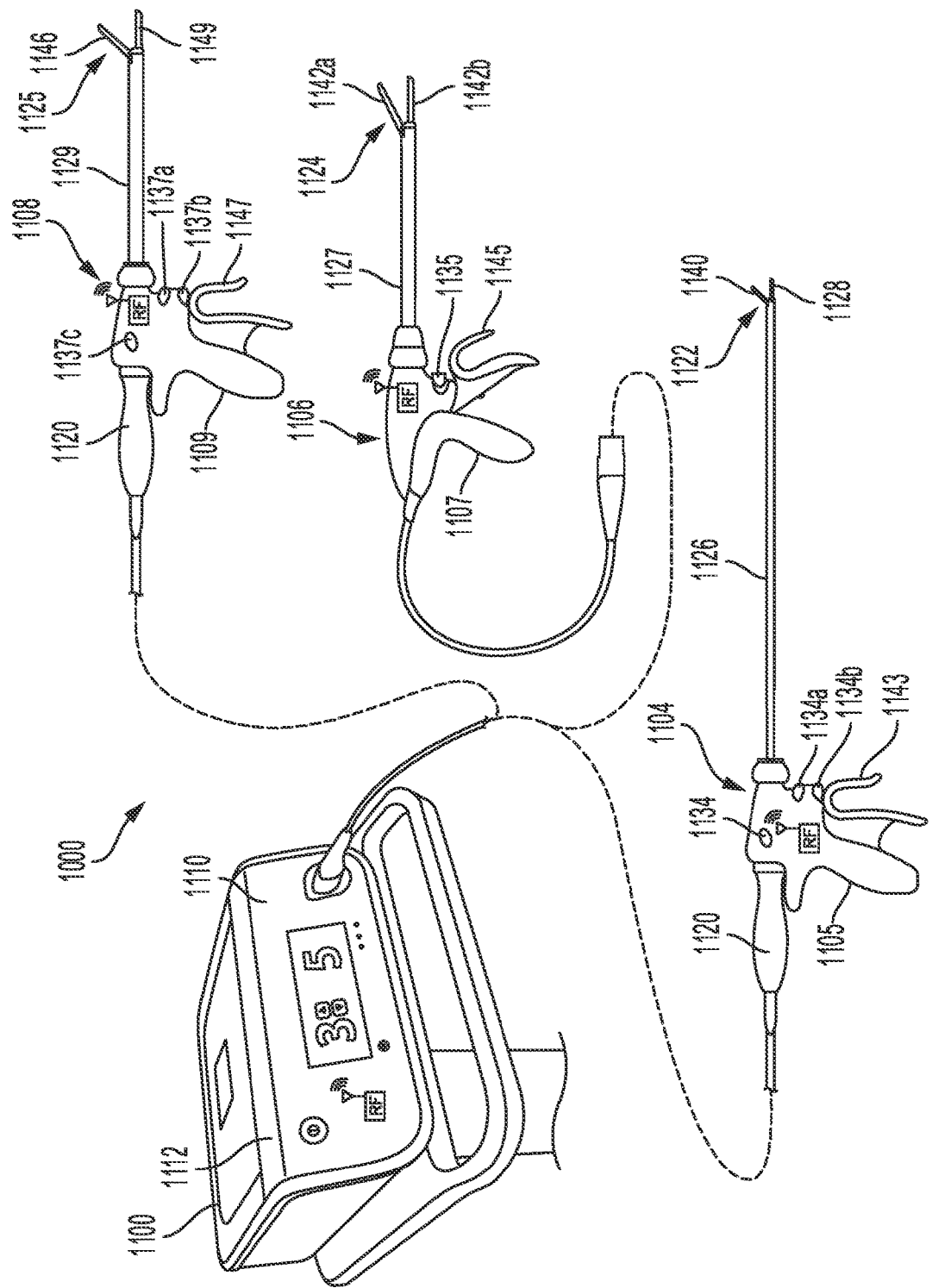
FIG. 22 is a surgical system comprising a generator and various surgical instruments usable therewith, in accordance with at least one aspect of the present disclosure.

FIG. 22 illustrates one form of a surgical system 1000 comprising a generator 1100 and various surgical instruments 1104, 1106, 1108 usable therewith, where the surgical instrument 1104 is an ultrasonic surgical instrument, the surgical instrument 1106 is an RF electrosurgical instrument, and the multifunction surgical instrument 1108 is a combination ultrasonic/RF electrosurgical instrument. The generator 1100 is configurable for use with a variety of surgical instruments. According to various forms, the generator 1100 may be configurable for use with different surgical instruments of different types including, for example, ultrasonic surgical instruments 1104, RF electrosurgical instruments 1106, and multifunction surgical instruments 1108 that integrate RF and ultrasonic energies delivered simultaneously from the generator 1100. Although in the form of FIG. 22 the generator 1100 is shown separate from the surgical instruments 1104, 1106, 1108 in one form, the generator 1100 may be formed integrally with any of the surgical instruments 1104, 1106, 1108 to form a unitary surgical system. The generator 1100 comprises an input device 1110 located on a front panel of the generator 1100 console. The input device 1110 may comprise any suitable device that generates signals suitable for programming the operation of the generator 1100. The generator 1100 may be configured for wired or wireless communication.

The generator 1100 is configured to drive multiple surgical instruments 1104, 1106, 1108. The first surgical instrument is an ultrasonic surgical instrument 1104 and comprises a handpiece 1105 (HP), an ultrasonic transducer 1120, a shaft 1126, and an end effector 1122. The end effector 1122 comprises an ultrasonic blade 1128 acoustically coupled to the ultrasonic transducer 1120 and a clamp arm 1140. The handpiece 1105 comprises a trigger 1143 to operate the clamp arm 1140 and a combination of the toggle buttons 1134*a*, 1134*b*, 1134*c* to energize and drive the ultrasonic blade 1128 or other function. The toggle buttons 1134*a*, 1134*b*, 1134*c* can be configured to energize the ultrasonic transducer 1120 with the generator 1100.

The generator 1100 also is configured to drive a second surgical instrument 1106. The second surgical instrument 1106 is an RF electrosurgical instrument and comprises a handpiece 1107 (HP), a shaft 1127, and an end effector 1124. The end effector 1124 comprises electrodes in clamp arms 1142*a*, 1142*b* and return through an electrical conductor portion of the shaft 1127. The electrodes are coupled to and energized by a bipolar energy source within the generator 1100. The handpiece 1107 comprises a trigger 1145 to operate the clamp arms 1142*a*, 1142*b* and an energy button 1135 to actuate an energy switch to energize the electrodes in the end effector 1124.

The generator 1100 also is configured to drive a multifunction surgical instrument 1108. The multifunction surgical instrument 1108 comprises a handpiece 1109 (HP), a shaft 1129, and an end effector 1125. The end effector 1125 comprises an ultrasonic blade 1149 and a clamp arm 1146. The ultrasonic blade 1149 is acoustically coupled to the ultrasonic transducer 1120. The handpiece 1109 comprises a trigger 1147 to operate the clamp arm 1146 and a combination of the toggle buttons 1137*a*, 1137*b*, 1137*c* to energize and drive the ultrasonic blade 1149 or other function. The toggle buttons 1137*a*, 1137*b*, 1137*c* can be configured to energize the ultrasonic transducer 1120 with the generator 1100 and energize the ultrasonic blade 1149 with a bipolar energy source also contained within the generator 1100.

The generator 1100 is configurable for use with a variety of surgical instruments. According to various forms, the generator 1100 may be configurable for use with different surgical instruments of different types including, for example, the ultrasonic surgical instrument 1104, the RF electrosurgical instrument 1106, and the multifunction surgical instrument 1108 that integrates RF and ultrasonic energies delivered simultaneously from the generator 1100. Although in the form of FIG. 22 the generator 1100 is shown separate from the surgical instruments 1104, 1106, 1108, in another form the generator 1100 may be formed integrally with any one of the surgical instruments 1104, 1106, 1108 to form a unitary surgical system. As discussed above, the generator 1100 comprises an input device 1110 located on a front panel of the generator 1100 console. The input device 1110 may comprise any suitable device that generates signals suitable for programming the operation of the generator 1100. The generator 1100 also may comprise one or more output devices 1112. Further aspects of generators for digitally generating electrical signal waveforms and surgical instruments are described in US patent publication US-2017-0086914-A1, which is herein incorporated by reference in its entirety.

Situational Awareness

Although an "intelligent" device including control algorithms that respond to sensed data can be an improvement over a "dumb" device that operates without accounting for sensed data, some sensed data can be incomplete or inconclusive when considered in isolation, i.e., without the context of the type of surgical procedure being performed or the type of tissue that is being operated on. Without knowing the procedural context (e.g., knowing the type of tissue being operated on or the type of procedure being performed), the control algorithm may control the modular device incorrectly or suboptimally given the particular context-free sensed data. For example, the optimal manner for a control algorithm to control a surgical instrument in response to a particular sensed parameter can vary according to the particular tissue type being operated on. This is due to the fact that different tissue types have different properties (e.g., resistance to tearing) and thus respond differently to actions taken by surgical instruments. Therefore, it may be desirable for a surgical instrument to take different actions even when the same measurement for a particular parameter is sensed. As one specific example, the optimal manner in which to control a surgical stapling and cutting instrument in response to the instrument sensing an unexpectedly high force to close its end effector will vary depending upon whether the tissue type is susceptible or resistant to tearing. For tissues that are susceptible to tearing, such as lung tissue, the instrument's control algorithm would optimally ramp down the motor in response to an unexpectedly high force to close to avoid tearing the tissue. For tissues that are resistant to tearing, such as stomach tissue, the instrument's control algorithm would optimally ramp up the motor in response to an unexpectedly high force to close to ensure that the end effector is clamped properly on the tissue. Without knowing whether lung or stomach tissue has been clamped, the control algorithm may make a suboptimal decision.

Figure 23:
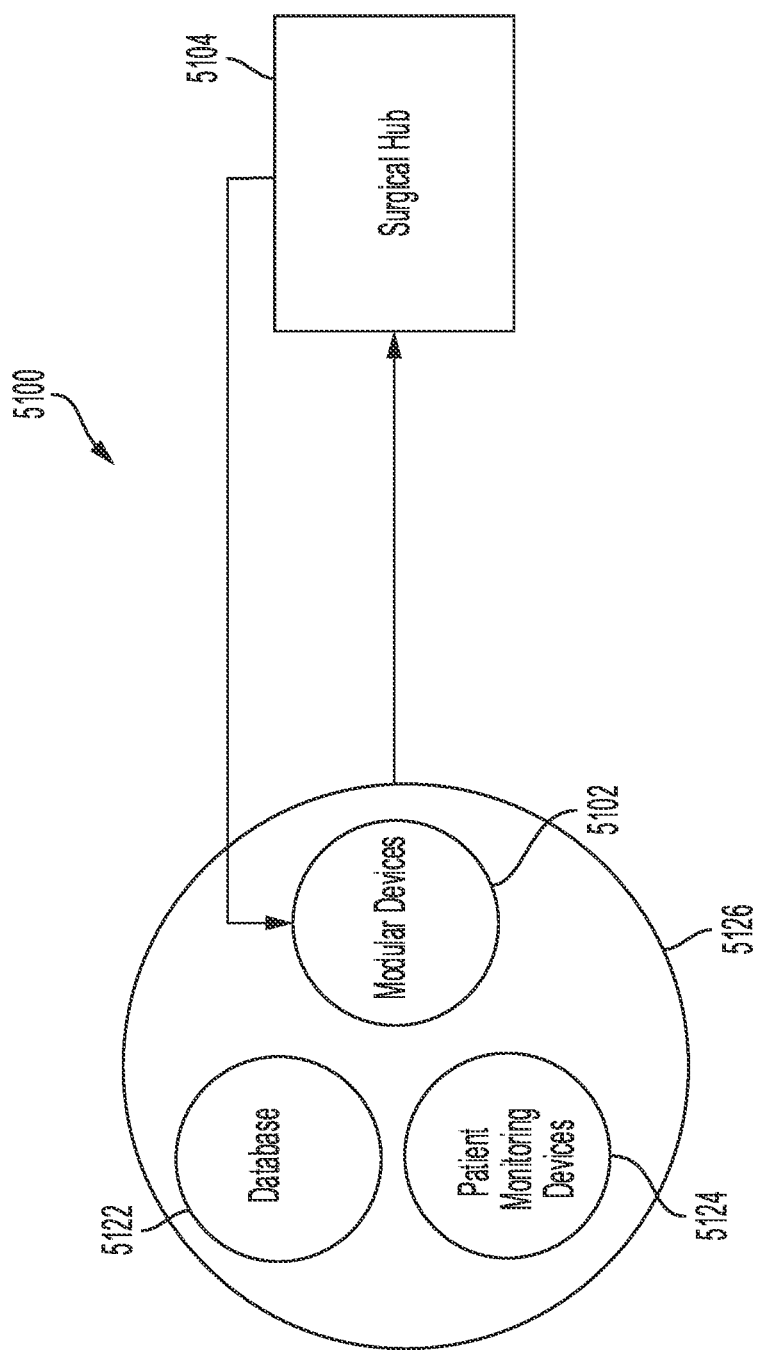
FIG. 23 is a diagram of a situationally aware surgical system, in accordance with at least one aspect of the present disclosure.

One solution utilizes a surgical hub including a system that is configured to derive information about the surgical procedure being performed based on data received from various data sources and then control the paired modular devices accordingly. In other words, the surgical hub is configured to infer information about the surgical procedure from received data and then control the modular devices paired to the surgical hub based upon the inferred context of the surgical procedure. FIG. 23 illustrates a diagram of a situationally aware surgical system 5100, in accordance with at least one aspect of the present disclosure. In some exemplifications, the data sources 5126 include, for example, the modular devices 5102 (which can include sensors configured to detect parameters associated with the patient and/or the modular device itself), databases 5122 (e.g., an EMR database containing patient records), and patient monitoring devices 5124 (e.g., a blood pressure (BP) monitor and an electrocardiography (EKG) monitor). The surgical hub 5104 can be configured to derive the contextual information pertaining to the surgical procedure from the data based upon, for example, the particular combination(s) of received data or the particular order in which the data is received from the data sources 5126. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 5104 to derive or infer information related to the surgical procedure from received data can be referred to as "situational awareness." In one exemplification, the surgical hub 5104 can incorporate a situational awareness system, which is the hardware and/or programming associated with the surgical hub 5104 that derives contextual information pertaining to the surgical procedure from the received data.

The situational awareness system of the surgical hub 5104 can be configured to derive the contextual information from the data received from the data sources 5126 in a variety of different ways. In one exemplification, the situational awareness system includes a pattern recognition system, or machine learning system (e.g., an artificial neural network), that has been trained on training data to correlate various inputs (e.g., data from databases 5122, patient monitoring devices 5124, and/or modular devices 5102) to corresponding contextual information regarding a surgical procedure. In other words, a machine learning system can be trained to accurately derive contextual information regarding a surgical procedure from the provided inputs. In another exemplification, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 5102. In one exemplification, the contextual information received by the situational awareness system of the surgical hub 5104 is associated with a particular control adjustment or set of control adjustments for one or more modular devices 5102. In another exemplification, the situational awareness system includes a further machine learning system, lookup table, or other such system, which generates or retrieves one or more control adjustments for one or more modular devices 5102 when provided the contextual information as input.

A surgical hub 5104 incorporating a situational awareness system provides a number of benefits for the surgical system 5100. One benefit includes improving the interpretation of sensed and collected data, which would in turn improve the processing accuracy and/or the usage of the data during the course of a surgical procedure. To return to a previous example, a situationally aware surgical hub 5104 could determine what type of tissue was being operated on; therefore, when an unexpectedly high force to close the surgical instrument's end effector is detected, the situationally aware surgical hub 5104 could correctly ramp up or ramp down the motor of the surgical instrument for the type of tissue.

As another example, the type of tissue being operated can affect the adjustments that are made to the compression rate and load thresholds of a surgical stapling and cutting instrument for a particular tissue gap measurement. A situationally aware surgical hub 5104 could infer whether a surgical procedure being performed is a thoracic or an abdominal procedure, allowing the surgical hub 5104 to determine whether the tissue clamped by an end effector of the surgical stapling and cutting instrument is lung (for a thoracic procedure) or stomach (for an abdominal procedure) tissue. The surgical hub 5104 could then adjust the compression rate and load thresholds of the surgical stapling and cutting instrument appropriately for the type of tissue.

As yet another example, the type of body cavity being operated in during an insufflation procedure can affect the function of a smoke evacuator. A situationally aware surgical hub 5104 could determine whether the surgical site is under pressure (by determining that the surgical procedure is utilizing insufflation) and determine the procedure type. As a procedure type is generally performed in a specific body cavity, the surgical hub 5104 could then control the motor rate of the smoke evacuator appropriately for the body cavity being operated in. Thus, a situationally aware surgical hub 5104 could provide a consistent amount of smoke evacuation for both thoracic and abdominal procedures.

As yet another example, the type of procedure being performed can affect the optimal energy level for an ultrasonic surgical instrument or radio frequency (RF) electrosurgical instrument to operate at. Arthroscopic procedures, for example, require higher energy levels because the end effector of the ultrasonic surgical instrument or RF electrosurgical instrument is immersed in fluid. A situationally aware surgical hub 5104 could determine whether the surgical procedure is an arthroscopic procedure. The surgical hub 5104 could then adjust the RF power level or the ultrasonic amplitude of the generator (i.e., "energy level") to compensate for the fluid filled environment. Relatedly, the type of tissue being operated on can affect the optimal energy level for an ultrasonic surgical instrument or RF electrosurgical instrument to operate at. A situationally aware surgical hub 5104 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 5104 can be configured to adjust the energy level for the ultrasonic surgical instrument or RF electrosurgical instrument throughout the course of a surgical procedure, rather than just on a procedure-by-procedure basis. A situationally aware surgical hub 5104 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

As yet another example, data can be drawn from additional data sources 5126 to improve the conclusions that the surgical hub 5104 draws from one data source 5126. A situationally aware surgical hub 5104 could augment data that it receives from the modular devices 5102 with contextual information that it has built up regarding the surgical procedure from other data sources 5126. For example, a situationally aware surgical hub 5104 can be configured to determine whether hemostasis has occurred (i.e., whether bleeding at a surgical site has stopped) according to video or image data received from a medical imaging device. However, in some cases the video or image data can be inconclusive. Therefore, in one exemplification, the surgical hub 5104 can be further configured to compare a physiologic measurement (e.g., blood pressure sensed by a BP monitor communicably connected to the surgical hub 5104) with the visual or image data of hemostasis (e.g., from a medical imaging device 124 (FIG. 2) communicably coupled to the surgical hub 5104) to make a determination on the integrity of the staple line or tissue weld. In other words, the situational awareness system of the surgical hub 5104 can consider the physiological measurement data to provide additional context in analyzing the visualization data. The additional context can be useful when the visualization data may be inconclusive or incomplete on its own.

Another benefit includes proactively and automatically controlling the paired modular devices 5102 according to the particular step of the surgical procedure that is being performed to reduce the number of times that medical personnel are required to interact with or control the surgical system 5100 during the course of a surgical procedure. For example, a situationally aware surgical hub 5104 could proactively activate the generator to which an RF electrosurgical instrument is connected if it determines that a subsequent step of the procedure requires the use of the instrument. Proactively activating the energy source allows the instrument to be ready for use a soon as the preceding step of the procedure is completed.

As another example, a situationally aware surgical hub 5104 could determine whether the current or subsequent step of the surgical procedure requires a different view or degree of magnification on the display according to the feature(s) at the surgical site that the surgeon is expected to need to view. The surgical hub 5104 could then proactively change the displayed view (supplied by, e.g., a medical imaging device for the visualization system 108) accordingly so that the display automatically adjusts throughout the surgical procedure.

As yet another example, a situationally aware surgical hub 5104 could determine which step of the surgical procedure is being performed or will subsequently be performed and whether particular data or comparisons between data will be required for that step of the surgical procedure. The surgical hub 5104 can be configured to automatically call up data screens based upon the step of the surgical procedure being performed, without waiting for the surgeon to ask for the particular information.

Another benefit includes checking for errors during the setup of the surgical procedure or during the course of the surgical procedure. For example, a situationally aware surgical hub 5104 could determine whether the operating theater is setup properly or optimally for the surgical procedure to be performed. The surgical hub 5104 can be configured to determine the type of surgical procedure being performed, retrieve the corresponding checklists, product location, or setup needs (e.g., from a memory), and then compare the current operating theater layout to the standard layout for the type of surgical procedure that the surgical hub 5104 determines is being performed. In one exemplification, the surgical hub 5104 can be configured to compare the list of items for the procedure (scanned by a scanner, for example) and/or a list of devices paired with the surgical hub 5104 to a recommended or anticipated manifest of items and/or devices for the given surgical procedure. If there are any discontinuities between the lists, the surgical hub 5104 can be configured to provide an alert indicating that a particular modular device 5102, patient monitoring device 5124, and/or other surgical item is missing. In one exemplification, the surgical hub 5104 can be configured to determine the relative distance or position of the modular devices 5102 and patient monitoring devices 5124 via proximity sensors, for example. The surgical hub 5104 can compare the relative positions of the devices to a recommended or anticipated layout for the particular surgical procedure. If there are any discontinuities between the layouts, the surgical hub 5104 can be configured to provide an alert indicating that the current layout for the surgical procedure deviates from the recommended layout.

As another example, a situationally aware surgical hub 5104 could determine whether the surgeon (or other medical personnel) was making an error or otherwise deviating from the expected course of action during the course of a surgical procedure. For example, the surgical hub 5104 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 5104 determined is being performed. In one exemplification, the surgical hub 5104 can be configured to provide an alert indicating that an unexpected action is being performed or an unexpected device is being utilized at the particular step in the surgical procedure.

Overall, the situational awareness system for the surgical hub 5104 improves surgical procedure outcomes by adjusting the surgical instruments (and other modular devices 5102) for the particular context of each surgical procedure (such as adjusting to different tissue types) and validating actions during a surgical procedure. The situational awareness system also improves surgeons' efficiency in performing surgical procedures by automatically suggesting next steps, providing data, and adjusting displays and other modular devices 5102 in the surgical theater according to the specific context of the procedure.

Modular Energy System

ORs everywhere in the world are a tangled web of cords, devices, and people due to the amount of equipment required to perform surgical procedures. Surgical capital equipment tends to be a major contributor to this issue because most surgical capital equipment performs a single, specialized task. Due to their specialized nature and the surgeons' needs to utilize multiple different types of devices during the course of a single surgical procedure, an OR may be forced to be stocked with two or even more pieces of surgical capital equipment, such as energy generators. Each of these pieces of surgical capital equipment must be individually plugged into a power source and may be connected to one or more other devices that are being passed between OR personnel, creating a tangle of cords that must be navigated. Another issue faced in modern ORs is that each of these specialized pieces of surgical capital equipment has its own user interface and must be independently controlled from the other pieces of equipment within the OR. This creates complexity in properly controlling multiple different devices in connection with each other and forces users to be trained on and memorize different types of user interfaces (which may further change based upon the task or surgical procedure being performed, in addition to changing between each piece of capital equipment). This cumbersome, complex process can necessitate the need for even more individuals to be present within the OR and can create danger if multiple devices are not properly controlled in tandem with each other. Therefore, consolidating surgical capital equipment technology into singular systems that are able to flexibly address surgeons' needs to reduce the footprint of surgical capital equipment within ORs would simplify the user experience, reduce the amount of clutter in ORs, and prevent difficulties and dangers associated with simultaneously controlling multiple pieces of capital equipment. Further, making such systems expandable or customizable would allow for new technology to be conveniently incorporated into existing surgical systems, obviating the need to replace entire surgical systems or for OR personnel to learn new user interfaces or equipment controls with each new technology.

As described in FIGS. 1-11, a surgical hub 106 can be configured to interchangeably receive a variety of modules, which can in turn interface with surgical devices (e.g., a surgical instrument or a smoke evacuator) or provide various other functions (e.g., communications). In one aspect, a surgical hub 106 can be embodied as a modular energy system 2000, which is illustrated in connection with FIGS. 24-30. The modular energy system 2000 can include a variety of different modules 2001 that are connectable together in a stacked configuration. In one aspect, the modules 2001 can be both physically and communicably coupled together when stacked or otherwise connected together into a singular assembly. Further, the modules 2001 can be interchangeably connectable together in different combinations or arrangements. In one aspect, each of the modules 2001 can include a consistent or universal array of connectors disposed along their upper and lower surfaces, thereby allowing any module 2001 to be connected to another module 2001 in any arrangement (except that, in some aspects, a particular module type, such as the header module 2002, can be configured to serve as the uppermost module within the stack, for example). In an alternative aspect, the modular energy system 2000 can include a housing that is configured to receive and retain the modules 2001, as is shown in FIGS. 3 and 4. The modular energy system 2000 can also include a variety of different components or accessories that are also connectable to or otherwise associatable with the modules 2001. In another aspect, the modular energy system 2000 can be embodied as a generator module 140, 240 (FIGS. 3 and 10) of a surgical hub 106. In yet another aspect, the modular energy system 2000 can be a distinct system from a surgical hub 106. In such aspects, the modular energy system 2000 can be communicably couplable to a surgical hub 206 for transmitting and/or receiving data therebetween.

Figure 24:
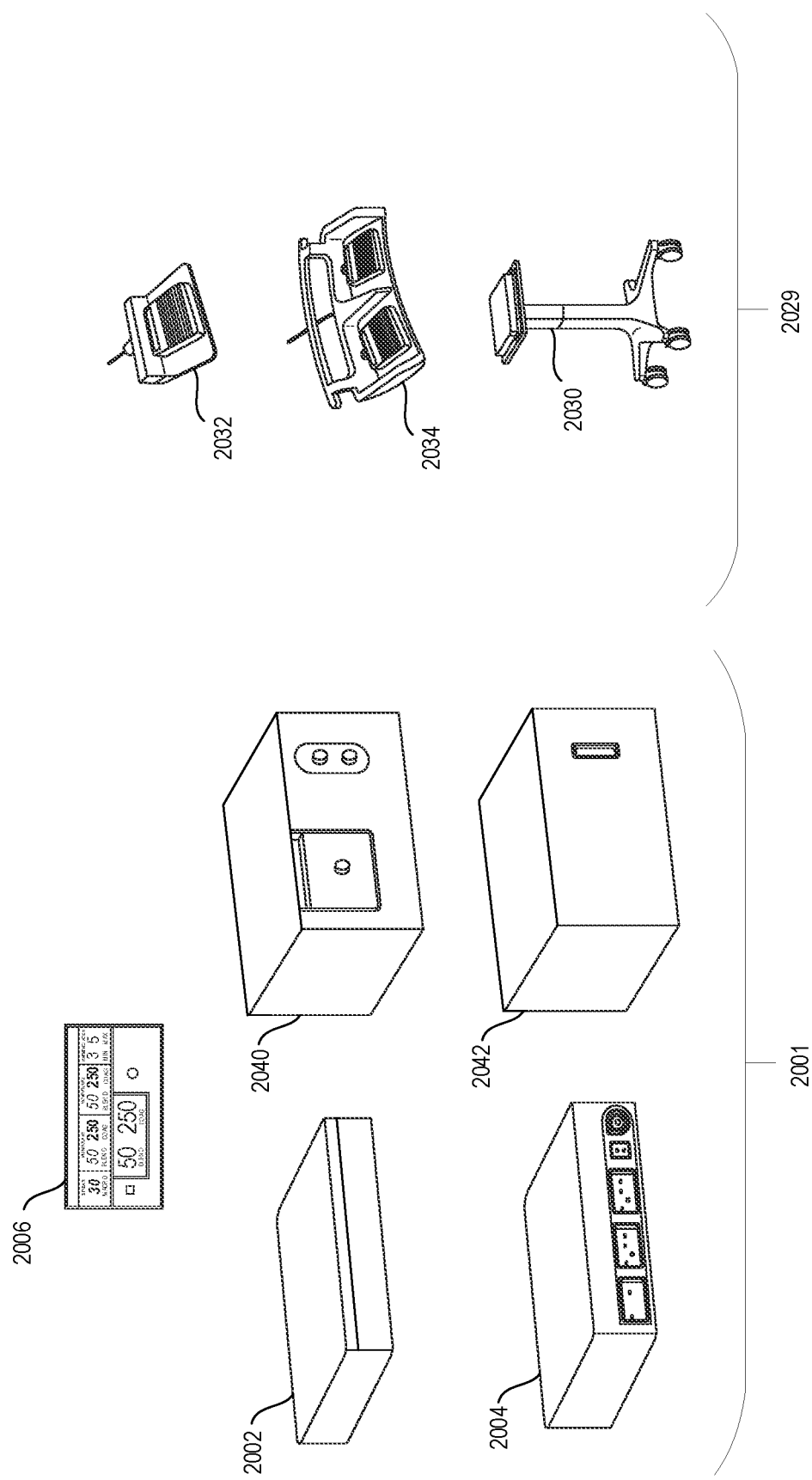
FIG. 24 is a diagram of various modules and other components that are combinable to customize modular energy systems, in accordance with at least one aspect of the present disclosure.

The modular energy system 2000 can be assembled from a variety of different modules 2001, some examples of which are illustrated in FIG. 24. Each of the different types of modules 2001 can provide different functionality, thereby allowing the modular energy system 2000 to be assembled into different configurations to customize the functions and capabilities of the modular energy system 2000 by customizing the modules 2001 that are included in each modular energy system 2000. The modules 2001 of the modular energy system 2000 can include, for example, a header module 2002 (which can include a display screen 2006), an energy module 2004, a technology module 2040, and a visualization module 2042. In the depicted aspect, the header module 2002 is configured to serve as the top or uppermost module within the modular energy system stack and can thus lack connectors along its top surface. In another aspect, the header module 2002 can be configured to be positioned at the bottom or the lowermost module within the modular energy system stack and can thus lack connectors along its bottom surface. In yet another aspect, the header module 2002 can be configured to be positioned at an intermediate position within the modular energy system stack and can thus include connectors along both its bottom and top surfaces. The header module 2002 can be configured to control the system-wide settings of each module 2001 and component connected thereto through physical controls 2011 thereon and/or a graphical user interface (GUI) 2008 rendered on the display screen 2006. Such settings could include the activation of the modular energy system 2000, the volume of alerts, the footswitch settings, the settings icons, the appearance or configuration of the user interface, the surgeon profile logged into the modular energy system 2000, and/or the type of surgical procedure being performed. The header module 2002 can also be configured to provide communications, processing, and/or power for the modules 2001 that are connected to the header module 2002. The energy module 2004, which can also be referred to as a generator module 140, 240 (FIGS. 3 and 10), can be configured to generate one or multiple energy modalities for driving electrosurgical and/or ultrasonic surgical instruments connected thereto, such as is described above in connection with the generator 900 illustrated in FIG. 21. The technology module 2040 can be configured to provide additional or expanded control algorithms (e.g., electrosurgical or ultrasonic control algorithms for controlling the energy output of the energy module 2004). The visualization module 2042 can be configured to interface with visualization devices (i.e., scopes) and accordingly provide increased visualization capabilities.

The modular energy system 2000 can further include a variety of accessories 2029 that are connectable to the modules 2001 for controlling the functions thereof or that are otherwise configured to work on conjunction with the modular energy system 2000. The accessories 2029 can include, for example, a single-pedal footswitch 2032, a dual-pedal footswitch 2034, and a cart 2030 for supporting the modular energy system 2000 thereon. The footswitches 2032, 2034 can be configured to control the activation or function of particular energy modalities output by the energy module 2004, for example.

By utilizing modular components, the depicted modular energy system 2000 provides a surgical platform that grows with the availability of technology and is customizable to the needs of the facility and/or surgeons. Further, the modular energy system 2000 supports combo devices (e.g., dual electrosurgical and ultrasonic energy generators) and supports software-driven algorithms for customized tissue effects. Still further, the surgical system architecture reduces the capital footprint by combining multiple technologies critical for surgery into a single system.

The various modular components utilizable in connection with the modular energy system 2000 can include monopolar energy generators, bipolar energy generators, dual electrosurgical/ultrasonic energy generators, display screens, and various other modules and/or other components, some of which are also described above in connection with FIGS. 1-11.

Figure 29:
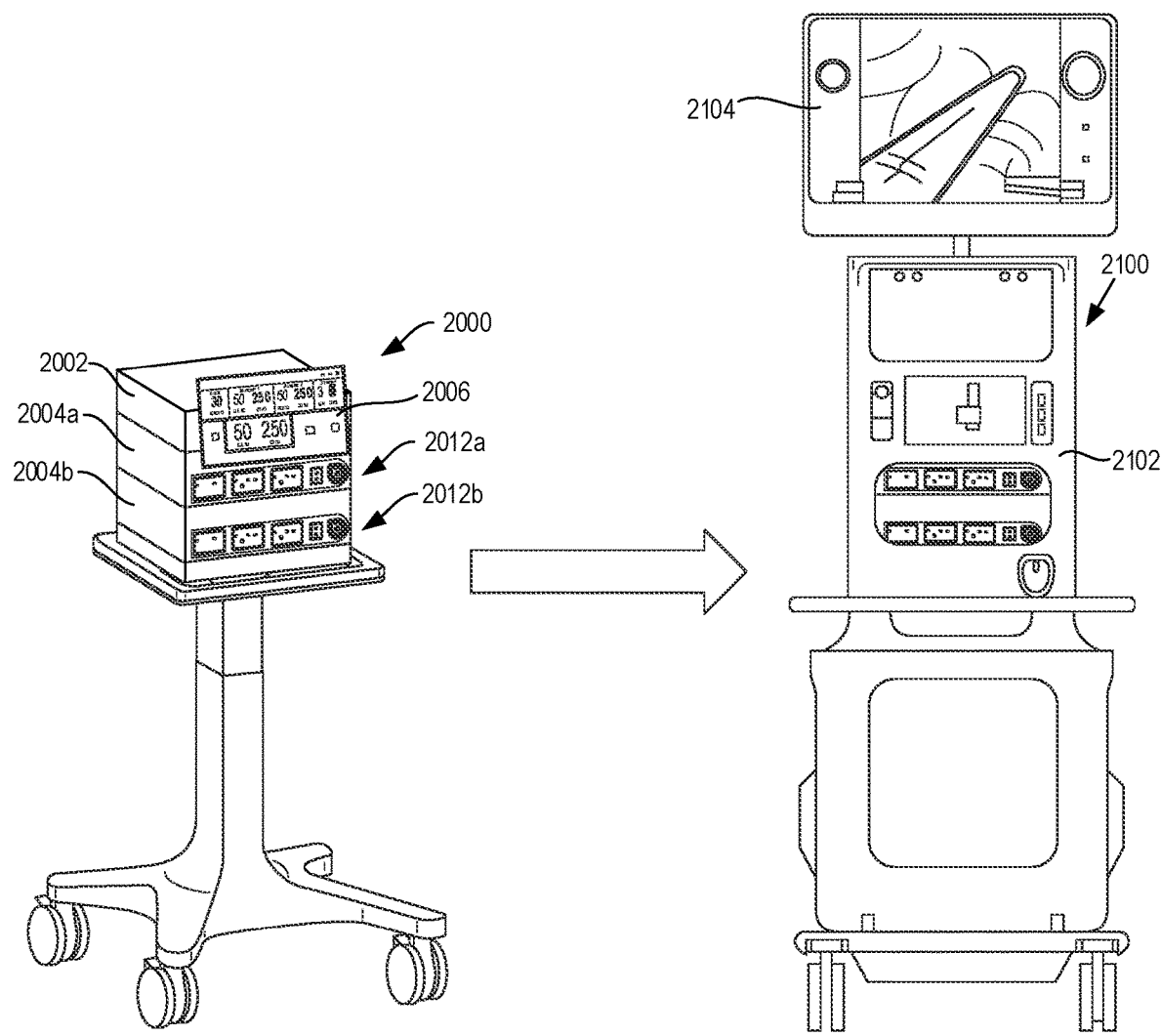
FIG. 29 is a diagram of a modular energy system including communicably connectable surgical platforms, in accordance with at least one aspect of the present disclosure.

Referring now to FIG. 25A, the header module 2002 can, in some aspects, include a display screen 2006 that renders a GUI 2008 for relaying information regarding the modules 2001 connected to the header module 2002. In some aspects, the GUI 2008 of the display screen 2006 can provide a consolidated point of control of all of the modules 2001 making up the particular configuration of the modular energy system 2000. Various aspects of the GUI 2008 are discussed in fuller detail below in connection with FIG. 30. In alternative aspects, the header module 2002 can lack the display screen 2006 or the display screen 2006 can be detachably connected to the housing 2010 of the header module 2002. In such aspects, the header module 2002 can be communicably couplable to an external system that is configured to display the information generated by the modules 2001 of the modular energy system 2000. For example, in robotic surgical applications, the modular energy system 2000 can be communicably couplable to a robotic cart or robotic control console, which is configured to display the information generated by the modular energy system 2000 to the operator of the robotic surgical system. As another example, the modular energy system 2000 can be communicably couplable to a mobile display that can be carried or secured to a surgical staff member for viewing thereby. In yet another example, the modular energy system 2000 can be communicably couplable to a surgical hub 2100 or another computer system that can include a display 2104, as is illustrated in FIG. 29. In aspects utilizing a user interface that is separate from or otherwise distinct from the modular energy system 2000, the user interface can be wirelessly connectable with the modular energy system 2000 as a whole or one or more modules 2001 thereof such that the user interface can display information from the connected modules 2001 thereon.

Referring still to FIG. 25A, the energy module 2004 can include a port assembly 2012 including a number of different ports configured to deliver different energy modalities to corresponding surgical instruments that are connectable thereto. In the particular aspect illustrated in FIGS. 24-30, the port assembly 2012 includes a bipolar port 2014, a first monopolar port 2016a, a second monopolar port 2018b, a neutral electrode port 2018 (to which a monopolar return pad is connectable), and a combination energy port 2020. However, this particular combination of ports is simply provided for illustrative purposes and alternative combinations of ports and/or energy modalities may be possible for the port assembly 2012.

As noted above, the modular energy system 2000 can be assembled into different configurations. Further, the different configurations of the modular energy system 2000 can also be utilizable for different surgical procedure types and/or different tasks. For example, FIGS. 25A and 25B illustrate a first illustrative configuration of the modular energy system 2000 including a header module 2002 (including a display screen 2006) and an energy module 2004 connected together. Such a configuration can be suitable for laparoscopic and open surgical procedures, for example.

Figure 26A:
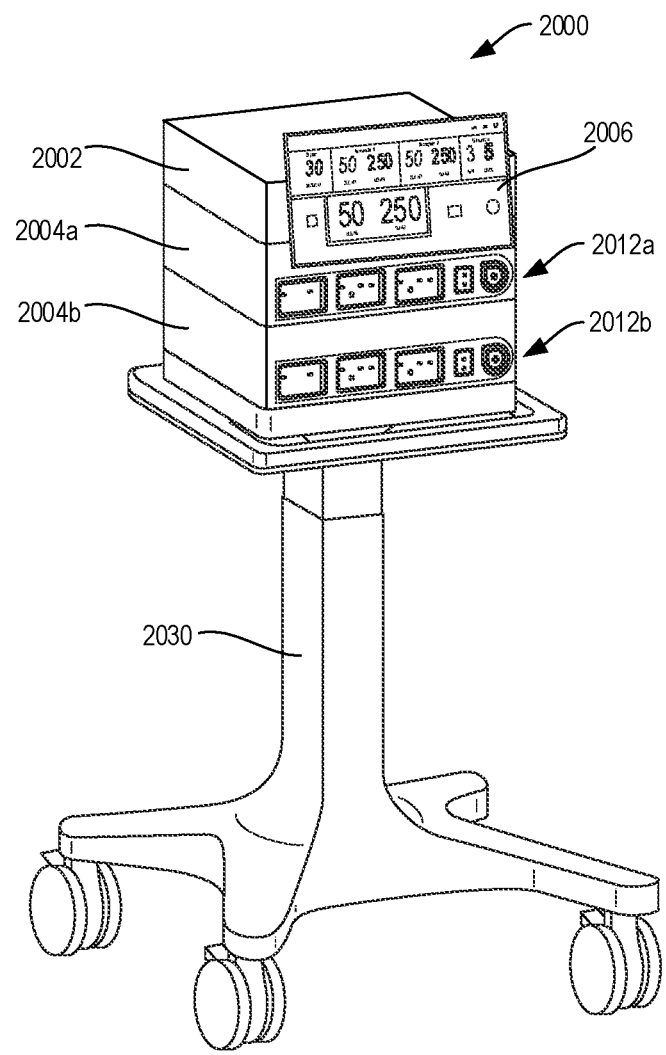
FIG. 26A is a second illustrative modular energy system configuration including a header module, a display screen, an energy module, and an expanded energy module connected together and mounted to a cart, in accordance with at least one aspect of the present disclosure.
Figure 26B:
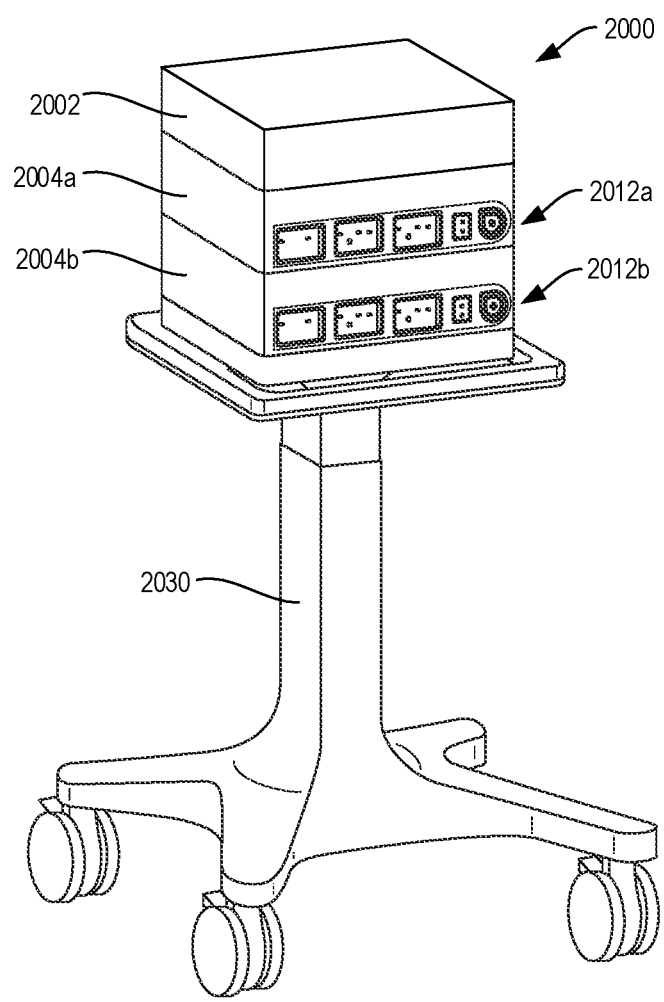
FIG. 26B is a third illustrative modular energy system configuration that is similar to the second configuration shown in FIG. 25A, except that the header module lacks a display screen, in accordance with at least one aspect of the present disclosure.

FIG. 26A illustrates a second illustrative configuration of the modular energy system 2000 including a header module 2002 (including a display screen 2006), a first energy module 2004a, and a second energy module 2004b connected together. By stacking two energy modules 2004a, 2004b, the modular energy system 2000 can provide a pair of port assemblies 2012a, 2012b for expanding the array of energy modalities deliverable by the modular energy system 2000 from the first configuration. The second configuration of the modular energy system 2000 can accordingly accommodate more than one bipolar/monopolar electrosurgical instrument, more than two bipolar/monopolar electrosurgical instruments, and so on. Such a configuration can be suitable for particularly complex laparoscopic and open surgical procedures. FIG. 26B illustrates a third illustrative configuration that is similar to the second configuration, except that the header module 2002 lacks a display screen 2006. This configuration can be suitable for robotic surgical applications or mobile display applications, as noted above.

Figure 27:
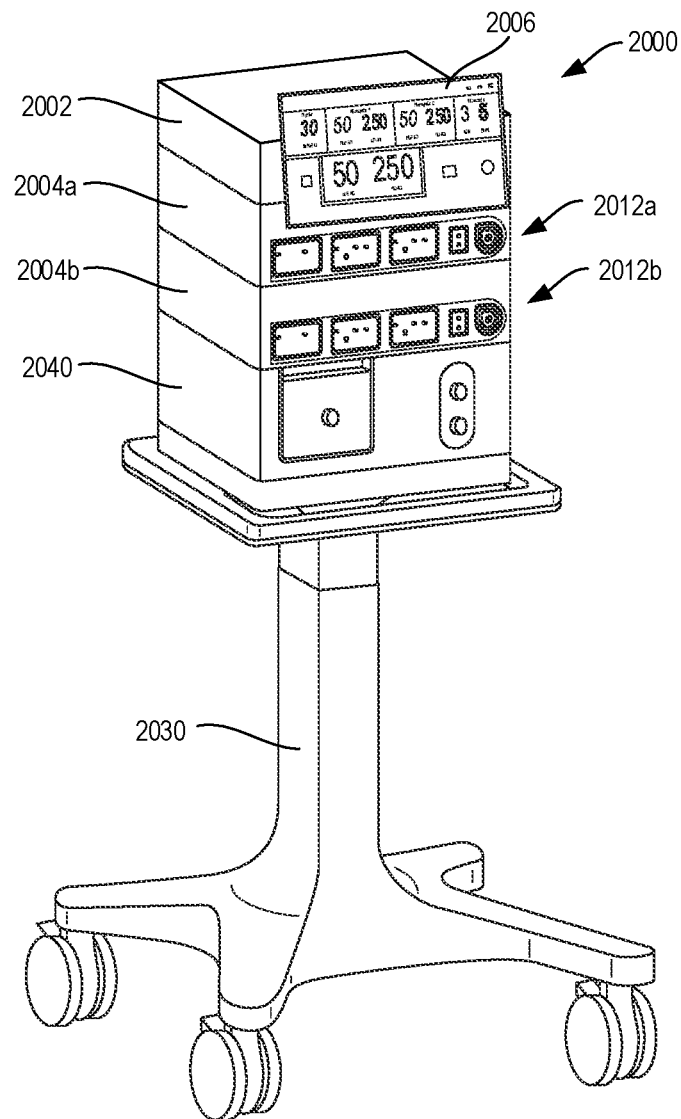
FIG. 27 is a fourth illustrative modular energy system configuration including a header module, a display screen, an energy module, an expanded energy module, and a technology module connected together and mounted to a cart, in accordance with at least one aspect of the present disclosure.

FIG. 27 illustrates a fourth illustrative configuration of the modular energy system 2000 including a header module 2002 (including a display screen 2006), a first energy module 2004a, a second energy module 2004b, and a technology module 2040 connected together. Such a configuration can be suitable for surgical applications where particularly complex or computation-intensive control algorithms are required. Alternatively, the technology module 2040 can be a newly released module that supplements or expands the capabilities of previously released modules (such as the energy module 2004).

Figure 28:
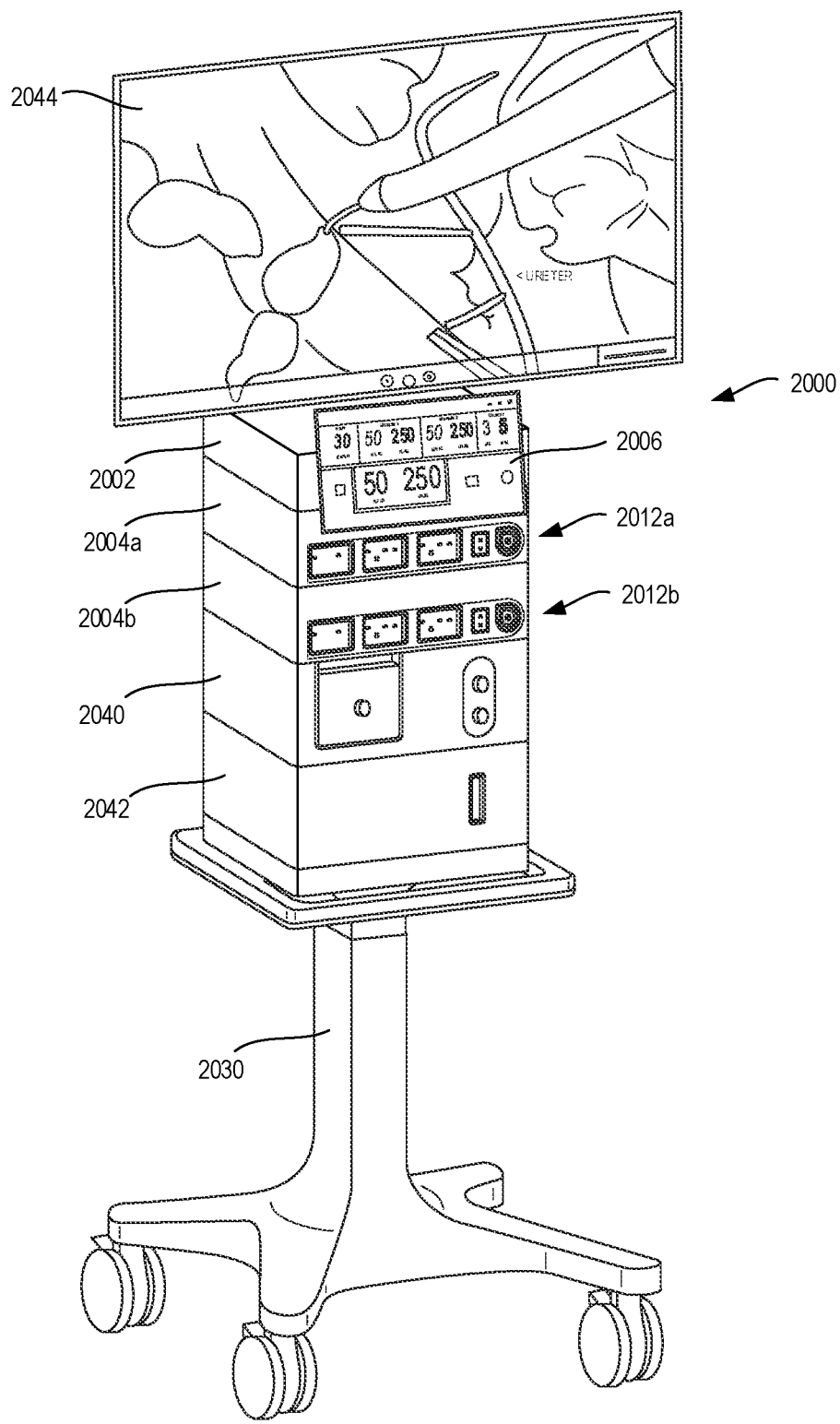
FIG. 28 is a fifth illustrative modular energy system configuration including a header module, a display screen, an energy module, an expanded energy module, a technology module, and a visualization module connected together and mounted to a cart, in accordance with at least one aspect of the present disclosure.

FIG. 28 illustrates a fifth illustrative configuration of the modular energy system 2000 including a header module 2002 (including a display screen 2006), a first energy module 2004a, a second energy module 2004b, a technology module 2040, and a visualization module 2042 connected together. Such a configuration can be suitable for endoscopic procedures by providing a dedicated surgical display 2044 for relaying the video feed from the scope coupled to the visualization module 2042. It should be noted that the configurations illustrated in FIGS. 25A-29 and described above are provided simply to illustrate the various concepts of the modular energy system 2000 and should not be interpreted to limit the modular energy system 2000 to the particular aforementioned configurations.

As noted above, the modular energy system 2000 can be communicably couplable to an external system, such as a surgical hub 2100 as illustrated in FIG. 29. Such external systems can include a display screen 2104 for displaying a visual feed from an endoscope (or a camera or another such visualization device) and/or data from the modular energy system 2000. Such external systems can also include a computer system 2102 for performing calculations or otherwise analyzing data generated or provided by the modular energy system 2000, controlling the functions or modes of the modular energy system 2000, and/or relaying data to a cloud computing system or another computer system. Such external systems could also coordinate actions between multiple modular energy systems 2000 and/or other surgical systems (e.g., a visualization system 108 and/or a robotic system 110 as described in connection with FIGS. 1 and 2).

Figure 30:
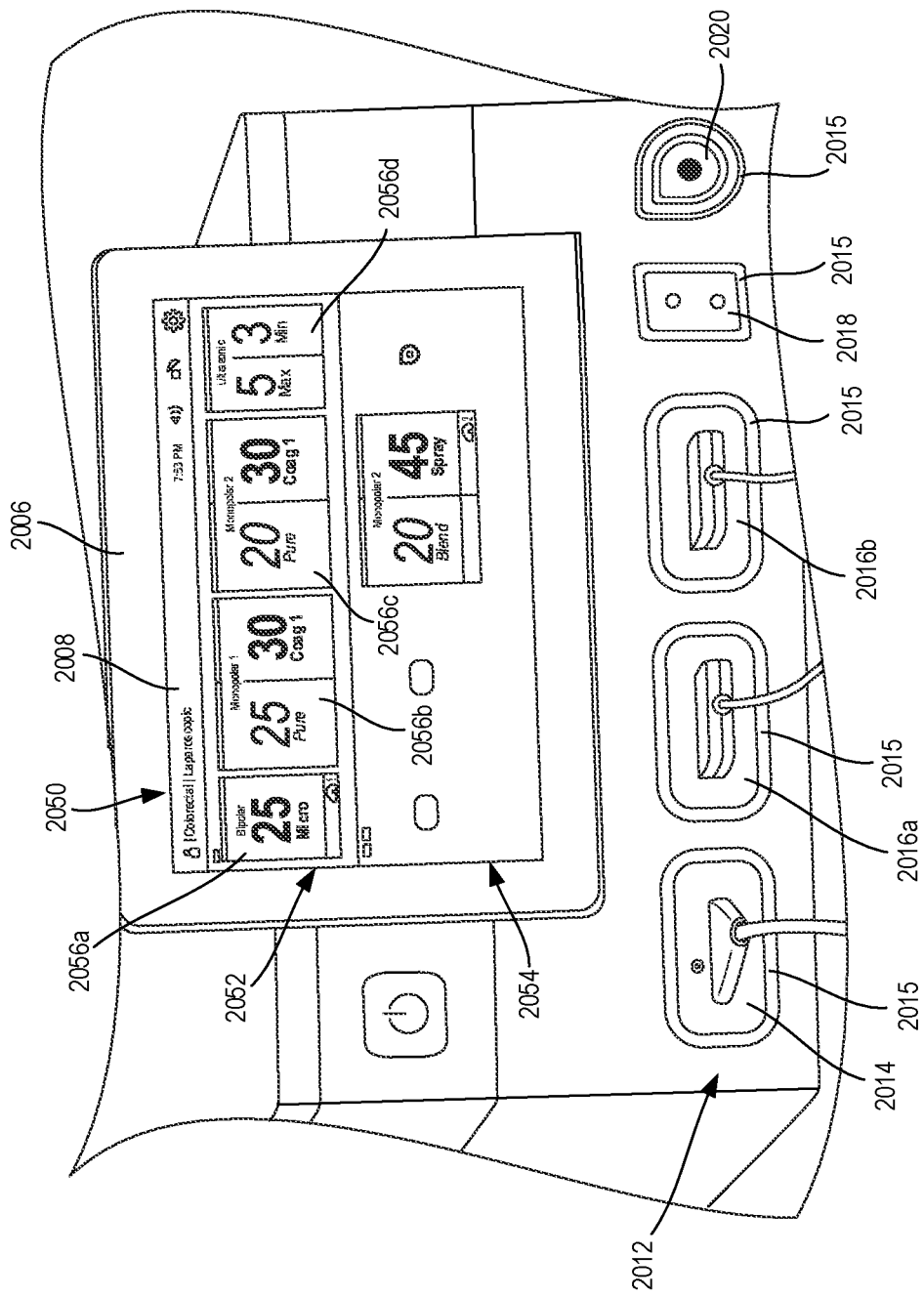
FIG. 30 is a perspective view of a header module of a modular energy system including a user interface, in accordance with at least one aspect of the present disclosure.

Referring now to FIG. 30, in some aspects, the header module 2002 can include or support a display 2006 configured for displaying a GUI 2008, as noted above. The display screen 2006 can include a touchscreen for receiving input from users in addition to displaying information. The controls displayed on the GUI 2008 can correspond to the module(s) 2001 that are connected to the header module 2002. In some aspects, different portions or areas of the GUI 2008 can correspond to particular modules 2001. For example, a first portion or area of the GUI 2008 can correspond to a first module and a second portion or area of the GUI 2008 can correspond to a second module. As different and/or additional modules 2001 are connected to the modular energy system stack, the GUI 2008 can adjust to accommodate the different and/or additional controls for each newly added module 2001 or remove controls for each module 2001 that is removed. Each portion of the display corresponding to a particular module connected to the header module 2002 can display controls, data, user prompts, and/or other information corresponding to that module. For example, in FIG. 30, a first or upper portion 2052 of the depicted GUI 2008 displays controls and data associated with an energy module 2004 that is connected to the header module 2002. In particular, the first portion 2052 of the GUI 2008 for the energy module 2004 provides first widget 2056a corresponding to the bipolar port 2014, a second widget 2056b corresponding to the first monopolar port 2016a, a third widget 2056c corresponding to the second monopolar port 2016b, and a fourth widget 2056d corresponding to the combination energy port 2020. Each of these widgets 2056a-d provides data related to its corresponding port of the port assembly 2012 and controls for controlling the modes and other features of the energy modality delivered by the energy module 2004 through the respective port of the port assembly 2012. For example, the widgets 2056a-d can be configured to display the power level of the surgical instrument connected to the respective port, change the operational mode of the surgical instrument connected to the respective port (e.g., change a surgical instrument from a first power level to a second power level and/or change a monopolar surgical instrument from a "spray" mode to a "blend" mode), and so on.

In one aspect, the header module 2002 can include various physical controls 2011 in addition to or in lieu of the GUI 2008. Such physical controls 2011 can include, for example, a power button that controls the activation of each module 2001 that is connected to the header module 2002 in the modular energy system 2000. Alternatively, the power button can be displayed as part of the GUI 2008. Therefore, the header module 2002 can serve as a single point of contact and obviate the need to individually activate and deactivate each individual module 2001 from which the modular energy system 2000 is constructed.

In one aspect, the header module 2002 can display still images, videos, animations, and/or information associated with the surgical modules 2001 of which the modular energy system 2000 is constructed or the surgical devices that are communicably coupled to the modular energy system 2000. The still images and/or videos displayed by the header module 2002 can be received from an endoscope or another visualization device that is communicably coupled to the modular energy system 2000. The animations and/or information of the GUI 2008 can be overlaid on or displayed adjacent to the images or video feed.

In one aspect, the modules 2001 other than the header module 2002 can be configured to likewise relay information to users. For example, the energy module 2004 can include light assemblies 2015 disposed about each of the ports of the port assembly 2012. The light assemblies 2015 can be configured to relay information to the user regarding the port according to their color or state (e.g., flashing). For example, the light assemblies 2015 can change from a first color to a second color when a plug is fully seated within the respective port. In one aspect, the color or state of the light assemblies 2015 can be controlled by the header module 2002. For example, the header module 2002 can cause the light assembly 2015 of each port to display a color corresponding to the color display for the port on the GUI 2008.

Figure 31:
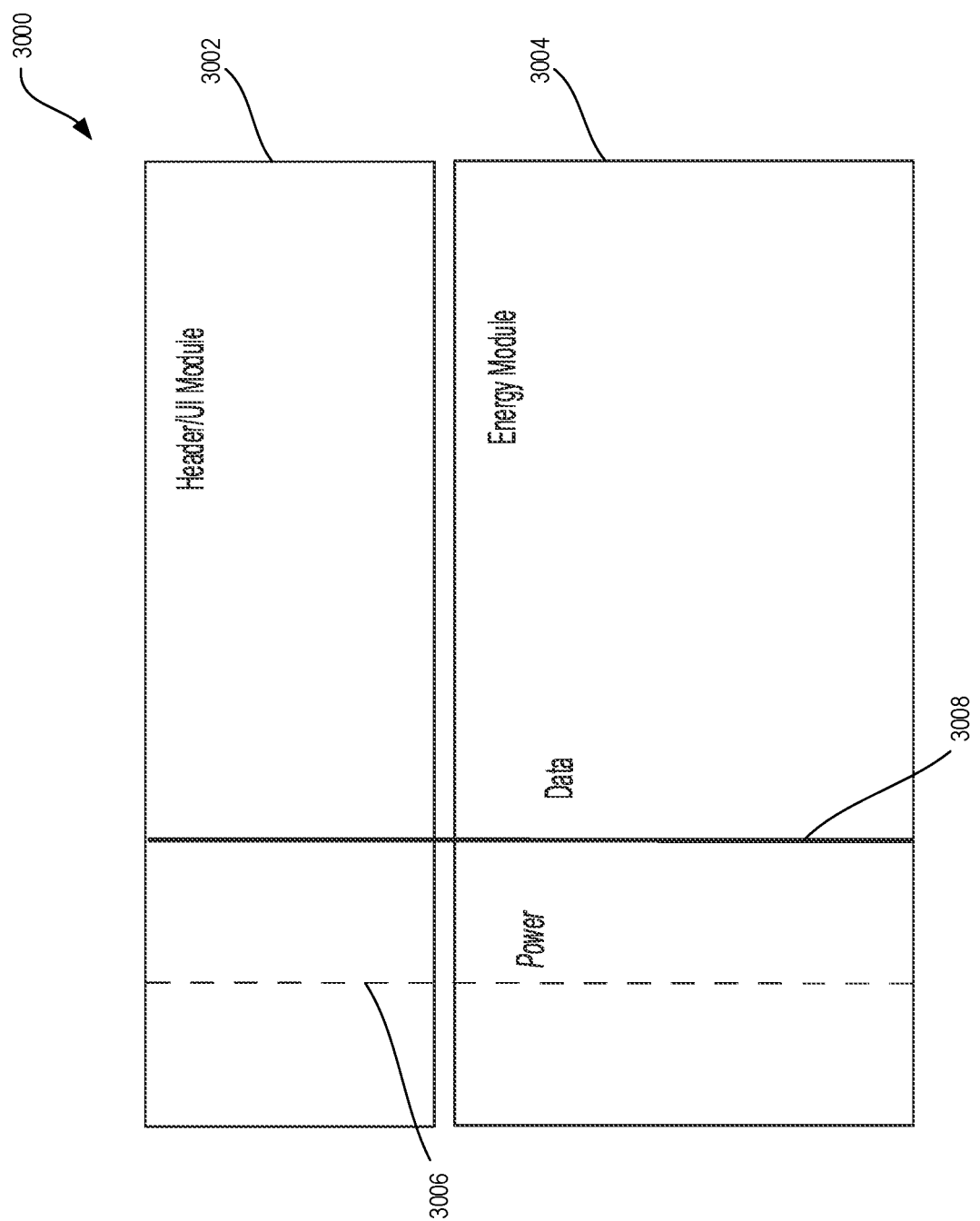
FIG. 31 is a block diagram of a stand-alone hub configuration of a modular energy system, in accordance with at least one aspect of the present disclosure.
Figure 32:
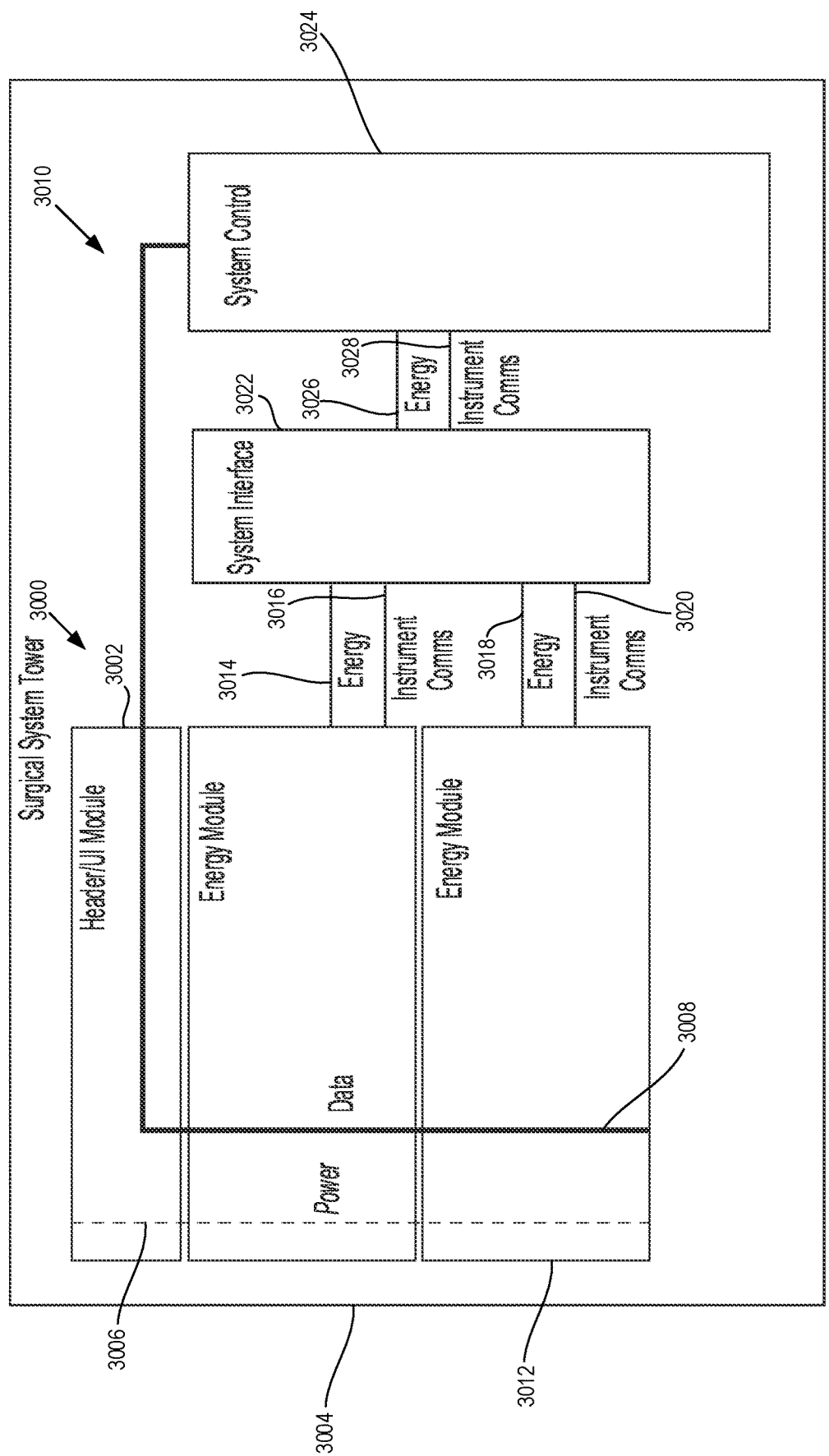
FIG. 32 is a block diagram of a hub configuration of a modular energy system integrated with a surgical control system, in accordance with at least one aspect of the present disclosure.

FIG. 31 is a block diagram of a stand-alone hub configuration of a modular energy system 3000, in accordance with at least one aspect of the present disclosure and FIG. 32 is a block diagram of a hub configuration of a modular energy system 3000 integrated with a surgical control system 3010, in accordance with at least one aspect of the present disclosure. As depicted in FIGS. 31 and 32, the modular energy system 3000 can be either utilized as stand-alone units or integrated with a surgical control system 3010 that controls and/or receives data from one or more surgical hub units. In the examples illustrated in FIGS. 31 and 32, the integrated header/UI module 3002 of the modular energy system 3000 includes a header module and a UI module integrated together as a singular module. In other aspects, the header module and the UI module can be provided as separate components that are communicatively coupled though a data bus 3008.

As illustrated in FIG. 31, an example of a stand-alone modular energy system 3000 includes an integrated header module/user interface (UI) module 3002 coupled to an energy module 3004. Power and data are transmitted between the integrated header/UI module 3002 and the energy module 3004 through a power interface 3006 and a data interface 3008. For example, the integrated header/UI module 3002 can transmit various commands to the energy module 3004 through the data interface 3008. Such commands can be based on user inputs from the UI. As a further example, power may be transmitted to the energy module 3004 through the power interface 3006.

In FIG. 32, a surgical hub configuration includes a modular energy system 3000 integrated with a control system 3010 and an interface system 3022 for managing, among other things, data and power transmission to and/or from the modular energy system 3000. The modular energy system depicted in FIG. 32 includes an integrated header module/UI module 3002, a first energy module 3004, and a second energy module 3012. In one example, a data transmission pathway is established between the system control unit 3024 of the control system 3010 and the second energy module 3012 through the first energy module 3004 and the header/UI module 3002 through a data interface 3008. In addition, a power pathway extends between the integrated header/UI module 3002 and the second energy module 3012 through the first energy module 3004 through a power interface 3006. In other words, in one aspect, the first energy module 3004 is configured to function as a power and data interface between the second energy module 3012 and the integrated header/UI module 3002 through the power interface 3006 and the data interface 3008. This arrangement allows the modular energy system 3000 to expand by seamlessly connecting additional energy modules to energy modules 3004, 3012 that are already connected to the integrated header/UI module 3002 without the need for dedicated power and energy interfaces within the integrated header/UI module 3002.

The system control unit 3024, which may be referred to herein as a control circuit, control logic, microprocessor, microcontroller, logic, or FPGA, or various combinations thereof, is coupled to the system interface 3022 via energy interface 3026 and instrument communication interface 3028. The system interface 3022 is coupled to the first energy module 3004 via a first energy interface 3014 and a first instrument communication interface 3016. The system interface 3022 is coupled to the second energy module 3012 via a second energy interface 3018 and a second instrument communication interface 3020. As additional modules, such as additional energy modules, are stacked in the modular energy system 3000, additional energy and communications interfaces are provided between the system interface 3022 and the additional modules.

As described in more detail hereinbelow, the energy modules 3004, 3012 are connectable to a hub and can be configured to generate electrosurgical energy (e.g., bipolar or monopolar), ultrasonic energy, or a combination thereof (referred to herein as an "advanced energy" module) for a variety of energy surgical instruments. Generally, the energy modules 3004, 3012 include hardware/software interfaces, an ultrasonic controller, an advanced energy RF controller, bipolar RF controller, and control algorithms executed by the controller that receives outputs from the controller and controls the operation of the various energy modules 3004, 3012 accordingly. In various aspects of the present disclosure, the controllers described herein may be implemented as a control circuit, control logic, microprocessor, microcontroller, logic, or FPGA, or various combinations thereof.

Figure 33:
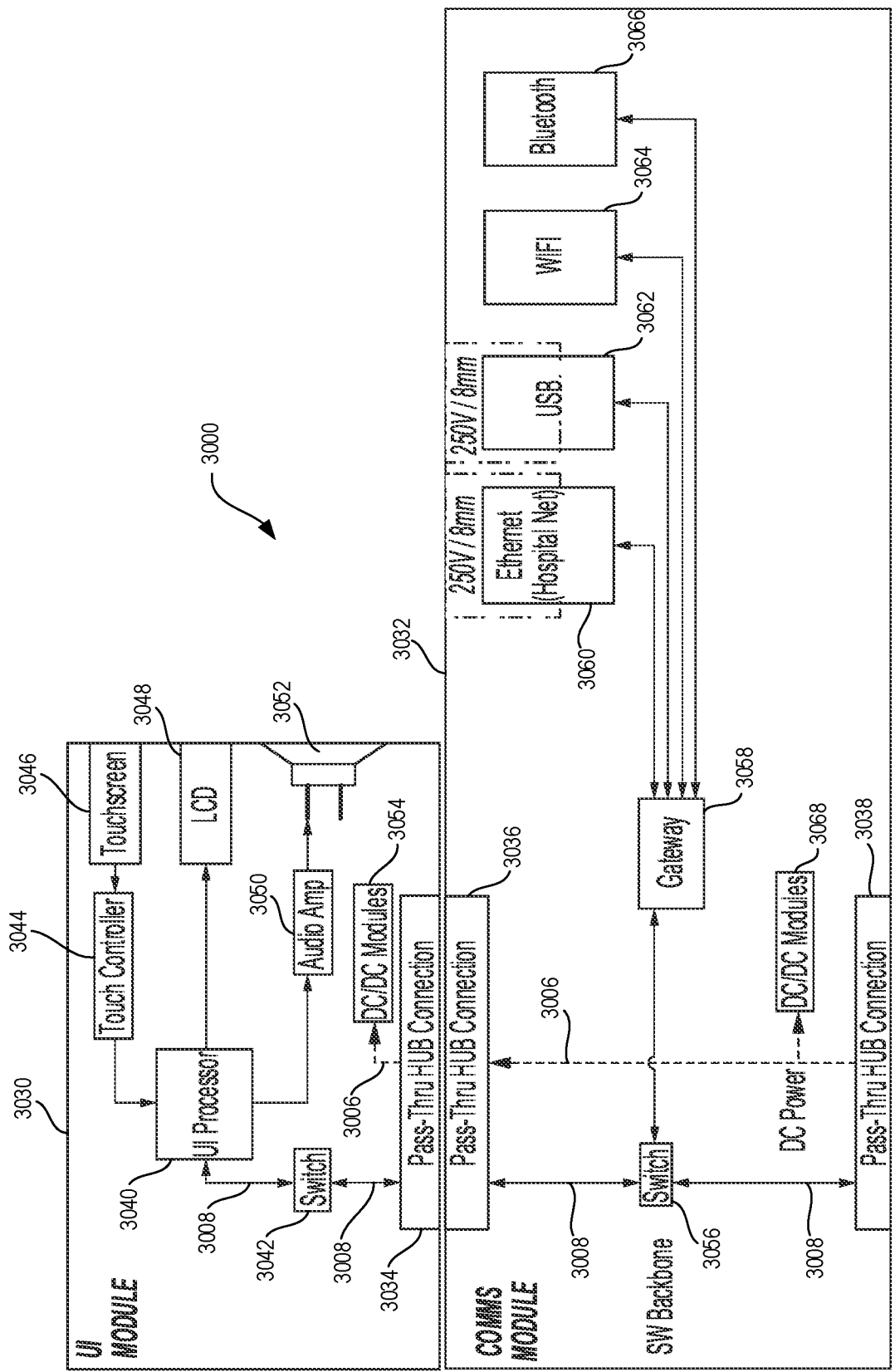
FIG. 33 is a block diagram of a user interface module coupled to a communications module of a modular energy system, in accordance with at least one aspect of the present disclosure.
Figure 34:
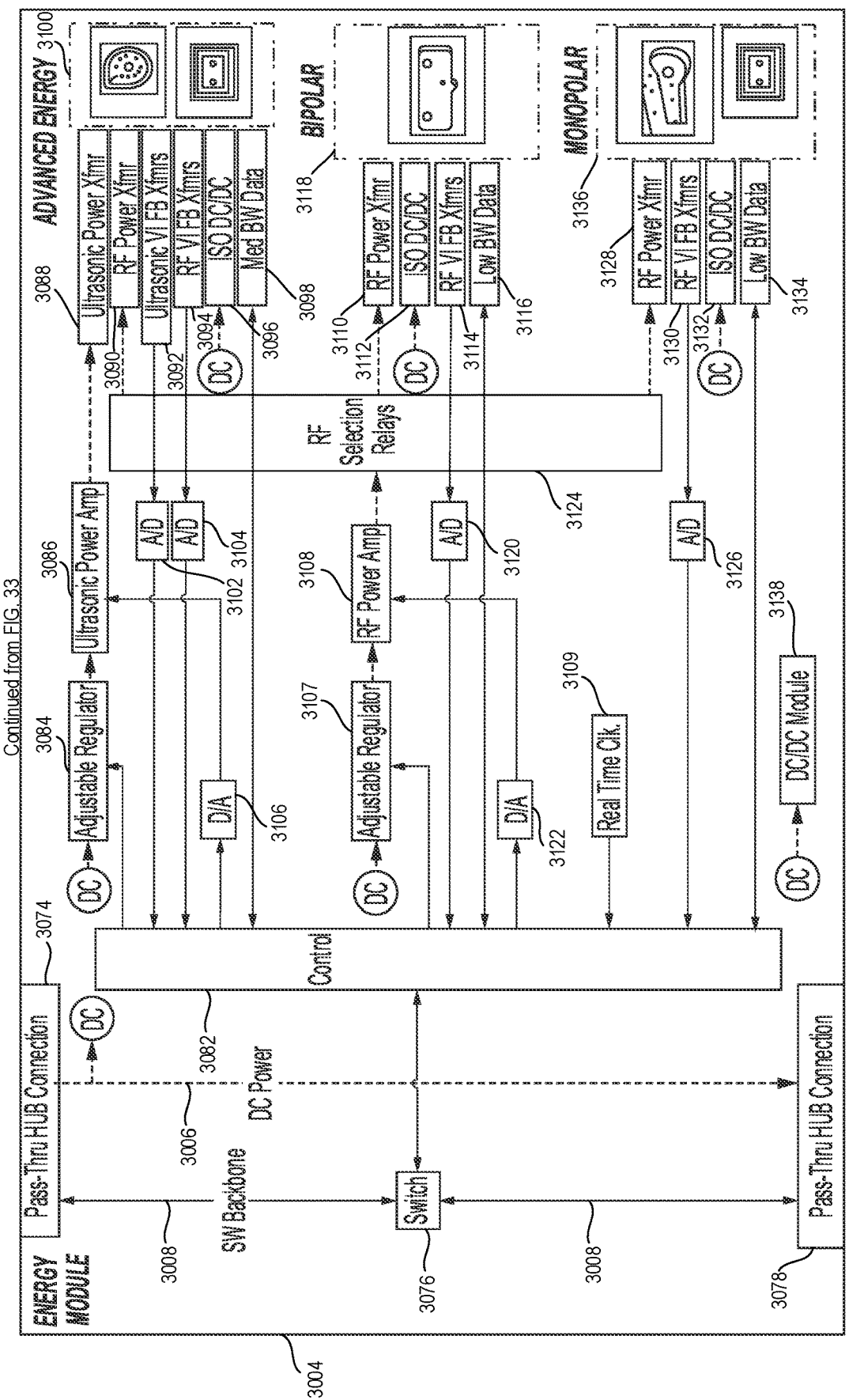
FIG. 34 is a block diagram of an energy module of a modular energy system, in accordance with at least one aspect of the present disclosure.
Figure 35A:
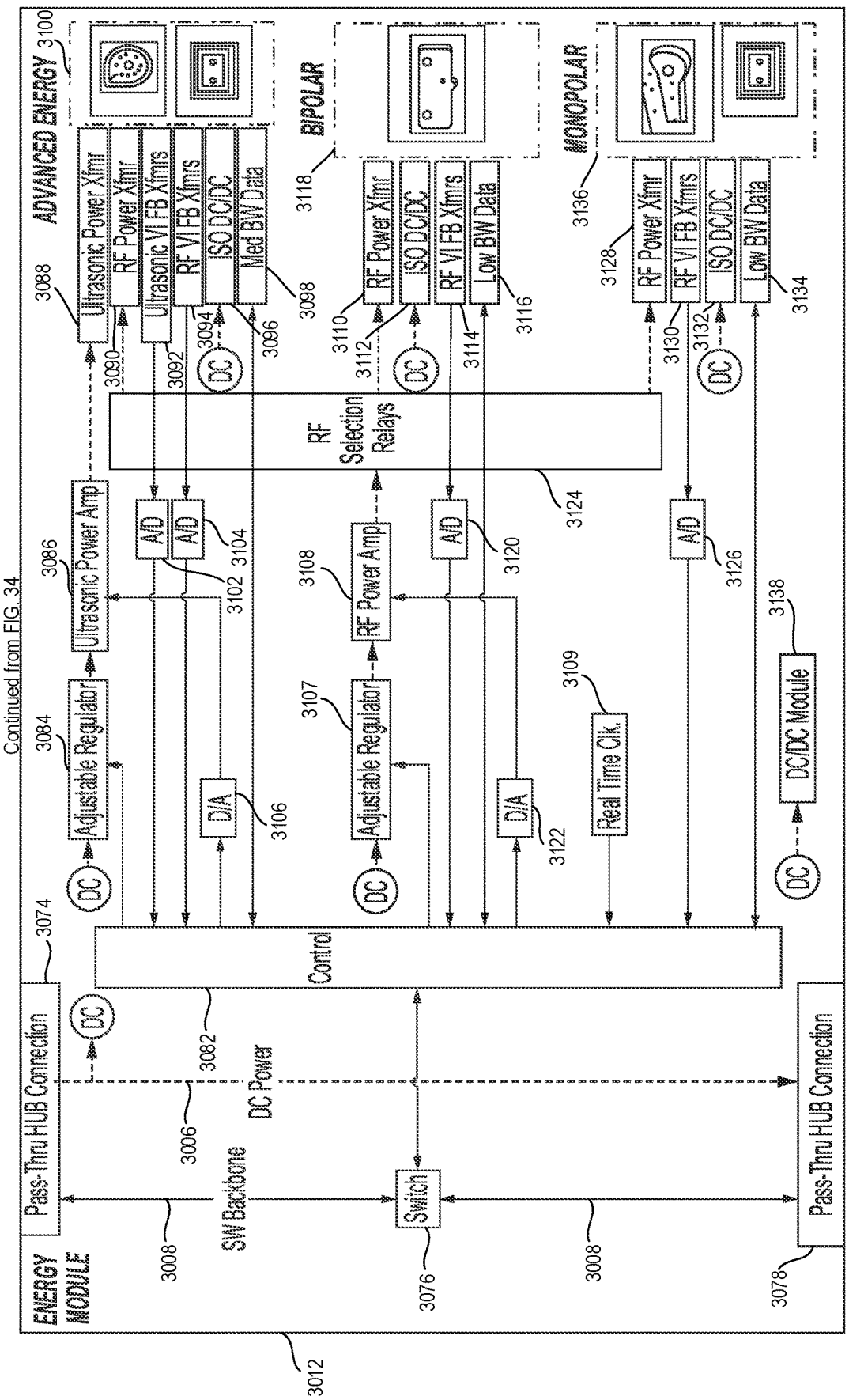
FIGS. 35A and 35B illustrate a block diagram of an energy module coupled to a header module of a modular energy system, in accordance with at least one aspect of the present disclosure.
Figure 35B:
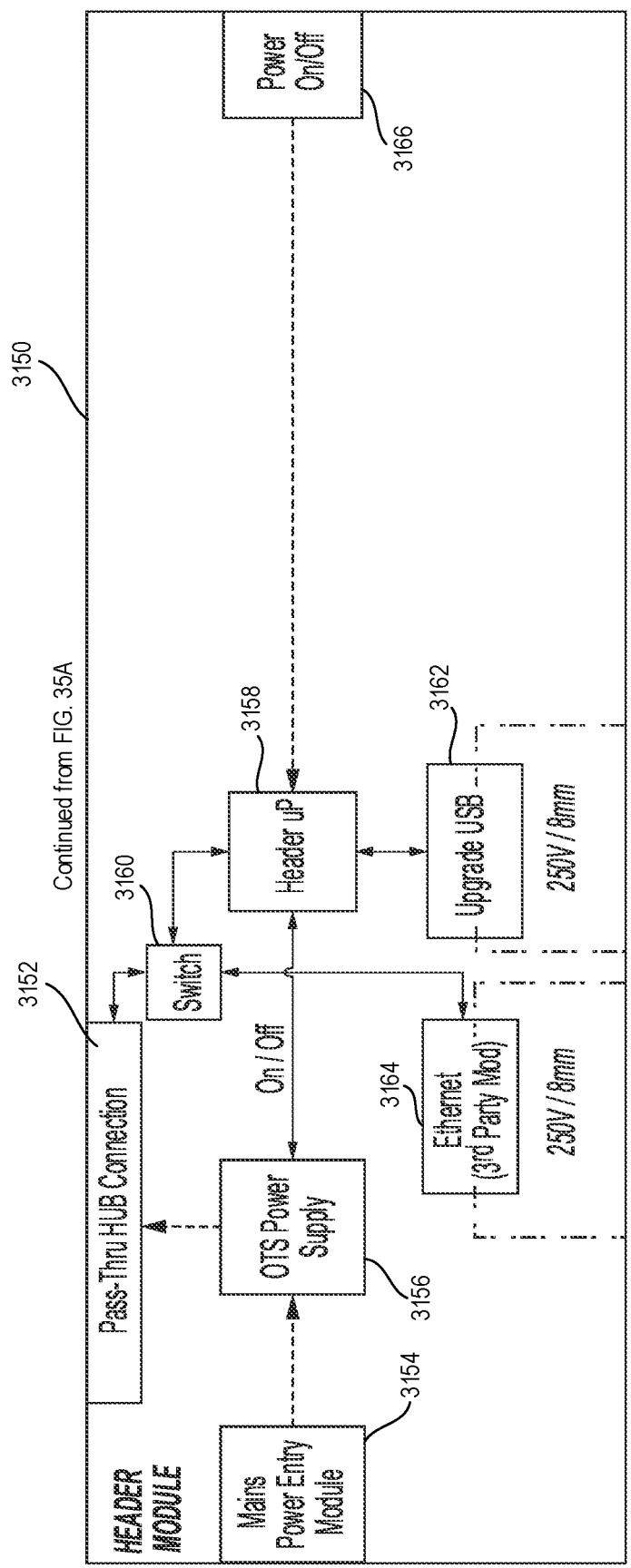

FIGS. 33-35 are block diagrams of various modular energy systems connected together to form a hub, in accordance with at least one aspect of the present disclosure. FIGS. 33-35 depict various diagrams (e.g., circuit or control diagrams) of hub modules. The modular energy system 3000 includes multiple energy modules 3004 (FIG. 34), 3012 (FIG. 35), a header module 3150 (FIG. 35), a UI module 3030 (FIG. 33), and a communications module 3032 (FIG.

33), in accordance with at least one aspect of the present disclosure. The UI module 3030 includes a touch screen 3046 displaying various relevant information and various user controls for controlling one or more parameters of the modular energy system 3000. The UI module 3030 is attached to the top header module 3150, but is separately housed so that it can be manipulated independently of the header module 3150. For example, the UI module 3030 can be picked up by a user and/or reattached to the header module 3150. Additionally, or alternatively, the UI module 3030 can be slightly moved relative to the header module 3150 to adjust its position and/or orientation. For example, the UI module 3030 can be tilted and/or rotated relative to the header module 3150.

In some aspects, the various hub modules can include light piping around the physical ports to communicate instrument status and also connect on-screen elements to corresponding instruments. Light piping is one example of an illumination technique that may be employed to alert a user to a status of a surgical instrument attached/connected to a physical port. In one aspect, illuminating a physical port with a particular light directs a user to connect a surgical instrument to the physical port. In another example, illuminating a physical port with a particular light alerts a user to an error related an existing connection with a surgical instrument.

Turning to FIG. 33, there is shown a block diagram of a user interface (UI) module 3030 coupled to a communications module 3032 via a pass-through hub connector 3034, in accordance with at least one aspect of the present disclosure. The UI module 3030 is provided as a separate component from a header module 3150 (shown in FIG. 35) and may be communicatively coupled to the header module 3150 via a communications module 3032, for example. In one aspect, the UI module 3030 can include a UI processor 3040 that is configured to represent declarative visualizations and behaviors received from other connected modules, as well as perform other centralized UI functionality, such as system configuration (e.g., language selection, module associations, etc.). The UI processor 3040 can be, for example, a processor or system on module (SOM) running a framework such as Qt, .NET WPF, Web server, or similar.

In the illustrated example, the UI module 3030 includes a touchscreen 3046, a liquid crystal display 3048 (LCD), and audio output 3052 (e.g., speaker, buzzer). The UI processor 3040 is configured to receive touchscreen inputs from a touch controller 3044 coupled between the touch screen 3046 and the UI processor 3040. The UI processor 3040 is configured to output visual information to the LCD display 3048 and to output audio information the audio output 3052 via an audio amplifier 3050. The UI processor 3040 is configured to interface to the communications module 3032 via a switch 3042 coupled to the pass-through hub connector 3034 to receive, process, and forward data from the source device to the destination device and control data communication therebetween. DC power is supplied to the UI module 3030 via DC/DC converter modules 3054. The DC power is passed through the pass-through hub connector 3034 to the communications module 3032 through the power bus 3006. Data is passed through the pass-through hub connector 3034 to the communications module 3032 through the data bus 3008. Switches 3042, 3056 receive, process, and forward data from the source device to the destination device.

Continuing with FIG. 33, the communications module 3032, as well as various surgical hubs and/or surgical systems can include a gateway 3058 that is configured to shuttle select traffic (i.e., data) between two disparate networks (e.g., an internal network and/or a hospital network) that are running different protocols. The communications module 3032 includes a first pass-through hub connector 3036 to couple the communications module 3032 to other modules. In the illustrated example, the communications module 3032 is coupled to the UI module 3030. The communications module 3032 is configured to couple to other modules (e.g., energy modules) via a second pass-through hub connector 3038 to couple the communications module 3032 to other modules via a switch 3056 disposed between the first and second pass-through hub connectors 3036, 3038 to receive, process, and forward data from the source device to the destination device and control data communication therebetween. The switch 3056 also is coupled to a gateway 3058 to communicate information between external communications ports and the UI module 3030 and other connected modules. The gateway 3058 may be coupled to various communications modules such as, for example, an Ethernet module 3060 to communicate to a hospital or other local network, a universal serial bus (USB) module 3062, a WFi module 3064, and a Bluetooth module 3066, among others. The communications modules may be physical boards located within the communications module 3032 or may be a port to couple to remote communications boards.

Figure 36A:
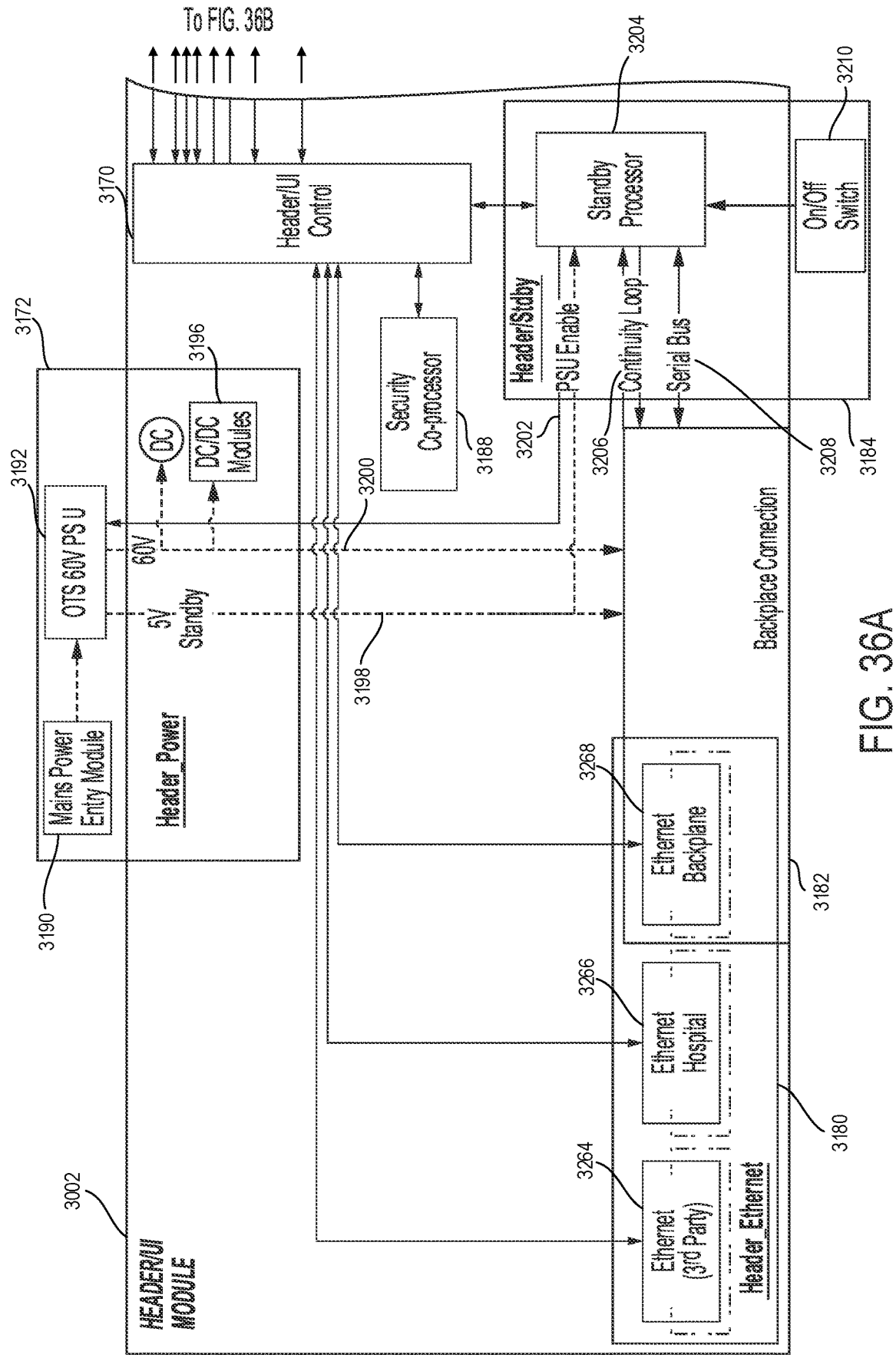
FIGS. 36A and 36B illustrate a block diagram of a header/user interface (UI) module of a modular energy system for a hub, such as the header module depicted in FIG. 33, in accordance with at least one aspect of the present disclosure.

In some aspects, all of the modules (i.e., detachable hardware) are controlled by a single UI module 3030 that is disposed on or integral to a header module. FIG. 35 shows a stand alone header module 3150 to which the UI module 3030 can be attached. FIGS. 31, 32, and 36 show an integrated header/UI Module 3002. Returning now to FIG. 33, in various aspects, by consolidating all of the modules into a single, responsive UI module 3002, the system provides a simpler way to control and monitor multiple pieces of equipment at once. This approach drastically reduces footprint and complexity in an operating room (OR).

Turning to FIG. 34, there is shown a block diagram of an energy module 3004, in accordance with at least one aspect of the present disclosure. The communications module 3032 (FIG. 33) is coupled to the energy module 3004 via the second pass-through hub connector 3038 of the communications module 3032 and a first pass-through hub connector 3074 of the energy module 3004. The energy module 3004 may be coupled to other modules, such as a second energy module 3012 shown in FIG. 35, via a second pass-through hub connector 3078. Turning back to FIG. 34, a switch 3076 disposed between the first and second pass-through hub connectors 3074, 3078 receives, processes, and forwards data from the source device to the destination device and controls data communication therebetween. Data is received and transmitted through the data bus 3008. The energy module 3032 includes a controller 3082 to control various communications and processing functions of the energy module 3004.

DC power is received and transmitted by the energy module 3004 through the power bus 3006. The power bus 3006 is coupled to DC/DC converter modules 3138 to supply power to adjustable regulators 3084, 3107 and isolated DC/DC converter ports 3096, 3112, 3132.

In one aspect, the energy module 3004 can include an ultrasonic wideband amplifier 3086, which in one aspect may be a linear class H amplifier that is capable of generating arbitrary waveforms and drive harmonic transducers at low total harmonic distortion (THD) levels. The ultrasonic wideband amplifier 3086 is fed by a buck adjustable regulator 3084 to maximize efficiency and controlled by the controller 3082, which may be implemented as a digital signal processor (DSP) via a direct digital synthesizer (DDS), for example. The DDS can either be embedded in the DSP or implemented in the field-programmable gate array (FPGA), for example. The controller 3082 controls the ultrasonic wideband amplifier 3086 via a digital-to-analog converter 3106 (DAC). The output of the ultrasonic wideband amplifier 3086 is fed to an ultrasonic power transformer 3088, which is coupled to an ultrasonic energy output portion of an advanced energy receptacle 3100. Ultrasonic voltage (V) and current (I) feedback (FB) signals, which may be employed to compute ultrasonic impedance, are fed back to the controller 3082 via an ultrasonic VI FB transformer 3092 through an input portion of the advanced energy receptacle 3100. The ultrasonic voltage and current feedback signals are routed back to the controller 3082 through an analog-to-digital converter 3102 (A/D). Also coupled to the controller 3082 through the advanced energy receptacle 3100 is the isolated DC/DC converter port 3096, which receives DC power from the power bus 3006, and a medium bandwidth data port 3098.

In one aspect, the energy module 3004 can include a wideband RF power amplifier 3108, which in one aspect may be a linear class H amplifier that is capable of generating arbitrary waveforms and drive RF loads at a range of output frequencies. The wideband RF power amplifier 3108 is fed by an adjustable buck regulator 3107 to maximize efficiency and controlled by the controller 3082, which may be implemented as DSP via a DDS. The DDS can either be embedded in the DSP or implemented in the FPGA, for example. The controller 3082 controls the wideband RF amplifier 3086 via a DAC 3122. The output of the wideband RF power amplifier 3108 can be fed through RF selection relays 3124. The RF selection relays 3124 are configured to receive and selectively transmit the output signal of the wideband RF power amplifier 3108 to various other components of the energy module 3004. In one aspect, the output signal of the wideband RF power amplifier 3108 can be fed through RF selection relays 3124 to an RF power transformer 3110, which is coupled to an RF output portion of a bipolar RF energy receptacle 3118. Bipolar RF voltage (V) and current (I) feedback (FB) signals, which may be employed to compute RF impedance, are fed back to the controller 3082 via an RF VI FB transformer 3114 through an input portion of the bipolar RF energy receptacle 3118. The RF voltage and current feedback signals are routed back to the controller 3082 through an A/D 3120. Also coupled to the controller 3082 through the bipolar RF energy receptacle 3118 is the isolated DC/DC converter port 3112, which receives DC power from the power bus 3006, and a low bandwidth data port 3116.

As described above, in one aspect, the energy module 3004 can include RF selection relays 3124 driven by the controller 3082 (e.g., FPGA) at rated coil current for actuation and can also be set to a lower hold-current via pulse-width modulation (PWM) to limit steady-state power dissipation. Switching of the RF selection relays 3124 is achieved with force guided (safety) relays and the status of the contact state is sensed by the controller 3082 as a mitigation for any single fault conditions. In one aspect, the RF selection relays 3124 are configured to be in a first state, where an output RF signal received from an RF source, such as the wideband RF power amplifier 3108, is transmitted to a first component of the energy module 3004, such as the RF power transformer 3110 of the bipolar energy receptacle 3118. In a second aspect, the RF selection relays 3124 are configured to be in a second state, where an output RF signal received from an RF source, such as the wideband RF power amplifier 3108, is transmitted to a second component, such as an RF power transformer 3128 of a monopolar energy receptacle 3136, described in more detail below. In a general aspect, the RF selection relays 3124 are configured to be driven by the controller 3082 to switch between a plurality of states, such as the first state and the second state, to transmit the output RF signal received from the RF power amplifier 3108 between different energy receptacles of the energy module 3004.

As described above, the output of the wideband RF power amplifier 3108 can also fed through the RF selection relays 3124 to the wideband RF power transformer 3128 of the RF monopolar receptacle 3136. Monopolar RF voltage (V) and current (I) feedback (FB) signals, which may be employed to compute RF impedance, are fed back to the controller 3082 via an RF VI FB transformer 3130 through an input portion of the monopolar RF energy receptacle 3136. The RF voltage and current feedback signals are routed back to the controller 3082 through an A/D 3126. Also coupled to the controller 3082 through the monopolar RF energy receptacle 3136 is the isolated DC/DC converter port 3132, which receives DC power from the power bus 3006, and a low bandwidth data port 3134.

The output of the wideband RF power amplifier 3108 can also fed through the RF selection relays 3124 to the wideband RF power transformer 3090 of the advanced energy receptacle 3100. RF voltage (V) and current (I) feedback (FB) signals, which may be employed to compute RF impedance, are fed back to the controller 3082 via an RF VI FB transformer 3094 through an input portion of the advanced energy receptacle 3100. The RF voltage and current feedback signals are routed back to the controller 3082 through an A/D 3104.

FIG. 35 is a block diagram of a second energy module 3012 coupled to a header module 3150, in accordance with at least one aspect of the present disclosure. The first energy module 3004 shown in FIG. 34 is coupled to the second energy module 3012 shown in FIG. 35 by coupling the second pass-through hub connector 3078 of the first energy module 3004 to a first pass-through hub connector 3074 of the second energy module 3012. In one aspect, the second energy module 3012 can a similar energy module to the first energy module 3004, as is illustrated in FIG. 35. In another aspect, the second energy module 2012 can be a different energy module compared to the first energy module, such as an energy module illustrated in FIG. 37, described in more detail. The addition of the second energy module 3012 to the first energy module 3004 adds functionality to the modular energy system 3000.

The second energy module 3012 is coupled to the header module 3150 by connecting the pass-through hub connector 3078 to the pass-through hub connector 3152 of the header module 3150. In one aspect, the header module 3150 can include a header processor 3158 that is configured to manage a power button function 3166, software upgrades through the upgrade USB module 3162, system time management, and gateway to external networks (i.e., hospital or the cloud) via an Ethernet module 3164 that may be running different protocols. Data is received by the header module 3150 through the pass-through hub connector 3152. The header processor 3158 also is coupled to a switch 3160 to receive, process, and forward data from the source device to the destination device and control data communication therebetween. The header processor 3158 also is coupled to an OTS power supply 3156 coupled to a mains power entry module 3154.

FIG. 36 is a block diagram of a header/user interface (UI) module 3002 for a hub, such as the header module depicted in FIG. 33, in accordance with at least one aspect of the present disclosure. The header/UI module 3002 includes a header power module 3172, a header wireless module 3174, a header USB module 3176, a header audio/screen module 3178, a header network module 3180 (e.g., Ethernet), a backplane connector 3182, a header standby processor module 3184, and a header footswitch module 3186. These functional modules interact to provide the header/UI 3002 functionality. A header/UI controller 3170 controls each of the functional modules and the communication therebetween including safety critical control logic modules 3230, 3232 coupled between the header/UI controller 3170 and an isolated communications module 3234 coupled to the header footswitch module 3186. A security co-processor 3188 is coupled to the header/UI controller 3170.

The header power module 3172 includes a mains power entry module 3190 coupled to an OTS power supply unit 3192 (PSU). Low voltage direct current (e.g., 5V) standby power is supplied to the header/UI module 3002 and other modules through a low voltage power bus 3198 from the OTS PSU 3192. High voltage direct current (e.g., 60V) is supplied to the header/UI module 3002 through a high voltage bus 3200 from the OTS PSU 3192. The high voltage DC supplies DC/DC converter modules 3196 as well as isolated DC/DC converter modules 3236. A standby processor 3204 of the header/standby module 3184 provides a PSU/enable signal 3202 to the OTS PSU 3192.

The header wireless module 3174 includes a WFi module 3212 and a Bluetooth module 3214. Both the WiFi module 3212 and the Bluetooth module 3214 are coupled to the header/UI controller 3170. The Bluetooth module 3214 is used to connect devices without using cables and the Wi-Fi module 3212 provides high-speed access to networks such as the Internet and can be employed to create a wireless network that can link multiple devices such as, for examples, multiple energy modules or other modules and surgical instruments, among other devices located in the operating room. Bluetooth is a wireless technology standard that is used to exchange data over short distances, such as, less than 30 feet.

The header USB module 3176 includes a USB port 3216 coupled to the header/UI controller 3170. The USB module 3176 provides a standard cable connection interface for modules and other electronics devices over short-distance digital data communications. The USB module 3176 allows modules comprising USB devices to be connected to each other with and transfer digital data over USB cables.

The header audio/screen module 3178 includes a touchscreen 3220 coupled to a touch controller 3218. The touch controller 3218 is coupled to the header/UI controller 3170 to read inputs from the touchscreen 3220. The header/UI controller 3170 drives an LCD display 3224 through a display/port video output signal 3222. The header/UI controller 3170 is coupled to an audio amplifier 3226 to drive one or more speakers 3228.

In one aspect, the header/UI module 3002 provides a touchscreen 3220 user interface configured to control modules connected to one control or header module 3002 in a modular energy system 3000. The touchscreen 3220 can be used to maintain a single point of access for the user to adjust all modules connected within the modular energy system 3000. Additional hardware modules (e.g., a smoke evacuation module) can appear at the bottom of the user interface LCD display 3224 when they become connected to the header/UI module 3002, and can disappear from the user interface LCD display 3224 when they are disconnected from the header/UI module 3002.

Further, the user touchscreen 3220 can provide access to the settings of modules attached to the modular energy system 3000. Further, the user interface LCD display 3224 arrangement can be configured to change according to the number and types of modules that are connected to the header/UI module 3002. For example, a first user interface can be displayed on the LCD display 3224 for a first application where one energy module and one smoke evacuation module are connected to the header/UI module 3002, and a second user interface can be displayed on the LCD display 3224 for a second application where two energy modules are connected to the header/UI module 3002. Further, the user interface can alter its display on the LCD display 3224 as modules are connected and disconnected from the modular energy system 3000.

In one aspect, the header/UI module 3002 provides a user interface LCD display 3224 configured to display on the LCD display coloring corresponds to the port lighting. In one aspect, the coloring of the instrument panel and the LED light around its corresponding port will be the same or otherwise correspond with each other. Each color can, for example, convey a unique meaning. This way, the user will be able to quickly assess which instrument the indication is referring to and the nature of the indication. Further, indications regarding an instrument can be represented by the changing of color of the LED light lined around its corresponding port and the coloring of its module. Still further, the message on screen and hardware/software port alignment can also serve to convey that an action must be taken on the hardware, not on the interface. In various aspects, all other instruments can be used while alerts are occurring on other instruments. This allows the user to be able to quickly assess which instrument the indication is referring to and the nature of the indication.

In one aspect, the header/UI module 3002 provides a user interface screen configured to display on the LCD display 3224 to present procedure options to a user. In one aspect, the user interface can be configured to present the user with a series of options (which can be arranged, e.g., from broad to specific). After each selection is made, the modular energy system 3000 presents the next level until all selections are complete. These settings could be managed locally and transferred via a secondary means (such as a USB thumb drive). Alternatively, the settings could be managed via a portal and automatically distributed to all connected systems in the hospital.

The procedure options can include, for example, a list of factory preset options categorized by specialty, procedure, and type of procedure. Upon completing a user selection, the header module can be configured to set any connected instruments to factory-preset settings for that specific procedure. The procedure options can also include, for example, a list of surgeons, then subsequently, the specialty, procedure, and type. Once a user completes a selection, the system may suggest the surgeon's preferred instruments and set those instrument's settings according to the surgeon's preference (i.e., a profile associated with each surgeon storing the surgeon's preferences).

In one aspect, the header/UI module 3002 provides a user interface screen configured to display on the LCD display 3224 critical instrument settings. In one aspect, each instrument panel displayed on the LCD display 3224 of the user interface corresponds, in placement and content, to the instruments plugged into the modular energy system 3000. When a user taps on a panel, it can expand to reveal additional settings and options for that specific instrument and the rest of the screen can, for example, darken or otherwise be de-emphasized.

In one aspect, the header/UI module 3002 provides an instrument settings panel of the user interface configured to comprise/display controls that are unique to an instrument and allow the user to increase or decrease the intensity of its output, toggle certain functions, pair it with system accessories like a footswitch connected to header footswitch module 3186, access advanced instrument settings, and find additional information about the instrument. In one aspect, the user can tap/select an "Advanced Settings" control to expand the advanced settings drawer displayed on the user interface LCD display 3224. In one aspect, the user can then tap/select an icon at the top right-hand corner of the instrument settings panel or tap anywhere outside of the panel and the panel will scale back down to its original state. In these aspects, the user interface is configured to display on the LCD display 3224 only the most critical instrument settings, such as power level and power mode, on the ready/home screen for each instrument panel. This is to maximize the size and readability of the system from a distance. In some aspects, the panels and the settings within can be scaled proportionally to the number of instruments connected to the system to further improve readability. As more instruments are connected, the panels scale to accommodate a greater amount of information.

The header network module 3180 includes a plurality of network interfaces 3264, 3266, 3268 (e.g., Ethernet) to network the header/UI module 3002 to other modules of the modular energy system 3000. In the illustrated example, one network interface 3264 may be a 3rd party network interface, another network interface 3266 may be a hospital network interface, and yet another network interface 3268 may be located on the backplane network interface connector 3182.

The header standby processor module 3184 includes a standby processor 3204 coupled to an On/Off switch 3210. The standby processor 3204 conducts an electrical continuity test by checking to see if electrical current flows in a continuity loop 3206. The continuity test is performed by placing a small voltage across the continuity loop 3206. A serial bus 3208 couples the standby processor 3204 to the backplane connector 3182.

The header footswitch module 3186 includes a controller 3240 coupled to a plurality of analog footswitch ports 3254, 3256, 3258 through a plurality of corresponding presence/ID and switch state modules 3242, 3244, 3246, respectively. The controller 3240 also is coupled to an accessory port 3260 via a presence/ID and switch state module 3248 and a transceiver module 3250. The accessory port 3260 is powered by an accessory power module 3252. The controller 3240 is coupled to header/UI controller 3170 via an isolated communication module 3234 and first and second safety critical control modules 3230, 3232. The header footswitch module 3186 also includes DC/DC converter modules 3238.

In one aspect, the header/UI module 3002 provides a user interface screen configured to display on the LCD display 3224 for controlling a footswitch connected to any one of the analog footswitch ports 3254, 3256, 3258. In some aspects, when the user plugs in a non hand-activated instrument into any one of the analog footswitch ports 3254, 3256, 3258, the instrument panel appears with a warning icon next to the footswitch icon. The instrument settings can be, for example, greyed out, as the instrument cannot be activated without a footswitch.

When the user plugs in a footswitch into any one of the analog footswitch ports 3254, 3256, 3258, a pop-up appears indicating that a footswitch has been assigned to that instrument. The footswitch icon indicates that a footswitch has been plugged in and assigned to the instrument. The user can then tap/select on that icon to assign, reassign, unassign, or otherwise change the settings associated with that footswitch. In these aspects, the system is configured to automatically assign footswitches to non hand-activated instruments using logic, which can further assign single or double-pedal footswitches to the appropriate instrument. If the user wants to assign/reassign footswitches manually there are two flows that can be utilized.

In one aspect, the header/UI module 3002 provides a global footswitch button. Once the user taps on the global footswitch icon (located in the upper right of the user interface LCD display 3224), the footswitch assignment overlay appears and the contents in the instrument modules dim. A (e.g., photo-realistic) representation of each attached footswitch (dual or single-pedal) appears on the bottom if unassigned to an instrument or on the corresponding instrument panel. Accordingly, the user can drag and drop these illustrations into, and out of, the boxed icons in the footswitch assignment overlay to assign, unassign, and reassign footswitches to their respective instruments.

In one aspect, the header/UI module 3002 provides a user interface screen displayed on the LCD display 3224 indicating footswitch auto-assignment, in accordance with at least one aspect of the present disclosure. As discussed above, the modular energy system 3000 can be configured to auto-assign a footswitch to an instrument that does not have hand activation. In some aspects, the header/UI module 3002 can be configured to correlate the colors displayed on the user interface LCD display 3224 to the lights on the modules themselves as means of tracking physical ports with user interface elements.

In one aspect, the header/UI module 3002 may be configured to depict various applications of the user interface with differing number of modules connected to the modular energy system 3000. In various aspects, the overall layout or proportion of the user interface elements displayed on the LCD display 3224 can be based on the number and type of instruments plugged into the header/UI module 3002. These scalable graphics can provide the means to utilize more of the screen for better visualization.

In one aspect, the header/UI module 3002 may be configured to depict a user interface screen on the LCD display 3224 to indicate which ports of the modules connected to the modular energy system 3000 are active. In some aspects, the header/UI module 3002 can be configured to illustrate active versus inactive ports by highlighting active ports and dimming inactive ports. In one aspect, ports can be represented with color when active (e.g., monopolar tissue cut with yellow, monopolar tissue coagulation with blue, bipolar tissue cut with blue, advanced energy tissue cut with warm white, and so on). Further, the displayed color will match the color of the light piping around the ports. The coloring can further indicate that the user cannot change settings of other instruments while an instrument is active. As another example, the header/UI module 3002 can be configured to depict the bipolar, monopolar, and ultrasonic ports of a first energy module as active and the monopolar ports of a second energy module as likewise active.

In one aspect, the header/UI module 3002 can be configured to depict a user interface screen on the LCD display 3224 to display a global settings menu. In one aspect, the header/UI module 3002 can be configured to display a menu on the LCD display 3224 to control global settings across any modules connected to the modular energy system 3000. The global settings menu can be, for example, always displayed in a consistent location (e.g., always available in upper right hand corner of main screen).

In one aspect, the header/UI module 3002 can be configured to depict a user interface screen on the LCD display 3224 configured to prevent changing of settings while a surgical instrument is in use. In one example, the header/UI module 3002 can be configured to prevent settings from being changed via a displayed menu when a connected instrument is active. The user interface screen can include, for example, an area (e.g., the upper left hand corner) that is reserved for indicating instrument activation while a settings menu is open. In one aspect, a user has opened the bipolar settings while monopolar coagulation is active. In one aspect, the settings menu could then be used once the activation is complete. In one aspect, the header/UI module 3002 can be is configured to never overlay any menus or other information over the dedicated area for indicating critical instrument information in order to maintain display of critical information.

In one aspect, the header/UI module 3002 can be configured to depict a user interface screen on the LCD display 3224 configured to display instrument errors. In one aspect, instrument error warnings may be displayed on the instrument panel itself, allowing user to continue to use other instruments while a nurse troubleshoots the error. This allows users to continue the surgery without the need to stop the surgery to debug the instrument.

In one aspect, the header/UI module 3002 can be configured to depict a user interface screen on the LCD display 3224 to display different modes or settings available for various instruments. In various aspects, the header/UI module 3002 can be configured to display settings menus that are appropriate for the type or application of surgical instrument(s) connected to the stack/hub. Each settings menu can provide options for different power levels, energy delivery profiles, and so on that are appropriate for the particular instrument type. In one aspect, the header/UI module 3002 can be configured to display different modes available for bipolar, monopolar cut, and monopolar coagulation applications.

In one aspect, the header/UI module 3002 can be configured to depict a user interface screen on the LCD display 3224 to display pre-selected settings. In one aspect, the header/UI module 3002 can be configured to receive selections for the instrument/device settings before plugging in instruments so that the modular energy system 3000 is ready before the patient enters the operating room. In one aspect, the user can simply click a port and then change the settings for that port. In the depicted aspect, the selected port appears as faded to indicate settings are set, but no instrument is plugged into that port.

Figure 37:
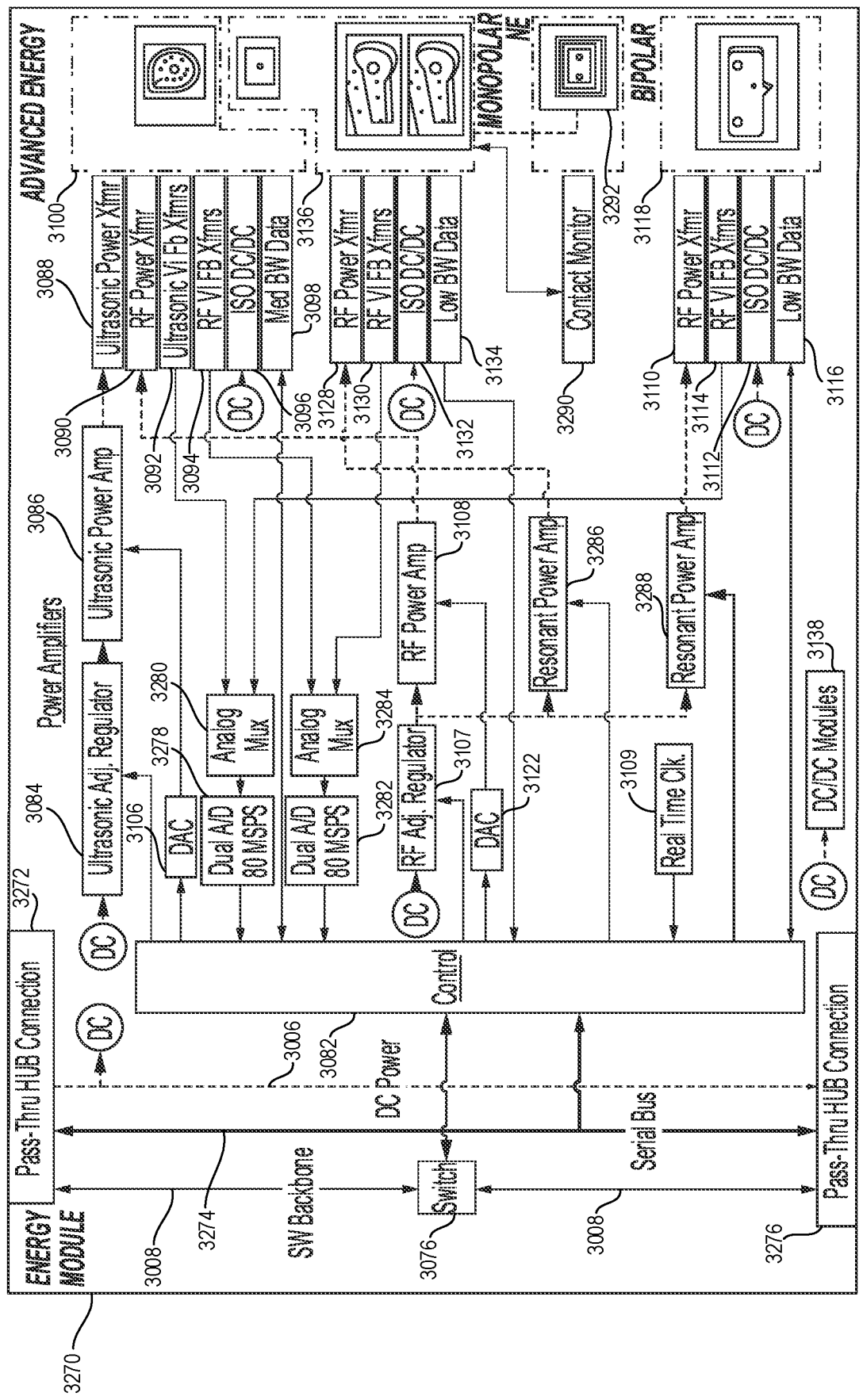
FIG. 37 is a block diagram of an energy module for a hub, such as the energy module depicted in FIGS. 31-36B, in accordance with at least one aspect of the present disclosure.

FIG. 37 is a block diagram of an energy module 3270 for a hub, such as the energy module depicted in FIGS. 31, 32, 34, and 35, in accordance with at least one aspect of the present disclosure. The energy module 3270 is configured to couple to a header module, header/UI module, and other energy modules via the first and second pass-through hub connectors 3272, 3276. A switch 3076 disposed between the first and second pass-through hub connectors 3272, 3276 receives, processes, and forwards data from the source device to the destination device and controls data communication therebetween. Data is received and transmitted through the data bus 3008. The energy module 3270 includes a controller 3082 to control various communications and processing functions of the energy module 3270.

DC power is received and transmitted by the energy module 3270 through the power bus 3006. The power bus 3006 is coupled to the DC/DC converter modules 3138 to supply power to adjustable regulators 3084, 3107 and isolated DC/DC converter ports 3096, 3112, 3132.

In one aspect, the energy module 3270 can include an ultrasonic wideband amplifier 3086, which in one aspect may be a linear class H amplifier that is capable of generating arbitrary waveforms and drive harmonic transducers at low total harmonic distortion (THD) levels. The ultrasonic wideband amplifier 3086 is fed by a buck adjustable regulator 3084 to maximize efficiency and controlled by the controller 3082, which may be implemented as a digital signal processor (DSP) via a direct digital synthesizer (DDS), for example. The DDS can either be embedded in the DSP or implemented in the field-programmable gate array (FPGA), for example. The controller 3082 controls the ultrasonic wideband amplifier 3086 via a digital-to-analog converter 3106 (DAC). The output of the ultrasonic wideband amplifier 3086 is fed to an ultrasonic power transformer 3088, which is coupled to an ultrasonic energy output portion of the advanced energy receptacle 3100. Ultrasonic voltage (V) and current (I) feedback (FB) signals, which may be employed to compute ultrasonic impedance, are fed back to the controller 3082 via an ultrasonic VI FB transformer 3092 through an input portion of the advanced energy receptacle 3100. The ultrasonic voltage and current feedback signals are routed back to the controller 3082 through an analog multiplexer 3280 and a dual analog-to-digital converter 3278 (A/D). In one aspect, the dual A/D 3278 has a sampling rate of 80 MSPS. Also coupled to the controller 3082 through the advanced energy receptacle 3100 is the isolated DC/DC converter port 3096, which receives DC power from the power bus 3006, and a medium bandwidth data port 3098.

In one aspect, the energy module 3270 can include a plurality of wideband RF power amplifiers 3108, 3286, 3288, among others, which in one aspect, each of the wideband RF power amplifiers 3108, 3286, 3288 may be linear class H amplifiers capable of generating arbitrary waveforms and drive RF loads at a range of output frequencies. Each of the wideband RF power amplifiers 3108, 3286, 3288 are fed by an adjustable buck regulator 3107 to maximize efficiency and controlled by the controller 3082, which may be implemented as DSP via a DDS. The DDS can either be embedded in the DSP or implemented in the FPGA, for example. The controller 3082 controls the first wideband RF power amplifier 3108 via a DAC 3122.

Unlike the energy modules 3004, 3012 shown and described in FIGS. 34 and 35, the energy module 3270 does not include RF selection relays configured to receive an RF output signal from the adjustable buck regulator 3107. In addition, unlike the energy modules 3004, 3012 shown and described in FIGS. 34 and 35, the energy module 3270 includes a plurality of wideband RF power amplifiers 3108, 3286, 3288 instead of a single RF power amplifier. In one aspect, the adjustable buck regulator 3107 can switch between a plurality of states, in which the adjustable buck regulator 3107 outputs an output RF signal to one of the plurality of wideband RF power amplifiers 3108, 3286, 3288 connected thereto. The controller 3082 is configured to switch the adjustable buck regulator 3107 between the plurality of states. In a first state, the controller drives the adjustable buck regulator 3107 to output an RF energy signal to the first wideband RF power amplifier 3108. In a second state, the controller drives the adjustable buck regulator 3107 to output an RF energy signal to the second wideband RF power amplifier 3286. In a third state, the controller drives the adjustable buck regulator 3107 to output an RF energy signal to the third wideband RF power amplifier 3288.

The output of the first wideband RF power amplifier 3108 can be fed to an RF power transformer 3090, which is coupled to an RF output portion of an advanced energy receptacle 3100. RF voltage (V) and current (I) feedback (FB) signals, which may be employed to compute RF impedance, are fed back to the controller 3082 via RF VI FB transformers 3094 through an input portion of the advanced energy receptacle 3100. The RF voltage and current feedback signals are routed back to the controller 3082 through the RF VI FB transformers 3094, which are coupled to an analog multiplexer 3284 and a dual A/D 3282 coupled to the controller 3082. In one aspect, the dual A/D 3282 has a sampling rate of 80 MSPS.

The output of the second RF wideband power amplifier 3286 is fed through an RF power transformer 3128 of the RF monopolar receptacle 3136. Monopolar RF voltage (V) and current (I) feedback (FB) signals, which may be employed to compute RF impedance, are fed back to the controller 3082 via RF VI FB transformers 3130 through an input portion of the monopolar RF energy receptacle 3136. The RF voltage and current feedback signals are routed back to the controller 3082 through the analog multiplexer 3284 and the dual A/D 3282. Also coupled to the controller 3082 through the monopolar RF energy receptacle 3136 is the isolated DC/DC converter port 3132, which receives DC power from the power bus 3006, and a low bandwidth data port 3134.

The output of the third RF wideband power amplifier 3288 is fed through an RF power transformer 3110 of a bipolar RF receptacle 3118. Bipolar RF voltage (V) and current (I) feedback (FB) signals, which may be employed to compute RF impedance, are fed back to the controller 3082 via RF VI FB transformers 3114 through an input portion of the bipolar RF energy receptacle 3118. The RF voltage and current feedback signals are routed back to the controller 3082 through the analog multiplexer 3280 and the dual A/D 3278. Also coupled to the controller 3082 through the bipolar RF energy receptacle 3118 is the isolated DC/DC converter port 3112, which receives DC power from the power bus 3006, and a low bandwidth data port 3116.

A contact monitor 3290 is coupled to an NE receptacle 3292. Power is fed to the NE receptacle 3292 from the monopolar receptacle 3136.

In one aspect, with reference to FIGS. 31-37, the modular energy system 3000 can be configured to detect instrument presence in a receptacle 3100, 3118, 3136 via a photo-interrupter, magnetic sensor, or other non-contact sensor integrated into the receptacle 3100, 3118, 3136. This approach prevents the necessity of allocating a dedicated presence pin on the MTD connector to a single purpose and instead allows multi-purpose functionality for MTD signal pins 6-9 while continuously monitoring instrument presence.

In one aspect, with reference to FIGS. 31-37, the modules of the modular energy system 3000 can include an optical link allowing high speed communication (10-50 Mb/s) across the patient isolation boundary. This link would carry device communications, mitigation signals (watchdog, etc.), and low bandwidth run-time data. In some aspects, the optical link(s) will not contain real-time sampled data, which can be done on the non-isolated side.

In one aspect, with reference to FIGS. 31-37, the modules of the modular energy system 3000 can include a multi-function circuit block which can: (i) read presence resistor values via A/D and current source, (ii) communicate with legacy instruments via hand switch Q protocols, (iii) communicate with instruments via local bus 1-Wire protocols, and (iv) communicate with CAN FD-enabled surgical instruments. When a surgical instrument is properly identified by an energy generator module, the relevant pin functions and communications circuits are enabled, while the other unused functions are disabled and set to a high impedance state.

In one aspect, with reference to FIGS. 31-37, the modules of the modular energy system 3000 can include an amplifier pulse/stimulation/auxiliary DC amplifier. This is a flexible-use amplifier based on a full-bridge output and incorporates functional isolation. This allows its differential output to be referenced to any output connection on the applied part (except, in some aspects, a monopolar active electrode). The amplifier output can be either small signal linear (pulse/stim) with waveform drive provided by a DAC or a square wave drive at moderate output power for DC applications such as DC motors, illumination, FET drive, etc. The output voltage and current are sensed with functionally isolated voltage and current feedback to provide accurate impedance and power measurements to the FPGA. Paired with a CAN FD-enabled instrument, this output can offer motor/motion control drive, while position or velocity feedback is provided by the CAN FD interface for closed loop control.

Passive Header Module Display

As discussed above under the heading MODULAR ENERGY SYSTEM, energy systems can be designed for modularity, which is to say that an energy system can be assembled from different numbers and types of modules according to users' needs for any given surgical procedure or task. In particular, a modular energy system 2000 (FIGS. 24-30) can include a header module 2002, which can in turn include a display screen 2006 for displaying/rendering a user interface (UI) 2050 (FIG. 30) that displays data associated with all of the modules 2001 (FIGS. 24-30) that are connected to the header module 2002. Accordingly, the header module 2002 provides a single, consolidated UI 2050 to display content for all of the modules 2001, which is beneficial for a number of reasons, some of which are described in U.S. patent application Ser. No. 16/562,123, titled METHOD FOR CONSTRUCTING AND USING A MODULAR SURGICAL ENERGY SYSTEM WITH MULTIPLE DEVICES, filed Sep. 5, 2019, now U.S. Patent Application Publication No. 2020/0100830, which is hereby incorporated by reference herein. However, an issue could potentially arise in such a system structure if the header module 2002 and the individual modules 2001 are both responsible for making calculations pertaining to data sensed with respect to the individual modules 2001. Namely, this introduces the possibility for errors if the system updates of the header module 2002 and the individual modules 2001 are mismatched. Stated differently, if the header module 2002 has downloaded the most recent system update, but the individual modules 2001 have not (or vice versa), then the mismatched system versions could create errors if both the header module 2002 and the individual modules 2001 are responsible for performing computations on sensed data. To address this potential issue, in one aspect, the individual modules 2001 can be configured to perform all computations on sensed data and the header module 2002 can be configured to passively display all of the data this is transmitted to it from the individual modules 2001. Utilizing a header module 2002 that simply passively renders or displays the received data, without performing independent computations with respect to the received data, addresses these potential issues with modules 2001 having mismatched system versions. However, such a system structure with a passive header module 2002 can potentially create a separate issue pertaining to the display of safety critical content (e.g., the power level at which the energy module 2004 (FIGS. 24-30)). Namely, if the header module 2002 is passively displaying content, then it would not know if the displayed safety critical content was correct. Accordingly, for the modules 2001 of that generate safety critical data that is then displayed via the header module 2002, the modular energy system 2000 must be configured to verify that the safety critical UI content is being displayed correctly because, although the modules 2001 may themselves know whether safety critical data/content is correct, this information may not be known by header module 2002. Therefore, a solution for the modular energy system 2000 is needed to verify (and correct, as needed) safety critical UI content generated from module data and displayed by the header module 2002 or UI module 3002 (FIG. 31) without prior, independent knowledge by the header module 2002 or UI module 3002 of whether the displayed content is correct.

In one general aspect, the modular energy system is configured to execute local verification loops between the modules to verify the proper display of safety critical UI content to achieve end-to-end monitoring and verification of safety critical UI content.

In another general aspect, a modular energy system includes a header module and one or more other modules, where each of the non-header modules generates data that is delivered to the header module, which in turn passively displays UI content based on the delivered data. Thus, the modules are can be referred to as "smart" and the header module can be referred to as "passive" use of a passive header module minimizes need and time to deliver software updates to the modular energy system because the header module need not be separately updated from the other modules in order for the modular energy system to function.

Figure 38:
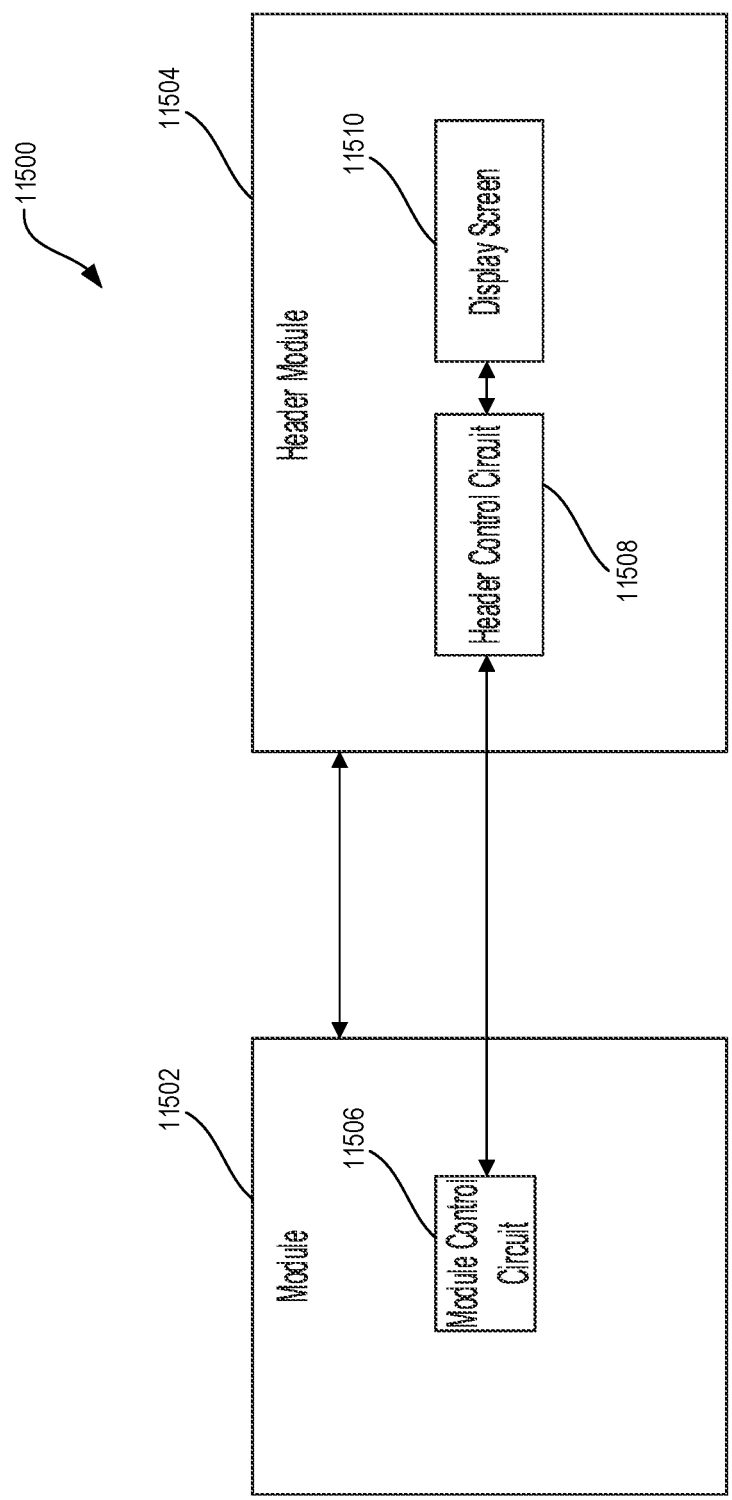
FIG. 38 is a block diagram of a modular energy system, in accordance with at least one aspect of the present disclosure.

FIG. 38 is a block diagram of a modular energy system 11500, in accordance with at least one aspect of the present disclosure. In one aspect, the modular energy system 11500 can include a header module 11504 that is connected to a module 11502, which can include a variety of different module types, such as the modules 2001 described above in connection with FIGS. 24-30. The module 11502 can include a control circuit 11506. The module control circuit 11506 can include a controller 3082 (FIG. 34), for example. The header module 11504 can include a control circuit 11508 and a display screen 11510 that is communicably coupled to the control circuit 11508. The header control circuit 11508 can include a UI processor 3040 (FIG. 33), for example. The display screen 11510 can be configured to display a UI 2050 for displaying operational information/parameters pertaining to the modular energy system 11500 and/or receiving input from the user, as described above. The header control circuit 11508 can be configured to control the display screen 11510 to cause the UI 2050 to display various UI elements or content (e.g., text, icons, or widgets) as dictated by the header control circuit 11508. When the module 11502 and the header module 11504 are connected, the module control circuit 11506 and the header control circuit 11508 can be communicably coupled such that they are able to send and receive data/signals therebetween. In one aspect, the header control circuit 11508 cause control the display screen 11510 to cause the UI 2050 to display UI content based on data received from the module 11502.

In various aspects, the modular energy system 11500 can be configured to execute a process to verify safety critical UI content generated from module data and displayed by the header module 11504 without prior, independent knowledge by the header module 11504 of whether the displayed content is correct. As one example, the module control circuit 11506 and/or header control circuit 11508 can be configured to execute a process 11600 illustrated in FIG. 39 for verifying displayed UI content, in accordance with at least one aspect of the present disclosure. The process 11600 can be embodied as, for example, instructions stored in one or more memories coupled to the module control circuit 11506 and/or header control circuit 11508 that, when executed by the module control circuit 11506 and/or header control circuit 11508, cause the module control circuit 11506 and/or header control circuit 11508 to perform the enumerated steps of the process 11600. In the following description of the process 11600, reference should also be made to FIG. 38.

Accordingly, the module control circuit 11506 executing, at least in part, the process 11600 can generate 11602 data pertaining to its own functions or other functions of the modular energy system 11500. Some of the generated 11602 data can include safety critical data. If, for example, the modular 11502 is an energy module 2204, the safety critical data could include the power level at which a particular energy modality driven by the energy module 2204 is set or the mode in which the energy modality is being driven (e.g., cut, coagulation, or spray). As one can imagine, the energy module power level or operational mode is safety critical because applying too much energy or the wrong type of energy to the patient can cause injuries (e.g., by cutting tissue when the surgeon had intended to coagulate the tissue). Other safety critical data can include whether the module 11502 has detected a loose electrical connection within, to, or from the module 11502; whether the power consumption of the module 11502 has exceeded a threshold (e.g., the power threshold rated for the module 11502 according to the modules, surgical instruments, and/or tools connected thereto); whether the current drawn by the module 11502 has exceeded a threshold; and/or detection of an improper operational parameter (e.g., whether the power level or mode is in appropriate for detected tissue parameters or whether an incorrect type of scope has been connected to the visualization module 2042 (FIG. 28) for the surgical procedure type). UI content to be rendered/displayed by the header module 11504 based on such safety critical data can be verified to ensure that it is being accurately reported to users via the UI 2050. The module control circuit 11506 can then transmit 11604 the generated data for receipt by the header module 11504 via, for example, the data bus/interface 3008 (FIGS. 33-35). Any data generated 11602 by the module 11502 that is determined to be safety critical can include a label, tag, or identifier indicating its status as safety critical data when transmitted 11604 to the header module 11504.

Accordingly, the module control circuit 11506 can verify 11606 that the transmitted data was fully and/or correctly received by the header module 11502. In one aspect, the module control circuit 11506 can verify 11606 the correct receipt of the data via a checksum to identify errors that may occur during transmission or storage of the data transmitted to the header module 11504. This step of confirming that the data was correctly received by the header module 11502 can ensure that, if there is determined to be an error in the displayed UI content later in the process 11600, the module control circuit 11506 and/or header control circuit 11508 can determine whether the source of the error was with the data transmission process or an error by the header module 11504 in displaying the UI content.

Accordingly, the header control circuit 11508 executing, at least in part, the process 11600 can render 11608, 11610 any non-safety critical content and any safety critical content on the display screen 11510 via the UI 2050. The content rendered via the UI 2050 can take the form of text, numerals, icons, widgets, and any other indicia or UI element. For example, if the transmitted data includes the energy mode power level and mode, then that data can be displayed in the form of text and numerical UI content, as is shown in FIG. 30, for example.

In one aspect, the header control circuit 11508 can further check 11612 the health of the display screen 11510. This may involve, for example, ensuring that all electrical connections to the display 11510 are properly made, that the display 11510 has a homogenous image display with smooth gradients, and/or that the display 11510 does not have improper response times. If there is an issue with the health of the display 11510, the header control circuit 11508 can generate an alert to the user, such as an audible alert (e.g., ringing sound), a tactile alert (e.g. vibration), or some other suitable alert provided via a touchscreen 3046 (FIG. 33), a LCD 3048 (FIG. 33), and/or an audio output 3052 (FIG. 33). This step of checking the health of the display screen 11510 can ensure that, if there is determined to be an error in the displayed UI content later in the process 11600, the module control circuit 11506 and/or header control circuit 11508 can determine whether the source of the error was with the display screen 11510 itself or an error by the header module 11504 in causing the display screen 11510 to display the UI content.

Accordingly, the header control circuit 11508 can transmit 11614 to the module 11502 any rendered UI content that was based on data that was indicated as safety critical by the module 11502. As with the initial transmission of the data, the safety critical UI content can be transmitted 11614 to the module 11502 via, for example, the data bus/interface 3008.

Accordingly, the module control circuit 11506 can determine 11616 whether the displayed safety critical UI content coincides with the transmitted safety critical data. If it is determined that the displayed safety critical UI content does not coincide with the transmitted safety critical data, then the module control circuit 11506 and/or header control circuit 11508 can take a variety of different actions, including providing a visual, audible, and/or haptic alert to the user (e.g., via the display screen 11510), deactivating the module 11502, and/or deactivating a surgical instrument or tool coupled to the module 11502. For example, if the module 11502 is an energy module 2004 and the module control circuit 11506 determines 11616 that the displayed energy module power level does not coincide with the actual energy module power level, then the module control circuit 11506 can cause the energy module 2004 to de-energize the surgical instrument connected to the energy module 2004 (i.e., stopping delivering power thereto) and the header control circuit 11508 can cause the display screen 11510 to display an alert.

In this way, the process 11600 by and between the module control circuit 11506 and/or header control circuit 11508 provides a verification loop that allows the header module 11504 to passively display safety critical data received from the module 11502 (obviating the need for the header module 11504 to always receive system updates in concert with the module 11502), while still ensuring that safety critical content is being properly and correctly displayed to users.

In one aspect, the display screen 11510 can be directly or physically coupled to the header module 11504. In another aspect, the display screen 11510 can be a remote UI, such as a nurse's screen in a control tower in the operating room or a video overlay on an endoscope monitor, for example.

In one aspect, the verification loop embodied by the process 11600 can be executed across a secondary bus/interface separate from the bus/interface 3008 described in connection with FIGS. 33-35, which may or may not be dedicated to the verification of the display of safety critical UI content. The secondary bus/interface could serve as a back up to the bus/interface 3008 in case of a failure of the bus/interface 3008 to ensure that the modular energy system 11500 is monitoring and verifying any displayed safety critical UI content even in the event that the primary bus/interface 3008 of the modular energy system 11500 has failed.

Figure 39:
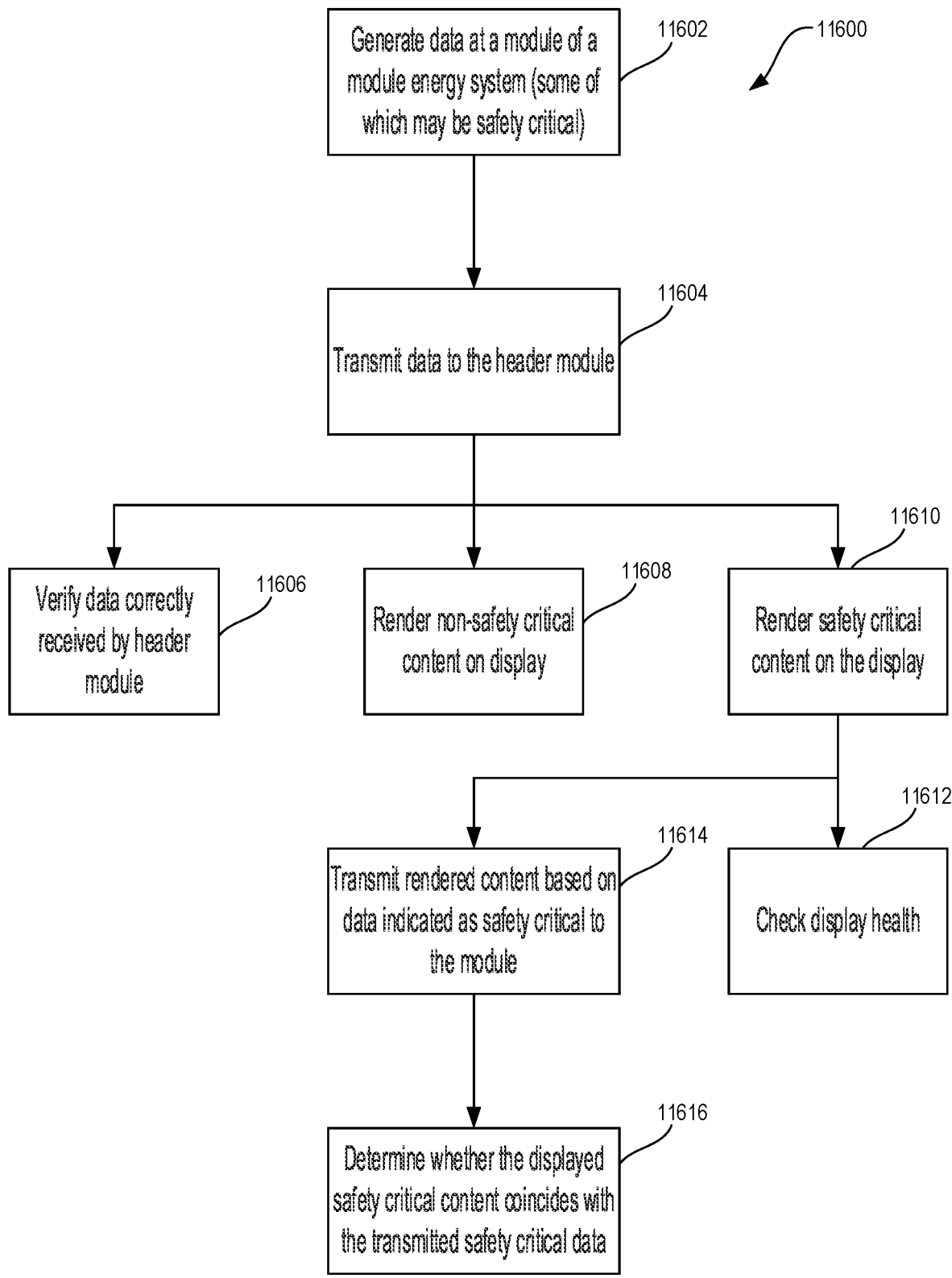
FIG. 39 is a logic flow diagram of a process for verifying displayed UI content, in accordance with at least one aspect of the present disclosure.

It should be further noted that although FIG. 38 illustrates a single module 11502 connected to the header module 11504 and the process 11600 described in connection with FIG. 39, the techniques described herein are equally applicable to modular energy systems 11500 including any number of modules connected to the header module 11504. In the event of there being more than one module being connected to the header module 11504, the described techniques can be executed by and between the header control circuit 11508 and any control circuits of the connected modules.

Energy Module Port Configurations

As discussed above under the heading MODULAR ENERGY SYSTEM, an energy module 2004 (FIGS. 24-30) can include a variety of different ports and associated circuitry that are configured to deliver various energy modalities, such as bipolar ports, monopolar ports, ultrasonic ports, and/or combination energy ports. Each type of energy port can have a different arrangement electrical contacts or pins, which can be referred to as a "pin out." In various aspects, the ports can have pin outs that allow them to engage with multiple types of electrical connectors having different plug or electrical connector arrangements. This can be beneficial because it allows ports to be able to flexible engage different types of electrical connectors, which in turn may have different numbers and/or arrangements of plugs or electrical connectors as dictated by the needs of the circuitry of the different surgical tools. However, ports that are able to engage multiple electrical connectors can create an issue because if a single port can engage with two different connector types, then the two different connectors could potentially be simultaneously engaged with the port unless the port's pin out is configured to prevent such a situation. Two electrical connectors for two different surgical instruments simultaneously being connected to and driven from a single port can be a dangerous situation because it can cause power fluctuations, arcing between the electrical connectors, and other issues.

In one general aspect, the monopolar port of an energy module can include a large diameter pin and a set of (e.g., three) small diameter pins that interfere so that a connector can only be engaged with one of the large diameter pin or the set of small diameter pins at a time.

Figure 40A:
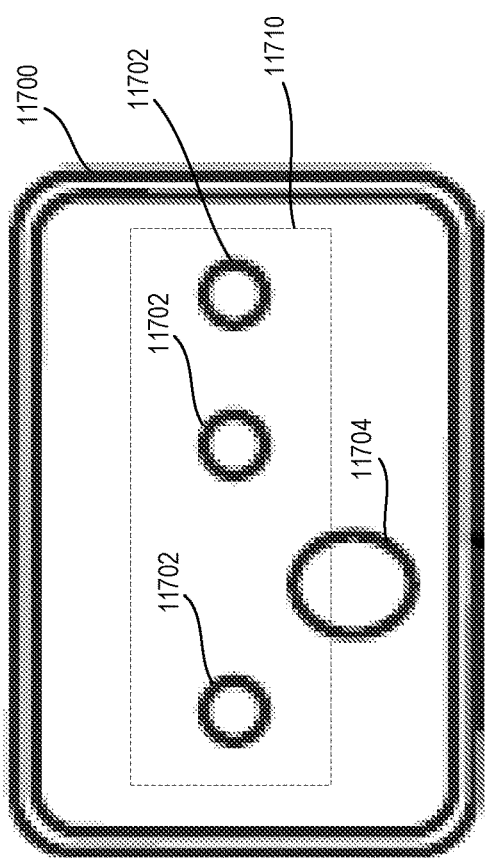
FIG. 40A is a monopolar port engaged with a first connector type, in accordance with at least one aspect of the present disclosure.
Figure 40B:
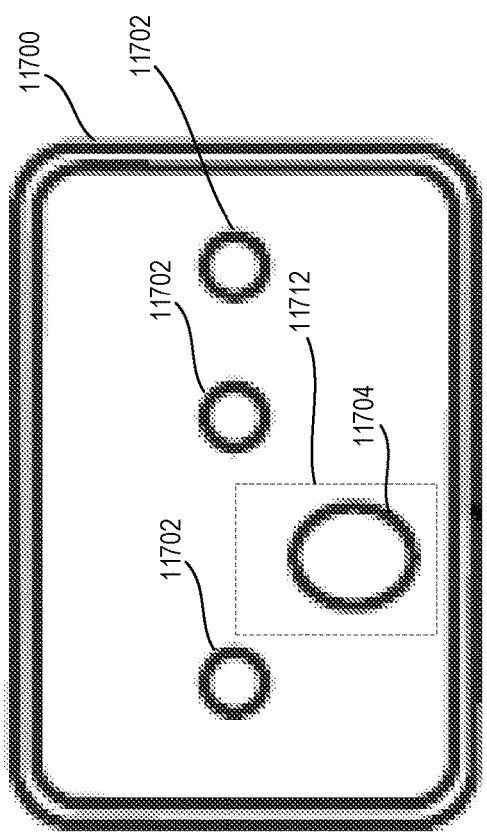
FIG. 40B is a monopolar port engaged with a second connector type, in accordance with at least one aspect of the present disclosure.

In one aspect, as shown in FIGS. 40A and 40B, the monopolar port 11700 can comprise different sets of electrical contacts that are configured to engage with different types of connectors. For example, the monopolar port 11700 can include a first set of one or more electrical contacts configured to engage a first connector type and a second set of one or more electrical contacts configured to engage a second connector type. The various electrical contacts can include receptacles or female contacts disposed on the surface of the monopolar port 11700 that are sized and shaped to receive a corresponding male contact of a particular connector type. The electrical contacts of the monopolar port 11700 can be circular or a variety of other shapes.

In the particular example shown in FIGS. 40A and 40B, the monopolar port 11700 can include a set of first electrical contacts 11702 that are configured to collectively engage with a first connector type 11710 and a second electrical contact 11704 that is configured to engage with a second connector 11712. The first electrical contacts 11702 can have a first diameter and the second electrical contacts 11704 can have a second diameter. In one aspect, the second diameter can be larger than the first diameter. Further, the first electrical contacts 11702 are positioned in a linear arrangement across the monopolar port 11700 and the second electrical contact 11704 is positioned offset from the longitudinal axis of the linearly arranged first electrical contacts 11702. The first electrical contacts 11702 and the second electrical contact 11704 are positioned relative to each other is selected such that a first connector 11710 engaged with the first electrical contacts 11702 obstructs the second electrical contact 11704, preventing or otherwise interfering with the ability of a second electrical connector 11712 to engage with the second electrical contact 11704, as is shown in FIG. 40A. Further, the first electrical contacts 11702 and the second electrical contact 11704 are positioned relative to each other is selected such that a second connector 11712 engaged with the second electrical contact 11704 obstructs the first electrical contacts 11702, preventing or otherwise interfering with the ability of a first electrical connector 11710 to engage with the first electrical contacts 11702, as is shown in FIG. 40B. In the particular example shown in FIGS. 40A and 40B, there are three first electrical contacts 11702 and the second electrical contact 11704 is arranged between a distal one of the first electrical contacts 11702 and a pair of the first electrical contacts 11702; however, different numbers and arrangements of the first and second electrical contacts 11702, 11704 are possible.

This interfering arrangement of the electrical contacts 11702, 11704 may advantageously improve the safety of a monopolar port 11700. Further, such an arrangement is additionally possible for other types of ports (i.e., ports configured to deliver different energy modalities). By preventing the user from inserting connectors for more than one monopolar electrosurgical surgical instrument, the risk of an electrical circuit overload of the monopolar energy port involving an electrical fire or unsafe power surge, for example, advantageously may be reduced or prevented.

Consolidated User Interface

One challenge with capital energy systems for surgical procedures is that they all include their own control interfaces. In addition to having to individually control each of the capital energy systems, users must also learn the individual nuances associated with controlling all of the various interfaces. This problem often cannot be avoided because surgical procedures regularly employ multiple different types of energy systems. Being forced to individually control every single energy system via a different control interface, each of which often has its own idiosyncrasies, slows down surgical procedures and introduces the possibility for errors if individuals are not fully accustomed to every single control interface with which they are forced to interact. As described above, the present disclosure describes a modular energy system configured to serve as a single, consolidated capital energy system for an OR. In conjunction with the modular energy system described hereinabove, it can further be beneficial to provide a single, consolidated UI for controlling all of the different modules that make up the modular energy system.

In various aspects, the present disclosure provides a visual interface for a modular energy system, which can include a header module that is removably connectable to a variety of different modules, such as an energy module, as is described above under the heading MODULAR ENERGY SYSTEM. The visual interface can be configured to change the appearance and size of module controls based on sensing connected module(s). Further, the visual interface can be configured to visually coordinate the activation status and ready status with the physical port of an energy module. The majority of the screen area of the visual interface can be dedicated to the main energy modules, with secondary modules placed in reduced menu states for occasional interaction. Further, the visual interface can provide alarms and notifications, which can overlap with the control interface(s) when alarms/notifications pop up.

In one aspect, the present disclosure also provides a modular energy system where user preferences can be stored and accessed through menus provided by the modular energy system visual interface in order to prepopulate device settings across multiple modules based on the procedure type selected by the user(s) (among other selection options).

Figure 41:
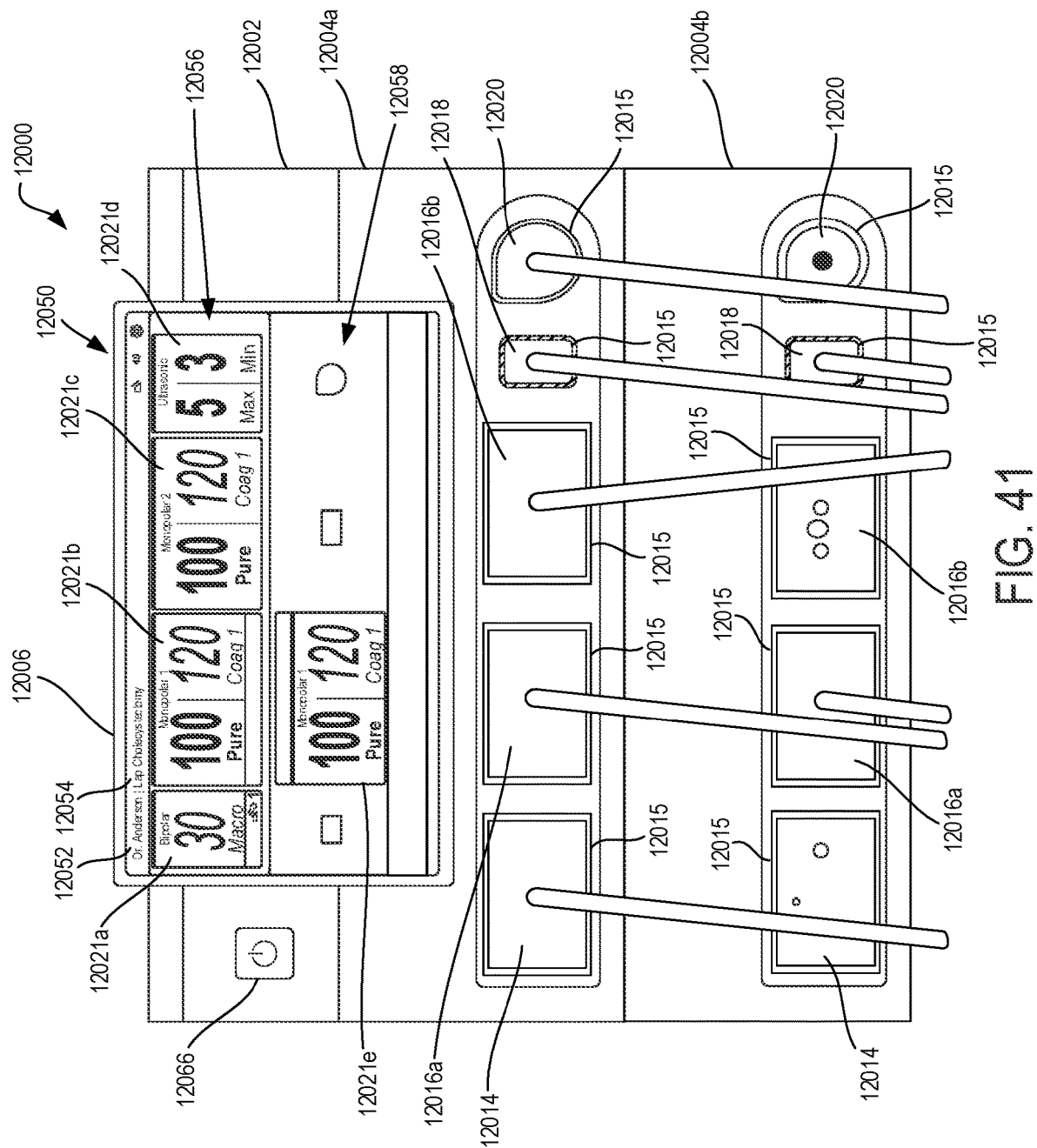
FIG. 41 is a front view of an illustrative modular energy system including a consolidated user interface (UI), in accordance with at least one aspect of the present disclosure.

FIG. 41 is a front view of an illustrative modular energy system 12000 including a consolidated UI, in accordance with at least one aspect of the present disclosure. The modular energy system 12000 can include multiple energy modules (shown in FIG. 41 with two energy modules 12004a, 12004b), a header module 12002, and a display screen 12006 supporting a UI 12050, as described above under the heading MODULAR ENERGY SYSTEM. The display screen 12006 can include a touchscreen for receiving user inputs and/or manipulating or controlling the UI 12050 displayed thereby. In some aspects, all of the modules that are connected to the header module 12002 can be controlled by a single UI (i.e., the UI 12050) that is disposed on or integral to the header module 12002. Consolidating all of the controls for the individual modules into a single, responsive UI that controls the module energy system 12000 as a whole provides a simpler way to control and monitor multiple pieces of surgical equipment at once. This approach drastically reduces footprint and complexity of surgical systems within an OR.

The modular energy system 12000 shown in FIG. 41 may be similar to other modular energy systems described herein such as modular energy system 2000. All of the modules that make up the modular energy system 12000 may be controlled by a single UI supported by or otherwise associated with the header module 12002. This may advantageously consolidate the control of all of the modules in the modular energy system 12000 into a single responsive UI, obviating the need to individually control each of the modules through their own UIs. As a result, the modular energy system 12000 beneficially may provide a simpler way to control and monitor multiples pieces of equipment simultaneously. In one aspect, the UI can be embodied as a graphical UI (GUI).

The modular energy system 12000 comprises a display screen 12006 that may be similar to other display screens described herein, such as the display screen 2006 described in connection with FIG. 30. In one aspect, the display screen 12006 can be structurally incorporated into the header module 12002 (which may be similar to header modules described herein, such as the header module 2002 described in connection with FIGS. 24-29). In other aspects, the display screen 12006 can be removably connectable to the header module 12002 and/or communicably connectable to the header module 2002 (e.g., via wired or wireless connections). The UI provided by the header module 12002 may comprise UI elements or components for displaying information to users and/or receiving inputs from users. The UI elements can include interactive components and/or noninteractive components, such as widgets, icons, or menus. The UI elements provided by the UI 12050 can be utilized to control system wide settings (e.g., system volume); settings, modes, or functions for energy modules 12004*a*, 12004*b* connected to the header module 12002; assignment or functions of accessories that are connected to the header module 12002; and so on. Further, the UI 12050 can be configured to indicate a variety of different information to users, such as the surgeon profile that is signed into the module energy system 12000, the surgical procedure type being performed, and so on. For example, as shown in FIG. 38, the UI 12050 displayed on the display screen 12006 can display the surgical procedure type 12054, which in the illustrated example is a laparoscopic cholecystectomy, and the name 12052 (or another identifier, such as an identification number or a user name) of the clinician performing the given surgical procedure. In addition to the UI 12050, the header module 12002 can additionally include physical controls for controlling the functions of the modular energy system 12000, such as a power button 12066.

To illustrate the concepts of the modular energy system UI, the modular energy system 12000 is depicted as including a first energy module 12004*a* and second energy module 12004*b* (which can be similar to energy modules described herein, such as the energy modules 3004,3012 described in connection with FIGS. 31-35) that are connected to the header module 12002 in a stacked configuration; however, the modular energy system 12000 is not limited to this or any other particular number, type, or arrangement of modules. As described above, the modular energy system 12000 can be arranged in a number of different configurations and include a variety of different modules. Further, the energy modules 12004*a*, 12004*b* can be configured to function as power and data interfaces between the header module 12002 and/or adjacent modules in the stacked configuration of the modular energy system 12002. Each of the energy modules 12004*a*, 12004*b* may include a port assembly 12012*a*, 12012*b*. The port assemblies 12012*a*, 12012*b* (which can be similar to the port assembly 2012 described in connection with FIG. 25A, for example) can include multiple different port types for delivering different energy modalities to corresponding surgical instruments that are connectable thereto, as described above. In one particular implementation, the port assemblies 12012*a*, 12012*b* may include a bipolar port 12014, a first monopolar port 12016*a*, a second monopolar port 12016*b*, a neutral electrode port 12018 (also referred to as a monopolar return pad port), and/or a combination energy port 12020; however, in other aspects, the port assemblies 12012*a*, 12012*b* can include other combinations of port types. Further, the modular energy system 12000 can include additional modules such as a technology module 2040 (FIG. 24) or a visualization module 2042 (FIG. 24), for example. These other modules can likewise serve as power and data interfaces between the header module 12002 and/or adjacent modules in the modular energy system 12002.

The UI 12050 displayed via the display screen 12006 may display a representation for each module connected to the modular energy system 12000. In one aspect, the UI 12050 can comprise UI components or elements that correspond to each of the modules connected to the header module 12002. As modules are connected and disconnected from the header module 12002, new UI elements for newly connected modules can be added to the UI 12050 and currently displayed UI elements fore disconnected modules can be removed from the UI 12050. Accordingly, the other UI elements displayed on the UI 12050 can be resized, repositioned, or otherwise reconfigured to accommodate the UI elements for newly connected modules or occupy the space on the UI 12050 vacated by the UI elements for disconnected modules. In other words, as modules are connected and disconnected from the modular energy system 12000, the illustrated graphical features on the UI 12050 can change. For example, the UI 12050 can alter to eliminate a display area for a module that is now disconnected from the modular energy system 12000. Conversely, as more modules are connected to the header module 12002, the display areas may scale or increase in number in corresponding relationship to the increase in connected modules. In general, the UI 12050 can provide a particular zone that is designated for each module connected to the header module 12002. Further, in one aspect, the arrangement or position of the modules' UI components within the UI 12050 can correspond to the physical arrangement of the modules within the stacked configuration of the modular energy system 12000 and/or the physical position of various components of the modules to which the UI components correspond, such that the UI 12050 visually coincides with the physical arrangement of the modular energy system 12000 so that the information and/or controls provide by the modules' UI elements can be easily located. Various techniques for detecting when modules are connected/disconnected from the modular energy system 12000 and modules' relative positions within the stack of the modular energy system 12000 are disclosed in U.S. patent application Ser. No. 16/562,142, titled METHOD FOR ENERGY DISTRIBUTION IN A SURGICAL MODULAR ENERGY SYSTEM, filed Sep. 5, 2019, now U.S. Patent Application Publication No. 2020/0078070, which is hereby incorporated by reference herein in its entirety.

As noted above, in one aspect, the UI 12050 can include a number of UI portions that correspond to the modules connected to the UI. For example, the UI 12050 illustrated in FIG. 41 includes a first UI portion 12056 that corresponds to the first module (which, in this particular example, is a first energy module 12004*a*) connected to the header module 12002 and a second UI portion 12058 that corresponds to the second module (which, in this particular example, is a second energy module 12004*b*) connected to the header module 12002. Further, in this particular example, the first UI portion 12056, which corresponds to the first energy module 12004*a*, can be located along an upper portion of the UI 12050 to coincide with the relative position of the first energy module 12004*a* within the modular energy system 12000. Similarly, the second UI portion 12058, which corresponds to the second energy module 12004*b*, can be located along a bottom portion of the UI 12050 to coincide with the relative position of the second energy module 12004*b* within the modular energy system 12000. Additionally, the various UI elements displayed in each UI portion can correspond to the type of module that the UI portion is dedicated to. For example, the first UI portion 12056, which corresponds to the first energy module 12004*a*, can include four UI elements 12021*a*-12021*d* that correspond to the bipolar port 12014, the first monopolar port 12016*a*, the second monopolar port 12016*b*, and the combination energy port 12020, respectively. In one aspect, the UI portion for a connected energy module can be configured to display the UI element 12021*a-d* corresponding to each of the ports 12014, 12016*a*, 12016*b*, 12020 of the first energy module 12014*a* only when a surgical instrument is connected thereto. In the example shown in FIG. 41, a surgical instrument is connected to each of the ports 12014, 12016*a*, 12016*b*, 12020; therefore, each of the corresponding UI elements 12021*a-d* are displayed on the UI portion 12056. Conversely, the second UI portion 12058 is only displaying a single UI element 12021*e* corresponding to the first monopolar port 12016*a* of the second energy module 12014*b* because the first monopolar port 12016*a* is the only port of the second energy module 12014*b* to which a surgical instrument is connected. When a surgical instrument is not connected to a particular port, the corresponding UI portion(s) 12056, 12058 can be configured to display, for example, static images, such as a shape corresponding to the shape of the unused port so that a user can easily ascertain which particular port type is unused. As with also be appreciated from the example shown in FIG. 41, the positions of the UI elements 12021*a-d* within the UI 12050 can further coincide with the relative physical position of the ports 12014, 12016*a*, 12016*b*, 12020.

The UI elements for energy modules can be configured to display information (e.g., operational parameters) related to the surgical instrument connected to the port 12014, 12016*a*, 12016*b*, 12020 associated with the particular UI element. For example, a first UI element 12021*a* indicates that the first energy module 12014*a* is set to energize the bipolar electrosurgical instrument connected thereto to deliver energy at 30 watts in a macro mode; a second UI element 12021*b* indicates that the first energy module 12014*a* is set to energize a first monopolar electrosurgical instrument connected thereto to deliver energy at 100 watts in a pure therapeutic cut mode and 120 watts in a first coagulation mode; a third UI element 12021*c* indicates that the first energy module 12014*a* is set to energize a second monopolar electrosurgical instrument connected thereto to deliver energy at 100 watts in the pure therapeutic cut mode and 120 watts in the first coagulation mode; a fourth UI element 12021*d* indicates that the first energy module 12014*a* is set to energize an ultrasonic surgical instrument connected thereto to deliver energy at a maximum power level five and a minimum power level three; and a fifth UI element 12021*e* indicates that the second energy module 12014*b* is set to energize a third electrosurgical monopolar instrument connected thereto to deliver energy at 100 watts in the pure therapeutic cut mode and 120 watts in the first coagulation mode. The power level of the ultrasonic instrument could be measured by the amperes of current delivered to the piezoelectric crystal contained within the instrument. Each of the various UI elements 12021*a-e* in the UI portions 12056, 12058 can display information associated with the respective energy module 12004*a-b* and/or surgical instrument connected thereto as long as that instrument is plugged into the modular energy system 12000. Further, the UI elements 12021*a-e* can also function as widgets that are manipulable or otherwise controllable by users to change the settings associated with the energy module 12004*a-b* and/or surgical instrument to which the UI element 12021*a-e* corresponds. For example, the UI elements 12021*a-e* can allow uses to change the amount of energy being delivered by the energy module 12004*a-b*, change the mode in which the surgical instrument is being operated.

Figure 36B:
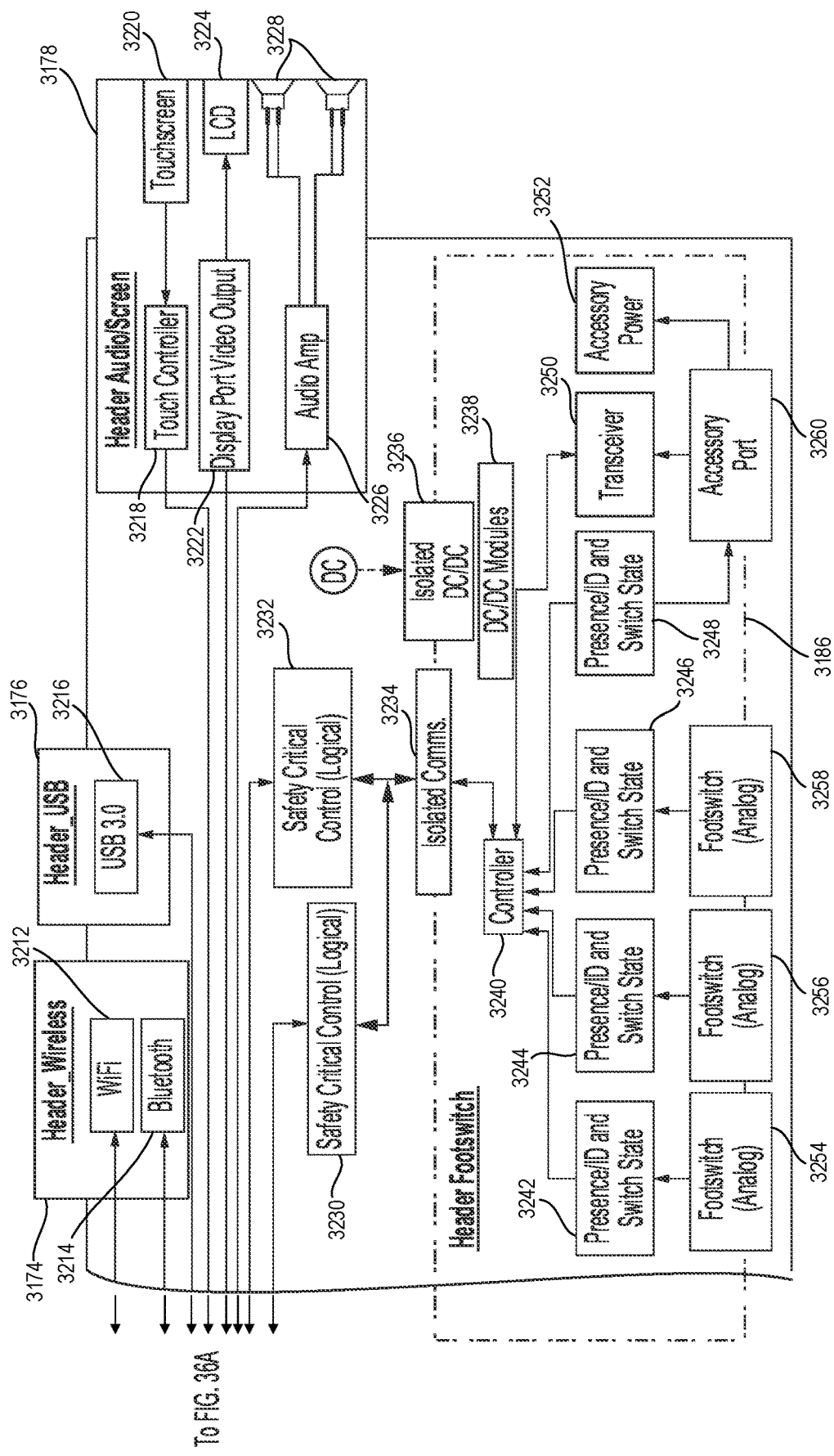
Figure 42:
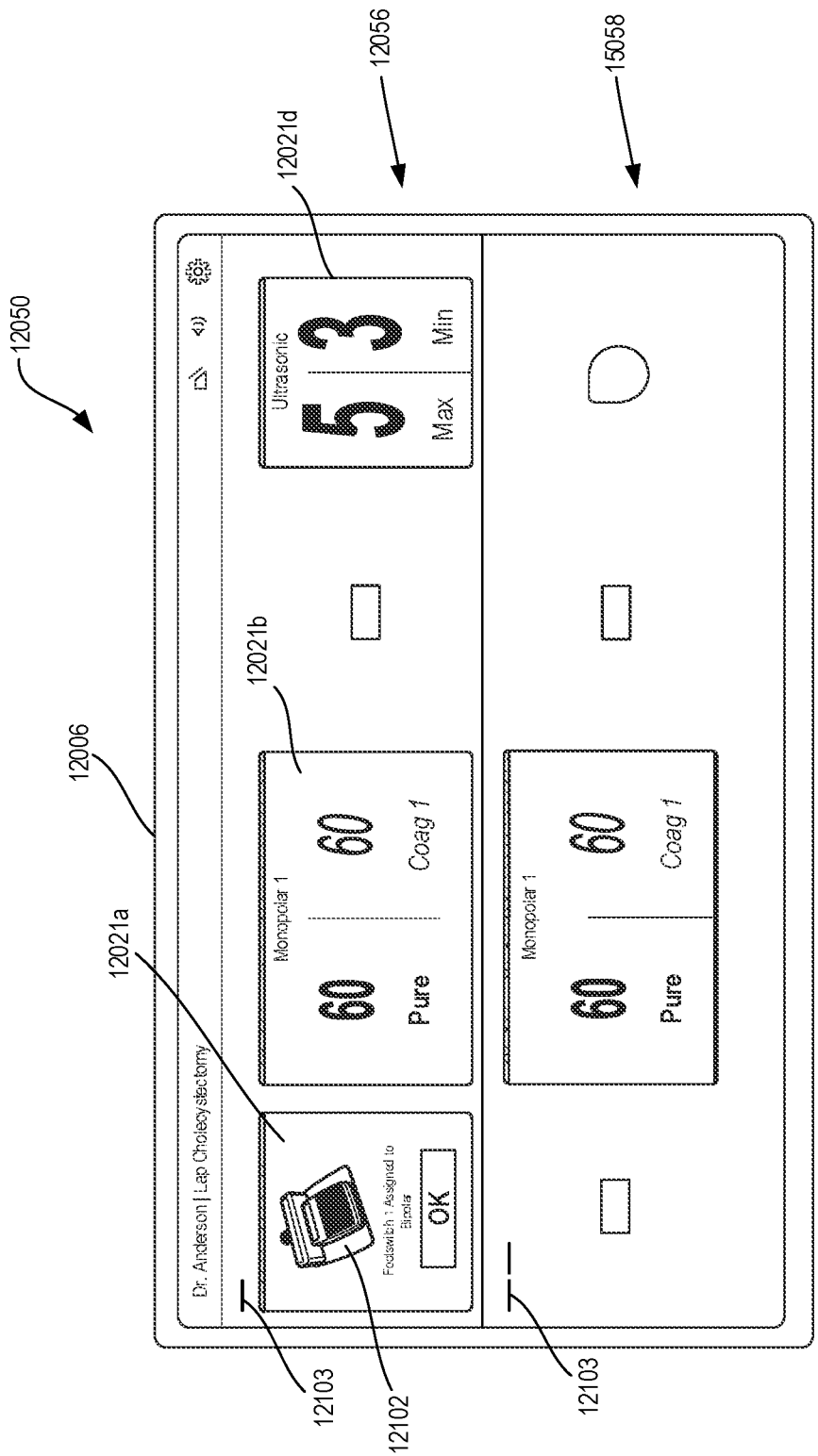
FIG. 42 is a view of a graphical UI of an illustrative modular energy system configuration, in accordance with at least one aspect of the present disclosure.

FIG. 42 is a view of a UI 12050 of an illustrative modular energy system configuration, in accordance with at least one aspect of the present disclosure. In one aspect, the UI 12050 comprises a footswitch assignment widget 12102. The UI 12050 can be configured to display the footswitch assignment widget 12102 when a user of the modular energy system 12000 has connected a surgical instrument or tool that requires connection to a footswitch, such as a single- or dual-pedal footswitch 2032, 2034 (FIG. 24). A control circuit of the modular energy system 12000, such as the control unit 3024 (FIG. 32) or the controller 3240 (FIG. 36B), can be configured to determine when a connected surgical instrument requires a footswitch and then control the UI 12050 to display a footswitch assignment widget 12102. In one aspect, the control circuit of the modular energy system 12000 can be configured to automatically assign a connected footswitch to a newly connected surgical instrument. As noted above, a footswitch or another accessory can be connected to the header module 12002 via an analog footswitch port 3254, 3256, 3258 (FIG. 36B). At this point, the footswitch assignment widget 12102 can be rendered on the UI 12050 to inform the user that a footswitch has been assigned to the connected surgical instrument, which, in the example shown in FIG. 42, is a bipolar surgical instrument. The footswitch assignment widget 12102 may be the same or similar to the control icon or widget displayed on the instrument settings panel of the surgical instrument that can be utilized to pair the surgical instrument with a system accessory, such as one of the footswitches 2032, 2034.

The UI 12050 can further comprise a location icon 12103*a-b* (or other UI element) indicating the position of the module within the stacked configuration of the modular energy system 12000 that the UI portions 12056, 12058 correspond to. As discussed above, the different UI portions 12056, 12058 of the UI 12050 can each correspond to a particular module connected to the header module 12002, in which each portion may display controls, data, user prompts, and other information corresponding to the particular module. In one aspect, the location icon 12103*a-b* can include a number of dashes or other indicia that indicates the particular module that the UI portion 12056, 12058 corresponds to. For example, one dash can correspond to the first or uppermost module within the stacked configuration of the modular energy system 12000, two dashes can correspond to the second energy module within the stacked configuration of the modular energy system 12000, and so on. Each dash of the location icon 12103 could also have a particular color or other indicia to differentiate the different location icons 12103 from each other. The color of the location icon 12103*a-b* can correspond to the UI portion or module with which it is associated. For example, the first UI portion 12056 and the corresponding first location icon 12103*a* could both include a first color (e.g., red), while the second UI portion 12056 and the corresponding second location icon 12103*b* could both include a second color (e.g., green).

In one aspect, the UI 12050 can be configured to coordinate the coloring of at least some of its UI components with the coloring of components of the modules connected to the header module 12002. For example, referring back to FIG. 41, each of the UI portions 12056, 12058 and/or associated UI elements 12021*a-e* can be configured to include or otherwise be coordinated with the colors emitted by light assemblies 12015 of the corresponding energy module 12004*a-b*. That is, the colors displayed by the UI 12050 can correspond to the port lighting of the energy modules 12004*a-b*. By coordinating the coloring between the physical components of the modules (e.g., the ports 12014, 12016*a*, 12016*b*, 12020 of the energy modules 12004*a-b*) and the UI components (e.g., the UI elements 12121*a-e*), the UI 12050 can allow users to quickly and easily ascertain which UI components are associated with which module components. The light assemblies 12015 may be similar to the light assemblies 2015 described above with respect to FIG. 30. Also, as described above, each of the light assemblies 12015 can be configured to change color when a plug of a surgical instrument or tool is fully inserted into a respective port of the port assembly, according to the mode or function of the surgical instrument, whether there is an error associated with the surgical instrument and/or the modules, and so on. Accordingly, the UI 12050 can be configured to change the coloring of the associated UI components to coincide therewith.

The UI portions 12056, 12058 and/or the UI elements 12021*a-e* rendered on the display screen 12006 can also change appearance and size based on sensing the connection of a module to the header module 12002. For example, the UI 12050 can change to display a first UI portion 12056 on the display screen 12006 that corresponds to the first energy module 12004*a* in response to the first energy module 12004*a* being connected to the header module 12002. Also, the lighting assemblies 12015 for each module and/or the UI portions 12056, 12058 can be used to visually coordinate the activation and ready status of the physical port that they are associated with. Further, the UI 12050 can further change to display a second UI portion 12058 of the display screen 12006 in response to the second energy module 12004*b* being connected to the header module 12002.

Figure 43:
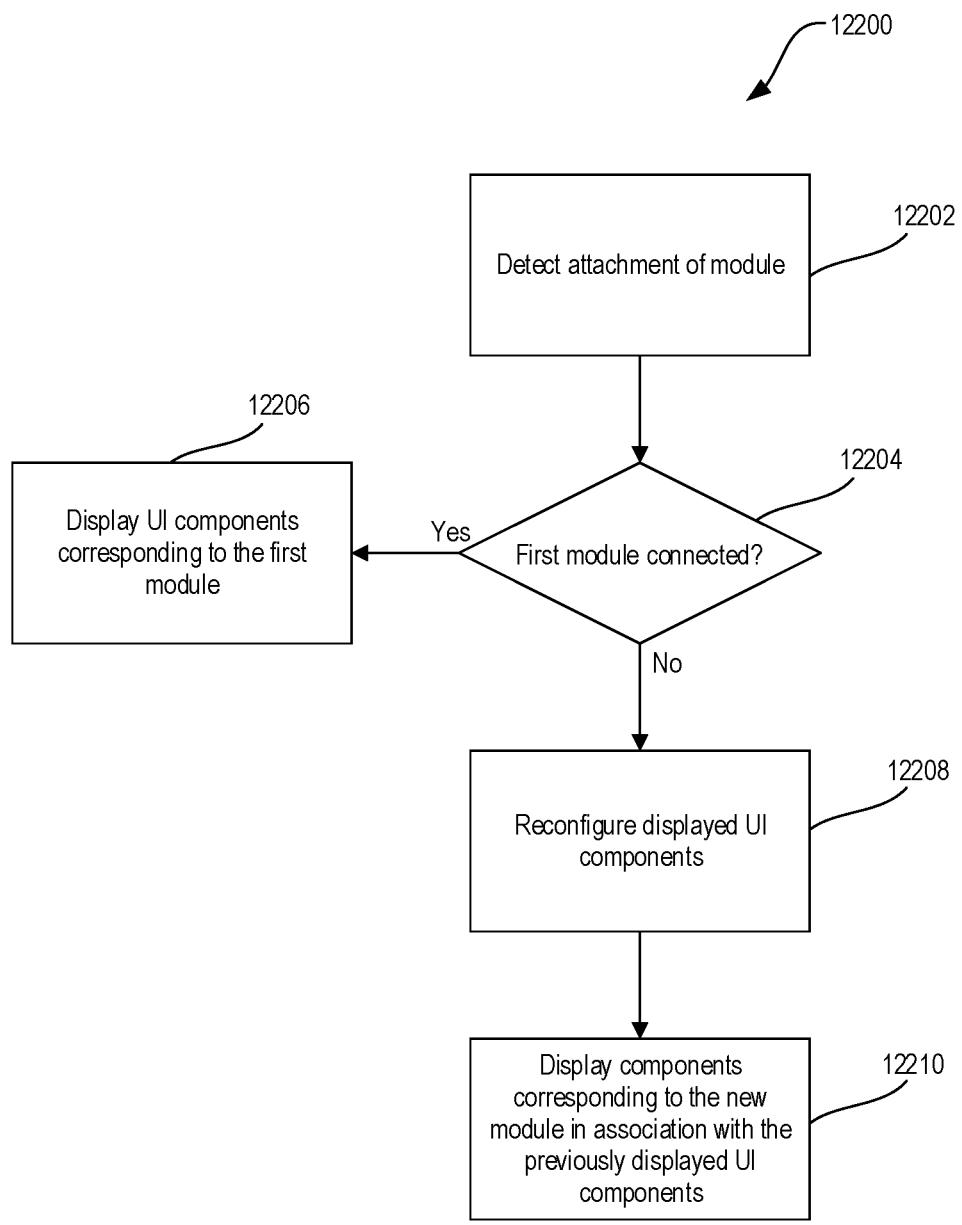
FIG. 43 is a logic flow diagram of a process for displaying UI components for connected modules, in accordance with at least one aspect of the present disclosure.

In one aspect, FIG. 43 is a logic flow diagram of a process 12200 for displaying UI components for connected modules, in accordance with at least one aspect of the present disclosure. The process 12200 can be embodied as, for example, instructions stored in a memory coupled to a control circuit (e.g., the control unit 3024 (FIG. 32) or the UI processor 3040 (FIG. 33)) that, when executed by the control circuit, cause the control circuit to perform the enumerated steps of the process 12200. In the following description of the process 12200, reference should also be made to FIGS. 41 and 42.

Accordingly, the control circuit detects 12202 attachment of a module, such as an energy module, to the header module 12002. The control circuit then determines 21204 whether the connected module is the first module that has been connected to the header module 12002, i.e., is the first module other than the header module 12002 in the modular energy system 12000 that is being assembled. If it is the first connected module, then the process 12200 proceeds along the YES branch and the control circuit, which is coupled to the display screen 12006, controls the display screen 12006 to display 12206 a UI component corresponding to the connected module type via the UI 12050. For example, the control circuit can cause the display screen 12006 to display the first UI portion 12056, including the associated UI elements 12021*a-d*, in response to the first energy module 12004*a* being connected to the header module 12002. If it is not the first connected module (i.e., there are already one or more modules connected to the header module 12002 in the modular energy system 12000), then the process 12200 proceeds along the NO branch and the control circuit controls the display screen 12006 to resize, reposition, or otherwise reconfigure 12208 the currently displayed UI components of the UI 12050 and display 12210 a UI component corresponding to the newly connected module type via the UI 12050. For example, the control circuit can cause the display screen 12006 to resize/reposition the first UI portion 12056 and its associated UI element(s) 12021*a-d* and correspondingly display the second UI portion 12058, including its associated UI element(s) 12021*e*, in response to the second energy module 12004*b* being added to the module stack of the modular energy system 12000. In this way, the UI 12050 can be configured to dynamically change according to the number and types of modules that are connected together to form the modular energy system 12000 and thereby provide a single, consolidated UI for collective controlling all of the connected modules.

Referring back to FIGS. 41 and 42, in one aspect, particular module types can be categorized within the UI 12050 as main or secondary modules. Secondary modules can be represented by smaller display areas on the display screen 12006. In particular, secondary modules can be placed in a reduced menu state so that they do not occupy an excessive amount of space on the display screen 12006 while remaining available for occasional user interaction. Further, the UI 12050 can comprise a particular area for displaying alarms and notifications as they are generated. For example, the alarms and notifications could be displayed along a top header portion of the display screen 12006.

In one aspect, the header module 12002 can further be configured to store user preferences, including prepopulated device settings across multiple modules in the modular energy system 12000. The UI 12050 can then be used to access these prepopulated device settings via UI menus. Additionally, the particular prepopulated settings can be determined by the modular energy system 12000 based on the surgical procedure selected by the user.

Modular Energy System Audio Techniques

Conventional surgical capital equipment can be designed to provide users with audiovisual feedback when surgical instruments driven thereby are activated or otherwise in use. For example, surgical capital equipment can be configured to output audible feedback when a surgical instrument is energized in order to ensure that the surgical staff is aware that the surgical instrument has been activated. In one implementation, this could take the form of an audio tone that is emitted by the capital equipment when an electrosurgical and/or ultrasonic surgical instrument connected thereto is energized. For conventional surgical capital equipment, when there are multiple different pieces of capital equipment within an OR that are actively in use, these activation tones can be distinguished from each other, even when the tones are very similar to each other, because of the fact that the capital equipment is located at different positions within the OR. Because the capital equipment generating the audio tones are located at different positions, this inherently creates different acoustic effects for each of the tones that allows the tones to be distinguished from each other. However, as is described above under the heading MODULAR ENERGY SYSTEM, the modular energy systems described herein are designed to replace the disparate pieces of surgical capital equipment and provide a single, consolidated system for driving all of the surgical instruments in use during a surgical procedure. This could create an issue with audio feedback because the different energy modules are located at a single location within the OR (namely, in the modular energy system stack), and thus, it could be challenging for users to differentiate between the same or similar tones being emitted from the modules because the tones are no longer originating from different locations within the OR. Therefore, there is a need for modular energy systems to implement various techniques to modulate audio feedback and/or generate unique audio feedback based upon the configuration of the modular energy system and other factors.

In one general aspect, a modular energy system can include at least two energy modules, which can each include multiple (e.g., four) ports. The modular energy system can be configured to construct unique audio signals for each port based on the number, type, and operational status of the connected modules. In one aspect, the signals can be constructed through modulation of at least two separate signals.

In one aspect, a modular energy system (e.g., the modular energy system(s) of FIGS. 24-37) can be configured to employ an audio control system that is configured to generate tones played by the modular energy system and confirm that the correct tone is being played for a given function being performed by the modular energy system. By ensuring that it is outputting the correct tone for each given function, the control system can prevent incorrect audio feedback from being provided to surgical staff members and other users during the course of a surgical procedure.

Figure 44:
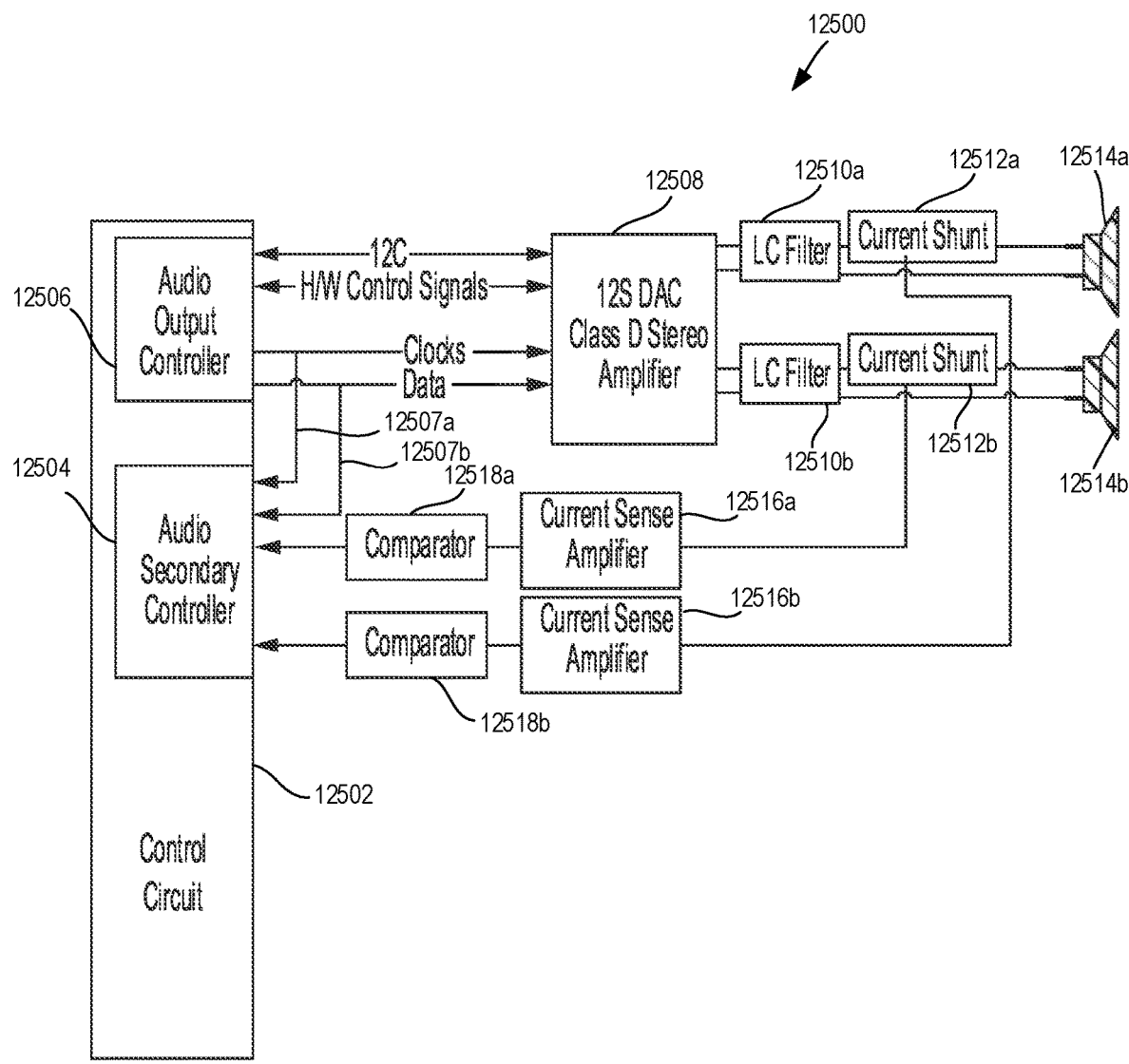
FIG. 44 is a block diagram of an audio control system for a modular energy system, in accordance with at least one aspect of the present disclosure.

For example, FIG. 44 is a block diagram of an audio control system 12500 for a modular energy system. The audio control system 12500 can include a control circuit 12502, which can in turn include an audio output controller 12506 and an audio secondary controller 12504. The audio output controller 12506 can be configured to generate audio signals, which can include digital audio signals, that are provided to an audio amplifier 12508 (e.g., a 12S digital-to-analog (DAC) class D stereo amplifier) for output by one or more audio output devices 12514*a-b* (e.g., speakers). The audio secondary controller 12504 is further coupled to the audio output controller 12506 via the circuit connections 12507*a-b*, such that the audio secondary controller 12504 receives the audio signals from the audio output controller 12506 prior to them being emitted by the audio output devices 12514*a-b*. In one aspect, the audio signal output by the audio output controller 12506 can include a segment that includes or represents an audio signal identifier (ID) that uniquely identifies the particular tone to which the audio signal corresponds. The audio signal output by the audio output controller 12506 can be generated from, for example, an audio file that includes the audio signal ID.

Accordingly, the audio secondary controller 12504 can receive, via the circuit connections 12507*a-b*, the signal, including the audio signal ID embedded therein, output by the audio output controller 12506. The audio signal ID, which can be embedded in extra bits of the digital audio signal output by the audio output controller 12506, can be used to confirm that the audio output controller 12506 is outputting an appropriate signal to the audio amplifier 12508 (i.e., that the audio output controller 12506 is attempting to play the proper tone). In one aspect, the audio secondary controller 12504 can be configured to compare the audio signal from the digital audio signal output by the audio output controller 12506 to an expected audio signal. In one further aspect, the audio secondary controller 12504 can be configured to compare the audio signal ID from the audio output controller 12506 to an expected audio signal ID to determine whether the correct signal is being output by the audio output controller 12506. In an alternative aspect, the audio secondary controller 12504 can be configured to compare the entirety of the output audio signal or the portion of the output audio signal utilized by the audio amplifier 12508 to create the audio tone to an expected audio signal to determine whether the correct signal is being output by the audio output controller 12506. The expected audio signal and/or audio signal ID against which the audio secondary controller 12506 compares the received actual output audio signal and/or signal ID can be determined by the audio secondary controller 12506 through independent knowledge of the modular energy system status or other processes.

The audio control system 12500 can further include one or more LC filters 12510*a-b* coupled to current shunts 12512*a-b* and the audio output devices 12514*a-b*. Further, the audio control system 12500 can include current sense amplifiers 12516*a-b* coupled to the current shunts 12512*a-b* and comparators 12518*a-b* coupled to the current sense amplifiers 12516*a-b*. The output of the comparators 12518*a-b* is coupled to the audio secondary controller 12504.

Accordingly, the audio secondary controller 12504 can receive, via the current shunts 12512*a-b* and associated components, a current measurement signal of the audio signal output by the audio amplifier 12508. In one aspect, the audio secondary controller 12504 can be configured to compare the current measurement signal to a threshold for determining if the audio amplifier output is within an expected intensity range. By determining whether the audio amplifier output is within the expected intensity range, the audio secondary controller 12504 can confirm that the audio amplifier 12508 is functioning at a sufficient level (i.e., is driving enough power to the audio output devices 12514*a-b*) and/or that the audio output devices 12514*a-b* are functioning and/or connected properly (i.e., the audio output devices 12514*a-b* are connected to the audio amplifier 12508 and based upon the lack of an open or short circuit).

In one aspect, the audio secondary controller 12504 can be configured to further or alternatively compare the direct output of the audio output controller 12506 and the output being fed to the audio output devices 21514*a-b* to confirm that the audio output devices 21514*a-b* are outputting the correct tone given the generated audio signal.

In yet another aspect, the audio secondary controller 12504 can be configured to identify the specific tone being output via the audio output devices 21514*a-b* according to the current measurement signal received from the current shunts 12512*a-b* and associated components. Accordingly, the audio secondary controller 12504 can be configured to determine whether the tone, which was determined via the current measurement signal, is appropriate for the given situation or modular energy system status. For example, the audio secondary controller 12504 can be configured to determine whether the correct activation tone is being played via the audio output devices 21514*a-b* when an instrument is activated/energized. Therefore, the audio secondary controller 12504 can ensure both that the tone is appropriate and that the audio amplifier 12508 is functioning properly.

Because a modular energy system (e.g., the modular energy system(s) of FIGS. 24-37) can include an energy module that can simultaneously energize multiple instruments and the activation or energization of each instrument can have a unique tone associated with it, the modular energy system can, in some situations, be outputting multiple overlapping tones. Further, the modular energy system could also output other tones associated with alerts or messages being provided to users that can overlap with other tones being output by the modular energy system. Because of the close proximity between the energy module(s) and the other audio-emitting modules of the modular energy system due to the nature of its stacked configuration, these overlapping tones could potentially interfere with each other or be difficult for users to audibly discern from each other. In one aspect, the modular energy system can be configured to generate unique audio outputs when multiple audio-emitting functions are being performed by the modular energy system. In other words, the modular energy system can be configured to generate a single unique audio output, rather than multiple overlapping audio outputs. Therefore, the modular energy system can ensure that all provided audible feedback is readily discernible by the users. In one further aspect, the unique audio output can be generated based upon the particular combination of tones that would otherwise have been output in an overlapping manner.

In one aspect, every audio file representing a tone output by the modular energy system can include an embedded ID that is unique to that audio file. The functions of the modular energy system that can be assigned audio files that are to be output when the functions are being formed can include, for example, energizing or activating a particular instrument type or providing a particular type of alert or message. Each different surgical instrument drivable by the modular energy system and alert/message that can be provided by the modular energy system could have a different tone associated with it in order to provide users confirmatory audible feedback as to each individual function type being performed by the modular energy system. In one aspect, each audio file can include a first series of bits (e.g., 16 bits) representing the digital audio signal for the tone and a second series of bits (e.g., 8 bits) representing the header or ID for the tone. Upon determining that a particular function is being performed by the modular energy system, the audio output controller 12506 can be configured to retrieve the appropriate audio file corresponding to the function and then pass a sequence of bits, including the digital audio signal and the associated ID to the amplifier 12508 (which ignores the ID bits when generating the output audio waveform). Accordingly, the audio secondary controller 12504 can be configured to read the output of the audio amplifier 12508 and ensure that the embedded ID corresponds to the appropriate audio file corresponding to a particular function being performed by the modular energy system, as is generally described above. The embedded audio file IDs can also be utilized in the process of generating unique tones from combinations of the individual audio files.

Figure 45:
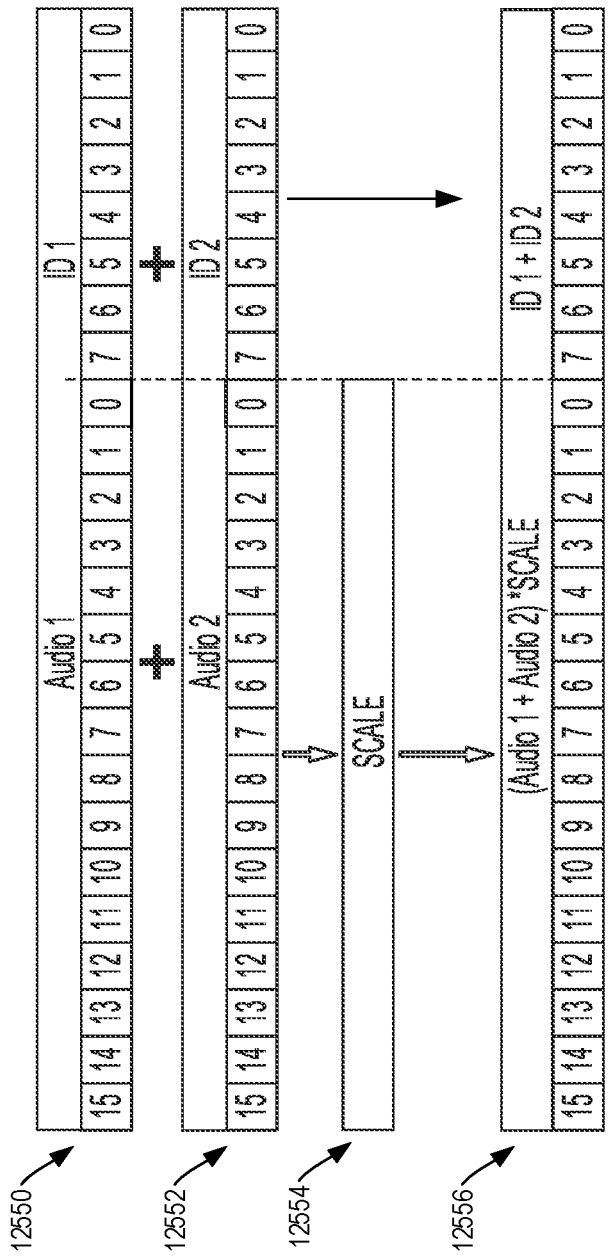
FIG. 45 is a diagram of a technique for generating unique audio outputs, in accordance with at least one aspect of the present disclosure.

In one aspect, the audio control system 12500 can be configured to generate unique tones that are based on particular combinations of individual tones for functions that are being simultaneously performed by the modular energy system. For example, FIG. 45 is a diagram of a technique for generating unique audio outputs. The technique embodied by FIG. 45 can be executed by the control circuit 12502 of the audio control system 12500 in FIG. 44, for example. In one aspect, the control circuit 12502 can be configured to generate a unique tone from a combination of individual tones that is output by the audio control system 12500 in lieu of the individual tones and provide a unique ID for confirming that the proper tone is being generated and output based upon the input individual tones.

In one aspect, the audio file IDs can be selected such that the sum of a given number of any of the IDs is not equal to any of the IDs. In other words, the IDs can be selected such that the sum of a given number of the IDs is a value that is unique from the selected IDs. One method for generating a list of such IDs is by considering each possible ID number from the lowest allowable ID to the highest allowable ID. In particular, each candidate ID can only added to a list of valid IDs if: (i) it is not equal to a sum of a combination of existing valid IDs and (ii) when summed with existing valid IDs (or a sum of a combination of existing IDs), the result is also not equal to other existing valid IDs or sums of combinations of IDs. This method guarantees that any number is either itself a unique individual ID or is a unique sum of a combination of IDs where the set of constituent individual IDs is exactly known. This method can be embodied as a set of steps, a closed-form or algorithmic mathematical expression, and so on. Ensuring that each combination of IDs is unique both from other combinations of the IDs and from the values of the IDs themselves allows the control circuit 12502 to differentiate between each particular combination of tones being generated by the audio control system 12500 and, thereby, verify that the correct tone is being played by the modular energy system for any combination of functions. For example, if two tones are being combined together, the IDs can include 1, 3, 7, 15, 25, 41, 61, 89, and so on. As can be seen in this example, the sum of any pair of the IDs is a unique value. Different IDs can be selected if three or more tones are being mixed or combined together, as the number of IDs being added together affects which particular values can be summed to produce unique values. TABLE 1, which is below, provides an approximation of the number of unique tone ID numbers that can be generated based upon the number of bits utilized for the audio file ID.

TABLE 1

| Number of ID Bits | Maximum Number of Unique Two-Tone Combinations | Maximum Number of Unique Three-Tone Combinations |
| --- | --- | --- |
| 8 | 15 | 7 |
| 16 | 137 | 52 |
| 20 | 388 | 145 |
| 24 | 647 | 393 |

Accordingly, the control circuit 12502 can retrieve a first audio file, represented by the first diagram element 12550, and a second audio file, represented by the second diagram element 12552. Each of the audio files includes a portion corresponding to the digital audio signal (i.e., "Audio 1" and "Audio 2"). In this particular example, the digital audio signal is 16 bits, but this is simply an example, and the audio portion is not limited to any particular number of bits. In an alternative aspect, instead of the audio portion representing a digital audio signal that is then fed to the amplifier 12508 for output thereby, the audio portion can represent a unique value or ID that corresponds to a tone that is retrievable by the control circuit 12502 from a memory. Further, each of the audio files includes a portion corresponding to the ID (i.e., "ID 1" and "ID 2") associated with each of the tones. In this particular example, the header or ID is 8 bits, but this is, once again, simply an example, and the ID portion is not limited to any particular number of bits (and indeed, TABLE 1 above provides examples of the ID alternatively being 16, 20, or 24 bits).

Accordingly, the control circuit 12502 can sum the IDs (e.g., using binary addition) from the retrieved audio files to generate a combination ID (i.e., "ID 1+ID 2"). Further, the control circuit 12502 can sum the audio portions (e.g., using binary addition) from the retrieved audio files and then apply a scale factor, represented by the third diagram element 12554, to generate a unique output tone (i.e., "(Audio 1+Audio 2)*SCALE"). The concatenated combined audio and ID portions are represented by the fourth diagram element 12556.

Accordingly, the audio output controller 12506 can be configured to pass the sequence of bits concatenated combined audio and ID portions, which are represented by the fourth diagram element 12556 and generated using the technique described above, to the amplifier 12508 (which ignores the ID bits when generating the output audio waveform). Accordingly, the audio secondary controller 12504 can be configured to read the output of the audio output controller 12506 and ensure that the embedded ID corresponds to the combined IDs of the audio files from which the audio output was generated. Because the audio file IDs were preselected such that each combination of the IDs produces a corresponding ID that is unique to that particular combination, the audio secondary controller 12504 can thus compare the output generated by the audio output controller 12506 to the summed IDs from the appropriate audio files and ensure that the output of the audio output controller 12506 is correct for the particular combination of tones.

It should be noted that although the technique illustrated in FIG. 45 is shown and described in the context of combining two individual tones to output a unique tone and ID, the technique should not be construed to be limited to the combination of two tones. As described above, the technique is also equally applicable to the combination of three or more individual tones to generate a unique tone and ID. Further, the technique illustrated in FIG. 45 can be either pre-generated or performed during run-time.

In one aspect, a modular energy system (e.g., the modular energy system(s) of FIGS. 24-37) can be configured to generate audio outputs that are differentiable by electronic systems according to an identifier signal embedded within a non-audible range of the generated audio output. Therefore, the modular energy system can be configured to confirm that it is playing the correct tone for a given action it is performing by isolating and comparing the identifier signal embedded within the audio output to the correct identifier for the action. Alternatively, other systems within the vicinity of the modular energy system could be configured to determine what actions the modular energy system is performing based upon the identifier signal embedded within the audio outputs thereof. Further, the identifier signal can be embedded within a non-audible frequency range so that the audible character of the tone is not altered.

Figure 46:
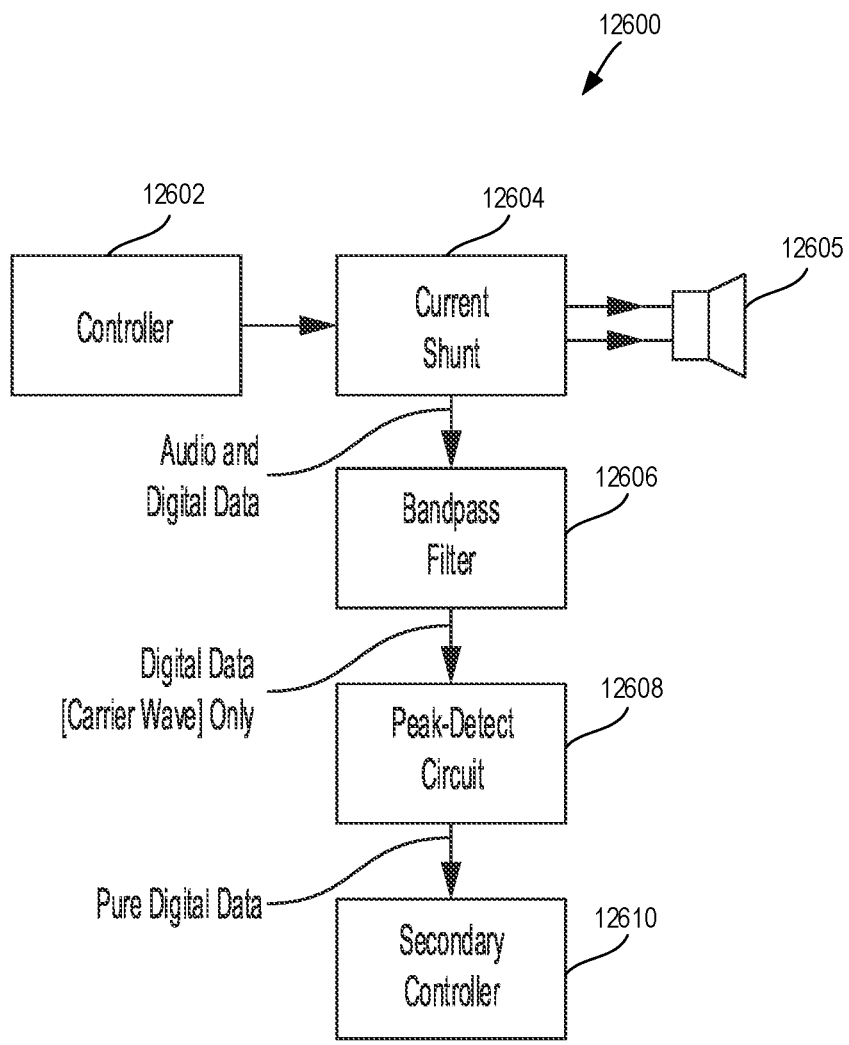
FIG. 46 is a block diagram of an audio control system for a modular energy system, in accordance with at least one aspect of the present disclosure.
Figure 47:
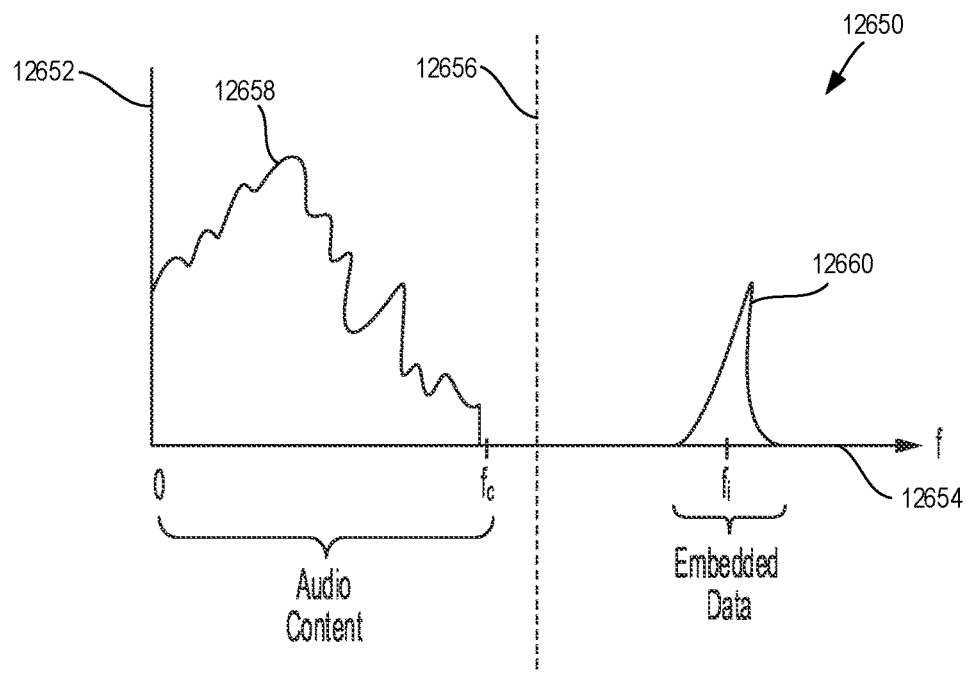
FIG. 47 is a graph of audio level versus frequency for an audio signal, in accordance with at least one aspect of the present disclosure.

For example, FIG. 46 is a block diagram of an audio control system 12600 for a modular energy system, in accordance with at least one aspect of the present disclosure. The audio control system 12600 includes a controller 12602 (e.g., a control circuit or a processor) coupled to an audio output device 12605. Further referring to FIG. 47, which is a graph of audio level (e.g., acoustic intensity level, which is measurable in dB), represented by the vertical axis 12652, versus frequency, which is represented by the horizontal axis 12654, for an audio signal, the controller 12602 can be configured to cause the audio output device 12605 to output an audible acoustic signal 12658, which is embodied as a tone or sound that is emitted based on the particular function or action that is being taken by the modular energy system (e.g., energizing a surgical instrument). This audible acoustic signal 12658 can vary depending upon the function of the modular energy system, the number and types of other tones being output by the modular energy system, and a variety of other factors, as described above. The audible acoustic signal 12658 can vary over a particular frequency range terminating at a frequency $f_c$, which is below the audible frequency threshold 12656 for human hearing. The controller 12602 can be further configured to embed an identifier acoustic signal 12660 within the audio output that is at a frequency or range of frequencies above an audible frequency threshold 12656 (e.g., 20 kHz). The identifier acoustic signal 12660 can be centered or based at a frequency $f_i$, which, as noted above, can be above the audible frequency threshold 12656 for human hearing.

Figure 48:
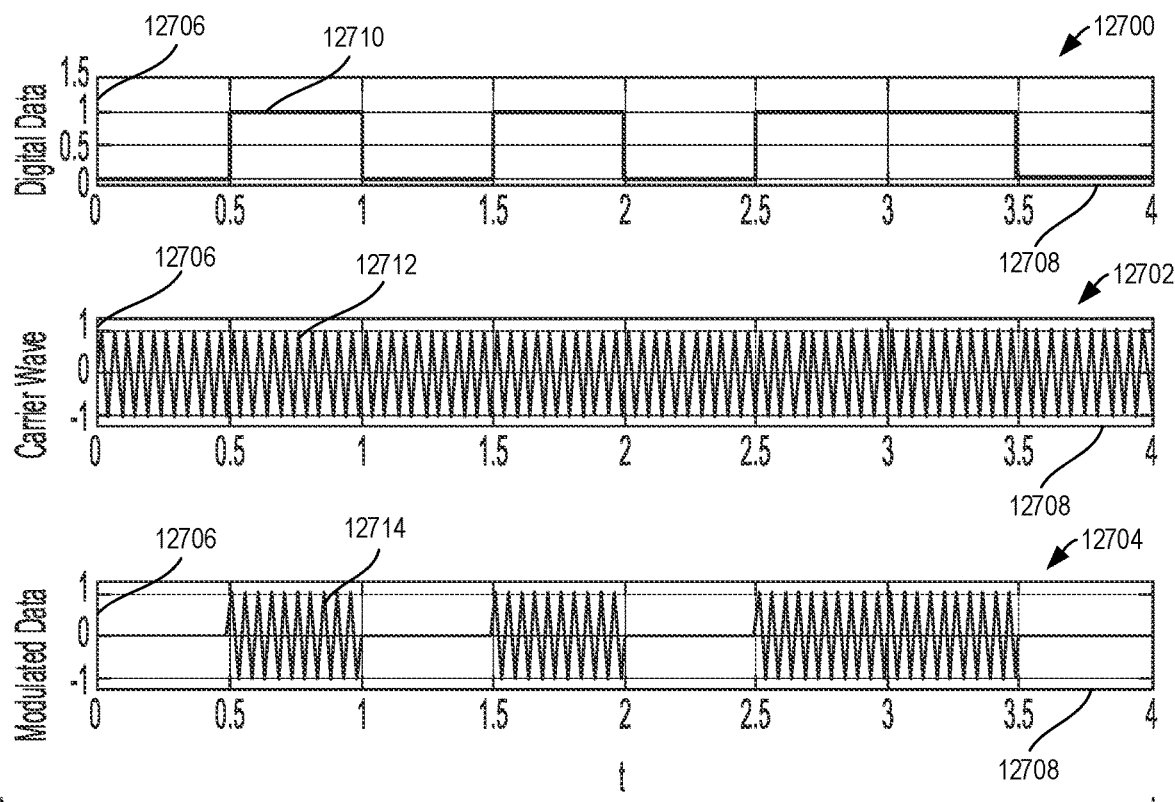
FIG. 48 is a series of graphs representative of a process for modulating a carrier wave to carry digital data, in accordance with at least one aspect of the present disclosure.

In one aspect, the identifier acoustic signal 12660 can be embodied as a digital signal encoding data, such as an identifier code indicating the function being performed by the modular energy system. The identifier acoustic signal 12660 can be embodied as a digital signal utilizing a variety of different techniques. For example, FIG. 48 is a series of graphs 12700, 12702, 12704 representative of a process for modulating a carrier wave 12712 to carry digital data. In each of the graphs 12700, 12702, 12704, the vertical axis 12706 represents signal amplitude, and the horizontal axis 12708 represents time. It should be noted that the values of the vertical and horizontal axes 12706, 12708 represent relative values and are provided only for illustrative purposes. The first graph 12700 represents the digital signal 12710 that can be output by the controller 12602. In this example, the digital signal 12710 represents an 8-bit identifier having a value of "01010110." Accordingly, this value can represent an identifier code unique to the action or function being performed by the modular energy system. Each different action or function can be assigned different identifiers so that they are uniquely differentiable by the modular energy system or an external system. Further, the second graph 12702 represents a carrier signal 12712, which can be at the frequency $f_i$, described above. Accordingly, the carrier signal 12712 can be modulated to encode the identifier represented by the digital signal 12710 to generate the modulated signal 12714 shown in the third graph 12704. Therefore, the modulated signal 12714, which is at the frequency $f_i$, can encode the identifier. In one aspect, this signal modulation technique can be performed "on the fly" by the audio control system 12600. In another aspect, the modulated signal 12714 can be pre-embedded within a file for the audio tone (e.g., a .wav file) so that the modulated signal 12714 is output by the modular energy system any time that the audio tone file is played.

Referring back to FIG. 46, the audio control system 12600 can further include a bandpass filter 12606 coupled to a current shunt 12604 coupling the controller 12602 to the audio output device 12605. The bandpass filter 12606 can be configured to pass frequencies within a particular range of the frequency $f_i$ of the identifier acoustic signal 12660, i.e., a range of $f_i$−x to $f_i$+y, where x and y are selected based upon the desired tuning of the bandpass filter 12606. Accordingly, the bandpass filter 12606 can pass the modulated signal 12714 for further processing. The audio control system 12600 can further include a peak-detection circuit 12608 and a secondary controller 12610 that are configured to detect the peak amplitude of the modulated signal 12714 for each particular time interval and thereby decode the modulated signal 12714 to ascertain the encoded identifier. In one aspect, the secondary controller 12610 can further be configured to determine the function being performed by the modular energy system for which the acoustic signal is being output, compare the decoded identifier to the stored identifier assigned to the function, and then determine whether the decoded identifier corresponds to the stored identifier. If the values do not correspond, then that can indicate that the modular energy system and/or the audio control system 12600 is causing the incorrect tone to be output for the given modular energy system function. The secondary controller 12610 can thereafter output a user warning (e.g., via a UI 2050 (FIG. 30)), cause the controller 12602 to change the tone being output via the audio output device 12605, and/or take another corrective action. Conversely, if the values do correspond, then that can indicate that the modular energy system and/or the audio control system 12600 is causing the correct tone to be output for the given modular energy system function. Accordingly, corrective actions are unnecessary and the second controller 12610 does not take any corrective actions. This process can be beneficial because it embeds an identifier within the audio output generated by the modular energy system without altering the audible character of the outputs, and a large number of digital identifiers can be encoded within the audio output (e.g., $2^n$ identifiers, where n is the number of bits in the digital signal 12710).

Figure 49:
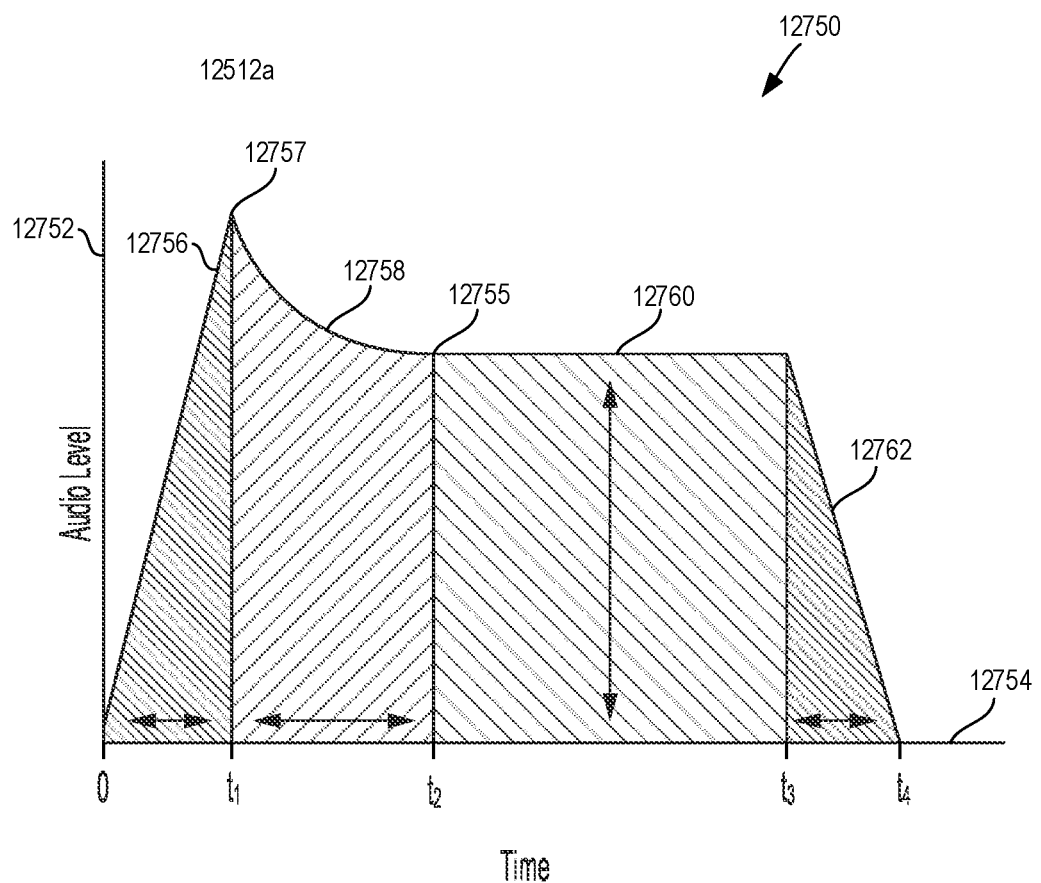
FIG. 49 is a graph of audio level versus time for an audio signal, in accordance with at least one aspect of the present disclosure.

In one aspect, a modular energy system (e.g., the modular energy system(s) of FIGS. 24-37) can be configured to modulate a generated tone to have distinct audio levels at different times of the tones. This can be utilized to, for example, cause the generated tones to have a higher audio level at the beginning of the tone in order to assist users in audibly distinguishing between multiple different tones that have been activated in a close proximity to each other or between tones that have been ongoing and newly activated tones. For example, FIG. 49 is a graph 12750 of audio level (e.g., acoustic intensity level, which is measurable in dB), represented by the vertical axis 12752, versus time, represented by the horizontal axis 12754, for an audio signal 12755. The audio signal 12755 can be generated by the audio control system 12500 illustrated in FIG. 44, the audio control system 12600 illustrated in FIG. 46, or any other such control systems.

In the illustrated implementation, the control system causes the audio level of the audio signal 12755 to increase sharply 12756 to a peak level 12757 during an initial time period from the point of initial activation of the audio signal 12755 to $t_1$. Thereafter, the control system causes the audio level to decay 12758 from time $t_1$ to time $t_2$ to a sustained level 12760, which is then maintained from time $t_2$ to time $t_3$. At time $t_3$, the control system then causes the audio level of the audio signal 12755 to decay 12762 to zero at time $t_4$ as the modular energy system completes the function associated with the audio signal 12755 or the audio signal 12755 is otherwise completed. For example, the control system can determine that a surgical instrument connected to the modular energy system has been activated, retrieve the appropriate audio file for the given surgical instrument type, and then cause the tone encoded by the audio file to be output at a higher audio level during an initial time period before decaying to a standard or sustained level for the tone. When the instrument is no longer activated, then the control system can halt playing the tone (i.e., the audio level for the phone will decay to zero, as shown in FIG. 49). By causing the audio signal 12755 to peak 12757 at a value higher than the sustained level 12760 during an initial time period, the control system can thus allow users to audibly distinguish between different tones being output by the modular energy system in a close proximity to each other because it creates an especially identifiable initial portion of the tone that coincides with the activation of the function with which the tone is associated. Therefore, users can distinguish between which tone corresponds to which function according to the sequence in which the initial portions of the tones are heard by the users. Further, users can distinguish between newly activated and ongoing tones according to the different audio levels of the initial portions of the newly activated tones and the ongoing tones.

Figure 50:
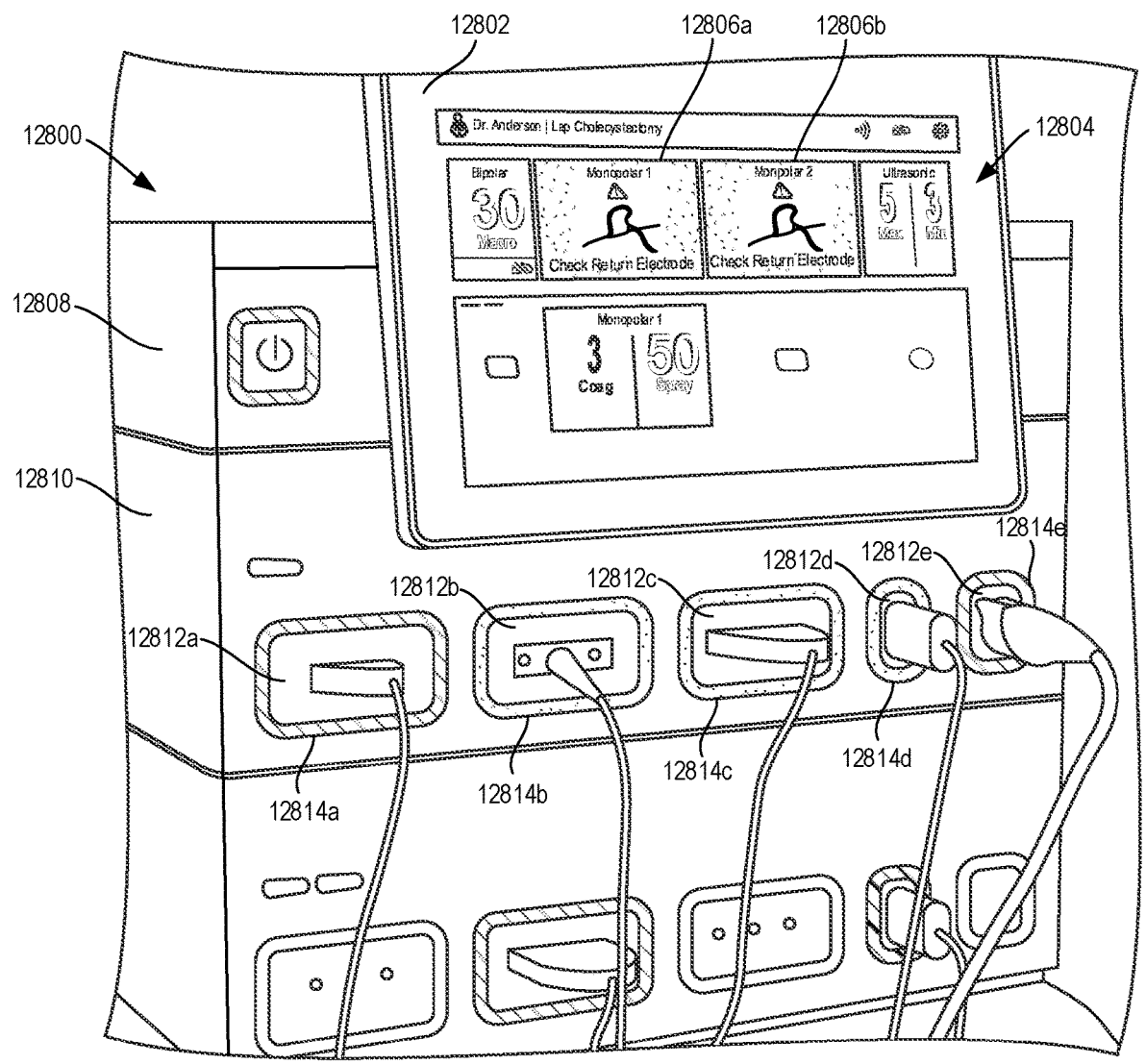
FIG. 50 is a perspective view of a modular energy system configured to provide audiovisual feedback to users, in accordance with at least one aspect of the present disclosure.

In one aspect, an example of which is shown in FIG. 50, a modular energy system 12800 can be configured to provide both audio and visual feedback in tandem with each other. As described above, a modular energy system 12800 can include a header module 12808 that can be connected to one or more energy modules 12810 or other module types. The header module 12808 and the energy modules 12810 can be configured to provide various types of visual feedback. For example, the header module 12808 can support or be associated with a display screen 12802, which can in turn display a UI 12804. The UI 12804 can in turn be configured to provide various information or alerts as feedback to users, such as "check return electrode" alerts 12806*a*, 12806*b*. Further, an energy module 12810 can include light piping elements 12814*a-e* disposed about its ports 12812*a-e*, which can be configured to light up in various colors, flash in particular patterns or sequences, or take other actions to convey information to users. In one aspect, the modular energy system 12800 can be configured to generate tones or audio signals in tandem with the visual feedback provided by the UI alerts, light piping elements 12814*a-e*, or other visual feedback provided by the modular energy system 12800. For example, the header module 12808 and/or energy module 12810 can be configured to determine when visual feedback is being provided and accordingly cause an appropriate tone to be generated by the modular energy system 12800. The generated tone can be generated or modulated by any of the techniques described hereinabove. For example, when a "check return electrode" alert 12806*a*, 12806*b* is being displayed on the UI 12804 and/or the light piping 12814*b-d* for the monopolar ports 12812*b-c* and the neutral electrode port 12812*d* is displaying an alert color indicating that there is an error with the return electrode, the modular energy system 12800 can be configured to correspondingly output a "check return electrode" tone. Further, the "check return electrode" tone can be unique and, thus, audibly distinguishable by users from other tones output by the modular energy system 12800 for other functions or alerts.

Footswitch Identification and Mapping

As surgical systems become more modular and capital equipment increases in capability and capacity, the number of permutations in which various pieces of surgical equipment can be connected and combined together is increasing. Additionally, more is required of surgical system accessories as the functionality of surgical systems increases. With conventional surgical equipment, users may have to continually disconnect and reconnect surgical system accessories between multiple different surgical systems (or components thereof) during the course of a surgical procedure. Therefore, there exists a need for surgical systems and accessories that are adaptable in their ability to connect to surgical systems (such as hubs and/or modular energy systems, as described above) and are configured to be electronically reassigned to various aspects of the surgical systems once physically connected thereto. Accordingly, in various non-limiting aspects of the present disclosure, a surgical system is provided that can adaptably connect to system accessories and reassign those system accessories once they are connected.

For example, in the non-limiting aspect of FIG. 25A, an energy module 2004 of a modular energy system includes a port assembly 2012 with a number of different ports configured to deliver different energy modalities to corresponding surgical instruments that are connectable thereto. A non-limiting example of an accessory that can be adaptably connected to such an energy module 2004 is a footswitch. Once connected, the footswitch could be electronically assigned and reassigned to any of the ports of the port assembly 2012 and used to activate various energy modalities of the energy module 2004. For example, a user may depress a pedal of a connected footswitch to activate a transducer, which causes a signal to be transmitted to the energy module 2004 to which the footswitch is connected, which in turn causes the generator to energize a surgical instrument connected to the port to which the footswitch is assigned. The footswitch could further include any number of pedals that can be configured to perform a particular function of the energy module. For example, in one non-limiting aspect, the footswitch could comprise a first pedal to activate and/or control an ultrasonic mode and a second pedal to activate and/or control an electrosurgical mode. As another example, the first pedal of the footswitch could be configured to activate and/or control a first monopolar mode and the second pedal could be configured to activate and/or control a second monopolar mode. These particular examples are provided for illustrative purposes only and other non-limiting aspects of the present disclosure include other pedals configured to perform other functions of an energy module of the surgical system. Accordingly, the footswitch pedals can be configured in various ways to accommodate a specific drive mode of the energy module or user preference.

In one aspect, the present disclosure provides a modular energy system that is configured to include multiple connected energy modules, which can each have at least one footswitch. The modular energy system can provide a footswitch interface configured to assign a compatible footswitch (or other control device) to a port on any of the connected modules, without physically changing the position of the footswitch connector.

Figure 51:
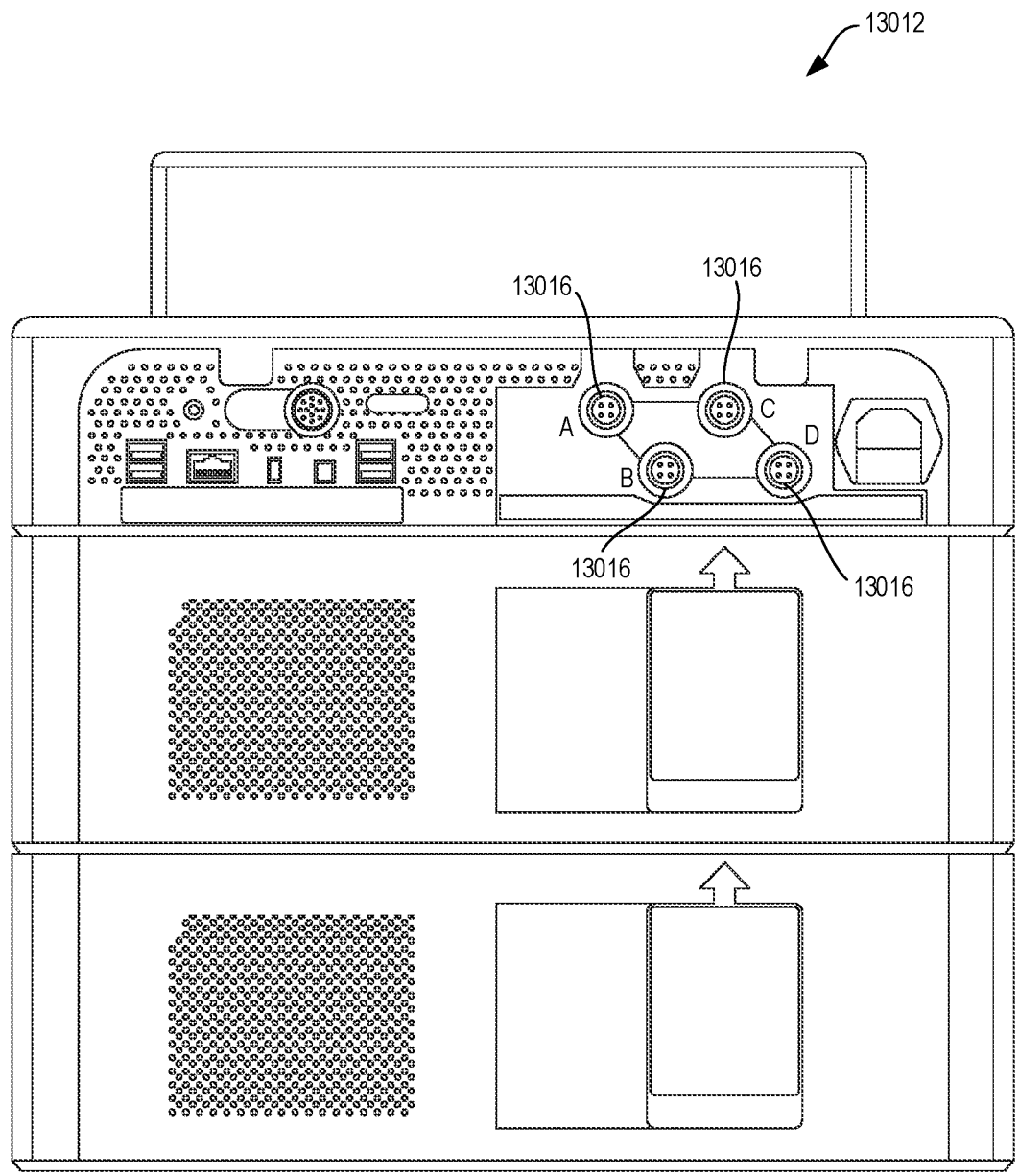
FIG. 51 is an energy module including a plurality of system accessory ports, in accordance with at least one aspect of the present disclosure.

Referring now to FIG. 51, a modular energy system 13012, including system accessory ports 13016 configured to accommodate the physical connection of a system accessory, is depicted in accordance with at least one aspect of the present disclosure. For example, a system accessory such as a footswitch can be connected to the modular energy system 13012 via the ports 13016. In one aspect, the ports 13016 of FIG. 51 are standardized and configured to accommodate any system accessory with a standardized connector. In other non-limiting aspects of the present disclosure, the ports are not standardized and each is specifically configured to accommodate a particular system accessory. The energy module of FIG. 51 includes four ports 13016. However, other aspects of the present disclosure include a varying numbers of ports 13016 configured to connect any number of footswitches. Likewise, although the ports 13016 of FIG. 51 are depicted on the back of a header module of the modular energy system 13012, other aspects of the present disclosure include ports located on the front, sides, and top of other modules of the energy module, among other locations. According to the aspect of FIG. 51, the ports 13016 can be labeled with indicia (e.g., "A," "B," "C," and "D") to better facilitate the physical tracking and mapping of the footswitches that are connected to the modular energy system 13012. For example, the user interface 13042 of FIG. 62 can include footswitch icons 13078 (FIG. 63) that include corresponding indicia (e.g., "A," "B," "C," and "D") that coincide with the ports 13016 of the modular energy system 13012, thereby indicating which footswitch icon 13078 corresponds to which connected footswitch. However, according to other non-limiting aspects of the present disclosure, alternate means of tracking and mapping each of the physical ports 13016 are used to track and map footswitches, including numbers, colors, textures, and other means of identification.

Figure 52:
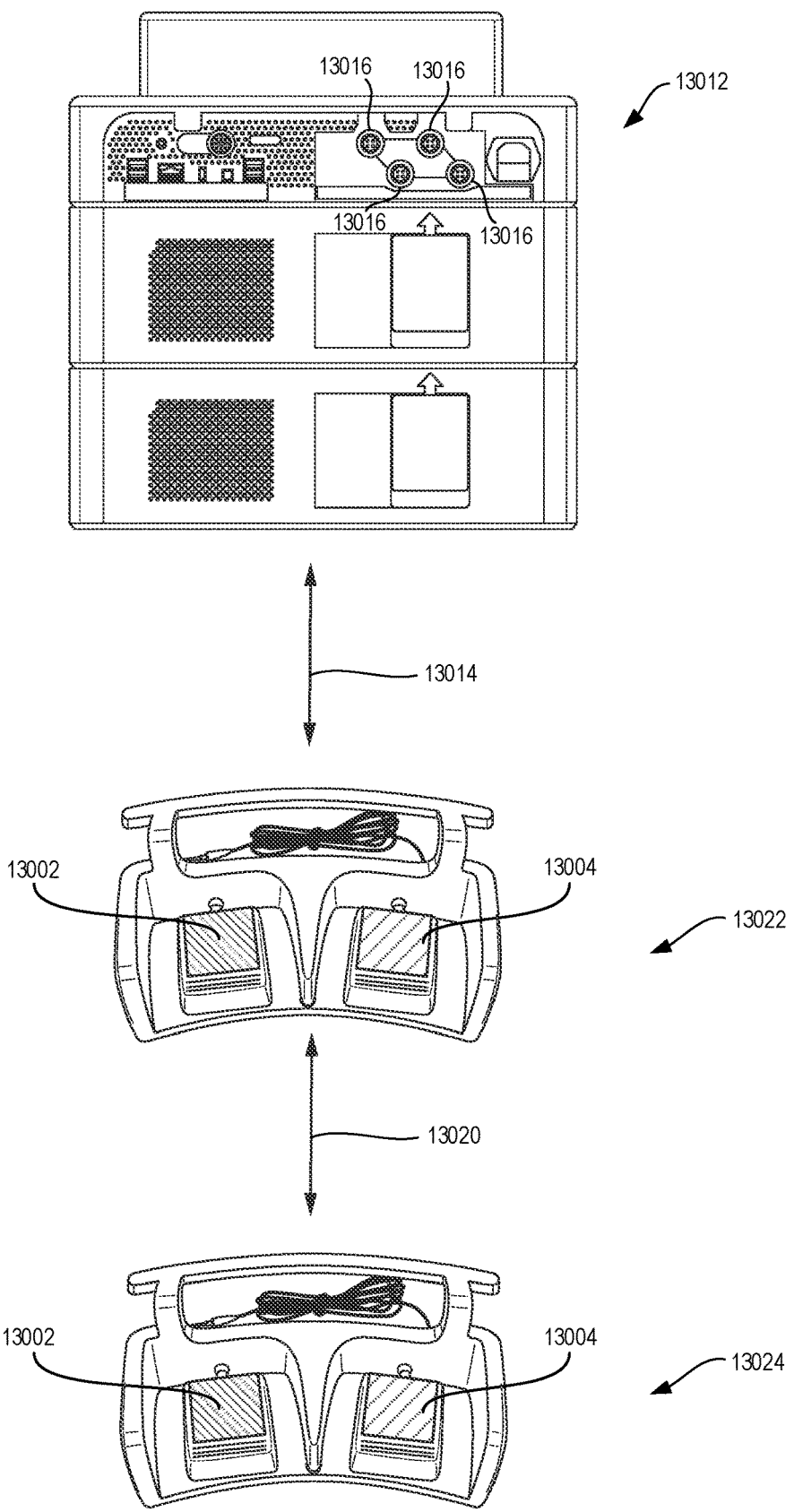
FIG. 52 is a diagram of footswitches physically connected to an energy module, in accordance with at least one aspect of the present disclosure.

Referring to FIG. 52, a diagram of a first footswitch 13022 and second footswitch 13024 physically connected to a modular energy system 13012 is depicted in accordance with at least one aspect of the present disclosure. According to the aspect of FIG. 52, the first footswitch 13022 and second footswitch 13024 can be physically connected via a first cable 13020, and one of the first footswitch 13022 or second footswitch 13024 can be physically connected to the modular energy system 13012 through one of the ports 13016 via a second cable 13014 such that both of the footswitches 13022, 13024 are physically connected to the modular energy system 13012 in a daisy-chained fashion. In other non-limiting aspects of the present disclosure, other footswitches and/or system accessories can be connected to the modular energy system 13012 through the first footswitch 13022 and/or second footswitch 13024. Accordingly, any number of footswitches and/or system accessories can be connected to the modular energy system 13012, regardless of how many ports 13016 the modular energy system 13012 includes.

Figure 53:
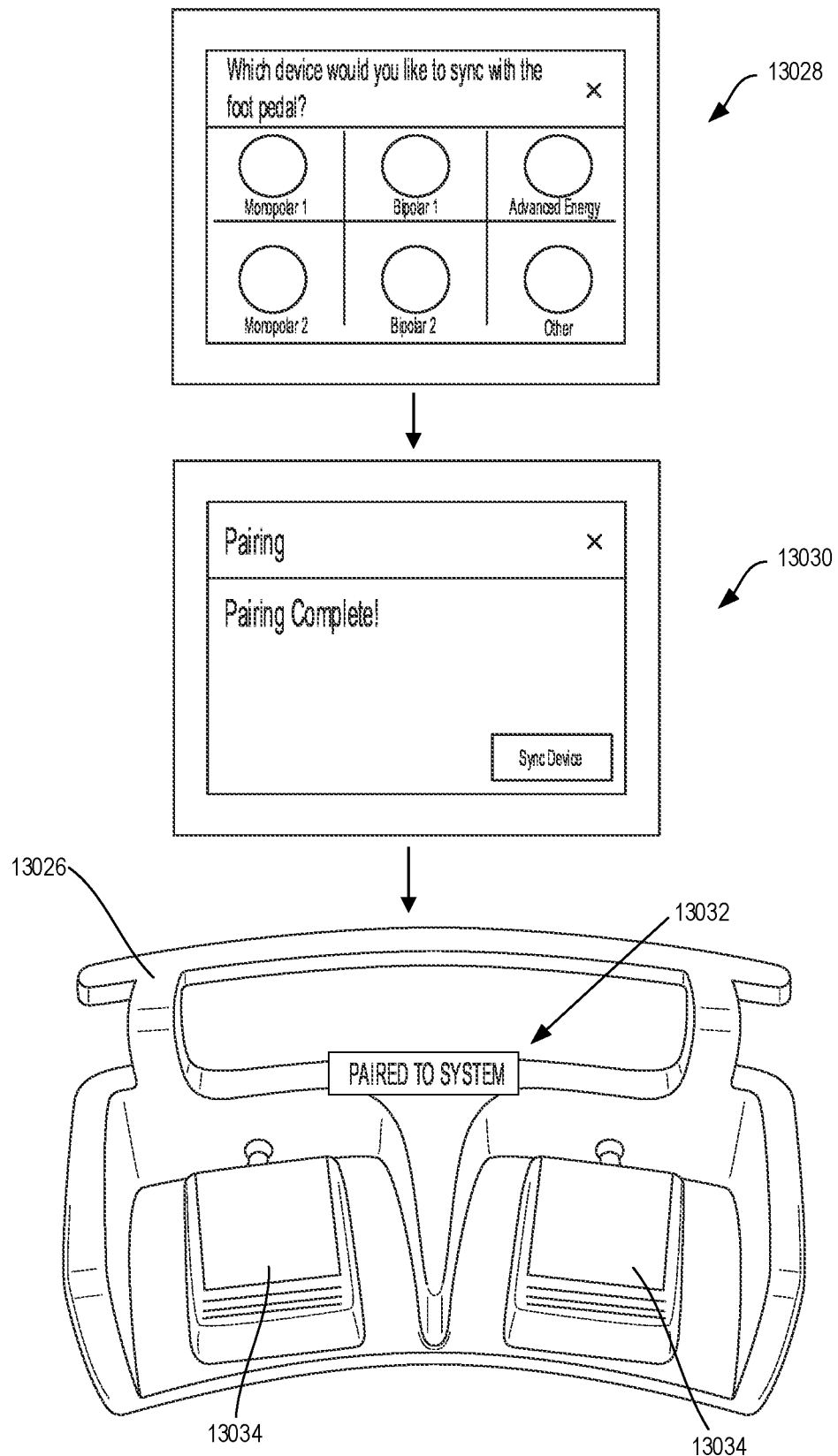
FIG. 53 is a diagram of a process of wirelessly connecting a footswitch to an energy module, in accordance with at least one aspect of the present disclosure.

Referring now to FIG. 53, a diagram of a process of wirelessly connecting a footswitch to an modular energy system is depicted in accordance with at least one aspect of the present disclosure. According to the non-limiting aspect of FIG. 53, a wirelessly enabled footswitch 13026 can include a wireless communication module and a wirelessly enabled modular energy system can includes wireless transceiver configured to receive and/or send a wireless signal. Thus, the wirelessly enabled footswitch 13026 can wirelessly communicate with and/or connect to a modular energy system via a variety of different wireless communication technologies, mediums (e.g., a wireless local access network (WLAN) or a cellular network), and/or communication protocols (e.g., Bluetooth or Wi-Fi). According to the aspect of FIG. 53, the wirelessly enabled footswitch 13026 can be connected to the modular energy system when a user initiates a pairing process via the user interface of the modular energy system. For example, the user interface can present the user with a pairing display 13028 that prompts the user to select a wirelessly enabled accessory, such as the footswitch 13026, that is recognized by the wirelessly enabled modular energy system. In FIG. 53, the user has selected the wirelessly enabled footswitch 13026 to pair with the wirelessly enabled modular energy system, and the user interface can present the user with a display 13030 confirming that the wireless connection was successful. Additionally, if the wirelessly enabled footswitch 13026 is configured with a reconfigurable display 13032, it can present the user with a confirmation that the wirelessly enabled footswitch 13026 has been successfully connected to the wirelessly enabled module energy system. The present disclosure further contemplates another aspect where the modular energy system 13012 and footswitches 13022, 13024 of FIG. 52 are wirelessly enabled in addition to being configured for physical connection. Accordingly, various system accessories and footswitches 13022, 13024 can be simultaneously connected to the modular energy system 13012, some via a physical connection and others via a wireless connection. As previously discussed, the modular energy system 13012 can automatically apply default settings to each of the first footswitch 13022 and second footswitch 13024 upon connection.

Referring now to FIGS. 54-58, various views of a modular energy system 13012 and user interface 13042 configured for use with a footswitch are shown in accordance with at least one aspect of the present disclosure. A footswitch and/or other system accessory can be connected to the modular energy system 13012 of FIGS. 54-58 using any of the aforementioned hardware and/or methods. Among other things, the modular energy system 13012 and user interface 13042 of FIGS. 54-58 can be used to assign and reassign connected footswitches and/or other system accessories to various ports of the energy modules 13041, 13043 without manipulating the physical connections and/or wireless connection settings between the system accessories and the modular energy system 13012. The modular energy system 13012 of FIGS. 54-58 includes a first energy module 13041 and a second energy module 13043. However, the present disclosure contemplates other aspects, including any number of energy modules. The energy modules 13041, 13043 include ports 13036, 13038a, 13038b, 13039, 13040 that are similar to those depicted in the port assembly of FIG. 25A. For example, the energy modules 13041, 13043 each include a bipolar port 13036, a first monopolar port 13038a, a second monopolar port 13038b, a neutral electrode port 13039, and a combination energy instrument port 13040. However, the principles discussed herein are not limited to the aforementioned ports and can be applied to any other port and/or combination of ports of the modular energy system 13012.

The modular energy system 13012 of FIGS. 54-58 further includes a user interface 13042, which displays an icon 13046, 13048a, 13048b, 13050 associated with some of the ports 13036, 13038a, 13038b, 13040 of each of the energy modules 13041, 13043. As used herein, an icon is a virtual representation of a component of the modular energy system 13012, system accessory, or instrument. For example, an icon can include an image, shape, color, and/or any combination thereof to help the user identify the component, system accessory, or instrument it represents. Specifically, for energy modules 13041, 13043 having the illustrated port arrangement, the user interface 13042 accordingly includes a bipolar port icon 13046, a first monopolar port icon 13048a, a second monopolar port icon 13048b, and a combination energy port icon 13050 for each of the energy modules 13041, 13043. The icons are arranged in a first row 13051 and a second row 13053, corresponding with the first energy module 13041 and the second energy module 13043, respectively. However, alternate arrangements of icons 13046, 13048a, 13048b, 13050 are further contemplated by the present disclosure. The user interface 13042 further displays whether a connected instrument is footswitch compatible via a global footswitch-enabled port icon 13045. Thus, the user can easily identify which of the ports 13036, 13038a, 13038b, 13040 are compatible with a footswitch and/or other system accessory by locating which of the various port icons 13046, 13048a, 13048b, 13050 are marked with or include a global footswitch-enabled port icon 13045.

Figure 54:
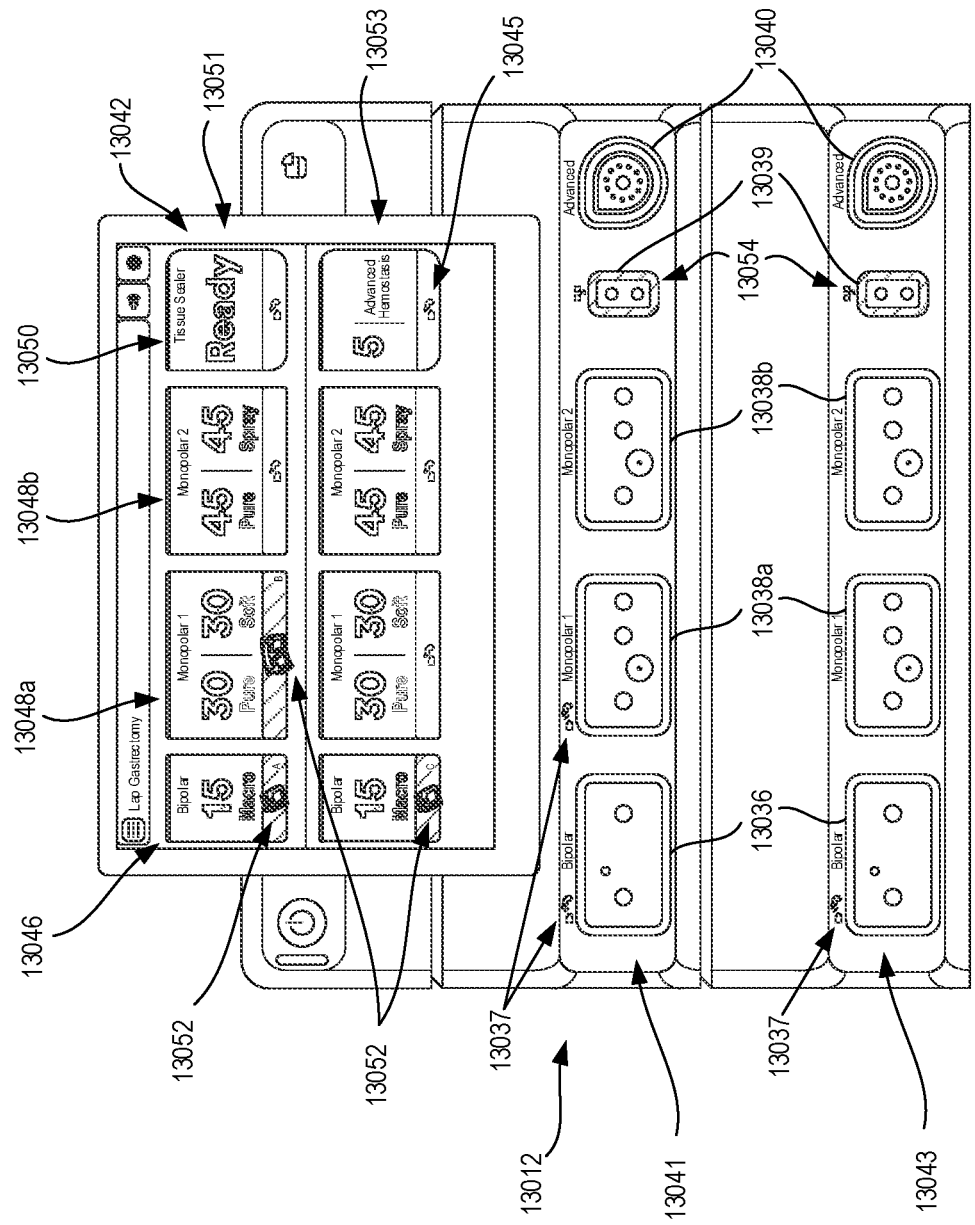
FIG. 54 is a front view of an energy module, in accordance with at least one aspect of the present disclosure.

The user interface 13042 of FIGS. 54-58 can be further configured to display a footswitch widget 13052 either on or in association with the various port icons 13046, 13048a, 13048b, 13050. The footswitch widget 13052 indicates that a footswitch has been assigned to the particular port 13036, 13038a, 13038b, 13040 corresponding to the port icon 13046, 13048a, 13048b, 13050 with which the footswitch widget 13052 is associated. Further, the footswitch widget 13052 can be manipulated by a user (through the display screen 2006, which can include a touchscreen) to electronically change which of the ports 13036, 13038a, 13038b, 13040 the particular footswitch is assigned to. As used herein, a widget is a software component that the user can interact with through direct manipulation, thereby directing a control circuit (e.g., the system control unit 3024 (FIG. 33) or the UI processor 3040 (FIG. 33)) configured to control the display screen 2006 (FIG. 30) and/or the user interface 13042 displayed thereon to execute a desired instruction. In FIG. 54, the user interface 13042 displays a footswitch widget 13052 on both bipolar port icons 13046 and the first monopolar port icon 13048a of the first row 13051. This indicates that footswitches have been assigned to the bipolar ports 13036 of the first and second energy modules 13041, 13043 and the first monopolar port icon 13048a of the first energy module 13041. The footswitch-assigned instrument port widget 13052 can be specifically tailored to correspond to the exact footswitch and/or other accessory that is assigned to the port. For example, the footswitch widget 13052 can include a visual display of a single-pedal footswitch or two-pedal footswitch, depending on what type of footswitch is assigned to that instrument.

In one aspect, the user interface 13042 can allow users to reassign any footswitches connected to the modular energy system 13012 by manipulating the widgets 13052 or other control elements displayed via the user interface 13042. For example, the user can drag and/or otherwise attach a footswitch-assigned port widget 13052 of FIG. 54 to any of the port icons 13046, 13048a, 13048b, 13050, including a footswitch-enabled port icon 13045, thereby instructing the control circuit to reassign that footswitch to a different port 13036, 13038a, 13038b, 13040. The control circuit can be coupled to the user interface 13042 and can be further configured to control the energy module(s) 13041, 13043 and/or surgical instrument(s) connected thereto based on the port icon 13046, 13048a, 13048b, 13050 on which the footswitch-assigned port widget 13052 is placed. This process will be described in further detail in the forthcoming discussion of FIGS. 46-50. After a footswitch has been reassigned to a new port, the user interface 13042 can be further configured to provide a confirmation that the reassignment was successful. Accordingly, the previously assigned port icons 13046, 13048a, 13048b, 13050 will no longer display a footswitch widget 13052 and will instead display a footswitch-enabled port icon 13045.

Still referring to FIG. 54, once a footswitch has been assigned to an instrument, the user interface will illuminate the port icon 13046, 13048a, 13048b, 13050 a "confirmation" color. The "confirmation" color is represented via crosshatching in FIG. 54. Likewise, the modular energy system 13012 can illuminate a light tube 13054 surrounding the port 13036, 13038a, 13038b, 13040 to which the assigned instrument is connected. In one aspect, the confirmation color displayed via the user interface 13042 for a particular port icon 13046, 13048a, 13048b, 13050 can coincide with the color that the light tube 13054 is illuminated for the corresponding port 13036, 13038a, 13038b, 13040. For example, the footswitch-assigned port widget 13052 and/or the port icons 13046, 13048a associated therewith can be illuminated a color (e.g., green), indicating that a footswitch has been assigned to the corresponding ports. In one aspect, the modular energy system 13012 can further or alternatively illuminate a footswitch assignment indicator 13037 associated with each of the bipolar ports 13036 of the first and second energy modules 13041, 13043, and a footswitch assignment indicator 13037 associated with the first monopolar port 13038a of the first energy module 13041 green, thereby confirming that a footswitch has been assigned to those ports. In another aspect, the light tubes 13054 surrounding the neutral electrode port 13039 of the first and second energy modules 13041, 13043 can also be illuminated a color (e.g., green), confirming that the neutral electrode return has been successfully connected to the modular energy system 13012. By having the colors directly associated with the energy ports (via the light tubes 13054) coincide with the colors indicated on the user interface 13042 for that port, the modular energy system 13012 can allow users to easily identify the instruments that have been assigned to the footswitch. The light tubes surrounding ports to which unassigned instruments are connected can remain unlit until the user reassigns the footswitch to those instruments. Therefore, the user has a clear visual indication as to exactly which instruments are assigned to a footswitch and which ports are actively in use at any point during the use of the modular energy system 13012.

Figure 55:
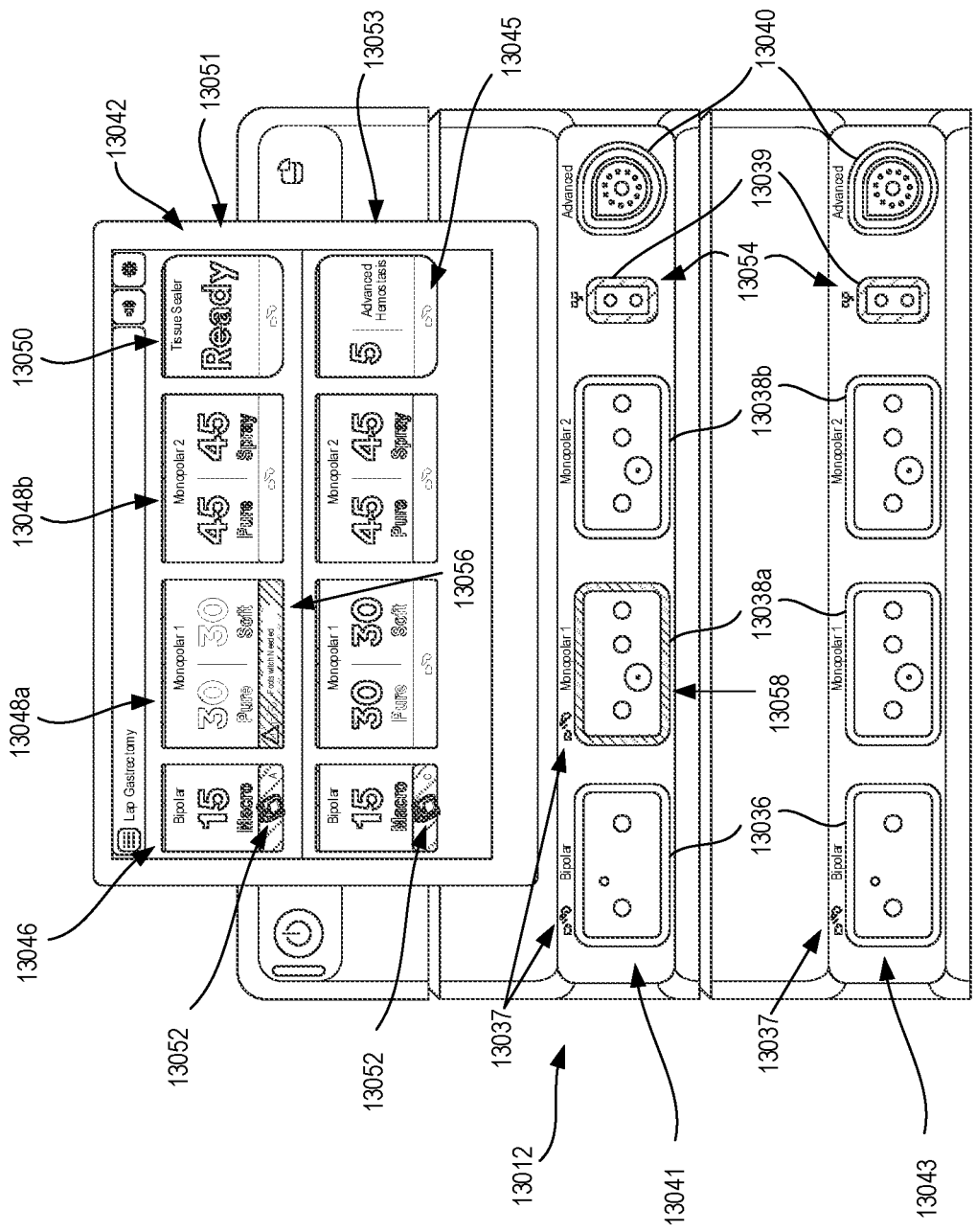
FIG. 55 is a front view of an energy module, in accordance with at least one aspect of the present disclosure.

Referring now to FIG. 55, a front view of the modular energy system 13012 of FIG. 54 is shown in accordance with another aspect of the present disclosure. Here, the user interface 13042 is communicating a "required assignment" notification 13056, indicating to the user that a footswitch has not been assigned to the first monopolar port 13038a. As used herein, a notification can include a text, colors, or an audible alert, among other things to communicate information to the user. In the aspect of FIG. 55, a non-hand-activated monopolar instrument was connected to the first energy module 13041, but no footswitch has been assigned to it yet. Accordingly, the "required assignment" notification 13056 displayed below the monopolar port icon 13048a is illuminated in a "required assignment" color. The "required assignment" can display various texts, images, or colors indicating what specifically is required. For example, the "required assignment" notification of FIG. 55 says "Footswitch Needed." The "required assignment" notification 13056 can include, for example, alternate crosshatching in a particular color (e.g., orange). Accordingly, the modular energy system 13012 can illuminate the footswitch assignment indicator 13037 associated with the bipolar port 13036 of the first and second energy modules 13041, 13043 a color (e.g., green), thereby confirming that a footswitch has been assigned to those ports. However, the footswitch assignment indicator 13037 associated with the first monopolar port 13038a of the first energy module 13041 can be illuminated in a color corresponding to the same color of the icon 13048a, indicating that a footswitch is not assigned to that port 13038a. Likewise, the modular energy system 13012 can illuminate a light tube 13058 surrounding the first monopolar instrument port 13038a of the first energy module 13041 corresponding to the same color of the icon 13048a. Light tubes 13054 surrounding the other ports can maintain their own individual colors, markings, and/or other indicia in accordance with their own individual statuses. Therefore, the user has a clear visual indication as to exactly which ports and/or instruments require attention and are implicated by the "required assignment" notification 13056 displayed by the user interface 13042.

Figure 56:
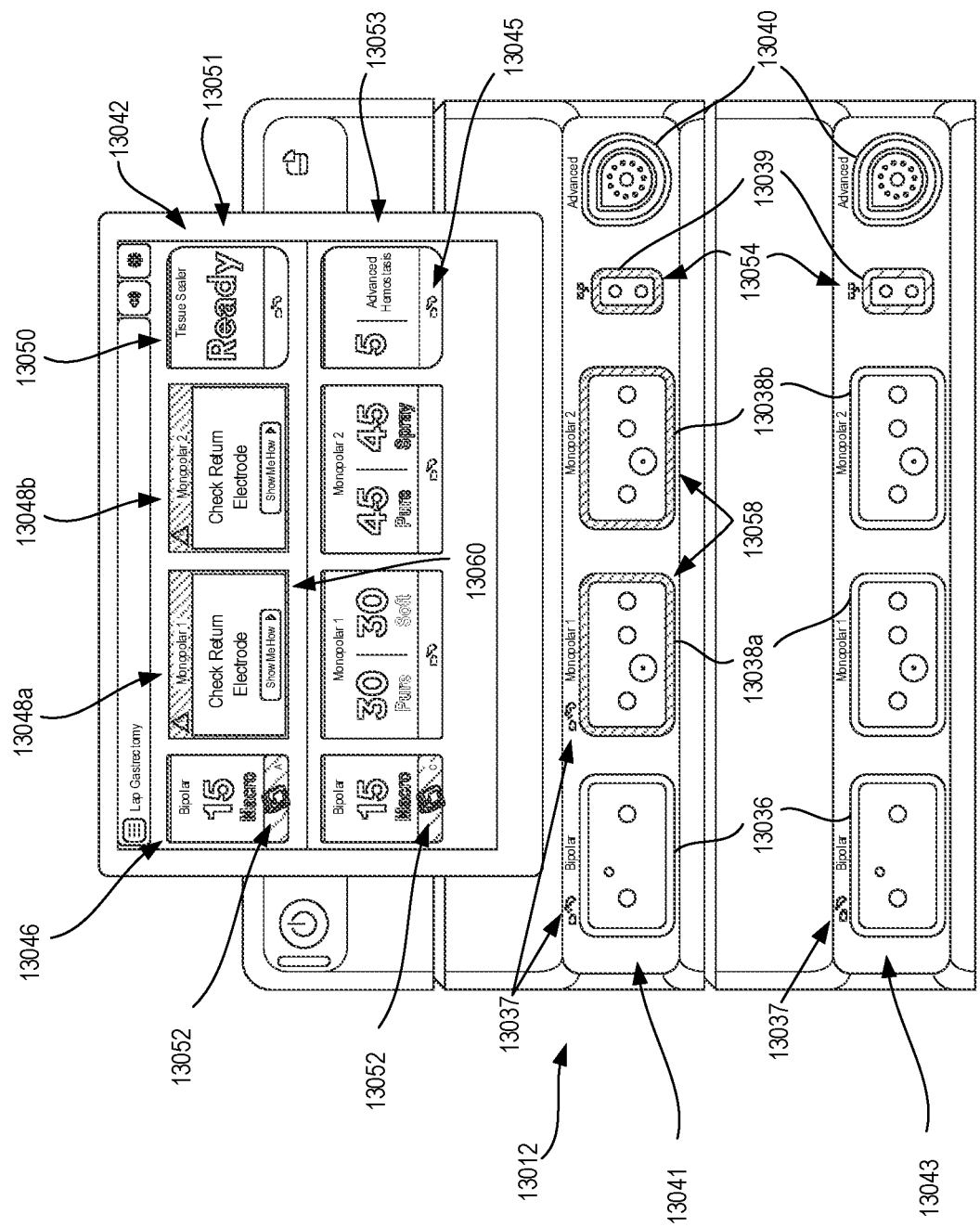
FIG. 56 is a front view of an energy module, in accordance with at least one aspect of the present disclosure.

Referring now to FIG. 56, a front view of the modular energy system 13012 of FIGS. 54 and 55 is shown in accordance with another aspect of the present disclosure. Here, the user interface 13042 is communicating an "instrument error" notification 13060, indicating to the user that an instrument is improperly connected or requires attention. In FIG. 56, the "instrument error" message 13060 is communicating to the user that a neutral electrode return is not properly connected to the neutral electrode port 13039 of the first energy module 13041. Accordingly, the "instrument error" notification 13060 is displayed below the first and second monopolar port icons 13048a, 13048b and the monopolar port icons 13048a, 13048b are illuminated an "instrument error" color. The "instrument error" notification 13060 can include, for example, alternate crosshatching in a particular color (e.g., red). Accordingly, the modular energy system 13012 can illuminate the footswitch assignment indicator 13037 associated with each of the bipolar ports 13036 of the first and second energy modules 13041, 13043, and a footswitch assignment indicator 13037 associated with the first monopolar port 13038a of the first energy module 13041 a color (e.g., green), thereby confirming that a footswitch has been assigned to those ports. However, the modular energy system 13012 can illuminate a light tube 13058 surrounding the first and second monopolar instrument ports 13038a, 13038b of the first energy module 13041 corresponding to the port icons 13048a, 13048b the same color. Therefore, the user has a clear visual indication as to exactly which instruments require attention and are implicated by the "instrument error" notification 13060 displayed by the user interface 13042 and whether or not the instrument is assigned to a footswitch.

Figure 57:
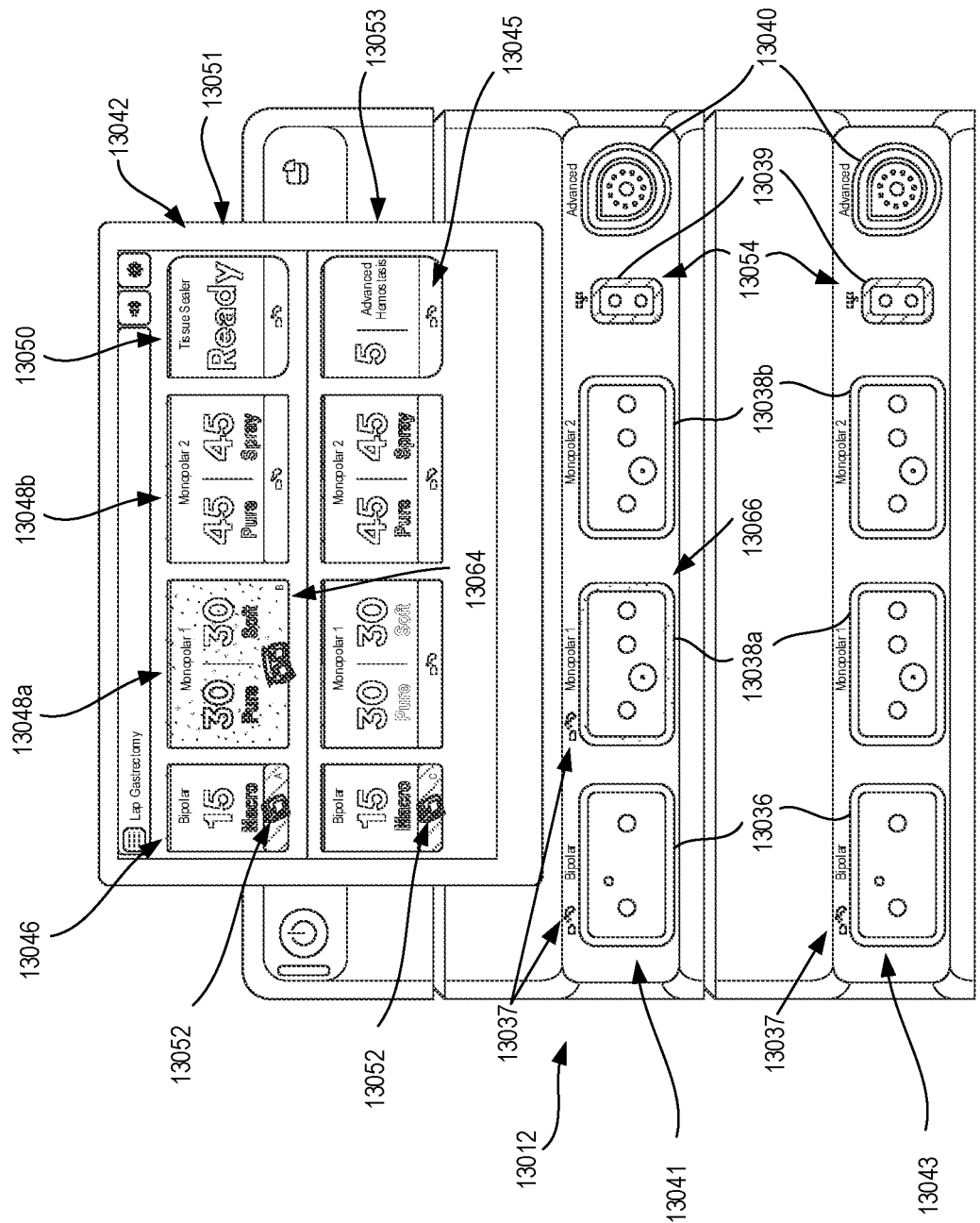
FIG. 57 is a front view of an energy module, in accordance with at least one aspect of the present disclosure.

Referring now to FIG. 57, a front view of the modular energy system 13012 of FIGS. 54-56 is shown in accordance with another aspect of the present disclosure. Here, the user interface 13042 is providing the user with an "activated port" notification 13064. The "activated port" notification can indicate which energy mode of energy module 13041, 13043 is activated, and specifically, which port 13036, 13038a, 13038b, 13040 of that energy module 13041, 13043 is activated for use. For example, in the aspect of FIG. 57, a "cut" mode of the first energy module 13041 is activated by the modular energy system 13012, thereby enabling an instrument connected to a first monopolar port 13038a to cut tissue. Accordingly, the "activated instrument" notification 13064 can be displayed within the monopolar port icon 13048a of the first row 13051 and the monopolar port icon 13048a can include a first indicia (e.g., a color). The "activated port" notification 13064 associated with the "cut" mode can include, for example, alternate crosshatching in a first color (e.g., yellow). Additionally and/or alternatively, the port icons 13046, 13048b, 13050 can be faded out, removed, or otherwise visually minimized by the user interface 13042. Likewise, the modular energy system 13012 can illuminate a light tube 13066 surrounding the activated port 13038a. Thus, the light tube 13066 and various elements of the user interface 13042 can communicate to the user which port 13036, 13038a, 13038b, 13040 of which energy module 13041, 13043 is activated.

Figure 58:
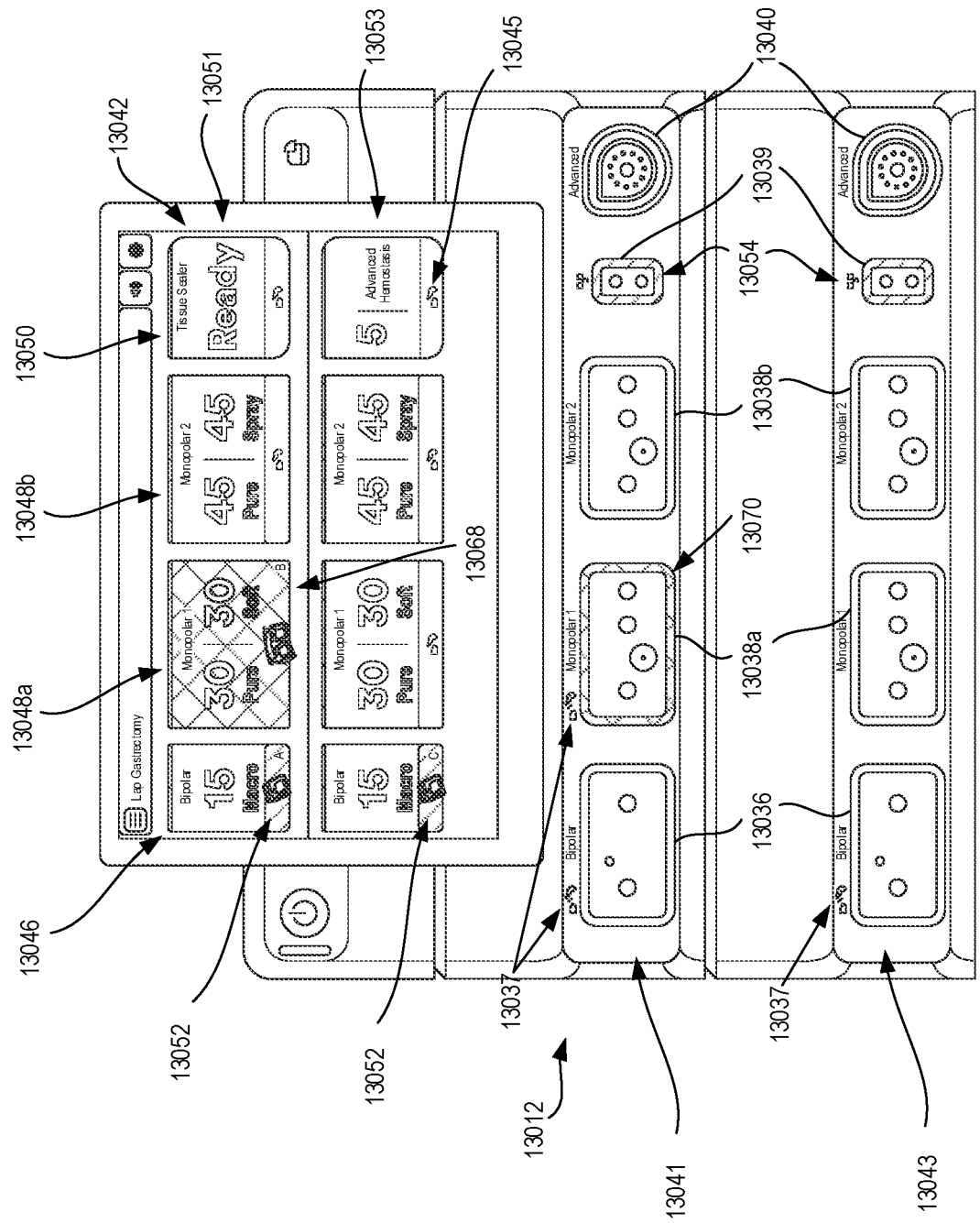
FIG. 58 is a front view of an energy module, in accordance with at least one aspect of the present disclosure.

FIG. 58 depicts a similar user interface 13042 to that of FIG. 57 in accordance with another aspect of the present disclosure. However, in the aspect of FIG. 58, a "coagulate" mode of the first energy module 13041 is activated by the modular energy system 13012, thereby enabling an instrument connected to a first monopolar port 13038a to coagulate tissue. Accordingly, the "activated instrument" notification 13068 can be displayed within the monopolar port icon 13048a of the first row 13051, and the monopolar port icon 13048a can include a second indicia. The second indicia can be different from the first indicia in order to visually distinguish the different modes in which a connected surgical instrument can operate. The "activated port" notification 13068 associated with a "coagulate" mode can include, for example, alternate crosshatching in a second color (e.g., blue). Additionally and/or alternatively, the port icons 13046, 13048*b*, 13050 can be faded out, removed, or otherwise visually minimized by the user interface 13042. Likewise, the modular energy system 13012 can illuminate a light tube 13070 surrounding the activated port 13038*a*.

Referring now to FIGS. 59-63, various displays of a user interface 13042 of an energy module are shown in accordance with at least one aspect of the present disclosure. In addition to the features depicted in FIGS. 59-63, the user interface is contemplated to further display an instrument settings panel that includes controls that are unique to each instrument. In some aspects, the user interface 13042 can include controls that allow the user to increase or decrease the intensity of an instrument's output 13071, adjust its functions 13073, and/or pair it with connected system accessories (e.g., a footswitch 13052). The user interface 13042 can further provide access to advanced instrument settings and access information about the instrument. For example, the instrument settings panel can be accessed by interacting with a settings icon 13075. These features, among others, are contemplated by the present disclosure, including various combinations thereof. Accordingly, the user interface 13042 can be extremely flexible and may be reconfigured to accommodate the specific needs of an electrosurgical procedure.

The user interface 13042 of FIGS. 59-63 is further configured to optimize the use of a connected footswitch. For example, if the user plugs in a non-hand-activated instrument, the user interface 13042 will display a warning if no footswitch is connected. Alternatively and/or additionally, the instrument settings are dimmed, as the instrument cannot be activated without a footswitch. Furthermore, the user interface 13042 is configured to notify the user when a footswitch has been assigned to an instrument, and allows the user to reassign, unassign, or otherwise change the settings associated with the connected footswitch in accordance with at least the aspects depicted in FIGS. 59-63. In other non-limiting aspects, the user interface 13042 is further configured to communicate with a control circuit and automatically assign footswitches to non-hand-activated instruments in accordance with default settings.

Figure 59:
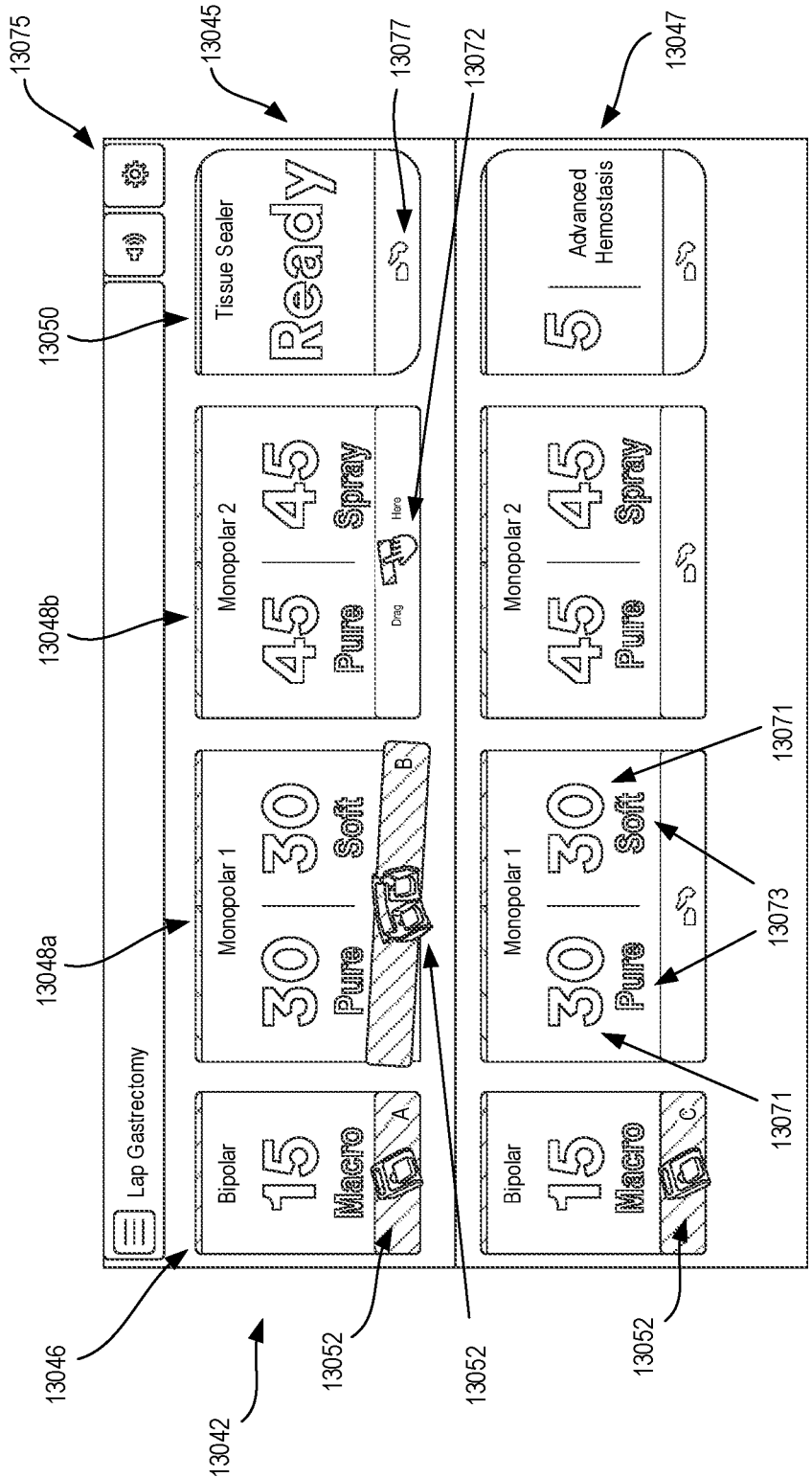
FIG. 59 is a display of a user interface, in accordance with at least one aspect of the present disclosure.

Referring now to FIG. 59, a display of the user interface 13042 of an energy module is shown in accordance with at least one aspect of the present disclosure. The user interface of FIG. 59 can display port icons 13046, 13048*a*, 13048*b*, 13050 associated with ports of a first energy module 13045 and second energy module 13047. Although the user interface of FIG. 59 is configured for use with two energy modules 13045, 13047, the present disclosure contemplates other aspects where the user interface is configured for use with any number of energy modules.

As depicted in FIG. 59, the port icons 13046, 13048*a*, 13048*b*, 13050 can include a global footswitch icon 13077, if the port is compatible for use with a footswitch or other system accessory. When a user wants to assign a footswitch to a specific port, they interact with the global footswitch icon 13077 of the desired port icon 13046, 13048*a*, 13048*b*, 13050. Accordingly, the user interface 13042 displays a footswitch assignment overlay that can allow the user to assign and reassign footswitches to the desired port icon 13046, 13048*a*, 13048*b*, 13050 using the footswitch widgets 13052. When the user interacts with the global footswitch icon 13077 of the desired port icon 13046, 13048*a*, 13048*b*, 13050, a "drag here" prompt 13072 will appear on that port icon 13046, 13048*a*, 13048*b*, 13050 and any footswitch widgets 13052 that can be reassigned to the selected port icon 13046, 13048*a*, 13048*b*, 13050 will be visually distinguished from footswitch widgets 13052 that cannot be reassigned to the selected port icon 13046, 13048*a*, 13048*b*, 13050. The user can move a compatible footswitch widget 13052 to the selected port icon 13046, 13048*a*, 13048*b*, 13050, thereby reassigning the footswitch to that port.

For example, in FIG. 59, the user has selected the global footswitch icon 13077 of the second monopolar port icon 13048*b* for the first energy module 13045, thereby initiating the process of assigning a footswitch to the second monopolar port of the first energy module 13045. In response, the second monopolar port icon 13048*b* displays a "drag here" prompt 13072. In response to being selected, the footswitch widget 13052 can be configured to visually confirm that it has been selected (e.g., by pivoting back and forth). In the illustrated example, the footswitch widget 13052 associated with the two-pedal footswitch assigned to the first monopolar port icon 13048*a* of the first energy module 13045 has begun to pivot back and forth, indicating that it can be reassigned to the second monopolar port icon 13048*b* of the first energy module 13045. Although the footswitch widget 13052 in FIG. 59 is pivoting back and forth, other methods of visually distinguishing compatible footswitch widgets 13052 are contemplated by the present disclosure (e.g., change color, become brighter, display text). Notably, the footswitch widgets 13052 associated with the single-pedal footswitches currently assigned to the bipolar instruments connected to the first and second energy modules 13045, 13047 are not pivoting, because they are not compatible for reassignment to the second monopolar port icon 13048*b*. However, other methods of visually distinguishing incompatible footswitch widgets 13052 are contemplated by the present disclosure (e.g., change color, become dimmer, display text). The user can drag the pivoting footswitch widget 13052 on the first monopolar port icon 13048*a* to the second monopolar port icon 13048*b*, thereby reassigning the footswitch from the first monopolar port icon 13048*a* to the second monopolar port icon 13048*b*. After the footswitch is reassigned, the user interface 13042 removes the footswitch assignment overlay. Although FIG. 59 depicts the assignment process for the second monopolar port icon 13048*b* of the first energy module 13045, selecting the global footswitch icon 13077 of any port icon 13046, 13048*a*, 13048*b*, 13050 will commence a similar process, wherein each footswitch widget 13052 associated with a connected footswitch that is compatible for assignment to the selected instrument will begin to pivot back and forth.

Figure 60:
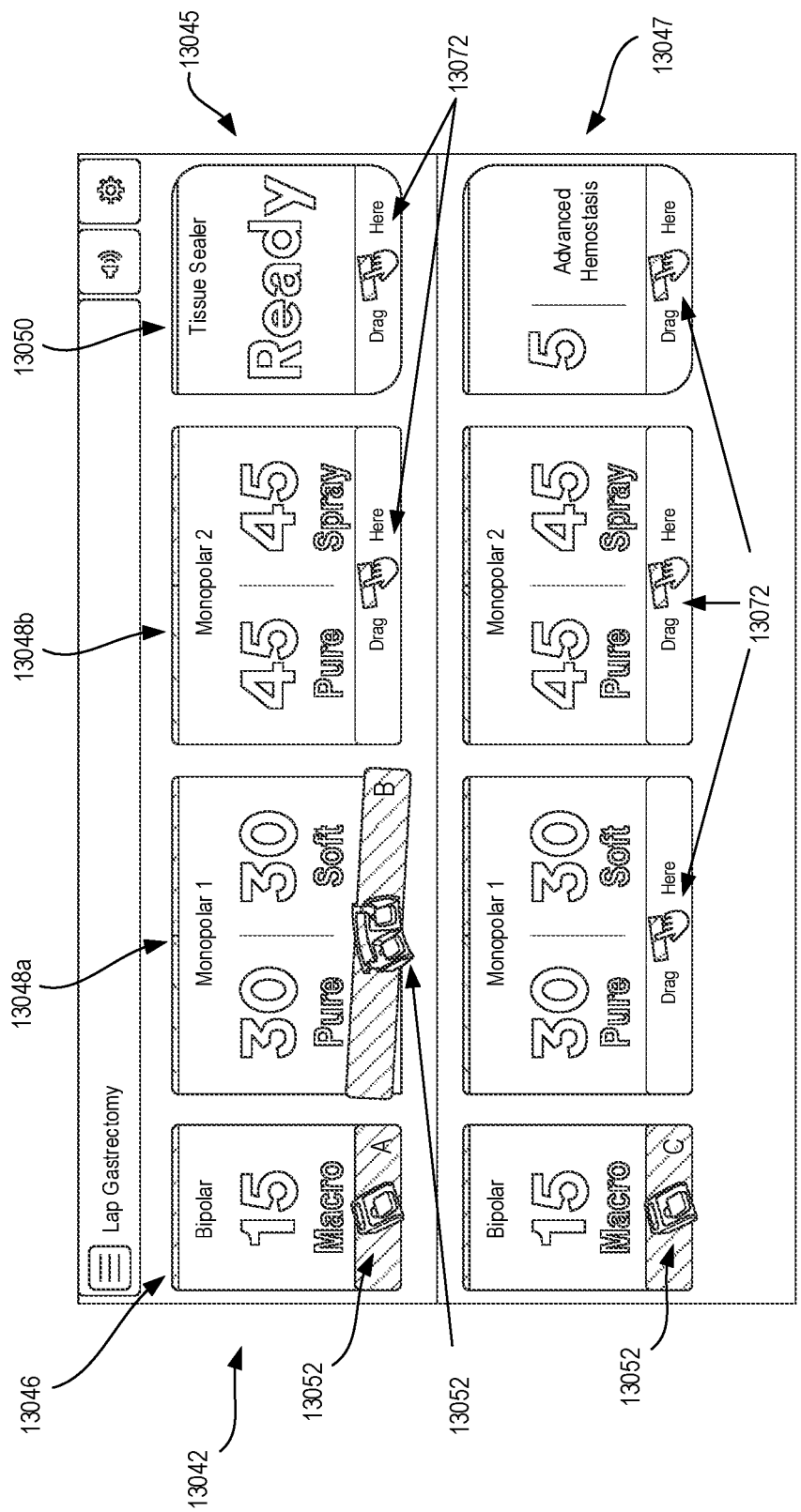
FIG. 60 is a display of a user interface, in accordance with at least one aspect of the present disclosure.

Referring now to FIG. 60, another display of the user interface 13042 of an energy module is shown in accordance with at least one aspect of the present disclosure. Contrary to the aspect of FIG. 59, the user has selected a footswitch widget 13052 that they want to reassign to a different port icon 13046, 13048*a*, 13048*b*, 13050. In response, the user interface 13042 can display a footswitch reassignment overlay distinguishing port icons 13046, 13048*a*, 13048*b*, 13050 that are compatible with the selected footswitch widget 13052. For example, in FIG. 60, the user has selected the footswitch widget 13052 currently assigned to the first monopolar port icon 13048*a* of the first energy module 13045. Accordingly, the second monopolar port icon 13048*b* and the combination energy port icon 13050 of the first energy module 13045 and the first monopolar port icon 13048*a*, the second monopolar port icon 13048*b*, and the combination energy port icon 13050 of the second energy module 13047 display a "drag here" prompt 13072 indicating that they are compatible with the selected footswitch for reassignment. The "drag here" prompts 13072 indicate to the user that the selected footswitch can be assigned to those ports. Although the compatible port icons 13048a, 13048b, 13050 of FIG. 60 display a "drag here" prompt, other methods of visually distinguishing compatible ports are contemplated by the present disclosure (e.g., change color, become brighter, display text). Additionally, the selected footswitch widget 13052 has begun to pivot back and forth, indicating which footswitch is selected and about to be reassigned. However, other methods of visually distinguishing the selected footswitch widget 13052 are contemplated by the present disclosure (e.g., change color, become brighter, display text). Because the selected footswitch widget 13052 is associated with a two-pedal footswitch, it is compatible with any of the connected instruments. However, if the user selected a footswitch widget 13052 associated with a single-pedal footswitch, the "drag here" prompt 13072 could appear on the bipolar port icons 13046 and combination energy port icons 13050.

Figure 61:
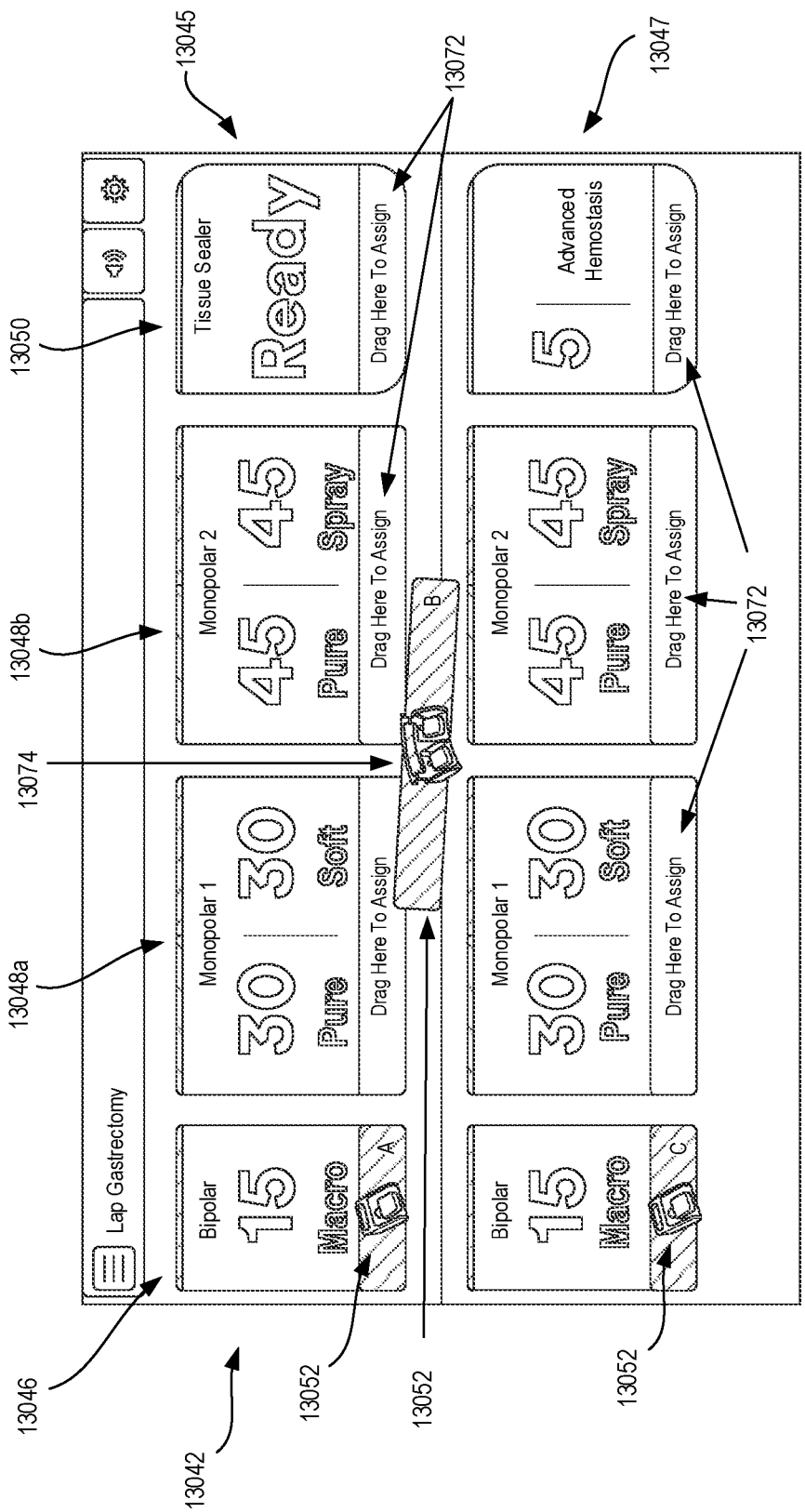
FIG. 61 is a display of a user interface, in accordance with at least one aspect of the present disclosure.

Referring now to FIG. 61, another display of the user interface 13042 of an energy module is shown in accordance with at least one aspect of the present disclosure. In FIG. 61, the user is in the process of reassigning a footswitch from the first monopolar port icon 13048a of the first energy module 13045 to the second monopolar port icon 13048b of the first energy module 13045, using the method depicted in FIG. 60. Specifically, the user has interacted with the footswitch widget 13052 previously assigned to the first monopolar port icon 13048a of the first energy module 13045, which initiated the footswitch reassignment overlay and resulted in the display of multiple "drag here" prompts 13072 on compatible port icons 13048a, 13048b, 13050. Notably, the bipolar port icons 13046 associated with the bipolar instruments connected to the top and bottom energy modules do not display a "drag here" prompt 13072, because single-pedal footswitches are currently assigned to them. Thus, they are unavailable for reassignment. The user is in the process of dragging the footswitch widget 13052 from the first monopolar port icon 13048a of the first energy module 13045 to the second monopolar port icon 13048b of the first energy module 13045. Although the user is dragging the footswitch widget 13052 in FIG. 61, alternate methods of moving the footswitch widget are contemplated by the present disclosure.

Figure 62:
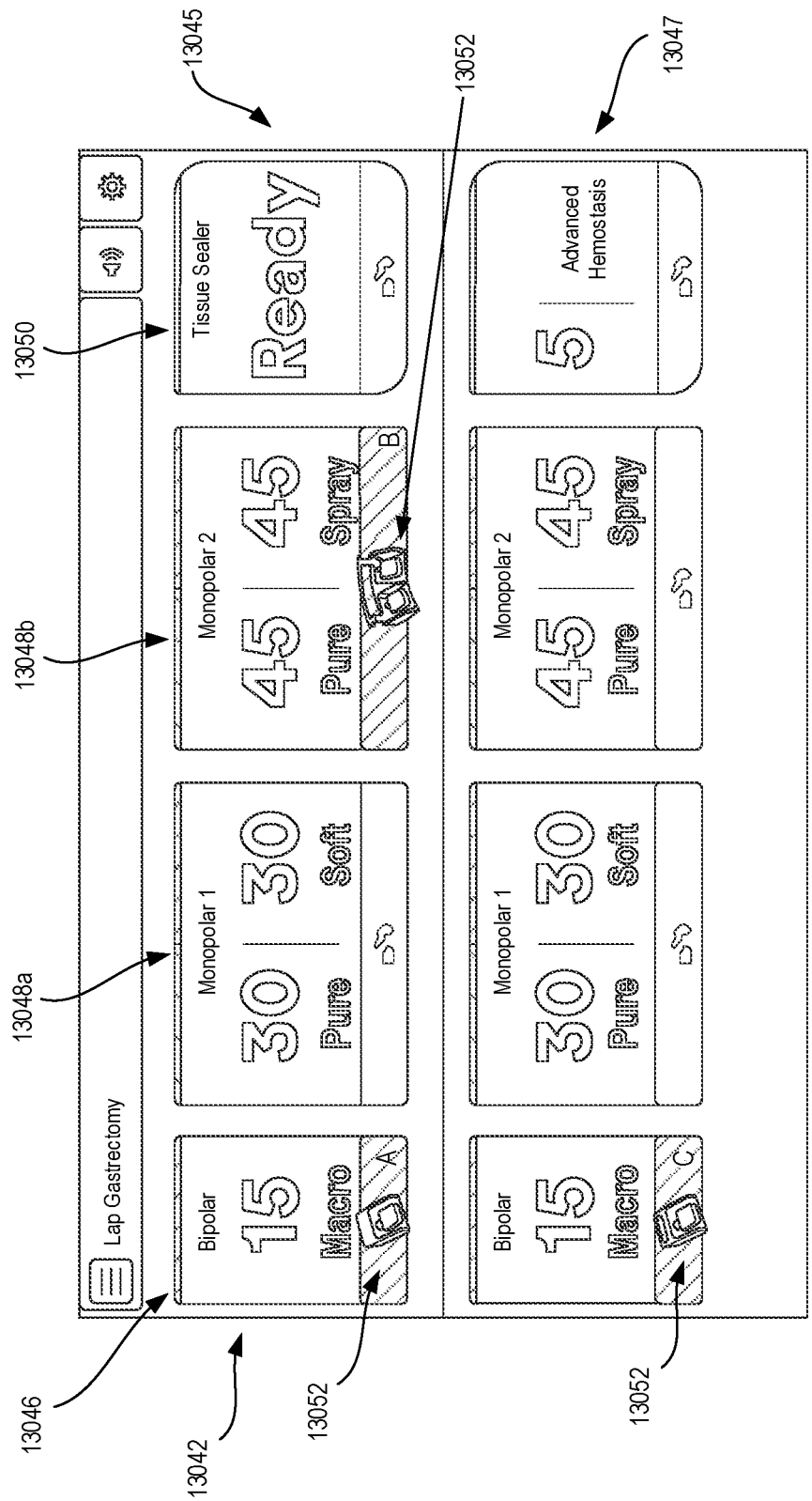
FIG. 62 is a display of a user interface, in accordance with at least one aspect of the present disclosure.

Referring now to FIG. 62, another display of the user interface 13042 of an energy module is shown in accordance with at least one aspect of the present disclosure. In FIG. 62, the user has completed the process of reassigning a footswitch from the first monopolar port icon 13048a of the first energy module 13045 to the second monopolar port icon 13048b of the first energy module 13045, as depicted in FIG. 61. Accordingly, the footswitch reassignment overlay is no longer displayed, the "drag here" prompts have disappeared, and the user interface has illuminated the second monopolar port icon 13048b the "confirmation" color. The "confirmation" color is represented via crosshatching in FIG. 62.

Figure 63:
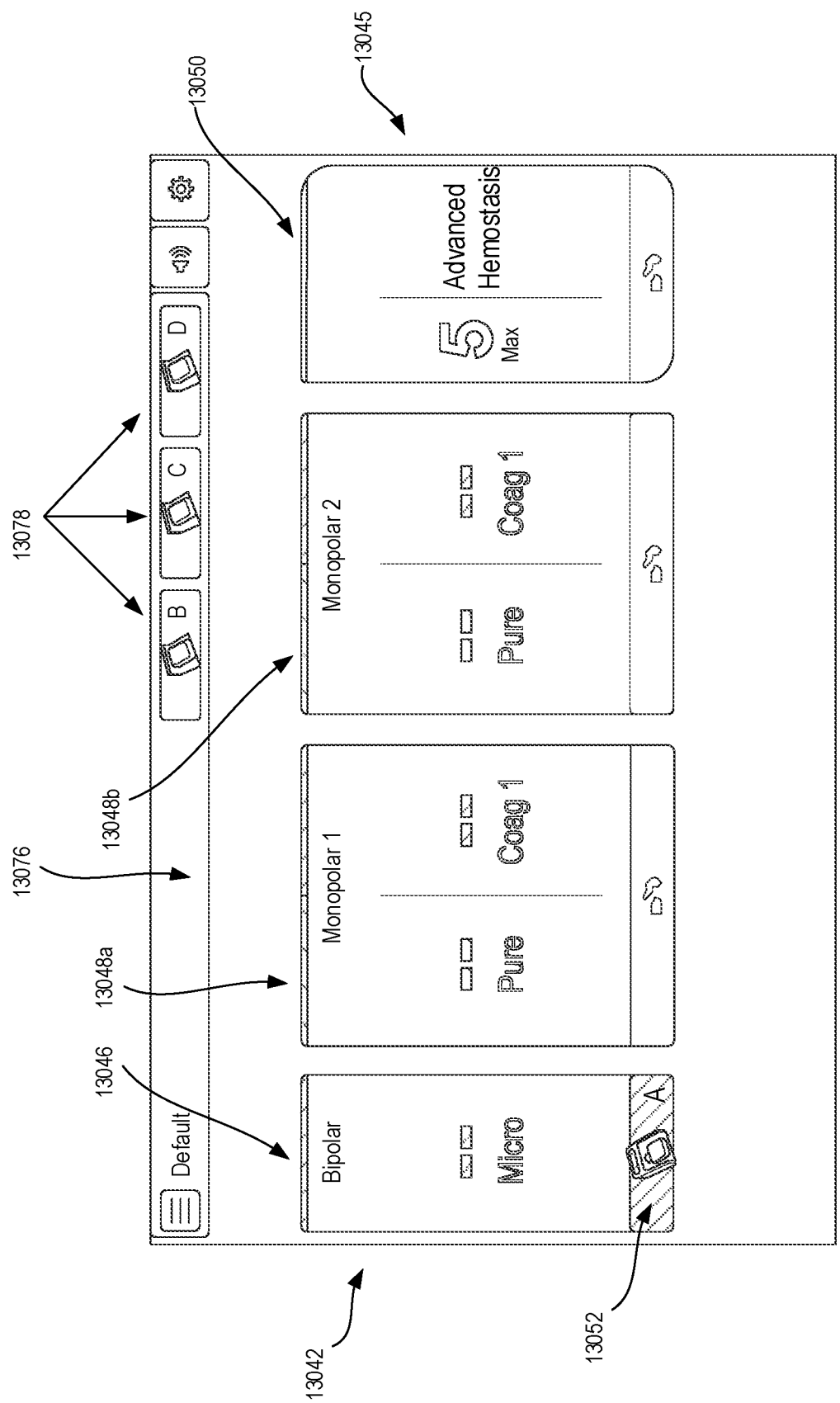
FIG. 63 is a display of a user interface, in accordance with at least one aspect of the present disclosure.

Referring now to FIG. 63, another display of the user interface 13042 of an energy module is shown in accordance with at least one aspect of the present disclosure. According to the aspect of FIG. 63, the user interface 13042 can have a designated area 13076 for unassigned footswitch icons 13078. Accordingly, if a footswitch is connected to the modular energy system, but has not been assigned to an instrument, an unassigned footswitch icon 13078 can appear on the user interface 13042 in the designated area 13076. Although the aspect of FIG. 63 depicts the designated area 13076 at the top of the display, other locations are contemplated by the present disclosure. When a user wants to assign an unassigned footswitch to an instrument, he or she can follow a process similar to those depicted in FIGS. 59-62. Specifically, the user can interact with either the unassigned footswitch icon 13078 or the desired port icon 13046, 13048a, 13048b, 13050, thereby initiating the footswitch reassignment overlay, and move the footswitch icon 13078 to the desired port icon 13046, 13048a, 13048b, 13050. Upon proper assignment, the user interface will illuminate the port icon 13046, 13048a, 13048b, 13050 to which the footswitch has been assigned the "confirmation" color. Although the modular energy system of FIG. 63 has only a first energy module 13045, the present disclosure contemplates other aspects where user interface 13042 displays port icons 13046, 13048a, 13048b, 13050 associated with the ports of any number of energy modules.

Figure 64:
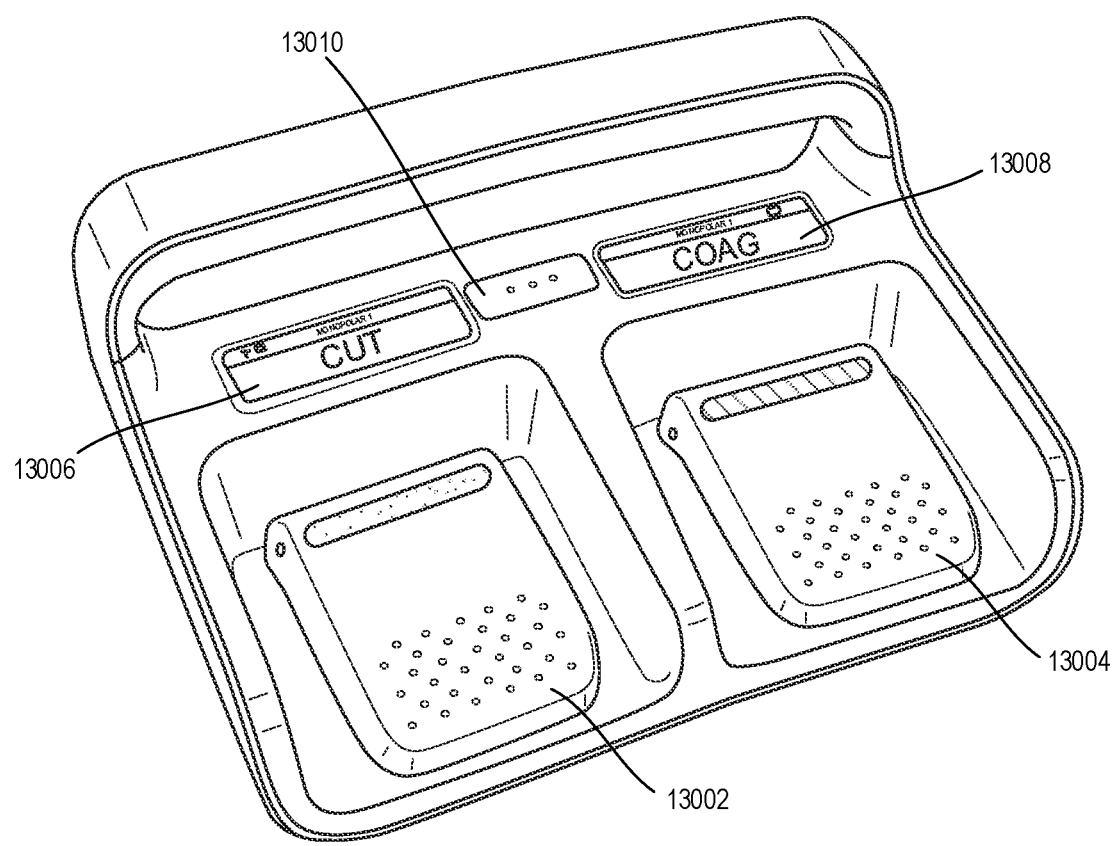
FIG. 64 is a perspective view of a footswitch, in accordance with at least one aspect of the present disclosure.

Referring to FIG. 64, a perspective view of a footswitch 13000 is shown in accordance with at least one aspect of the present disclosure. The footswitch 13000 is interchangeably compatible with different energy ports, energy modules, drive modes, and/or instruments. As previously discussed and depicted in FIGS. 59-63, the footswitch 13000 of FIG. 64 can be reassigned by the user interface of a modular energy system. For example, although the footswitch 13000 can be connected through a single port of the surgical system via a corresponding accessory port 13016, as depicted in FIGS. 51 and 52, it can be reassigned for use during a monopolar, bipolar, or combination energy mode of the modular energy system without altering the connection.

According to the aspect of FIG. 64, the footswitch 13000 includes a first foot pedal 13002 and second foot pedal 13004. The first foot pedal 13002 and second foot pedal 13004 can activate an instrument connected to a port of the modular energy system to perform a variety of functions. For example, in FIG. 64, the first foot pedal 13002 can be assigned to activate a cut energy mode of the energy module, and the second foot pedal 13004 can be assigned to activate a coagulation energy mode of the energy module. However, each of the first foot pedal 13002 and second foot pedal 13004 can be reassigned to activate a different function of the modular energy system via the user interface. Although the footswitch 13000 of FIG. 64 includes a first foot pedal 13002 and second foot pedal 13004, this particular example is merely for illustrative purposes and other non-limiting aspects of the present disclosure include a single foot pedal. For example, in one non-limiting aspect, a footswitch includes a single foot pedal assignable to bipolar or combination energy ports of the modular energy system. Still other non-limiting aspects of the present disclosure include more than two foot pedals. For example, in one non-limiting aspect, a footswitch includes three pedals assignable to activate a variety of energy modes of the modular energy system. Accordingly, the footswitch 13000 can be configured to include any number of foot pedals depending the intended application.

In further reference to FIG. 64, the footswitch 13000 includes a first reconfigurable display 13006 and second reconfigurable display 13008 positioned above each of the first foot pedal 13002 and second foot pedal 13004. The first reconfigurable display 13006 and second reconfigurable display 13008 can inform the user of the energy mode that each of the first foot pedal 13002 and second foot pedal 13004 are assigned to activate. Accordingly, the text, color, or other indicia displayed by the reconfigurable displays 13006, 13008 can correspond to the particular mode or function to which the respective foot pedal 13002, 13004 is assigned. The reconfigurable displays 13006, 13008 employ any number of display technologies, including, but not limited to: light-emitting diode displays (LED), liquid crystal displays (LCD), electroluminescent displays (ELD), electronic paper, and digital light processing displays (DLP), among others. In the particular aspect of FIG. 64, the first foot pedal 13002 is configured to activate a connected electrosurgical instrument to cut tissue. Accordingly, the first reconfigurable display 13006 can display the word "CUT." Likewise, the second foot pedal 13004 is configured to activate a connected electrosurgical instrument to coagulate tissue. Accordingly, the second reconfigurable display 13008 can display the word "COAG." However, when the user interface assigns each of the first foot pedal 13002 or second foot pedal 13004 to activate a different energy mode of the modular energy system, each of the first reconfigurable display 13006 and second reconfigurable display 13008 is reconfigured to display the new function. The reconfigurable displays 13006, 13008 can be automatically reconfigured by the modular energy system or manually changed by the user. Although the footswitch 13000 of FIG. 64 includes two reconfigurable displays, one for each of its two foot pedals, other non-limiting aspects of the present disclosure include fewer reconfigurable displays than foot pedals, wherein the reconfigurable displays can inform the user of an assigned function of any of the foot pedals on the footswitch. Still other non-limiting aspects of the present disclosure forego a reconfigurable display altogether, using the user interface and/or display of the modular energy system to display the function of each foot pedal. Other non-limiting aspects of the present disclosure omit reconfigurable displays in preference for audible or haptic feedback to inform the user of the configured function of each foot pedal. Still other aspects of the footswitch include a combination of configurable displays, audible, and haptic feedback to communicate with the user.

According to the aspect of FIG. 64, the footswitch 13000 includes an additional function button 13010 configured to interface with the modular energy system to perform a number of programmed functions related to the ports, modules, drive modes, and/or connected instruments. For example, the additional function button 13010 of FIG. 64 can reassign the footswitch 13000 a different port of the modular energy system. If the procedure requires the use of a different instrument, the user could push the additional function button 13010 to reassign the footswitch 13000 to activate a second port of the modular energy system, without having to alter the physical connection or traverse the OR to access the user interface. Similar to the first foot pedal 13002 and second foot pedal 13004, the user interface can be used to reassign the additional function button 13010 to perform any number of alternate functions. For example, the additional function button 13010 can be configured to reassign the footswitch 13000 to an alternate module or drive mode of the modular surgical system. Alternatively, the additional function button 13010 can be configured to reassign the first foot pedal 13002 or second foot pedal 13004 to activate an alternate energy mode of the modular energy system.

The user interface can automatically apply default settings upon connection of the footswitch 13000 to the modular energy system. The user can select the default settings via the user interface of the surgical system, which are subsequently stored in a data storage device in communication with the surgical system. Upon connection, the modular energy system can identify the footswitch (e.g., via resistor identification). Accordingly, the modular energy system can automatically assign an identified footswitch 13000 to a particular port of an energy module based on the default settings. The default settings can further take into account the particular configuration of the surgical system (e.g., the number and types of energy modules from which the modular surgical system is formed, the number and types of footswitches 13000 coupled to the modular energy system, the number and arrangement of foot pedals collectively available across the footswitch(es) 13000 coupled to the modular energy system). In certain aspects of the present disclosure, the automatic identification and assignment of the footswitch 13000 in accordance with default settings serves as a failsafe. For example, bipolar and monopolar lap instruments generally require a footswitch 13000 prior to operation. In one aspect, a default setting is established to prevent the energy module from functioning prior to the identification and assignment of the required footswitch 13000. Thus, the user will have to connect a footswitch 13000 prior to commencing surgery. However, once connected, the footswitch 13000 and foot pedals 13002, 13004, will be automatically assigned. Accordingly, the default settings can be modified by the user to conform to preference and/or surgical requirements.

As another example, if the modular energy system is configured for bipolar surgery, the default settings will automatically configure a first single foot pedal footswitch for bipolar activation upon connection, based on the default settings. If a second single foot pedal footswitch is subsequently connected, the modular energy system will recognize that the first footswitch is already assigned to a bipolar port and automatically assign the second footswitch for combination energy port upon connection, based on the default settings. Alternatively, if the modular energy system is configured for monopolar surgery, the default settings could automatically assign a first footswitch with two foot pedals to activate a first monopolar port upon connection, based on the default settings. If a second footswitch with two foot pedals is subsequently connected, the modular energy system could recognize that the first footswitch is already assigned to the first monopolar port and automatically assign the second footswitch to activate a second monopolar port upon connection, based on the default settings. If a third footswitch with two foot pedals is subsequently connected, the modular energy system could recognize that the first footswitch is already assigned to the first monopolar port and that the second footswitch is already assigned to second monopolar port and automatically assign the third footswitch to a combination energy port upon connection, based on the default settings. Accordingly, the reconfigurable displays of each footswitch can inform the user of each foot pedal function as the modular energy system automatically assigns the footswitches, allowing for convenient confirmation that the default settings have been appropriately applied. Although the default settings can automatically assign each footswitch 13000 upon connection, reassignment is possible via the user interface. Accordingly, if the user decides to change the settings, he or she may do so by using the user interfaces or, in some aspects, by toggling settings via the additional function button 13010.

EXAMPLES

Various aspects of the subject matter described herein are set out in the following numbered examples:

Example 1

A method for controlling a user interface (UI) of a modular energy system, the modular energy system comprising a header module and a display screen on which the UI is displayed, the method comprising: detecting attachment of a first module to the modular energy system; controlling the UI to display one or more first UI elements corresponding to the first module, the one or more first UI elements configured to provide information or controls pertaining to the first module; detecting attachment of a second module to the modular energy system; controlling the UI to resize the one or more first UI elements to accommodate display of one or more second UI elements corresponding to the second module; and controlling the UI to display the one or more second UI elements, the one or more second UI elements configured to display information or controls provide information or controls pertaining to the second module.

Example 2

The method of Example 1, wherein the one or more first UI elements comprises a widget, the widget configured to control a function of the first module.

Example 3

The method of Example 2, wherein: the first module comprises an energy module; and the widget is configured to control a power level of an energy modality delivered by a surgical instrument connected to the energy modality.

Example 4

The method of Example 3, wherein: the energy module comprises a plurality of ports configured to deliver a plurality of energy modalities; the one or more first UI elements each correspond to one of the plurality of ports; and the widget is configured to control the power level of the energy modality corresponding to a port to which the widget corresponds.

Example 5

The method of Example 2, wherein: the first module comprises an energy module; and the widget is configured to control an operational mode of an energy modality delivered by a surgical instrument connected to the energy modality.

Example 6

The method of Example 5, wherein: the energy module comprises a plurality of ports configured to deliver a plurality of energy modalities; the one or more first UI elements each correspond to one of the plurality of ports; and the widget is configured to control the operational mode of the energy modality corresponding to a port to which the widget corresponds.

Example 7

The method of any one of Examples 1-6, further comprising: controlling the UI to display the one or more first UI elements and the one or more second UI elements according to a relative position of the first module and the second module within the modular energy system.

Example 8

The method of Example 7, wherein: the first module and the second module are configured to removably connect to each other in a stacked configuration in which the first module is positioned above the second module; the one or more first UI elements are displayed at a first row on the UI; the one or more second UI elements are displayed at a second row on the UI; and the first row is above the second row.

Example 9

The method of any one of Examples 1-8, wherein: the first module comprises an energy module; and the one or more first UI elements are displayed in a color corresponding to an operational mode of the energy module.

Example 10

The method of Example 9, wherein the operational mode comprises a first operational mode and the color comprises a first color, the method further comprising: determining that the energy module has been changed from the first operational mode to a second operational mode; and controlling the UI to change the one or more first UI elements from the first color to a second color corresponding to the second operational mode.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The invention claimed is:

1. A method for controlling a user interface (UI) of a modular energy system, the modular energy system comprising a header module and a display screen on which the UI is displayed, the method comprising:
    detecting attachment of a first module to the modular energy system;
    controlling the UI to display one or more first UI elements corresponding to the first module, the one or more first UI elements configured to provide information or controls pertaining to the first module;
    detecting attachment of a second module to the modular energy system;
    controlling the UI to resize the one or more first UI elements to accommodate display of one or more second UI elements corresponding to the second module; and controlling the UI to display the one or more second UI elements, the one or more second UI elements configured to provide information or controls pertaining to the second module.

2. The method of claim 1, wherein the one or more first UI elements comprises a widget, the widget configured to control a function of the first module.

3. The method of claim 2, wherein:
the first module comprises an energy module; and
the widget is configured to control a power level of an energy modality delivered by a surgical instrument connected to the energy module.

4. The method of claim 3, wherein:
the energy module comprises a plurality of ports configured to deliver a plurality of energy modalities;
the one or more first UI elements each correspond to one of the plurality of ports; and
the widget is configured to control the power level of the energy modality corresponding to a port of the plurality of ports to which the widget corresponds.

5. The method of claim 2, wherein:
the first module comprises an energy module; and
the widget is configured to control an operational mode of an energy modality delivered by a surgical instrument connected to the energy module.

6. The method of claim 5, wherein:
the energy module comprises a plurality of ports configured to deliver a plurality of energy modalities;
the one or more first UI elements each correspond to one of the plurality of ports; and
the widget is configured to control the operational mode of the energy modality corresponding to a port of the plurality of ports to which the widget corresponds.

7. The method of claim 1, further comprising:
controlling the UI to display the one or more first UI elements and the one or more second UI elements according to a relative position of the first module and the second module within the modular energy system.

8. The method of claim 7, wherein:
the first module and the second module are configured to removably connect to each other in a stacked configuration in which the first module is positioned above the second module;
the one or more first UI elements are displayed at a first row on the UI;
the one or more second UI elements are displayed at a second row on the UI; and
the first row is above the second row.

9. The method of claim 1, wherein:
the first module comprises an energy module; and
the one or more first UI elements are displayed in a color corresponding to an operational mode of the energy module.

10. The method of claim 9, wherein the operational mode comprises a first operational mode and the color comprises a first color, the method further comprising:
determining that the energy module has been changed from the first operational mode to a second operational mode; and
controlling the UI to change the one or more first UI elements from the first color to a second color corresponding to the second operational mode.

11. A method for controlling a user interface (UI) of a modular energy system, the modular energy system comprising a header module and a display screen on which the UI is displayed, the method comprising:
coupling a first module to the modular energy system;
displaying a first UI element corresponding to the first module, the first UI element configured to provide information or controls associated with the first module;
coupling a second module to the modular energy system;
adjusting the first UI element to accommodate display of a second UI element corresponding to the second module; and
displaying the second UI element, the second UI element configured to provide information or controls associated with the second module.

12. The method of claim 11, wherein the first UI element comprises a widget configured to control a function of the first module.

13. The method of claim 12, wherein:
the first module comprises an energy module; and
the widget is configured to control a power level of an energy modality delivered by a surgical instrument connected to the energy module.

14. The method of claim 13, wherein:
the energy module comprises a port configured to deliver an energy modality;
the first UI element corresponding to the of port; and
the widget is configured to control the power level of the energy modality.

15. The method of claim 12, wherein:
the first module comprises an energy module; and
the widget is configured to control an operational mode of an energy modality delivered by a surgical instrument connected to the energy module.

16. The method of claim 15, wherein:
the energy module comprises a port configured to deliver an energy modality;
the first UI element corresponds to the port; and
the widget is configured to control the operational mode of the energy modality.

17. The method of claim 11, further comprising displaying the first UI element and the second UI element according to a relative position of the first module and the second module within the modular energy system.

18. The method of claim 17, wherein:
the first module and the second module are configured to removably connect to each other in a stacked configuration in which the first module is positioned above the second module;
the first UI element is displayed at a first row on the UI;
the second UI element is displayed at a second row on the UI; and
the first row is above the second row.

19. The method of claim 11, wherein:
the first module comprises an energy module; and
the first UI element is displayed in a color corresponding to an operational mode of the energy module.

20. The method of claim 19, wherein the operational mode comprises a first operational mode and the color comprises a first color, the method further comprising:
changing the energy module from the first operational mode to a second operational mode; and
changing the first UI element from the first color to a second color corresponding to the second operational mode.

* * * * *